(12) United States Patent
Jewett et al.

(10) Patent No.: US 10,017,728 B2
(45) Date of Patent: Jul. 10, 2018

(54) METHODS FOR MAKING RIBOSOMES

(71) Applicant: NORTHWESTERN UNIVERSITY, Evanston, IL (US)

(72) Inventors: Michael Christopher Jewett, Evanston, IL (US); Brian Robert Fritz, Chicago, IL (US); Laura Elyse Timmerman, Chicago, IL (US); Yi Liu, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/786,972

(22) PCT Filed: Apr. 24, 2014

(86) PCT No.: PCT/US2014/035376
§ 371 (c)(1),
(2) Date: Oct. 24, 2015

(87) PCT Pub. No.: WO2014/176469
PCT Pub. Date: Oct. 30, 2014

(65) Prior Publication Data
US 2016/0083688 A1  Mar. 24, 2016

Related U.S. Application Data

(60) Provisional application No. 61/815,631, filed on Apr. 24, 2013.

(51) Int. Cl.
*C12P 19/34* (2006.01)
*C12P 21/02* (2006.01)
*C12N 1/20* (2006.01)
*C12P 21/00* (2006.01)

(52) U.S. Cl.
CPC ............... *C12N 1/20* (2013.01); *C12P 19/34* (2013.01); *C12P 21/00* (2013.01); *C12P 21/02* (2013.01)

(58) Field of Classification Search
None
See application file for complete search history.

(56) References Cited

U.S. PATENT DOCUMENTS

| 4,458,066 A | 7/1984 | Caruthers et al. |
| 5,494,810 A | 2/1996 | Barany et al. |
| 2004/0038273 A1 * | 2/2004 | Merryman ............. C07H 21/02 435/6.12 |
| 2011/0195451 A1 * | 8/2011 | Proudfoot ............. C07K 14/805 435/69.1 |
| 2012/0171720 A1 | 7/2012 | Church et al. |

OTHER PUBLICATIONS

Schwartz, Nat. Protoc. 2(11):2945-2957, 2007.*
Jewett et al., Mol Syst. Biol. 4, Article No. 220, pp. 1-10, 2008.*
Oswald, http://bitesizebio.com/1005/what-you-need-to-know-about-od600, retrieved 2017.*
Barrett, O.P. and Chin, J.W. (2010) Evolved orthogonal ribosome purification for in vitro characterization. Nucleic Acids Res, 38, 2682-2691.
Beaucage, S.L. and Caruthers, M.H. (1981) Deoxynucleoside Phosphoramidites—A New class of Key Intermediates for Deoxypolynucleotide Synthesis. Tetrahedron Letters, vol. 22, No. 20, 1859-1862.
Brown, E. et al. (1979) Chemical Synthesis and Cloning of aTyrosine tRNA Gene. Methodes in Enzymology, 68, 109-151.
Cochella, L. and Green, R. (2004) Isolation of antibiotic resistance mutations in the rRNA by using an in vitro selection system. Proceedings of the National Academy of Sciences of the United States of America, 101, 3786-3791.
Goodchild, J. (1990) Conjugates of Oligonucleotides and Modified Oligonucleotides: A Review of Their Synthesis and Properties, Bioconjugate Chemistry, 1, 165-187.
Green, R. and Noller, H.F. (1996) In vitro complementation analysis localizes 23S rRNA posttranscriptional modifications that are required for *Escherichia coli* 50S ribosomal subunit assembly and function. RNA, 2, 1011-1021.
Innis, Michael. (1990) Optimization of PCRs. PCR Protocols: A Guide to Methods and Applications. San Diego: Academic Press, Inc.
Jewett, M.C., Fritz, B.R., Timmerman, L.E. and Church, G.M. (2013) In vitro integration of ribosomal RNA synthesis, ribosome assembly, and translation. Mol Syst Biol, Submitted.
Maki, J.A. and Culver, G.M. (2005) Recent developments in factor-facilitated ribosome assembly. Methods, 36, 313-320.
Narang, S. et al. (1979) Improved Phosphotriester Method for the Synthesis of Gene Fragments. Methods in Enzymology, 68, 90-98.
Nierhaus KH (1990) Reconstitution of ribosomes, in Ribosomes and Protein Synthesis, A Practical Approach, Oxford: Oxford University Press.
Nierhaus KH & Dohme F, "Total reconstitution of functionally active 50s ribosomal subunits from *Escherichia coli*." Proc. Natl. Acad. Sci., U.S.A. 71, 4713-1717 (1974).
Owczarzy et al. (2008) Predicting Stability of DNA Duplexes in Solutions Containing Monovalent Cations. Biochemisty, 47, 5336-5353.
Sambrook, J. et al. (1989) Molecular Cloning, A Labratory Manual. New York: Cold Spring Harbor Laboratory Press.
Semrad, K. and Green, R. (2002) Osmolytes stimulate the reconstitution of functional 50S ribosomes from in vittranscripts of *Escherichia coli* 23S rRNA. RNA, 8, 401-411.
Swartz, J.R., Jewett, M.G. and Woodrow, K.A. (2004) Cell-free protein synthesis with prokaryotic combined transcription-translation. Methods Mol Biol, 267, 169-182.

(Continued)

*Primary Examiner* — Nancy Treptow
(74) *Attorney, Agent, or Firm* — Andrus Intellectual Property Law, LLP

(57) ABSTRACT

A platform for preparing a sequence defined biopolymer in vitro is disclosed. The platform includes a ribosome-depleted cellular extract ribosomal RNAs prepared by in vitro transcription and purified ribosomal proteins depleted of ribosomal RNAs. A method of synthesizing and assembling ribosomes in vitro for use in the platform is provided, as well as a method for preparing a sequence defined biopolymer in vitro using assembling ribosomes and the platform.

20 Claims, 27 Drawing Sheets

(56) References Cited

OTHER PUBLICATIONS

Traub P, Nomura M (1968) Structure and function of *E. coli* ribosomes. V. Reconstitution of functionally active 30S ribosomal particles from RNA and proteins. Proc Natl Acad Sci U S A 59: 777-784.
Wetmur, James G. (1991) DNA Probes: Applications of the Principles of Nucleic Acid Hybridization. Critical Reviews in Biochemistry and Molecular Biology, 26, 227-259.
Wilson, D.N. and Nierhaus, K.H. (2007) The weird and wonderful world of bacterial ribosome regulation. Critical reviews in biochemistry and molecular biology, 42, 187-219.
Blanchard, et al., "tRNA dynamics on the ribosome during translation", PNAS, vol. 101, No. 35, Aug. 31, 2004, pp. 12893-12898.
Jewett, et al., "In vitro integration of ribosomal RNA synthesis, ribosome assembly, and translation", Molecular Systems Biology, 9:678, 2013 (Including Supplemental Report).
Nierhaus, et al., "Total Reconstitution of Functionally Active 50S Ribosomal Subunits from *Escherichia coli*", Proc. Nat. Acad. Sci. USA, vol. 71, No. 12, Dec. 1974, pp. 4713-4717.
Powers, et al., "A functional pseudoknot in 16S ribosomal RNA", EMBO Journal, vol. 10, No. 8, 1991, pp. 2203-2214.
Traub, et al., "Structure and Function of *E. coli* Ribosomes, V. Reconstitution of Functionally Active 30S Ribosomal Particles from RNA and Proteins", Laboratory of Genetics, University of Wisconsin, Madison, Jan. 16, 1968, pp. 777-784.

\* cited by examiner

C.

SEQUENCE LISTING

<160> NUMBER OF SEQ ID NOS: 31

<210> SEQ ID NO 1
<211> LENGTH: 4366
<212> TYPE: DNA
<213> ORGANISM: Artificial Sequence
<220> FEATURE:
<223> OTHER INFORMATION: pK7Luc DNA

<400> SEQUENCE: 1

```
tcgacggatc gttccactga gcgtcagacc ccgtagaaaa gatcaaagga tcttcttgag      60
atccttttt  tctgcgcgta atctgctgct tgcaaacaaa aaaaccaccg ctaccagcgg     120
tggtttgttt gccggatcaa gagctaccaa ctcttttcc  gaaggtaact ggcttcagca     180
gagcgcagat accaaatact gtccttctag tgtagccgta gttaggccac cacttcaaga     240
actctgtagc accgcctaca tacctcgctc tgctaatcct gttaccagtg gctgctgcca     300
gtggcgataa gtcgtgtctt accgggttgg actcaagacg atagttaccg gataaggcgc     360
agcggtcggg ctgaacgggg ggttcgtgca cacagcccag cttggagcga acgacctaca     420
ccgaactgag atacctacag cgtgagcatt gagaaagcgc cacgcttccc gaagggagaa     480
aggcggacag gtatccggta agcggcaggg tcggaacagg agagcgcacg agggagcttc     540
cagggggaaa cgcctggtat ctttatagtc ctgtcgggtt cgccacctc  tgacttgagc     600
gtcgattttt gtgatgctcg tcaggggggc ggagcctatg gaaaaacgcc agcaacgcgg     660
cctttttacg gttcctggcc ttttgctggc cttttgctca catgttcttt cctgcgttat     720
ccctgattc  tgtggataac cgtattaccg cctttgagtg agctgatacc gctcgccgca     780
gccgaacgac cgagcgcagc gagtcagtga gcgaggaagc ggaagaagct cgcacgccaa     840
tacgcaaacc gcctctcccc gcgcgttggc cgattcatta atgcagctgg cacgacaggt     900
ttcccgactg gaaagcgggc agtgagcgca acgcaattaa tgtgagttag ctcactcatt     960
aggcacccca ggctttacac tttatgcttc cggctcgtat gttgtgtgga attgtgagcg    1020
gataacaatt tcacacagga aacagctatg accatgatta cgaattcaga tctcgatccc    1080
gcgaaattaa tacgactcac tatagggaga ccacaacggt ttccctctag aaataatttt    1140
gtttaacttt aagaaggaga tatacatatg gaagacgcca aaaacataaa gaaaggcccg    1200
gcgccattct atccgctaga ggatggaacc gctggagagc aactgcataa ggctatgaag    1260
agatacgccc tggttcctgg aacaattgct tttacagatg cacatatcga ggtgaacatc    1320
acgtacgcgg aatacttcga aatgtccgtt cggttggcag aagctatgaa acgatatggg    1380
ctgaatacaa atcacagaat cgtcgtatgc agtgaaaact ctcttcaatt ctttatgccg    1440
gtgttgggcg cgttatttat cggagttgca gttgcgcccg cgaacgacat ttataatgaa    1500
cgtgaattgc tcaacagtat gaacatttcg cagcctaccg tagtgtttgt ttccaaaaag    1560
gggttgcaaa aaattttgaa cgtgcaaaaa aaattaccaa taatccagaa aattattatc    1620
atggattcta aaacggatta ccagggattt cagtcgatgt acacgttcgt cacatctcat    1680
ctacctcccg gttttaatga atacgatttt gtaccagagt cctttgatcg tgacaaaaca    1740
attgcactga taatgaactc ctctggatct actgggttac ctaagggtgt ggcccttccg    1800
catagaactg cctgcgtcag attctcgcat gccagagatc ctatttttgg caatcaaatc    1860
```

```
attccggata ctgcgatttt aagtgttgtt ccattccatc acggttttgg aatgtttact    1920
acactcggat atttgatatg tggatttcga gtcgtcttaa tgtatagatt tgaagaagag    1980
ctgtttttac gatcccttca ggattacaaa attcaaagtg cgttgctagt accaacccta    2040
ttttcattct tcgccaaaag cactctgatt gacaaatacg atttatctaa tttacacgaa    2100
attgcttctg ggggcgcacc tctttcgaaa gaagtcgggg aagcggttgc aaaacgcttc    2160
catcttccag ggatacgaca aggatatggg ctcactgaga ctacatcagc tattctgatt    2220
acacccgagg gggatgataa accgggcgcg gtcggtaaag ttgttccatt ttttgaagcg    2280
aaggttgtgg atctggatac cgggaaaacg ctgggcgtta atcagagagg cgaattatgt    2340
gtcagaggac ctatgattat gtccggttat gtaaacaatc cggaagcgac caacgccttg    2400
attgacaagg atggatggct acattctgga gacatagctt actgggacga agacgaacac    2460
ttcttcatag ttgaccgctt gaagtcttta attaaataca aaggatacca ggtggccccc    2520
gctgaattgg agtcgatatt gttacaacac cccaacatct tcgacgcggg cgtggcaggt    2580
cttcccgacg atgacgccgg tgaacttccc gccgccgttg ttgttttgga gcacggaaag    2640
acgatgacgg aaaagagat cgtggattac gtcgccagtc aagtaacaac cgccaaaaag    2700
ttgcgcggag gagttgtgtt tgtggacgaa gtaccgaaag gtcttaccgg aaaactcgac    2760
gcaagaaaaa tcagagagat cctcataaag gccaagaagg gcggaaagtc caaattgtaa    2820
gtcgaccggc tgctaacaaa gcccgaaagg aagctgagtt ggctgctgcc accgctgagc    2880
aataactagc ataacccctt ggggcctcta acgggtctt gagggttttt tgctgaaag    2940 gaggaactat atccggataa cctcgagctg cagggcatgc aagcttggca ctggccgtcg    3000
ttttacaacg tcgtgactgg gaaaaccctg gcgttaccca acttaatcgc cttgcagcac    3060
atcccccttt cgccagctgg cgtaatagcg aagaggcccg caccgatcgc ccttcccaac    3120
agttgcgcag cctgaatggc gaatgcgatt tattcaacaa agccgccgtc ccgtcaagtc    3180
agcgtaatgc tctgccagtg ttacaaccaa ttaaccaatt ctgattagaa aaactcatcg    3240
agcatcaaat gaaactgcaa tttattcata tcaggattat caataccata ttttttgaaaa    3300 agccgtttct gtaatgaagg agaaaactca ccgaggcagt tccataggat ggcaagatcc    3360
tggtatcggt ctgcgattcc gactcgtcca acatcaatac aacctattaa tttcccctcg    3420
tcaaaaataa ggttatcaag tgagaaatca ccatgagtga cgactgaatc cggtgagaat    3480
ggcaaaagct tatgcatttc tttccagact tgttcaacag gccagccatt acgctcgtca    3540
tcaaaatcac tcgcatcaac caaaccgtta ttcattcgtg attgcgcctg agcgagacga    3600
aatacgcgat cgctgttaaa aggacaatta caaacaggaa tcgaatgcaa ccggcgcagg    3660
aacactgcca gcgcatcaac aatattttca cctgaatcag gatattcttc taatacctgg    3720
aatgctgttt tcccggggat cgcagtggtg agtaaccatg catcatcagg agtacggata    3780
aaatgcttga tggtcggaag aggcataaat tccgtcagcc agtttagtct gaccatctca    3840
tctgtaacat cattggcaac gctacctttg ccatgtttca gaaacaactc tggcgcatcg    3900
ggcttcccat acaatcgata gattgtcgca cctgattgcc cgacattatc gcgagcccat    3960
ttatacccat ataaatcagc atccatgttg gaatttaatc gcggcttcga gcaagacgtt    4020
tcccgttgaa tatggctcat aacacccctt gtattactgt ttatgtaagc agacagtttt    4080
attgttcatg atgatatatt tttatcttgt gcaatgtaac atcagagatt ttgagacaca    4140
acgtggcttt gttgaataaa tcgaactttt gctgagttga aggatcagat cacgcatctt    4200
cccgacaacg cagaccgttc cgtggcaaag caaaagttca aaatcaccaa ctggcccacc    4260
```

```
tacaacaaag ctctcatcaa ccgtggctcc ctcactttct ggctggatga tggggcgatt      4320
caggcctggt atgagtcagc aacaccttct tcacgaggca gacctc                    4366
```

<210> SEQ ID NO 2
<211> LENGTH: 1829
<212> TYPE: RNA
<213> ORGANISM: Artificial Sequence
<220> FEATURE:
<223> OTHER INFORMATION: Luciferase mRNA

<400> SEQUENCE: 2

```
gggagaccac aacgguuucc cucuagaaau aauuuuguuu aacuuuaaga aggagauaua        60
cauauggaag acgccaaaaa cauaaagaaa ggcccggcgc cauucuaucc gcuagaggau       120
ggaaccgcug gagagcaacu gcauaaggcu augaagagau acgccccuggu uccuggaaca     180 auugcuuuua cagaugcaca uaucgaggug aacaucacgu acgcggaaua cuucgaaaug      240
uccguucggu uggcagaagc uaugaaacga uaugggcuga auacaaauca cagaaucguc       300
guaugcagug aaaacucucu ucaauucuuu augccggugu ugggcgcguu auuuaucgga      360
guugcaguug cgcccgcgaa cgacauuuau augaacgug aauugcucaa caguaugaac       420
auuucgcagc cuaccguagu guuuguuucc aaaaaggggu ugcaaaaaau uuugaacgug      480 caaaaaaau uaccaauaau ccagaaaauu auuaucaugg auucuaaaac ggauuaccag       540
ggauuucagu cgauguacac guucgucaca ucucaucuac cucccgguuu uaaugaauac     600
gauuuuguac cagagucuu ugaucgugac aaaacaauug cacugauaau gaacuccucu       660
ggaucuacug gguuaccuaa ggguguggcc cuuccgcaua aacugccug cgucagauuc       720 ucgcaugcca gagauccuau uuuuggcaau caaucauuc cggauacugc gauuuuaagu      780
guuguuccau uccaucacgg uuuuggaaug uuuacuacac ucggauauuu gauaugggga     840
uuucgagucg ucuuaaugua uagauuugaa gaagagcugu uuuuacgauc cuucaggau      900 uacaaaauuc aaagugcguu gcuaguacca acccuauuuu cauucuucgc caaaagcacu    960
cugauugaca aauacgauuu aucuaauuua cacgaaauug cuucgggggg cgcaccucuu   1020
ucgaaagaag ucgggaagc gguugcaaaa cgcuuccauc uuccagggau acgacaagga     1080
uaugggcuca cugagacuac aucagcuauu cugauuacac ccgagggga ugauaaaccg     1140 ggcgcggucg guaaaguugu uccauuuuu gaagcgaagg uugugaucu ggauaccggg     1200 aaaacgcugg gcguuaauca gagaggcgaa uuaugugca gaggaccuau gauuaugucc    1260
gguuauguaa caauccgga agcgaccaac gccuugauuu acaaggaugg auggcuacau    1320
ucuggagaca uagcuuacug ggacgaagac gaacacuucu ucauaguuga ccgcuugaag    1380
ucuuuaauua aauacaaagg auaccaggug gcccccgcug aauuggaguc gauauuguua    1440 caacaccca acaucuucga gcgggcgug gcaggucuuc ccgacgauga cgccggugaa    1500
cuucccgccg ccguuguugu uuuggagcac ggaaagacga ugacggaaaaa agagaucgug   1560 gauuacgucg ccagucaagu aacaaccgcc aaaaaguugc gcggaggagu uguguuugug    1620
gacgaaguac cgaaaggucu uaccggaaaa cucgacgcaa gaaaaaucag agagauccuc     1680
auaaaggcca gaagggcgg aaaguccaaa uuguaagucg accggcugcu aacaaagccc    1740
gaaaggaagc ugaguuggcu gcugccaccg cugagcaaua acuagcauaa ccccuugggg   1800
ccucuaaacg ggucuugagg gguuuuuug                                   1829
```

<210> SEQ ID NO 3

```
<211> LENGTH: 550
<212> TYPE: PRT
<213> ORGANISM: Artificial Sequence
<220> FEATURE:
<223> OTHER INFORMATION: Luciferase Protein

<400> SEQUENCE: 3

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
370                 375                 380
```

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 4
<211> LENGTH: 2480
<212> TYPE: DNA
<213> ORGANISM: Artificial Sequence
<220> FEATURE:
<223> OTHER INFORMATION: pY71sfGFP

<400> SEQUENCE: 4
ggatcctgca gttgagatcc ttttttttctg cgcgtaatct gctgcttgca aacaaaaaaa     60
ccaccgctac cagcggtggt ttgtttgccg gatcaagagc taccaactct ttttccgaag    120
gtaactggct tcagcagagc gcagatacca aatactgtcc ttctagtgta gccgtagtta    180
ggccaccact tcaagaactc tgtagcaccg cctacatacc tcgctctgct aatcctgtta    240
ccagtggctg ctgccagtgg cgataagtcg tgtcttaccg ggttggactc aagacgatag    300
ttaccggata aggcgcagcg gtcgggctga acggggggtt cgtgcacaca gcccagcttg    360
gagcgaacga cctacaccga actgagatac ctacagcgtg agcattgaga aagcgccacg    420
cttcccgaag ggagaaaggc ggacaggtat ccggtaagcg gcagggtcgg aacaggagag    480
cgcacgaggg agcttccagg gggaaacgcc tggtatcttt atagtcctgt cgggtttcgc    540
cacctctgac ttgagcgtcg atttttgtga tgctcgtcag gggggcggag cctatggaaa    600
cgaattcaga tctcgatccc gcgaaattaa tacgactcac tatagggaga ccacaacggt    660
ttccctctag aaataatttt gtttaacttt aagaaggaga tatacatatg agcaaaggtg    720
aagaactgtt taccggcgtt gtgccgattc tggtggaact ggatggcgat gtgaacggtc    780
acaaattcag cgtgcgtggt gaaggtgaag gcgatgccac gattggcaaa ctgacgctga    840
aatttatctg caccaccggc aaactgccgg tgccgtggcc gacgctggtg accaccctga    900
cctatggcgt tcagtgtttt agtcgctatc cggatcacat gaaacgtcac gatttcttta    960
aatctgcaat gccggaaggc tatgtgcagg aacgtacgat tagctttaaa gatgatggca   1020
aatataaaac gcgcgccgtt gtgaaatttg aaggcgatac cctggtgaac cgcattgaac   1080

```
tgaaaggcac ggattttaaa gaagatggca atatcctggg ccataaactg gaatacaact    1140
ttaatagcca taatgtttat attacggcgg ataaacagaa aaatggcatc aaagcgaatt    1200
ttaccgttcg ccataacgtt gaagatggca gtgtgcagct ggcagatcat tatcagcaga    1260
ataccccgat tggtgatggt ccggtgctgc tgccggataa tcattatctg agcacgcaga    1320
ccgttctgtc taaagatccg aacgaaaaag gcacccggga ccacatggtt ctgcacgaat    1380
atgtgaatgc ggcaggtatt acgtggagcc atccgcagtt cgaaaaataa gtcgaccggc    1440
tgctaacaaa gcccgaaagg aagctgagtt ggctgctgcc accgctgagc aataactagc    1500
ataccccctt ggggcctcta acgggtctt gaggggtttt tgctgaaag ccaattctga    1560 ttagaaaaac tcatcgagca tcaaatgaaa ctgcaattta ttcatatcag gattatcaat    1620
accatatttt tgaaaaagcc gtttctgtaa tgaaggagaa aactcaccga gcagttcca    1680 taggatggca agatcctggt atcggtctgc gattccgact cgtccaacat caatacaacc    1740
tattaatttc ccctcgtcaa aaataaggtt atcaagtgag aaatcaccat gagtgacgac    1800
tgaatccggt gagaatggca aaagcttatg catttctttc cagacttgtt caacaggcca    1860
gccattacgc tcgtcatcaa aatcactcgc atcaaccaaa ccgttattca ttcgtgattg    1920
cgcctgagcg agacgaaata cgcgatcgct gttaaaagga caattacaaa caggaatcga    1980
atgcaaccgg cgcaggaaca ctgccagcgc atcaacaata ttttcacctg aatcaggata    2040
ttcttctaat acctggaatg ctgttttccc ggggatcgca gtggtgagta accatgcatc    2100
atcaggagta cggataaaat gcttgatggt cggaagaggc ataaattccg tcagccagtt    2160
tagtctgacc atctcatctg taacatcatt ggcaacgcta cctttgccat gtttcagaaa    2220
caactctggc gcatcgggct tcccatacaa tcgatagatt gtcgcacctg attgcccgac    2280
attatcgcga gcccatttat acccatataa atcagcatcc atgttggaat ttaatcgcgg    2340
cttcgagcaa gacgtttccc gttgaatatg gctcataaca ccccttgtat tactgtttat    2400
gtaagcagac agttttattg ttcatgatga tatattttta tcttgtgcaa tgtaacatca    2460
gagattttga gacacaacgt                                               2480
```

<210> SEQ ID NO 5
<211> LENGTH: 899
<212> TYPE: RNA
<213> ORGANISM: Artificial Sequence
<220> FEATURE:
<223> OTHER INFORMATION: sfGFP mRNA

<400> SEQUENCE: 5

```
gggagaccac aacgguuucc cucuagaaau aauuuguuu aacuuuaaga aggagauaua     60
cauaugagca aaggugaaga acuguuuacc ggcguugugc cgauucuggu ggaacuggau    120
ggcgauguga acggucacaa auucagcgug cguggugaag ugaaggcga ugccacgauu    180 ggcaaacuga cgcugaaauu uaucugcacc accggcaaac ugccggugcc guggccgacg    240
cuggugacca cccugaccua uggcguucag uguuuagguc gcuauccgga ucacaugaaa    300
cgucacgauu ucuuuaaauc ugcaaugccg gaaggcuaug ucaggaacg uacgauuagc    360 uuuaaagaug auggcaaaua uaaaacgcgc gccguuguga aauuugaagg cgauacccug    420
gugaaccgca uugaacugaa aggcacggau uuuaagaag auggcaauau ccugggccau    480
aaacuggaau acaacuuuaa uagccauaau guuuauauua cggcggauaa acagaaaaau    540
ggcaucaaag cgaauuuuac cguucgccau aacguugaag auggcagugu gcagcuggca    600
```

```
gaucauuauc agcagaauac cccgauuggu gaugguccgg ugcugcugcc ggauaaucau   660
uaucugagca cgcagaccgu ucugucuaaa gauccgaacg aaaaaggcac ccgggaccac   720
augguucugc acgaauaugu gaaugcggca gguauuacgu ggagccaucc gcaguucgaa   780
aaauaagucg accggcugcu aacaaagccc gaaaggaagc ugaguuggcu gcugccaccg   840
cugagcaaua acuagcauaa ccccuugggg ccucuaaacg ggucuugagg gguuuuuug    899
```

<210> SEQ ID NO 6
<211> LENGTH: 240
<212> TYPE: PRT
<213> ORGANISM: Artificial Sequence
<220> FEATURE:
<223> OTHER INFORMATION: sfGFP Protein

<400> SEQUENCE: 6

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Thr Arg Asp His Met Val Leu His Glu
    210                 215                 220

Tyr Val Asn Ala Ala Gly Ile Thr Trp Ser His Pro Gln Phe Glu Lys
225                 230                 235                 240
```

<210> SEQ ID NO 7
<211> LENGTH: 2435
<212> TYPE: DNA
<213> ORGANISM: Artificial Sequence
<220> FEATURE:
<223> OTHER INFORMATION: pY71mRFP1 DNA

<400> SEQUENCE: 7

```
ggatcctgca gttgagatcc ttttttttctg cgcgtaatct gctgcttgca aacaaaaaaa   60
ccaccgctac cagcggtggt ttgtttgccg gatcaagagc taccaactct ttttccgaag  120
```

```
gtaactggct tcagcagagc gcagatacca aatactgtcc ttctagtgta gccgtagtta    180
ggccaccact tcaagaactc tgtagcaccg cctacatacc tcgctctgct aatcctgtta    240
ccagtggctg ctgccagtgg cgataagtcg tgtcttaccg ggttggactc aagacgatag    300
ttaccggata aggcgcagcg gtcgggctga acgggggggtt cgtgcacaca gcccagcttg    360
gagcgaacga cctacaccga actgagatac ctacagcgtg agcattgaga aagcgccacg    420
cttcccgaag ggagaaaggc ggacaggtat ccggtaagcg gcagggtcgg aacaggagag    480
cgcacgaggg agcttccagg gggaaacgcc tggtatcttt atagtcctgt cgggtttcgc    540
cacctctgac ttgagcgtcg attttttgtga tgctcgtcag gggggcggag cctatggaaa    600
cgaattcaga tctcgatccc gcgaaattaa tacgactcac tataggagag ccacaacggt    660
ttccctctag aaataatttt gtttaacttt aagaaggaga tatacatatg gcttcctccg    720
aagacgttat caagagagttc atgcgtttca agttcgtat ggaaggttcc gttaacggtc    780
acgagttcga aatcgaaggt gaaggtgaag gtcgtccgta cgaaggtacc cagaccgcta    840
aactgaaagt taccaaaggt ggtccgctgc cgttcgcttg gacatcctg tccccgcagt    900
tccagtacgg ttccaaagct tacgttaaac acccggctga catcccggac tacctgaaac    960
tgtccttccc ggaaggtttc aaatgggaac gtgttatgaa cttcgaagac ggtggtgttg   1020
ttaccgttac ccaggactcc tccctgcaag acggtgagtt catctacaaa gttaaactgc   1080
gtggtaccaa cttcccgtcc gacggtccgg ttatgcagaa aaaaccatg ggttgggaag    1140
cttccaccga acgtatgtac ccggaagacg gtgctctgaa aggtgaaatc aaaatgcgtc   1200
tgaaactgaa agacggtggt cactacgacg ctgaagttaa aaccacctac atggctaaaa   1260
aaccggttca gctgccgggt gcttacaaaa ccgacatcaa actggacatc acctcccaca   1320
acgaagacta caccatcgtt gaacagtacg aacgtgctga aggtcgtcac tccaccggtg   1380
cttaagtcga ccggctgcta acaaagcccg aaggaagct gagttggctg ctgccaccgc    1440
tgagcaataa ctagcataac cccttggggc ctctaaacgg gtcttgaggg gtttttgct    1500
gaaagccaat tctgattaga aaaactcatc gagcatcaaa tgaaactgca atttattcat   1560
atcaggatta tcaataccat atttttgaaa aagccgtttc tgtaatgaag gagaaaactc   1620
accgaggcag ttccatagga tggcaagatc ctggtatcgg tctgcgattc cgactcgtcc   1680
aacatcaata caacctatta atttccctc gtcaaaaata aggttatcaa gtgagaaatc    1740
accatgagtg acgactgaat ccggtgagaa tggcaaaagc ttatgcattt ctttccagac   1800
ttgttcaaca ggccagccat tacgctcgtc atcaaaatca ctcgcatcaa ccaaaccgtt   1860
attcattcgt gattgcgcct gagcgagacg aaatacgcga tcgctgttaa aaggacaatt   1920
acaaacagga tcgaatgcaa ccggcgcag gaacactgcc agcgcatcaa caatattttc    1980
acctgaatca ggatattctt ctaatacctg gaatgctgtt ttcccgggga tcgcagtggt   2040
gagtaaccat gcatcatcag gagtacggat aaaatgcttg atggtcggaa gaggcataaa   2100
ttccgtcagc cagtttagtc tgaccatctc atctgtaaca tcattggcaa cgctacctt    2160
gccatgtttc agaaacaact ctggcgcatc gggcttccca tacaatcgat agattgtcgc   2220
acctgattgc ccgacattat cgcgagccca tttatacccca tataaatcag catccatgtt   2280
ggaatttaat cgcggcttcg agcaagacgt ttcccgttga atatggctca taacacccct   2340
tgtattactg tttatgtaag cagacagttt tattgttcat gatgatatat ttttatcttg   2400
tgcaatgtaa catcagagat tttgagacac aacgt                              2435
```

<210> SEQ ID NO 8
<211> LENGTH: 854
<212> TYPE: RNA
<213> ORGANISM: Artificial Sequence
<220> FEATURE:
<223> OTHER INFORMATION: mRFP1 mRNA

<400> SEQUENCE: 8

```
gggagaccac aacgguuucc cucuagaaau aauuuuguuu aacuuuaaga aggagauaua      60
cauauggcuu ccuccgaaga cguuaucaaa gaguucaugc guuucaaagu ucguauggaa     120
gguuccguua acgucacga guucgaaauc gaaggugaag gugaaggucg uccguacgaa      180
gguacccaga ccgcuaaacu gaaaguuacc aaaggugguc cgcugccguu cgcuggggac     240
auccugnccc cgcaguucca guacgguucc aaagcuuacg uuaaacaccc ggcugacauc     300
ccggacuacc ugaaacuguc cuucccggaa gguuucaaau gggaacgugu uaugaacuuc     360
gaagacggug uguuguuuac cguuacccag cacuccuccc ugcaagacgg ugaguucauc     420
uacaaaguua aacugcgugg uaccaacuuc ccguccgacg guccgguuau gcagaaaaaa     480
accaugggut gggaagcuuc caccgaacgu auguacccgg aagacggugc ucugaagggu     540
gaaaucaaaa ugcgcucgaa acugaaagac gguggucacu acgacgcuga aguuaaaacc     600
accuacaugg cuaaaaaccc gguucagcug ccggugcuuc acaaaccga caucaaacug      660
gacaucaccu cccacaacga agacuacacc aucguugaac aguacgaacg ugcugaaggu     720
cgucacucca ccggugcuua agcgaccgg cugcuaacaa agcccgaaag gaagcugagu     780
uggcugcugc caccgcugag caauaacuag cauaaccccu ugggccucu aaacgggucu      840
ugagggguuu uuug                                                       854
```

<210> SEQ ID NO 9
<211> LENGTH: 225
<212> TYPE: PRT
<213> ORGANISM: Artificial Sequence
<220> FEATURE:
<223> OTHER INFORMATION: mRFP1 Protein

<400> SEQUENCE: 9

```
Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Thr Glu Arg Met Tyr Pro Glu Asp Gly Ala Leu Lys Gly Glu
145                 150                 155                 160
```

Ile Lys Met Arg Leu Lys Leu Lys Asp Gly Gly His Tyr Asp Ala Glu
            165                 170                 175

Val Lys Thr Thr Tyr Met Ala Lys Lys Pro Val Gln Leu Pro Gly Ala
        180                 185                 190

Tyr Lys Thr Asp Ile Lys Leu Asp Ile Thr Ser His Asn Glu Asp Tyr
    195                 200                 205

Thr Ile Val Glu Gln Tyr Glu Arg Ala Glu Gly Arg His Ser Thr Gly
210                 215                 220

Ala
225

<210> SEQ ID NO 10
<211> LENGTH: 4241
<212> TYPE: DNA
<213> ORGANISM: Artificial Sequence
<220> FEATURE:
<223> OTHER INFORMATION: pWK1 DNA

<400> SEQUENCE: 10

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acctaatacg     420
actcactata gggagattga agagtttgat catggctcag attgaacgct ggcggcaggc     480
ctaacacatg caagtcgaac ggtaacagga agaagcttgc ttctttgctg acgagtggcg     540
gacgggtgag taatgtctgg gaaactgcct gatggagggg gataactact ggaaacggta     600
gctaataccg cataacgtcg caagaccaaa gagggggacc ttcgggcctc ttgccatcgg     660
atgtgcccag atgggattag ctagtaggtg gggtaacggc tcacctaggc gacgatccct     720
agctggtctg agaggatgac cagccacact ggaactgaga cacggtccag actcctacgg     780
gaggcagcag tggggaatat tgcacaatgg gcgcaagcct gatgcagcca tgccgcgtgt     840
atgaagaagg ccttcgggtt gtaaagtact ttcagcgggg aggaagggag taaagttaat     900
acctttgctc attgacgtta cccgcagaag aagcaccggc taactccgtg ccagcagccg     960
cggtaatacg gagggtgcaa gcgttaatcg gaattactgg gcgtaaagcg cacgcaggcg    1020
gtttgttaag tcagatgtga atccccgggc tcaacctgg gaactgcatc tgatactggc    1080
aagcttgagt ctcgtagagg ggggtagaat tccaggtgta gcggtgaaat gcgtagagat    1140
ctggaggaat accggtggcg aaggcggccc cctggacgaa gactgacgct caggtgcgaa    1200
agcgtgggga gcaaacagga ttagataccc tggtagtcca cgccgtaaac gatgtcgact    1260
tggaggttgt gcccttgagg cgtggcttcc ggagctaacg cgttaagtcg accgcctggg    1320
gagtacggcc gcaaggttaa aactcaaatg aattgacggg ggcccgcaca agcggtggag    1380
catgtggttt aattcgatgc aacgcgaaga accttacctg gtcttgacat ccacggaagt    1440
tttcagagat gagaatgtgc cttcgggaac cgtgagacag gtgctgcatg gctgtcgtca    1500
gctcgtgttg tgaaatgttg ggttaagtcc cgcaacgagc gcaaccctta tcctttgttg    1560
ccagcggtcc ggccgggaac tcaaaggaga ctgccagtga taaactggag gaaggtgggg    1620
```

-continued

```
atgacgtcaa gtcatcatgg cccttacgac cagggctaca cacgtgctac aatggcgcat    1680
acaaagagaa gcgacctcgc gagagcaagc ggacctcata aagtgcgtcg tagtccggat    1740
tggagtctgc aactcgactc catgaagtcg gaatcgctag taatcgtgga tcagaatgcc    1800
acggtgaata cgttcccggg ccttgtacac accgcccgtc acaccatggg agtgggttgc    1860
aaaagaagta ggtagcttaa ccttcgggag ggcgcttacc actttgtgat tcatgactgg    1920
ggtgaagtcg taacaaggta accgtagggg aacctgcggt tggatcacct ccttaggtct    1980
agagtcgacc tgcaggcatg caagcttggc gtaatcatgg tcatagctgt ttcctgtgtg    2040
aaattgttat ccgctcacaa ttccacacaa catacgagcc ggaagcataa agtgtaaagc    2100
ctggggtgcc taatgagtga gctaactcac attaattgcg ttgcgctcac tgcccgcttt    2160
ccagtcggga acctgtcgt gccagctgca ttaatgaatc ggccaacgcg cggggagagg    2220
cggtttgcgt attgggcgct cttccgcttc ctcgctcact gactcgctgc gctcggtcgt    2280
tcggctgcgg cgagcggtat cagctcactc aaaggcggta atacggttat ccacagaatc    2340
aggggataac gcaggaaaga acatgtgagc aaaaggccag caaaaggcca ggaaccgtaa    2400
aaaggccgcg ttgctggcgt ttttccatag gctccgcccc cctgacgagc atcacaaaaa    2460
tcgacgctca agtcagaggt ggcgaaaccc gacaggacta taaagatacc aggcgtttcc    2520
ccctggaagc tccctcgtgc gctctcctgt tccgaccctg ccgcttaccg gatacctgtc    2580
cgcctttctc ccttcgggaa gcgtggcgct ttctcatagc tcacgctgta ggtatctcag    2640
ttcggtgtag gtcgttcgct ccaagctggg ctgtgtgcac gaaccccccg ttcagcccga    2700
ccgctgcgcc ttatccggta actatcgtct gagtccaac ccgtaagac acgacttatc    2760 gccactggca gcagccactg gtaacaggat tagcagagcg aggtatgtag gcggtgctac    2820
agagttcttg aagtggtggc ctaactacgg ctacactaga agaacagtat ttggtatctg    2880
cgctctgctg aagccagtta ccttcggaaa aagagttggt agctcttgat ccggcaaaca    2940
aaccaccgct ggtagcggtg gtttttttgt ttgcaagcag cagattacgc gcagaaaaaa    3000
aggatctcaa gaagatcctt tgatcttttc tacggggtct gacgctcagt ggaacgaaaa    3060
ctcacgttaa gggattttgg tcatgagatt atcaaaaagg atcttcacct agatcctttt    3120
aaattaaaaa tgaagtttta aatcaatcta agtatatat gagtaaactt ggtctgacag    3180
ttaccaatgc ttaatcagtg aggcaccat ctcagcgatc tgtctatttc gttcatccat    3240
agttgcctga ctccccgtcg tgtagataac tacgatacgg gagggcttac catctggccc    3300
cagtgctgca atgataccgc gagacccacg ctcaccggct ccagatttat cagcaataaa    3360
ccagccagcc ggaagggccg agcgcagaag tggtcctgca actttatccg cctccatcca    3420
gtctattaat tgttgccggg aagctagagt aagtagttcg ccagttaata gtttgcgcaa    3480
cgttgttgcc attgctacag gcatcgtggt gtcacgctcg tctttggta tggcttcatt    3540 cagctccggt tcccaacgat caaggcgagt tacatgatcc cccatgttgt gcaaaaaagc    3600
ggttagctcc ttcggtcctc cgatcgttgt cagaagtaag ttggccgcag tgttatcact    3660
catggttatg gcagcactgc ataattctct tactgtcatg ccatccgtaa gatgcttttc    3720
tgtgactggt gagtactcaa ccaagtcatt ctgagaatag tgtatgcggc gaccgagttg    3780
ctcttgcccg gcgtcaatac gggataatac cgcgccacat agcagaactt taaaagtgct    3840
catcattgga aaacgttctt cggggcgaaa actctcaagg atcttaccgc tgttgagatc    3900
cagttcgatg taacccactc gtgcacccaa ctgatcttca gcatctttta ctttcaccag    3960
cgtttctggg tgagcaaaaa caggaaggca aaatgccgca aaaaagggaa taagggcgac    4020
```

```
acggaaatgt tgaatactca tactcttcct ttttcaatat tattgaagca tttatcaggg    4080
ttattgtctc atgagcggat acatatttga atgtatttag aaaaataaac aaatagggt     4140 tccgcgcaca tttccccgaa aagtgccacc tgacgtctaa gaaaccatta ttatcatgac    4200
attaacctat aaaaataggc gtatcacgag gccctttcgt c                        4241
```

<210> SEQ ID NO 11
<211> LENGTH: 1542
<212> TYPE: RNA
<213> ORGANISM: Artificial Sequence
<220> FEATURE:
<223> OTHER INFORMATION: pWK1 16S RNA

<400> SEQUENCE: 11

```
agauugaaga guuugaucau ggcucagauu gaacgcuggc ggcaggccua acacaugcaa      60
gucgaacggu aacaggaaga agcuugcuuc uuugcugacg aguggcggac ggguagaguaa    120 ugucugggaa acugccugau ggaggggau aacuacugga aacgguagcu aauaccgcau      180
aacgucgcaa gaccaaagag ggggaccuuc gggccucuug ccaucggaug ugcccagaug     240
ggauuagcua guaggugggg uaacggcuca ccuaggcgac gaucccuagc uggucugaga    300
ggaugaccag ccacacugga acugagacac gguccagacu ccuacgggag gcagcagugg    360
ggaauauugc acaaugggcg caagccugau gcagccaugc cgcguguaug aagaaggccu    420
ucggguugua aguacuuuc agcggggagg aaggaguaa aguuaauacc uuugcucauu       480
gacguuaccc gcagaagaag caccggcuaa cuccgugcca gcagccgcgg uaauacggag     540
ggugcaagcg uuaaucggaa uuacugggcg uaaagcgcac gcaggcgguu uguuaaguca    600
gaugugaaau ccccgggcuc aaccuggaa cugcaucuga uacuggcaag cuugagcuc      660 guagaggggg guagaauucc aggguagcg ugaaaugcg uagagaucug gaggaauacc      720
gguggcgaag gcggcccccu ggacgaagac ugacgcucag gugcgaaagc guggggagca    780
aacaggauua gauacccugg uaguccacgc cguaaacgau gucgacuugg agguugugcc     840
cuugaggcgu ggcuuccgga gcuaacgcgu uaagucgacc gccugggag uacggccgca    900 agguuaaaac ucaaugaau ugacggggc ccgcacaagc gguggagcau guggguuaau       960
ucgaugcaac gcgaagaacc uuaccugguc uugacaucca cggaaguuuu cagagaugag    1020
aaugugccuu cgggaaccgu gagacaggug cugcauggcu gucgcagcu cguguuguga    1080 aauguugggu uaagucccgc aacgagcgca acccuuaucc uuuguugcca gcgguccggc    1140
cgggaacuca aaggagacug ccagugauaa acuggaggaa ggugggagug acgucaagu     1200 aucauggccc uuacgaccag ggcuacacac gugcuacaau ggcgcauaca aagagaagcg    1260
accucgcgag agcaagcgga ccucauaaag ugcgucuag uccggauugg agucugcaac    1320
ucgacuccau gaagucggaa ucgcuaguaa ucguggauca gaaugccacg gugaauacgu    1380 ucccggccu guacacacc gcccgucaca ccauggagu ggguugcaaa agaaguaggu        1440
agcuuaaccu ucggggaggc gcuuaccacu uugugauuca ugacuggggu gaagucguaa    1500
caagguaacc guaggggaac cugcgguugg aucaccuccu ua                        1542
```

<210> SEQ ID NO 12
<211> LENGTH: 5589
<212> TYPE: DNA
<213> ORGANISM: Artificial Sequence
<220> FEATURE:
<223> OTHER INFORMATION: pCW1 DNA

```
<400> SEQUENCE: 12
taatacgact cactataggt taagcgacta agcgtacacg gtggatgccc tggcagtcag    60
aggcgatgaa ggacgtgcta atctgcgata agcgtcggta aggtgatatg aaccgttata   120
accggcgatt tccgaatggg gaaacccagt gtgtttcgac acactatcat taactgaatc   180
cataggttaa tgaggcgaac cggggggaact gaaacatcta agtaccccga ggaaaagaaa   240
tcaaccgaga ttcccccagt agcggcgagc gaacggggag cagcccagag cctgaatcag   300
tgtgtgtgtt agtggaagcg tctggaaagg cgcgcgatac agggtgacag ccccgtacac   360
aaaaatgcac atgctgtgag ctcgatgagt agggcgggac acgtggtatc ctgtctgaat   420
atgggggac catcctccaa ggctaaatac tcctgactga ccgatagtga accagtaccg   480
tgagggaaag gcgaaaagaa ccccggcgag gggagtgaaa agaacctga aaccgtgtac   540
gtacaagcag tgggagcacg cttaggcgtg tgactgcgta ccttttgtat aatgggtcag   600
cgacttatat tctgtagcaa ggttaaccga ataggggagc cgaagggaaa ccgagtctta   660
actgggcgtt aagttgcagg gtatagaccc gaaacccgt gatctagcca tgggcaggtt   720
gaaggttggg taacactaac tggaggaccg aaccgactaa tgttgaaaaa ttagcggatg   780
acttgtggct gggggtgaaa ggccaatcaa accgggagat agctggttct ccccgaaagc   840
tatttaggta gcgcctcgtg aattcatctc cgggggtaga gcactgtttc ggcaagggg   900
tcatcccgac ttaccaaccc gatgcaaaact gcgaataccg gagaatgtta tcacgggaga   960
cacacggcgg gtgctaacgt ccgtcgtgaa gagggaaaca acccagaccg ccagctaagg  1020
tcccaaagtc atggttaagt gggaaacgat gtggaaggc ccagacagcc aggatgttgg  1080
cttagaagca gccatcattt aaagaaagcg taatagctca ctggtcgagt cggcctgcgc  1140
ggaagatgta acgggctaa accatgcacc gaagctgcgg cagcgacgct tatgcgttgt  1200
tgggtagggg agcgttctgt aagcctgcga aggtgtgctg tgaggcatgc tggaggtatc  1260
agaagtgcga atgctgacat aagtaacgat aaagcgggtg aaaagcccgc tcgccggaag  1320
accaagggtt cctgtccaac gttaatcggg gcagggtgag tcgacccta aggcgaggcc  1380
gaaaggcgta gtcgatggga aacaggttaa tattcctgta cttggtgtta ctgcgaaggg  1440
gggacggaga aggctatgtt ggccgggcga cggttgtccc ggtttaagcg tgtaggctgg  1500
ttttccaggc aaatccggaa aatcaaggct gaggcgtgat gacgaggcac tacggtgctg  1560
aagcaacaaa tgccctgctt ccaggaaaag cctctaagca tcaggtaaca tcaaatcgta  1620
ccccaaaccg acacaggtgg tcaggtagag aataccaagg cgcttgagag aactcgggtg  1680
aaggaactag gcaaaatggt gccgtaactt cgggagaagg cacgctgata tgtaggtgag  1740
gtccctcgcg gatggagctg aaatcagtcg aagataccag ctggctgcaa ctgtttatta  1800
aaaacacagc actgtgcaaa cacgaaagtg gacgtatacg gtgtgacgcc tgcccggtgc  1860
cggaaggtta attgatgggg ttagcgcaag cgaagctctt gatcgaagcc ccggtaaacg  1920
gcggccgtaa ctataacggt cctaaggtag cgaaattcct tgtcgggtaa gttccgacct  1980
gcacgaatgg cgtaatgatg gccaggctgt ctccacccga gactcagtga aattgaactc  2040
gctgtgaaga tgcagtgtac ccgcggcaag acggaaagac cccgtgaacc tttactatag  2100
cttgacactg aacattgagc cttgatgtgt aggataggtg ggaggctttg aagtgtggac  2160
gccagtctgc atggagccga ccttgaaata ccacccttta atgtttgatg ttctaacgtt  2220
gacccgtaat ccgggttgcg gacagtgtct ggtgggtagt ttgactgggg cggtctcctc  2280
ctaaagagta acggaggagc acgaaggttg gctaatcctg gtcggacatc aggaggttag  2340
```

```
tgcaatggca taagccagct tgactgcgag cgtgacggcg cgagcaggtg cgaaagcagg    2400
tcatagtgat ccggtggttc tgaatggaag ggccatcgct caacgdataa aaggtactcc    2460
ggggataaca ggctgatacc gcccaagagt tcatatcgac ggcggtgttt ggcacctcga    2520
tgtcggctca tcacatcctg gggctgaagt aggtcccaag ggtatggctg ttcgccattt    2580
aaagtggtac gcgagctggg tttagaacgt cgtgagacag ttcggtccct atctgccgtg    2640
ggcgctggag aactgagggg ggctgctcct agtacgagag gaccggagtg gacgcatcac    2700
tggtgttcgg gttgtcatgc caatggcact gcccggtagc taaatgcgga agagataagt    2760
gctgaaagca tctaagcacg aaacttgccc cgagatgagt tctccctgac cctttaaggg    2820
tcctgaagga acgttgaaga cgacgacgtt gataggccgg gtgtgtaagc gcagcgatgc    2880
gttgagctaa ccggtactaa tgaaccgtga ggcttaacct taagctgcag gcatgcaagc    2940
ttggcgtaat catggtcata gctgtttcct gtgtgaaatt gttatccgct cacaattcca    3000
cacaacatac gagccggaag cataaagtgt aaagcctggg gtgcctaatg agtgagctaa    3060
ctcacattaa ttgcgttgcg ctcactgccc gctttccagt cgggaaacct gtcgtgccag    3120
ctgcattaat gaatcggcca acgcgcgggg agaggcggtt tgcgtattgg gcgctcttcc    3180
gcttcctcgc tcactgactc gctgcgctcg tcgttcggc tgcggcgagc ggtatcagct    3240
cactcaaagg cggtaatacg gttatccaca gaatcagggg ataacgcagg aaagaacatg    3300
tgagcaaaag gccagcaaaa ggccaggaac cgtaaaaagg ccgcgttgct ggcgtttttc    3360
cataggctcc gccccctga cgagcatcac aaaaatcgac gctcaagtca gaggtggcga    3420
aacccgacag gactataaag ataccaggcg tttccccctg gaagctccct cgtgcgctct    3480
cctgttccga ccctgccgct taccggatac ctgtccgcct ttctcccttc gggaagcgtg    3540
gcgctttctc atagctcacg ctgtaggtat ctcagttcgg tgtaggtcgt tcgctccaag    3600
ctgggctgtg tgcacgaacc ccccgttcag cccgaccgct cgccttatc cggtaactat    3660 cgtcttgagt ccaacccggt aagacacgac ttatcgccac tggcagcagc cactggtaac    3720
aggattagca gagcgaggta tgtaggcggt gctacagagt tcttgaagtg gtggcctaac    3780
tacggctaca ctagaagaac agtatttggt atctgcgctc tgctgaagcc agttaccttc    3840
ggaaaaagag ttggtagctc ttgatccggc aaacaaacca ccgctggtag cggtggtttt    3900
tttgtttgca agcagcagat tacgcgcaga aaaaaaggat ctcaagaaga tcctttgatc    3960
ttttctacgg ggtctgacgc tcagtggaac gaaaactcac gttaagggat tttggtcatg    4020
agattatcaa aaaggatctt cacctagatc cttttaaatt aaaaatgaag ttttaaatca    4080
atctaaagta tatatgagta aacttggtct gacagttacc aatgcttaat cagtgaggca    4140
cctatctcag cgatctgtct atttcgttca tccatagttg cctgactccc cgtcgtgtag    4200
ataactacga tacgggaggg cttaccatct ggccccagtg ctgcaatgat accgcgagac    4260
ccacgctcac cggctccaga tttatcagca ataaaccagc cagccggaag ggccgagcgc    4320
agaagtggtc ctgcaacttt atccgcctcc atccagtcta ttaattgttg ccgggaagct    4380
agagtaagta gttcgccagt taatagtttg cgcaacgttg ttgccattgc tacaggcatc    4440
gtggtgtcac gctcgtcgtt tggtatggct tcattcagct ccggttccca acgatcaagg    4500
cgagttacat gatcccccat gttgtgcaaa aaagcggtta gctccttcgg tcctccgatc    4560
gttgtcagaa gtaagttggc cgcagtgtta tcactcatgg ttatggcagc actgcataat    4620
tctcttactg tcatgccatc cgtaagatgc ttttctgtga ctggtgagta ctcaaccaag    4680
```

```
tcattctgag aatagtgtat gcggcgaccg agttgctctt gcccggcgtc aatacgggat    4740
aataccgcgc cacatagcag aactttaaaa gtgctcatca ttggaaaacg ttcttcgggg    4800
cgaaaactct caaggatctt accgctgttg agatccagtt cgatgtaacc cactcgtgca    4860
cccaactgat cttcagcatc ttttactttc accagcgttt ctgggtgagc aaaaacagga    4920
aggcaaaatg ccgcaaaaaa gggaataagg gcgacacgga aatgttgaat actcatactc    4980 ttccttttc aatattattg aagcatttat cagggttatt gtctcatgag cggatacata    5040
tttgaatgta tttagaaaaa taaacaaata ggggttccgc gcacatttcc ccgaaaagtg    5100
ccacctgacg tctaagaaac cattattatc atgacattaa cctataaaaa taggcgtatc    5160
acgaggccct ttcgtctcgc gcgtttcggt gatgacggtg aaaacctctg acacatgcag    5220
ctcccggaga cggtcacagc ttgtctgtaa gcggatgccg ggagcagaca gcccgtcag    5280 ggcgcgtcag cgggtgttgg cgggtgtcgg gctggctta actatgcggc atcagagcag    5340
attgtactga gagtgcacca tatgcggtgt gaaataccgc acagatgcgt aaggagaaaa    5400
taccgcatca ggcgccattc gccattcagg ctgcgcaact gttgggaagg gcgatcggtg    5460
cgggcctctt cgctattacg ccagctggcg aaggggggat gtgctgcaag gcgattaagt    5520
tgggtaacgc cagggttttc ccagtcacga cgttgtaaaa cgacggccag tgaattcgag    5580
ctcggtacc                                                           5589
```

<210> SEQ ID NO 13
<211> LENGTH: 2904
<212> TYPE: RNA
<213> ORGANISM: Artificial Sequence
<220> FEATURE:
<223> OTHER INFORMATION: pCW1 23S RNA

<400> SEQUENCE: 13

```
gguuaagcga cuaagcguac acgguggaug cccuggcagu cagaggcgau gaaggacgug      60
cuaaucugcg auaagcgucg guaaggugau augaaccguu auaaccggcg auuuccgaau     120
ggggaaaccc aguguguuuc gacacacuau cauuaacuga auccauaggu uaaugaggcg     180
aaccggggga acugaaacau cuaaguaccc cgaggaaaag aaaucaaccg agauuccccc     240
aguagcggcg agcgaacggg gagcagccca gagccugaau cagugugugu guuaguggaa     300
gcgucuggaa aggcgcgcga uacaggguga cagccccgua cacaaaaaug cacaugcugu     360
gagcucgaug aguagggcgg gacacguggu auccugucug aauaugggggg gaccauccuc     420 caaggcuaaa uacuccugac ugaccgauag ugaaccagua ccgugaggga aaggcgaaaa     480
gaaccccggc gaggggagug aaaaagaacc ugaaccgug acguacaag caguggggagc     540 acgcuuaggc gugugacugc guaccuuuug uauaauggu cagcgacuua uauucuguag     600
caagguuaac cgauaggggg agccgaaggg aaaccgaguc uuaacugggc guuaaguugc     660
aggguauaga cccgaaaccc ggugaucuag ccaugggcag guugaagguu ggguaacacu     720
aacuggagga ccgaaccgac uaauguugaa aaauuagcgg augacuugug cugggggug     780 aaaggccaau caaaccggga gauagcuggu ucuccccgaa agcuauuuag guagcgccuc     840
gugaauucau cuccggggu agagcacugu uucggcaagg gggucauccc gacuuaccaa     900
cccgaugcaa acugcgaaua ccggagaaug uuaucacggg agacacacgg cgggugcuaa     960
cguccgucgu gaagagggaa acaacccaga ccgccagcua agucccaaa gucaugguua    1020 aguggggaaac gaugugggaa ggcccagaca gccaggaugu uggcuagaa gcagccauca    1080 uuuaaagaaa gcguaauagc ucacuggucg agucggccug cgcggaagau guaacggggc    1140
```

| | |
|---|---|
| uaaaccaugc accgaagcug cggcagcgac gcuuaugcgu uguuggguag gggagcguuc | 1200 |
| uguaagccug cgaaggugug cugugaggca ugcuggaggu aucagaagug cgaaugcuga | 1260 |
| cauaaguaac gauaaagcgg gugaaaagcc cgcucgccgg aagaccaagg guuccugucc | 1320 |
| aacguuaauc ggggcagggu gagucgaccc cuaaggcgag gccgaaaggc guagucgaug | 1380 |
| ggaaacaggu aauauuuccu guacuuggug uuacugcgaa gggggggacgg agaaggcuau | 1440 |
| guuggccggg cgacgguugu cccgguuuaa gcguguaggc ugguuuucca ggcaaauccg | 1500 |
| gaaaaucaag gcugaggcgu gaugacgagg cacuacggug cugaagcaac aaaugcccug | 1560 |
| cuuccaggaa aagccucuaa gcaucaggua acaucaaauc guaccccaaa ccgacacagg | 1620 |
| uggucaggua gagaauacca aggcgcuuga gagaacucgg gugaaggaac uaggcaaaau | 1680 |
| ggugccguaa cuucgggaga aggcacgcug auauguaggu gagguccucu cgcggauggag | 1740 |
| cugaaaucag ucgaagauac cagcuggcug caacuguuua uuaaaaacac agcacugugc | 1800 |
| aaacacgaaa guggacguau acggugugac gccugcccgg ugccggaagg uuaauugaug | 1860 |
| ggguuagcgc aagcgaagcu cuugaucgaa gccccgguaa acggcggccg uaacuauaac | 1920 |
| gguccuaagg uagcgaaauu ccuugucggg uaaguuccga ccugcacgaa uggcguaaug | 1980 |
| auggccaggc ugucuccacc cgagacucag ugaaauugaa cucgcuguga agaugcagug | 2040 |
| uacccgcggc aagacggaaa gacccccguga accuuuacua uagcuugaca cugaacauug | 2100 |
| agccuugaug uguaggauag gugggaggcu uugaagugug gacgccaguc ugcauggagc | 2160 |
| cgaccuugaa auaccacccu uuaauguuug auguucuaac guugacccgu aauccggguu | 2220 |
| gcggacagug ucuggugggu aguuugacug gggcggucuc cuccuaaaga guaacggagg | 2280 |
| agcacgaagg uuggcuaauc cuggucggac aucaggaggu uagugcaaug gcauaagcca | 2340 |
| gcuugacugc gagcgugacg gcgcgagcag gugcgaaagc aggucauagu gauccggugg | 2400 |
| uucugaaugg aagggccauc gcucaacgga uaaaagguac uccggggaua acaggcugau | 2460 |
| accgcccaag aguucauauc gacggcggug uuuggcaccu cgaugucggc ucaucacauc | 2520 |
| cuggggcuga aguaggucccc aagggguaugg cuguucgcca uuuaaagugg uacgcgagcu | 2580 |
| ggguuuagaa cgucgugaga caguucgguc ccuaucugcc guggggcgcug gagaacugag | 2640 |
| gggggcugcu ccuaguacga gaggaccgga guggacgcau cacuggguguu cggguugucsa | 2700 |
| ugccaauggc acugcccggu agcuaaaugc ggaagagaua agugcugaaa gcaucuaagc | 2760 |
| acgaaacuug ccccgagaug aguucucccu gacccuuuaa ggguccugaa ggaacguuga | 2820 |
| agacgacgac guugauaggc cgggugugua agcgcagcga ugcguugagc uaaccgguac | 2880 |
| uaaugaaccg ugaggcuuaa ccuu | 2904 |

<210> SEQ ID NO 14
<211> LENGTH: 4289
<212> TYPE: DNA
<213> ORGANISM: Artificial Sequence
<220> FEATURE:
<223> OTHER INFORMATION: p16S-T DNA

<400> SEQUENCE: 14

| | |
|---|---|
| taatacgact cactataggg agattgaaga gtttgatcat ggctcagatt gaacgctggc | 60 |
| ggcaggccta acacatgcaa gtcgaacggt aacaggaaga agcttgcttc tttgctgacg | 120 |
| agtggcggac gggtgagtaa tgtctgggaa actgcctgat ggagggggat aactactgga | 180 |
| aacggtagct aataccgcat aacgtcgcaa gaccaaagag ggggaccttc gggcctcttg | 240 |

```
ccatcggatg tgcccagatg ggattagcta gtaggtgggg taacggctca cctaggcgac    300
gatccctagc tggtctgaga ggatgaccag ccacactgga actgagacac ggtccagact    360
cctacgggag gcagcagtgg ggaatattgc acaatgggcg caagcctgat gcagccatgc    420
cgcgtgtatg aagaaggcct tcgggttgta aagtactttc agcggggagg aagggagtaa    480
agttaatacc tttgctcatt gacgttaccc gcagaagaag caccggctaa ctccgtgcca    540
gcagccgcgg taatacggag ggtgcaagcg ttaatcggaa ttactgggcg taaagcgcac    600
gcaggcggtt tgttaagtca gatgtgaaat ccccgggctc aacctgggaa ctgcatctga    660
tactggcaag cttgagtctc gtagaggggg gtagaattcc aggtgtagcg gtgaaatgcg    720
tagagatctg gaggaatacc ggtggcgaag gcggccccct ggacgaagac tgacgctcag    780
gtgcgaaagc gtggggagca acaggatta gatccctgg tagtccacgc cgtaaacgat    840
gtcgacttgg aggttgtgcc cttgaggcgt ggcttccgga gctaacgcgt taagtcgacc    900
gcctggggag tacggccgca aggttaaaac tcaaatgaat tgacggggc ccgcacaagc    960 ggtggagcat gtggtttaat tcgatgcaac gcgaagaacc ttacctggtc ttgacatcca    1020
cggaagtttt cagagatgag aatgtgcctt cgggaaccgt gagacaggtg ctgcatggct    1080
gtcgtcagct cgtgttgtga atgttgggt taagtcccgc aacgagcgca acccttatcc    1140
tttgttgcca gcggtccggc cgggaactca aaggagactg ccagtgataa actggaggaa    1200
ggtggggatg acgtcaagtc atcatggccc ttacgaccag ggctacacac gtgctacaat    1260
ggcgcataca aagagaagcg acctcgcgag agcaagcgga cctcataaag tgcgtcgtag    1320
tccggattgg agtctgcaac tcgactccat gaagtcggaa tcgctagtaa tcgtggatca    1380
gaatgccacg gtgaatacgt tcccgggcct tgtacacacc gcccgtcaca ccatgggagt    1440
gggttgcaaa agaagtaggt agcttaacct tcgggagggc gcttaccact ttgtgattca    1500
tgactggggt gaagtcgtaa caaggtaacc gtagggaac ctgcggttgg atcacctcct    1560
taggctagca taaccccttg gggcctctaa acgggtcttg agggtttttt tgtctagagt    1620
cgacctgcag gcatgcaagc ttggcgtaat catggtcata gctgtttcct gtgtgaaatt    1680
gttatccgct cacaattcca cacaacatac gagccggaag cataaagtgt aaagcctggg    1740
gtgcctaatg agtgagctaa ctcacattaa ttgcgttgcg ctcactgccc gctttccagt    1800
cgggaaacct gtcgtgccag ctgcattaat gaatcggcca acgcgcgggg agaggcggtt    1860
tgcgtattgg gcgctcttcc gcttcctcgc tcactgactc gctgcgctcg gtcgttcggc    1920
tgcggcgagc ggtatcagct cactcaaagg cggtaatacg gttatccaca gaatcagggg    1980
ataacgcagg aaagaacatg tgagcaaaag gccagcaaaa ggccaggaac cgtaaaaagg    2040
ccgcgttgct ggcgtttttc cataggctcc gcccccctga cgagcatcac aaaaatcgac    2100
gctcaagtca gaggtggcga aacccgacag gactataaag ataccaggcg tttccccctg    2160
gaagctccct cgtgcgctct cctgttccga ccctgccgct taccggatac ctgtccgcct    2220
ttctcccttc gggaagcgtg gcgctttctc atagctcacg ctgtaggtat ctcagttcgg    2280
tgtaggtcgt tcgctccaag ctgggctgtg tgcacgaacc cccgttcag cccgaccgct    2340 gcgccttatc cggtaactat cgtcttgagt ccaacccggt aagacacgac ttatcgccac    2400
tggcagcagc cactggtaac aggattagca gagcgaggta tgtaggcggt gctacagagt    2460
tcttgaagtg gtggcctaac tacggctaca ctagaagaac agtatttggt atctgcgctc    2520
tgctgaagcc agttaccttc ggaaaaagag ttggtagctc ttgatccggc aaacaaacca    2580
ccgctggtag cggtggtttt tttgtttgca agcagcagat tacgcgcaga aaaaaaggat    2640
```

| | |
|---|---|
| ctcaagaaga tcctttgatc ttttctacgg ggtctgacgc tcagtggaac gaaaactcac | 2700 |
| gttaagggat tttggtcatg agattatcaa aaaggatctt cacctagatc cttttaaatt | 2760 |
| aaaaatgaag ttttaaatca atctaaagta tatatgagta aacttggtct gacagttacc | 2820 |
| aatgcttaat cagtgaggca cctatctcag cgatctgtct atttcgttca tccatagttg | 2880 |
| cctgactccc cgtcgtgtag ataactacga tacgggaggg cttaccatct ggccccagtg | 2940 |
| ctgcaatgat accgcgagac ccacgctcac cggctccaga tttatcagca ataaaccagc | 3000 |
| cagccggaag ggccgagcgc agaagtggtc ctgcaacttt atccgcctcc atccagtcta | 3060 |
| ttaattgttg ccgggaagct agagtaagta gttcgccagt taatagtttg cgcaacgttg | 3120 |
| ttgccattgc tacaggcatc gtggtgtcac gctcgtcgtt tggtatggct tcattcagct | 3180 |
| ccggttccca acgatcaagg cgagttacat gatcccccat gttgtgcaaa aaagcggtta | 3240 |
| gctccttcgg tcctccgatc gttgtcagaa gtaagttggc cgcagtgtta tcactcatgg | 3300 |
| ttatggcagc actgcataat tctcttactg tcatgccatc cgtaagatgc ttttctgtga | 3360 |
| ctggtgagta ctcaaccaag tcattctgag aatagtgtat gcggcgaccg agttgctctt | 3420 |
| gcccggcgtc aatacgggat aataccgcgc cacatagcag aactttaaaa gtgctcatca | 3480 |
| ttggaaaacg ttcttcgggg cgaaaactct caaggatctt accgctgttg agatccagtt | 3540 |
| cgatgtaacc cactcgtgca cccaactgat cttcagcatc ttttactttc accagcgttt | 3600 |
| ctgggtgagc aaaaacagga aggcaaaatg ccgcaaaaaa gggaataagg gcgacacgga | 3660 |
| aatgttgaat actcatactc ttcctttttc aatattattg aagcatttat cagggttatt | 3720 |
| gtctcatgag cggatacata tttgaatgta tttagaaaaa taaacaaata ggggttccgc | 3780 |
| gcacatttcc ccgaaaagtg ccacctgacg tctaagaaac cattattatc atgacattaa | 3840 |
| cctataaaaa taggcgtatc acgaggccct ttcgtctcgc gcgtttcggt gatgacggtg | 3900 |
| aaaacctctg acacatgcag ctcccggaga cggtcacagc ttgtctgtaa gcggatgccg | 3960 |
| ggagcagaca agcccgtcag ggcgcgtcag cgggtgttgg cgggtgtcgg ggctggctta | 4020 |
| actatgcggc atcagagcag attgtactga gagtgcacca tatgcggtgt gaaataccgc | 4080 |
| acagatgcgt aaggagaaaa taccgcatca ggcgccattc gccattcagg ctgcgcaact | 4140 |
| gttgggaagg gcgatcggtg cgggcctctt cgctattacg ccagctggcg aaagggggat | 4200 |
| gtgctgcaag gcgattaagt tgggtaacgc cagggttttc ccagtcacga cgttgtaaaa | 4260 |
| cgacggccag tgaattcgag ctcggtacc | 4289 |

<210> SEQ ID NO 15
<211> LENGTH: 1592
<212> TYPE: RNA
<213> ORGANISM: Artificial Sequence
<220> FEATURE:
<223> OTHER INFORMATION: p16S-T 16S RNA

<400> SEQUENCE: 15

| | |
|---|---|
| agauugaaga guuugaucau ggcucagauu gaacgcuggc ggcaggccua acacaugcaa | 60 |
| gucgaacggu aacaggaaga agcuugcuuc uuugcugacg aguggcggac gggugaguaa | 120 |
| ugucugggaa acugccugau ggagggggau aacuacugga aacgguagcu aauaccgcau | 180 |
| aacgucgcaa gaccaaagag ggggaccuuc gggccucuug ccaucggaug ugcccagaug | 240 |
| ggauuagcua guaggugggg uaacggcuca ccuaggcgac gaucccuagc uggucugaga | 300 |
| ggaugaccag ccacacugga acugagacac gguccagacu ccuacgggag gcagcagugg | 360 |

```
ggaauauugc acaaugggcg caagccugau gcagccaugc cgcguguaug aagaaggccu    420
ucggguugua aaguacuuuc agcggggagg aagggaguaa aguuaauacc uuugcucauu    480
gacguuaccc gcagaagaag caccggcuaa cuccgugcca gcagccgcgg uaauacggag    540
ggugcaagcg uuaaucggaa uuacuggggcg uaaagcgcac gcaggcgguu uguuaaguca   600
gaugugaaau ccccgggcuc aaccugggaa cugcaucuga uacuggcaag cuugagucuc    660 guagagggg guagaauucc aggugguagcg gugaaaugcg uagagaucug gaggaauacc    720 ggugcgaag gcggccccu ggacgaagac ugacgcucag gugcgaaagc gugggagca      780 aacaggauua gauacccugg uagaaagac ugacgcucag gucgacuugg agguugcc      840 cuugaggcgu ggcuuccgga gcuaacgcgu uaagucgacc gccugggag uacggccgca    900 agguuaaaac ucaaaugaau ugacggggggc ccgcacaagc ggtggagcau ggguuuaau    960 ucgaugcaac gcgaagaacc uuaccugguc uugacaucca cggaaguuu cagagaugag    1020 aaugugccuu cgggaaccgu gagacaggug cugcauggcu gucgucagcu cguguuguga   1080
aauguugggu uaagucccgc aacgagcgca acccuuaucc uuuguugcca gcggccggc    1140 cgggaacuca aaggagacug ccagugauaa acuggaggaa ggugggggaug acgucaaguc   1200 aucauggccc uuacgaccag ggcuacacac gugcuacaau ggcgcauaca aagagaagcg    1260
accucgcgag agcaagcgga ccucauaaag ugcgucguag uccggauugg agucugcaac   1320
ucgacuccau gaagucggaa ucgcuaguaa ucguggauca gaaugccacg gugaauacgu    1380
ucccgggccu guacacacc gcccgucaca ccauggggagu ggguugcaaa agaaguaggu    1440
agcuuaaccu ucgggagggc gcuuaccacu uugugauuca ugacuggggu gaagucguaa    1500
caagguaacc guaggggaac cugcggcuugg aucaccuccu uaggcuagca uaaccccuug    1560
gggccucuaa acgggucuug aggguuuuu ug                                  1592

<210> SEQ ID NO 16
<211> LENGTH: 5637
<212> TYPE: DNA
<213> ORGANISM: Artificial Sequence
<220> FEATURE:
<223> OTHER INFORMATION: p23S-T DNA

<400> SEQUENCE: 16
taatacgact cactataggt taagcgacta agcgtacacg gtggatgccc tggcagtcag     60
aggcgatgaa ggacgtgcta atctgcgata agcgtcggta aggtgatatg aaccgttata    120
accggcgatt tccgaatggg gaaacccagt gtgtttcgac acactatcat taactgaatc    180
cataggttaa tgaggcgaac cggggaact gaaacatcta agtaccccga ggaaaagaaa    240
tcaaccgaga ttcccccagt agcggcgagc gaacggggag cagcccagag cctgaatcag    300
tgtgtgtgtt agtggaagcg tctggaaagg cgcgcgatac agggtgacag ccccgtacac    360
aaaaatgcac atgctgtgag ctcgatgagt agggcgggac acgtggtatc ctgtctgaat    420 atgggggggac catcctccaa ggctaaatac tcctgactga ccgatagtga accagtaccg    480
tgagggaaag gcgaaaagaa ccccggcgag gggagtgaaa agaacctgaa accgtgtac    540 gtacaagcag tggagcacg cttaggcgtg tgactgcgta ccttttgtat aatgggtcag    600
cgacttatat tctgtagcaa ggttaaccga ataggggagc cgaaggaaa ccgagtctta    660 actgggcgtt aagttgcagg gtatagaccc gaaacccggt gatctagcca tgggcaggtt    720
gaaggttggg taacactaac tggaggaccg aaccgactaa tgttgaaaaa ttagcggatg    780
acttgtggct gggggtgaaa ggccaatcaa accgggagat agctggttct ccccgaaagc    840
```

```
tatttaggta gcgcctcgtg aattcatctc cggggtaga gcactgtttc ggcaagggg      900
tcatcccgac ttaccaaccc gatgcaaact gcgaataccg gagaatgtta tcacgggaga    960
cacacggcgg gtgctaacgt ccgtcgtgaa gagggaaaca acccagaccg ccagctaagg   1020
tcccaaagtc atggttaagt gggaaacgat gtgggaaggc ccagacagcc aggatgttgg   1080
cttagaagca gccatcattt aaagaaagcg taatagctca ctggtcgagt cggcctgcgc   1140
ggaagatgta acgggctaa accatgcacc gaagctgcgg cagcgacgct tatgcgttgt    1200
tgggtagggg agcgttctgt aagcctgcga aggtgtgctg tgaggcatgc tggaggtatc   1260
agaagtgcga atgctgacat aagtaacgat aaagcgggtg aaaagcccgc tcgccggaag   1320
accaagggtt cctgtccaac gttaatcggg gcagggtgag tcgaccccta aggcgaggcc   1380
gaaaggcgta gtcgatggga aacaggttaa tattcctgta cttggtgtta ctgcgaaggg   1440
gggacggaga aggctatgtt ggccgggcga cggttgtccc ggtttaagcg tgtaggctgg   1500
ttttccaggc aaatccggaa atcaaggct gaggcgtgat gacgaggcac tacggtgctg    1560
aagcaacaaa tgccctgctt ccaggaaaag cctctaagca tcaggtaaca tcaaatcgta   1620
ccccaaaccg acacaggtgg tcaggtagag aataccaagg cgcttgagag aactcgggtg   1680
aaggaactag gcaaaatggt gccgtaactt cgggagaagg cacgctgata tgtaggtgag   1740
gtccctcgcg gatggagctg aaatcagtcg aagataccag ctggctgcaa ctgtttatta   1800
aaaacacagc actgtgcaaa cacgaaagtg gacgtatacg gtgtgacgcc tgcccggtgc   1860
cggaaggtta attgatgggg ttagcgcaag cgaagctctt gatcgaagcc ccggtaaacg   1920
gcggccgtaa ctataacggt cctaaggtag cgaaattcct tgtcgggtaa gttccgacct   1980
gcacgaatgg cgtaatgatg gccaggctgt ctccacccga gactcagtga aattgaactc   2040
gctgtgaaga tgcagtgtac ccgcggcaag acggaaagac cccgtgaacc tttactatag   2100
cttgacactg aacattgagc cttgatgtgt aggataggtg ggaggctttg aagtgtggac   2160
gccagtctgc atggagccga ccttgaaata ccacccttta atgtttgatg ttctaacgtt   2220
gacccgtaat ccgggttgcg acagtgtct ggtgggtagt ttgactgggg cggtctcctc    2280
ctaaagagta acggaggagc acgaaggttg gctaatcctg gtcggacatc aggaggttag   2340
tgcaatggca taagccagct tgactgcgag cgtgacggcg cgagcaggtg cgaaagcagg   2400
tcatagtgat ccggtggttc tgaatggaag ggccatcgct caacggataa aaggtactcc   2460
ggggataaca ggctgatacc gcccaagagt tcatatcgac ggcggtgttt ggcacctcga   2520
tgtcggctca tcacatcctg gggctgaagt aggtcccaag ggtatggctg ttcgccatt   2580
aaagtggtac gcgagctggg tttagaacgt cgtgagacag ttcggtccct atctgccgtg   2640
ggcgctggag aactgagggg ggctgctcct agtacgagag gaccggagtg gacgcatcac   2700
tggtgttcgg gttgtcatgc caatggcact gcccggtagc taaatgcgga agagataagt   2760
gctgaaagca tctaagcacg aaacttgccc cgagatgagt tctccctgac cctttaaggg   2820
tcctgaagga acgttgaaga cgacgacgtt gataggccgg gtgtgtaagc gcagcgatgc   2880
gttgagctaa ccggtactaa tgaaccgtga ggcttaacct tctagcataa ccccttgggg   2940
cctctaaacg ggtcttgagg ggtttttga agctgcaggc atgcaagctt ggcgtaatca    3000
tggtcatagc tgtttcctgt gtgaaattgt tatccgctca caattccaca caacatacga   3060
gccgaagca taaagtgtaa agcctggggt gcctaatgag tgagctaact cacattaatt    3120
gcgttgcgct cactgcccgc tttccagtcg ggaaacctgt cgtgccagct gcattaatga   3180
```

```
atcggccaac gcgcggggag aggcggtttg cgtattgggc gctcttccgc ttcctcgctc   3240
actgactcgc tgcgctcggt cgttcggctg cggcgagcgg tatcagctca ctcaaaggcg   3300
gtaatacggt tatccacaga atcaggggat aacgcaggaa agaacatgtg agcaaaaggc   3360
cagcaaaagg ccaggaaccg taaaaaggcc gcgttgctgg cgtttttcca taggctccgc   3420
ccccctgacg agcatcacaa aaatcgacgc tcaagtcaga ggtggcgaaa cccgacagga   3480
ctataaagat accaggcgtt tccccctgga agctccctcg tgcgctctcc tgttccgacc   3540
ctgccgctta ccggatacct gtccgccttt ctcccttcgg aagcgtggc gctttctcat   3600
agctcacgct gtaggtatct cagttcggtg taggtcgttc gctccaagct gggctgtgtg   3660
cacgaacccc ccgttcagcc cgaccgctgc gccttatccg gtaactatcg tcttgagtcc   3720
aacccggtaa gacacgactt atcgccactg gcagcagcca ctggtaacag gattagcaga   3780
gcgaggtatg taggcggtgc tacagagttc ttgaagtggt ggcctaacta cggctacact   3840
agaagaacag tatttggtat ctgcgctctg ctgaagccag ttaccttcgg aaaaagagtt   3900
ggtagctctt gatccggcaa acaaaccacc gctggtagcg tggttttttt tgtttgcaag   3960
cagcagatta cgcgcagaaa aaaggatct caagaagatc ctttgatctt ttctacgggg   4020
tctgacgctc agtggaacga aaactcacgt taagggattt tggtcatgag attatcaaaa   4080
aggatcttca cctagatcct tttaaattaa aaatgaagtt ttaaatcaat ctaaagtata   4140
tatgagtaaa cttggtctga cagttaccaa tgcttaatca gtgaggcacc tatctcagcg   4200
atctgtctat ttcgttcatc catagttgcc tgactccccg tcgtgtagat aactacgata   4260
cgggagggct taccatctgg ccccagtgct gcaatgatac cgcgagaccc acgctcaccg   4320
gctccagatt tatcagcaat aaaccagcca gccggaaggg ccgagcgcag aagtggtcct   4380
gcaactttat ccgcctccat ccagtctatt aattgttgcc gggaagctag agtaagtagt   4440
tcgccagtta atagtttgcg caacgttgtt gccattgcta caggcatcgt ggtgtcacgc   4500
tcgtcgtttg gtatggcttc attcagctcc ggttcccaac gatcaaggcg agttacatga   4560
tcccccatgt tgtgcaaaaa agcggttagc tccttcggtc ctccgatcgt tgtcagaagt   4620
aagttggccg cagtgttatc actcatggtt atggcagcac tgcataattc tcttactgtc   4680
atgccatccg taagatgctt ttctgtgact ggtgagtact caaccaagtc attctgagaa   4740
tagtgtatgc ggcgaccgag ttgctcttgc ccggcgtcaa tacgggataa taccgcgcca   4800
catagcagaa ctttaaaagt gctcatcatt ggaaaacgtt cttcggggcg aaaactctca   4860
aggatcttac cgctgttgag atccagttcg atgtaaccca ctcgtgcacc caactgatct   4920
tcagcatctt ttactttcac cagcgtttct gggtgagcaa aaacaggaag gcaaaatgcc   4980
gcaaaaaagg gaataagggc gacacggaaa tgttgaatac tcatactctt cctttttcaa   5040
tattattgaa gcatttatca gggttattgt ctcatgagcg gatacatatt tgaatgtatt   5100
tagaaaaata aacaaatagg ggttccgcgc acatttcccc gaaaagtgcc acctgacgtc   5160
taagaaacca ttattatcat gacattaacc tataaaaata ggcgtatcac gaggcccttt   5220
cgtctcgcgc gtttcggtga tgacggtgaa aacctctgac acatgcagct cccggagacg   5280
gtcacagctt gtctgtaagc ggatgccggg agcagacaag cccgtcaggg cgcgtcagcg   5340
ggtgttggcg ggtgtcgggg ctggcttaac tatgcggcat cagagcagat tgtactgaga   5400
gtgcaccata tgcggtgtga atacccgcac agatgcgtaa ggagaaaata ccgcatcagg   5460
cgccattcgc cattcaggct gcgcaactgt tgggaagggc gatcggtgcg ggcctcttcg   5520
ctattacgcc agctggcgaa agggggatgt gctgcaaggc gattaagttg ggtaacgcca   5580
```
gggttttccc agtcacgacg ttgtaaaacg acggccagtg aattcgagct cggtacc    5637

<210> SEQ ID NO 17
<211> LENGTH: 2952
<212> TYPE: RNA
<213> ORGANISM: Artificial Sequence
<220> FEATURE:
<223> OTHER INFORMATION: p23S-T 23S RNA

<400> SEQUENCE: 17

```
gguuaagcga cuaagcguac acgguggaug cccuggcagu cagaggcgau gaaggacgug     60
cuaaucugcg auaagcgucg guaaggugau augaaccguu auaaccggcg auuuccgaau    120
ggggaaaccc agugguguuuc gacacacuau cauuaacuga auccauaggu uaaugaggcg    180
aaccggggga acugaaacau cuaaguaccc cgaggaaaag aaaucaaccg agauuccccc    240
aguagcggcg agcgaacggg gagcagccca gagccugaau cagugugugu guuaguggaa    300
gcgucuggaa aggcgcgcga uacaggguga cagccccgua cacaaaaaug cacaugcugu    360
gagcucgaug aguagggcgg gacacguggu auccugucug aauaugggg gaccauccuc    420
caaggcuaaa uacuccugac ugaccgauag ugaaccagua ccgugaggga aaggcgaaaa    480
gaaccccggc gaggggagug aaaaagaacc ugaaccgug acguacaag caguggggagc    540
acgcuuaggc gugugacugc guaccuuuug uauaauggu cagcgacuua uaucguag      600
caagguuaac cgauaugggg agccgaaggg aaaccgaguc uuaacugggc guuaaguugc    660
agggauauga cccgaaaccc ggugaucuag ccaugggcag guugaaggu ggguaacacu     720
aacuggagga ccgaaccgac uaauguugaa aaauuagcgg augacuugug gcuggggug    780
aaaggccaau caaaccggga gauagcuggu ucucccgaa agcuauuuag guagcgccuc    840
gugaauucau cuccggggu agagcacugu uucggcaagg ggucaucccc gacuuaccaa    900
cccgaugcaa acugcgaaua ccggagaaug uuaucacggg agacacacgg cgggugcuaa    960
cguccgucgu gaagagggaa acaacccaga ccgccagcua agguucccaaa gucauggu    1020
aguggaaac gaugugggaa ggcccagaca gccaggaugu uggcuugaaa gcagccauca   1080
uuuaagaaa gcguaauagc ucacuggucg agucggccgc gcggaagau guaacggggc    1140
uaaaccaugc accgaagcug cggcagcgac gcuuaugcgu uguugguag ggagcguuc    1200
uguaagccug cgaaggugug cugugaggca ugcuggaggu aucagaagug cgaaugcuga   1260
cauaaguaac gauaaagcgg gugaaaagcc cgcucgccgg aagaccaagg guuccugucc    1320
aacguuaauc ggggcagggu gagucgaccc cuaaggcgag gccgaaaggc guaucgaug    1380
ggaaacaggu uaauauuccu guacuggug uuacugcgaa ggggggacgg agaaggcuau    1440
guuggccggg cgacgguugu cccgguuuaa gcguguaggc ugguuuucca ggcaaauccg    1500
gaaaaucaag gcugaggcgu gaugacgagg cacuacgguug cugaagcaac aaaugcccug    1560
cuuccaggaa aagccucuaa gcaucaggua acaucaaauc guaccccaaa ccgacacagg    1620
uggucaggua gagaauacca aggcgcuuga gagaacucgg ugaaggaac uaggcaaaau    1680
ggugccguaa cuucgggaga aggcacgcug auauguaggu gaggucccuc gcggauggag    1740
cugaaaucag ucgaagauac cagcggcug caacuguuua uuaaaacac agcacugugc    1800
aaacacgaaa guggacguau acggugugac gccugcccgg ugccggaagg uuaauugaug    1860
ggguuagcgc aagcgaagcu cuugaucgaa gccccgguaa acggcggccg uaacuauaac    1920
gguccuaagg uagcgaaauu ccuugucggg uaaguuccga ccugcacgaa uggcguaaug    1980
```

```
auggccaggc ugucuccacc cgagacucag ugaaauugaa cucgcuguga agaugcagug   2040
uacccgcggc aagacggaaa gaccccguga accuuuacua uagcuugaca cugaacauug   2100
agccuugaug uguaggauag gugggaggcu uugaagugug gacgccaguc ugcauggagc   2160
cgaccuugaa auaccacccu uuaauguuug auguucuaac guugacccgu aauccggguu   2220
gcggacagug ucuggugggu aguuugacug gggcggucuc cuccuaaaga guaacggagg   2280
agcacgaagg uuggcuaauc cuggucggac aucaggaggu uagugcaaug gcauaagcca   2340
gcuugacugc gagcgugacg gcgcgagcag gugcgaaagc aggucauagu gauccggugg   2400
uucugaaugg aagggccauc gcucaacgga uaaaagguac uccggggaua acaggcugau   2460
accgcccaag aguucauauc gacggcggug uuuggcaccu cgaugucggc ucaucacauc   2520
cuggggcuga aguaggucccc aagggauaugg cguucgcca uuuaaagugg uacgcgagcu   2580
ggguuuagaa cgucgugaga caguucgguc ccuaucugcc gugggcgcug gagaacugag   2640
gggggcugcu ccuagaacga gaggaccgga gugacgcau cacugguguu cggguuguca   2700
ugccaauggc acugcccggu agcuaaaugc ggaagagaua agugcugaaa gcaucuaagc   2760
acgaaacuug ccccgagaug aguucucccu gacccuuuaa gggugccugaa ggaacguuga   2820 agacgacgac guugauaggc cggguguguua agcgcagcga ugcguugagc uaaccgguac   2880
uaaugaaccg ugaggcuuaa ccuucuagca uaaccccuug gggccucuaa acgggucuug   2940 aggggguuuuuu ug                                                     2952
```

<210> SEQ ID NO 18
<211> LENGTH: 4340
<212> TYPE: DNA
<213> ORGANISM: Artificial Sequence
<220> FEATURE:
<223> OTHER INFORMATION: p16S-HH DNA

<400> SEQUENCE: 18

```
taatacgact cactataggg agattgaaga gtttgatcat ggctcagatt gaacgctggc     60
ggcaggccta acacatgcaa gtcgaacggt aacaggaaga agcttgcttc tttgctgacg    120
agtggcggac gggtgagtaa tgtctgggaa actgcctgat ggaggggggat aactactgga   180 aacggtagct aataccgcat aacgtcgcaa gaccaaagag ggggaccttc gggcctcttg    240
ccatcggatg tgcccagatg ggattagcta gtaggtgggg taacggctca cctaggcgac    300
gatccctagc tggtctgaga ggatgaccag ccacactgga actgagacac ggtccagact    360
cctacgggag gcagcagtgg ggaatattgc acaatgggcg caagcctgat gcagccatgc    420
cgcgtgtatg aagaaggcct tcgggttgta aagtactttc agcggggagg aagggagtaa    480
agttaatacc tttgctcatt gacgttaccc gcagaagaag caccggctaa ctccgtgcca    540
gcagccgcgg taatacggag ggtgcaagcg ttaatcggaa ttactgggcg taaagcgcac    600
gcaggcggtt tgttaagtca gatgtgaaat cccggggctc aacctgggaa ctgcatctga    660
tactggcaag cttgagtctc gtagaggggg gtagaattcc aggtgtagcg gtgaaatgcg    720
tagagatctg gaggaatacc ggtggcgaag gcggccccct ggacgaagac tgacgctcag    780
gtgcgaaagc gtgggagca aacaggatta gataccctgg tagtccacgc cgtaaacgat    840
gtcgacttgg aggttgtgcc cttgaggcgt ggcttccgga gctaacgcgt taagtcgacc    900
gcctggggag tacggccgca aggttaaaac tcaaatgaat tgacggggc ccgcacaagc    960 ggtggagcat gtggtttaat tcgatgcaac gcgaagaacc ttacctggtc ttgacatcca   1020
cggaagtttt cagagatgag aatgtgcctt cgggaaccgt gagacaggtg ctgcatggct   1080
```

-continued

```
gtcgtcagct cgtgttgtga aatgttgggt taagtcccgc aacgagcgca acccttatcc    1140
tttgttgcca gcggtccggc cgggaactca aaggagactg ccagtgataa actggaggaa    1200
ggtggggatg acgtcaagtc atcatggccc ttacgaccag ggctacacac gtgctacaat    1260
ggcgcataca aagagaagcg acctcgcgag agcaagcgga cctcataaag tgcgtcgtag    1320
tccggattgg agtctgcaac tcgactccat gaagtcggaa tcgctagtaa tcgtggatca    1380
gaatgccacg gtgaatacgt tcccgggcct tgtacacacc gcccgtcaca ccatgggagt    1440
gggttgcaaa agaagtaggt agcttaacct tcgggagggc gcttaccact ttgtgattca    1500
tgactggggt gaagtcgtaa caaggtaacc gtaggggaac ctgcggttgg atcacctcct    1560
taggtctgag cgtgataccc gctcactgaa gatggcccgg tagggccgaa acctactagc    1620
ataccccctt ggggcctcta acgggtctt gaggggtttt ttgtctagag tcgacctgca    1680
ggcatgcaag cttggcgtaa tcatggtcat agctgtttcc tgtgtgaaat tgttatccgc    1740
tcacaattcc acacaacata cgagccggaa gcataaagtg taaagcctgg ggtgcctaat    1800
gagtgagcta actcacatta attgcgttgc gctcactgcc cgctttccag tcgggaaacc    1860
tgtcgtgcca gctgcattaa tgaatcggcc aacgcgcggg gagaggcggt ttgcgtattg    1920
ggcgctcttc cgcttcctcg ctcactgact cgctgcgctc ggtcgttcgg ctgcggcgag    1980
cggtatcagc tcactcaaag gcggtaatac ggttatccac agaatcaggg gataacgcag    2040
gaaagaacat gtgagcaaaa ggccagcaaa aggccaggaa ccgtaaaaag gccgcgttgc    2100
tggcgttttt ccataggctc cgcccccctg acgagcatca caaaaatcga cgctcaagtc    2160
agaggtggcg aaacccgaca ggactataaa gataccaggc gtttccccct ggaagctccc    2220
tcgtgcgctc tcctgttccg accctgccgc ttaccggata cctgtccgcc tttctccctt    2280
cgggaagcgt ggcgctttct catagctcac gctgtaggta tctcagttcg gtgtaggtcg    2340
ttcgctccaa gctgggctgt gtgcacgaac cccccgttca gcccgaccgc tgcgccttat    2400
ccggtaacta tcgtcttgag tccaacccgg taagacacga cttatcgcca ctggcagcag    2460
ccactggtaa caggattagc agagcgaggt atgtaggcgg tgctacagag ttcttgaagt    2520
ggtggcctaa ctacggctac actagaagaa cagtatttgg tatctgcgct ctgctgaagc    2580
cagttacctt cggaaaaaga gttggtagct cttgatccgg caaacaaacc accgctggta    2640
gcggtggttt ttttgtttgc aagcagcaga ttacgcgcag aaaaaaagga tctcaagaag    2700
atcctttgat cttttctacg gggtctgacg ctcagtggaa cgaaaactca cgttaaggga    2760
ttttggtcat gagattatca aaaaggatct tcacctagat ccttttaaat taaaaatgaa    2820
gttttaaatc aatctaaagt atatatgagt aaacttggtc tgacagttac caatgcttaa    2880
tcagtgaggc acctatctca gcgatctgtc tatttcgttc atccatagtt gcctgactcc    2940
ccgtcgtgta gataactacg atacgggagg gcttaccatc tggccccagt gctgcaatga    3000
taccgcgaga cccacgctca ccggctccag atttatcagc aataaaccag ccagccggaa    3060
gggccgagcg cagaagtggt cctgcaactt tatccgcctc catccagtct attaattgtt    3120
gccgggaagc tagagtaagt agttcgccag ttaatagttt gcgcaacgtt gttgccattg    3180
ctacaggcat cgtggtgtca cgctcgtcgt ttggtatggc ttcattcagc tccggttccc    3240
aacgatcaag gcgagttaca tgatccccca tgttgtgcaa aaaagcggtt agctccttcg    3300
gtcctccgat cgttgtcaga agtaagttgg ccgcagtgtt atcactcatg gttatggcag    3360
cactgcataa ttctcttact gtcatgccat ccgtaagatg cttttctgtg actggtgagt    3420
```

```
actcaaccaa gtcattctga gaatagtgta tgcggcgacc gagttgctct tgcccggcgt    3480
caatacggga taataccgcg ccacatagca gaactttaaa agtgctcatc attggaaaac    3540
gttcttcggg gcgaaaactc tcaaggatct taccgctgtt gagatccagt tcgatgtaac    3600
ccactcgtgc acccaactga tcttcagcat cttttacttt caccagcgtt tctgggtgag    3660
caaaaacagg aaggcaaaat gccgcaaaaa agggaataag ggcgacacgg aaatgttgaa    3720
tactcatact cttccttttt caatattatt gaagcattta tcagggttat tgtctcatga    3780
gcggatacat atttgaatgt atttagaaaa ataaacaaat aggggttccg cgcacatttc    3840
cccgaaaagt gccacctgac gtctaagaaa ccattattat catgacatta acctataaaa    3900
ataggcgtat cacgaggccc tttcgtctcg cgcgtttcgg tgatgacggt gaaaacctct    3960
gacacatgca gctcccggag acggtcacag cttgtctgta gcggatgcc gggagcagac     4020 aagcccgtca gggcgcgtca gcgggtgttg gcgggtgtcg ggctggctt aactatgcgg     4080 catcagagca gattgtactg agagtgcacc atatgcggtg tgaaataccg cacagatgcg    4140
taaggagaaa ataccgcatc aggcgccatt cgccattcag gctgcgcaac tgttgggaag    4200
ggcgatcggt gcgggcctct tcgctattac gccagctggc gaaagggga tgtgctgcaa     4260 ggcgattaag ttgggtaacg ccaggttttt cccagtcacg acgttgtaaa acgacggcca    4320
gtgaattcga gctcggtacc                                                4340

<210> SEQ ID NO 19
<211> LENGTH: 1643
<212> TYPE: RNA
<213> ORGANISM: Artificial Sequence
<220> FEATURE:
<223> OTHER INFORMATION: p16S-HH 16S RNA

<400> SEQUENCE: 19
agauugaaga guuugaucau ggcucagauu gaacgcuggc ggcaggccua acacaugcaa      60
gucgaacggu aacaggaaga agcuugcuuc uuugcugacg aguggcggac ggguagauaa    120
ugucugggaa acugccugau ggaggggau aacuacugga aacgguagcu aauaccgcau     180
aacgucgcaa gaccaaagag ggggaccuuc gggccucuug ccaucggaug ugcccagaug    240
ggauuagcua guaggugggg uaacggcuca ccuaggcgac gaucccuagc uggucugaga    300
ggaugaccag ccacacugga acugagacac gguccagacu ccuacgggag gcagcagugg    360
ggaauauugc acaaugggcg caagccugau gcagccaugc cgcguguaug aagaaggccu    420
ucgguuugua aaguacuuuc agcggggagg aaggagauaa aguuaauacc uuugcucauu    480
gacguuaccc gcagaagaag caccggcuaa cuccgugcca gcagccgcgg uaauacggag    540
ggugcaagcg uuaaucgaa uuacugggcg uaaagcgcac gcaggcgguu uguuaaguca    600
gaugugaaau ccccgggcuc aaccugggaa cugcaucuga uacuggcaag cuugagucuc    660 guagagggggg guagaauucc agguguagcg ugaaaugcg uagagaucug gaggaauacc    720 ggugcgaag gcggccccu ggacgaagac ugacgcucag gugcgaaagc gugggagca      780 aacaggauua gauacccugg uaguccacgc cguaaacgau gucgacuugg agguugugcc    840
cuugaggcgu ggcuuccgga gcuaacgcgu uaagucgacc gccuggggag uacggccgca    900
agguuaaaac ucaaaugaau ugacggggc cgcacaagc ggguggagcau gugguuuaau    960 ucgaugcaac gcgaagaacc uuaccugguc uugacaucca cggaaguuuu cagagaugag   1020
aaugugccuu cgggaaccgu gagacagguug cugcauggcu gucgucagcu cguugugga    1080 aauguugggu uaagucccgc aacgagcgca acccuuaucc uuuguugcca gcggucggc    1140
```

```
cgggaacuca aaggagacug ccagugauaa acuggaggaa ggugggggaug acgucaaguc    1200 aucauggccc uuacgaccag ggcuacacac gugcuacaau ggcgcauaca aagagaagcg    1260
accucgcgag agcaagcgga ccucauaaag ugcgucguag uccggauugg agucugcaac    1320
ucgacuccau gaagucggaa ucgcuaguaa ucguggauca gaaugccacg gugaauacgu    1380
ucccgggccu uguacacacc gcccgucaca ccauggggagu ggguugcaaa agaaguaggu    1440
agcuuaaccu ucgggagggc gcuuaccacu uugugauuca ugacuggggu gaagucguaa    1500 caaggugaacc guagggggaac cugcgguugg auccauccuu uaggucugag cgugauaccc    1560
gcucacugaa gauggcccgg uagggccgaa accuacuagc auaaccccuu ggggccucua    1620
aacgggucuu gaggggguuuu uug                                           1643
```

<210> SEQ ID NO 20
<211> LENGTH: 5691
<212> TYPE: DNA
<213> ORGANISM: Artificial Sequence
<220> FEATURE:
<223> OTHER INFORMATION: p23S-HH DNA

<400> SEQUENCE: 20

```
taatacgact cactataggt taagcgacta agcgtacacg gtggatgccc tggcagtcag      60
aggcgatgaa ggacgtgcta atctgcgata agcgtcggta aggtgatatg aaccgttata     120
accggcgatt tccgaatggg gaaacccagt gtgtttcgac acactatcat taactgaatc     180
cataggttaa tgaggcgaac cgggggaact gaaacatcta agtaccccga ggaaaagaaa     240
tcaaccgaga ttcccccagt agcggcgagc gaacggggag cagcccagag cctgaatcag     300
tgtgtgtgtt agtggaagcg tctggaaagg cgcgcgatac agggtgacag ccccgtacac     360
aaaaatgcac atgctgtgag ctcgatgagt agggcgggac acgtggtatc ctgtctgaat     420 atgggggggac catcctccaa ggctaaatac tcctgactga ccgatagtga accagtaccg     480
tgagggaaag gcgaaaagaa cccggcgag ggagtgaaa aagaacctga aaccgtgtac     540
gtacaagcag tgggagcacg cttaggcgtg tgactgcgta ccttttgtat aatgggtcag     600
cgacttatat tctgtagcaa ggttaaccga ataggggagc gaagggaaa ccgagtctta     660 actgggcgtt aagttgcagg gtatagaccc gaaacccggt gatctagcca tgggcaggtt     720
gaaggttggg taacactaac tggaggaccg aaccgctaa tgttgaaaaa ttagcggatg     780
acttgtggct gggggtgaaa ggccaatcaa accgggagat agctggttct ccccgaaagc     840
tatttaggta gcgcctcgtg aattcatctc gggggtaga gcactgtttc ggcaaggggg     900
tcatcccgac ttaccaaccc gatgcaaact gcgataccg gagaatgtta tcacgggaga     960
cacacgcgcg gtgctaacgt ccgtcgtgaa gagggaaaca acccagaccg ccagctaagg    1020
tcccaaagtc atggttaagt gggaaacgat gtgggaaggc ccagacagcc aggatgttgg    1080
cttagaagca gccatcattt aaagaaagcg taatagctca ctggtcgagt cggcctgcgc    1140
ggaagatgta acgggctaa accatgcacc gaagctgcgg cagcgacgct tatgcgttgt    1200
tgggtagggg agcgttctgt aagcctgcga aggtgtgctg tgaggcatgc tggaggtatc    1260
agaagtgcga atgctgacat aagtaacgat aaagcgggtg aaaagcccgc tcgccggaag    1320
accaagggtt cctgtccaac gttaatcggg gcagggtgag tcgacccccta aggcgaggcc    1380 gaaaggcgta gtcgatggga aacaggttaa tattcctgta cttggtgtta ctgcgaaggg    1440
gggacggaga aggctatgtt ggccgggcga cggttgtccc ggtttaagcg tgtaggctgg    1500
```

```
ttttccaggc aaatccggaa aatcaaggct gaggcgtgat gacgaggcac tacggtgctg   1560
aagcaacaaa tgccctgctt ccaggaaaag cctctaagca tcaggtaaca tcaaatcgta   1620
ccccaaaccg acacaggtgg tcaggtagag aataccaagg cgcttgagag aactcgggtg   1680
aaggaactag gcaaaatggt gccgtaactt cgggagaagg cacgctgata tgtaggtgag   1740
gtccctcgcg gatggagctg aaatcagtcg aagataccag ctggctgcaa ctgtttatta   1800
aaaacacagc actgtgcaaa cacgaaagtg gacgtatacg gtgtgacgcc tgcccggtgc   1860
cggaaggtta attgatgggg ttagcgcaag cgaagctctt gatcgaagcc ccggtaaacg   1920
gcggccgtaa ctataacggt cctaaggtag cgaaattcct tgtcgggtaa gttccgacct   1980
gcacgaatgg cgtaatgatg gccaggctgt ctccacccga gactcagtga aattgaactc   2040
gctgtgaaga tgcagtgtac ccgcggcaag acggaaagac cccgtgaacc tttactatag   2100
cttgacactg aacattgagc cttgatgtgt aggataggtg ggaggctttg aagtgtggac   2160
gccagtctgc atggagccga ccttgaaata ccaccctta atgtttgatg ttctaacgtt   2220
gacccgtaat ccgggttgcg gacagtgtct ggtgggtagt ttgactgggg cggtctcctc   2280
ctaaagagta acgaggagc acgaaggttg gctaatcctg tcggacatc aggaggttag    2340 tgcaatggca taagccagct tgactgcgag cgtgacggcg cgagcaggtg cgaaagcagg   2400
tcatagtgat ccggtggttc tgaatggaag ggccatcgct caacggataa aaggtactcc   2460
ggggataaca ggctgatacc gcccaagagt tcatatcgac ggcggtgttt ggcacctcga   2520
tgtcggctca tcacatcctg gggctgaagt aggtcccaag ggtatggctg ttcgccattt   2580
aaagtggtac gcgagctggg tttagaacgt cgtgagacag ttcggtccct atctgccgtg   2640
ggcgctggag aactgagggg ggctgctcct agtacgagag gaccggagtg gacgcatcac   2700
tggtgttcgg gttgtcatgc caatggcact gcccggtagc taaatgcgga agagataagt   2760
gctgaaagca tctaagcacg aaacttgccc cgagatgagt tctccctgac cctttaaggg   2820
tcctgaagga acgttgaaga cgacgacgtt gataggccgg gtgtgtaagc gcagcgatgc   2880
gttgagctaa ccggtactaa tgaaccgtga ggcttaacct taagtctgag cgtgatacc   2940 gctcactgaa gatggcccgg tagggccgaa acttactagc ataacccctt ggggcctcta   3000
aacgggtctt gagggggtttt ttgaagctgc aggcatgcaa gcttggcgta atcatggtca   3060
tagctgtttc ctgtgtgaaa ttgttatccg ctcacaattc cacacaacat acgagccgga   3120
agcataaagt gtaaagcctg gggtgcctaa tgagtgagct aactcacatt aattgcgttg   3180
cgctcactgc ccgctttcca gtcgggaaac ctgtcgtgcc agctgcatta atgaatcggc   3240
caacgcgcgg ggagaggcgg tttgcgtatt gggcgctctt ccgcttcctc gctcactgac   3300
tcgctgcgct cggtcgttcg gctgcggcga gcggtatcag ctcactcaaa ggcggtaata   3360
cggttatcca cagaatcagg ggataacgca ggaaagaaca tgtgagcaaa aggccagcaa   3420
aaggccagga accgtaaaaa ggccgcgttg ctggcgtttt tccataggct ccgcccccct   3480
gacgagcatc acaaaaatcg acgctcaagt cagaggtggc gaaacccgac aggactataa   3540
agataccagg cgtttccccc tggaagctcc ctcgtgcgct ctcctgttcc gaccctgccg   3600
cttaccggat acctgtccgc ctttctccct tcgggaagcg tggcgctttc tcatagctca   3660
cgctgtaggt atctcagttc ggtgtaggtc gttcgctcca agctgggctg tgtgcacgaa   3720 cccccgttc agcccgaccg ctgcgcctta tccggtaact atcgtcttga gtccaacccg   3780
gtaagacacg acttatcgcc actggcagca gccactggta acaggattag cagagcgagg   3840
tatgtaggcg gtgctacaga gttcttgaag tggtggccta actacggcta cactagaaga   3900
```

```
acagtatttg gtatctgcgc tctgctgaag ccagttacct tcggaaaaag agttggtagc   3960
tcttgatccg gcaaacaaac caccgctggt agcggtggtt ttttgtttg caagcagcag   4020
attacgcgca gaaaaaaagg atctcaagaa gatcctttga tcttttctac ggggtctgac   4080
gctcagtgga acgaaaactc acgttaaggg attttggtca tgagattatc aaaaaggatc   4140
ttcacctaga tccttttaaa ttaaaaatga agttttaaat caatctaaag tatatatgag   4200
taaacttggt ctgacagtta ccaatgctta atcagtgagg cacctatctc agcgatctgt   4260
ctatttcgtt catccatagt tgcctgactc cccgtcgtgt agataactac gatacgggag   4320
ggcttaccat ctggccccag tgctgcaatg ataccgcgag acccacgctc accggctcca   4380
gatttatcag caataaacca gccagccgga agggccgagc gcagaagtgg tcctgcaact   4440
ttatccgcct ccatccagtc tattaattgt tgccgggaag ctagagtaag tagttcgcca   4500
gttaatagtt tgcgcaacgt tgttgccatt gctacaggca tcgtggtgtc acgctcgtcg   4560
tttggtatgg cttcattcag ctccggttcc caacgatcaa ggcgagttac atgatccccc   4620
atgttgtgca aaaaagcggt tagctccttc ggtcctccga tcgttgtcag aagtaagttg   4680
gccgcagtgt tatcactcat ggttatggca gcactgcata attctcttac tgtcatgcca   4740
tccgtaagat gcttttctgt gactggtgag tactcaacca agtcattctg agaatagtgt   4800
atgcggcgac cgagttgctc ttgcccggcg tcaatacggg ataataccgc gccacatagc   4860
agaactttaa aagtgctcat cattggaaaa cgttcttcgg ggcgaaaact ctcaaggatc   4920
ttaccgctgt tgagatccag ttcgatgtaa cccactcgtg cacccaactg atcttcagca   4980
tcttttactt tcaccagcgt ttctgggtga gcaaaaacag gaaggcaaaa tgccgcaaaa   5040
aagggaataa gggcgacacg gaaatgttga atactcatac tcttcctttt tcaatattat   5100
tgaagcattt atcagggtta ttgtctcatg agcggataca tatttgaatg tatttagaaa   5160
aataaacaaa taggggttcc gcgcacattt ccccgaaaag tgccacctga cgtctaagaa   5220
accattatta tcatgacatt aacctataaa aataggcgta tcacgaggcc ctttcgtctc   5280
gcgcgtttcg gtgatgacgg tgaaaacctc tgacacatgc agctcccgga gacggtcaca   5340
gcttgtctgt aagcggatgc cgggagcaga caagcccgtc agggcgcgtc agcgggtgtt   5400
ggcgggtgtc ggggctggct taactatgcg gcatcagagc agattgtact gagagtgcac   5460
catatgcggt gtgaaatacc gcacagatgc gtaaggagaa ataccgcat caggcgccat   5520
tcgccattca ggctgcgcaa ctgttgggaa gggcgatcgg tgcgggcctc ttcgctatta   5580
cgccagctgg cgaaaggggg atgtgctgca aggcgattaa gttgggtaac gccagggttt   5640
tcccagtcac gacgttgtaa aacgacggcc agtgaattcg agctcggtac c            5691
```

<210> SEQ ID NO 21
<211> LENGTH: 3006
<212> TYPE: RNA
<213> ORGANISM: Artificial Sequence
<220> FEATURE:
<223> OTHER INFORMATION: p23S-HH 23S RNA

<400> SEQUENCE: 21

```
gguuaagcga cuaagcguac acgguggaug cccuggcagu cagaggcgau gaaggacgug    60
cuaaucugcg auaagcgucg guaaggugau augaaccguu auaaccggcg auuuccgaau   120
ggggaaaccc agugguuuc gacacacuau cauuaacuga auccauaggu uaugaggcg    180
aaccggggga acugaaacau cuaaguaccc cgaggaaaag aaaucaaccg agauucccc    240
```

-continued

```
aguagcggcg agcgaacggg gagcagccca gagccugaau cagugugugu guuaguggaa    300
gcgucuggaa aggcgcgcga uacaggguga cagccccgua cacaaaaaug cacaugcugu    360
gagcucgaug aguagggcgg gacacguggu auccugucug aauauggggg gaccauccuc    420
caaggcuaaa uacuccugac ugaccgauag ugaaccagua ccgugaggga aaggcgaaaa    480
gaaccccggc gagggagug aaaaagaacc ugaaccgug uacguacaag caguggagc     540 acgcuuaggc gugugacugc guaccuuuug uauaaugggu cagcgacuua uauucuguag    600
caagguuaac cgauagggg agccgaaggg aaaccgaguc uuaacgggc guuaaguugc     660 agggauauga cccgaaaccc ggugaucuag ccaugggcag guugaagguu gguaacacu    720 aacuggagga ccgaaccgac uaauguugaa aaauuagcgg augacuugug gcuggggug     780 aaaggccaau caaaccggga gauagcuggu ucuccccgaa agcuauuuag guagcgccuc    840
gugaauucau cuccgggggu agagcacugu uucggcaagg gggucauccc gacuuaccaa    900
cccgaugcaa acugcgaaua ccggagaaug uuaucacggg agacacacgg cgggugcuaa    960
cguccgucgu gaagagggaa acaacccaga ccgccagcua agguccccaa aa gucauggguua   1020 agugggaaac gaugugggaa ggcccagaca gccaggaugu uggcuuagaa gcagccauca    1080
uuuaaagaaa gcguaauagc ucacggghucg agucggccug cgcggaagau guaacggggc    1140
uaaaccaugc accgaagcug cggcagcgac gcuuaugcgu uguugggguag gggagcguuc    1200 uguaagccug cgaaggugug cugugaggca ugcuggaggu aucagaagug cgaaugcuga    1260
cauaaguaac gauaaagcgg gugaaaagcc cgcucgccgg aagaccaagg guuccugucc    1320
aacguuaauc ggggcaggu gagucgaccc cuaaggcgag gccgaaaggc guaguucgaug    1380 ggaaacaggu uaauauuccu guacuuggug uuacugcgaa gggggggacgg agaaggcuau    1440 guuggccggg cgacguuugu cccgguuua gcguguaggc ugguuuucca ggcaaauccg    1500
gaaaaucaag gcugaggcgu gaugacgagg cacuacggug cugaagcaac aaaugcccug    1560
cuuccaggaa aagccucuaa gcaucaggua acaucaaauc guaccccaaaa ccgacacagg    1620 uggucaggua gagaauacca aggcgcuuga gagaacucgg uugaaggaac uaggcaaaau    1680
ggugccguaa cuucgggaga aggcacgcug auaguaggu gagucccuc gcggauggag    1740 cugaaaucag ucgaagauac cagcuggcug caacuguuua uuaaaaacac agcacugugc    1800
aaacacgaaa guggacguau acggugugac gccugcccgg ugccggaagg uuaauugaug    1860
ggguuagcgc aagcgaagcu cuugaucgaa gccccguaa acggcggccg uaacuauaac    1920
gguccuaagg uagcgaaauu ccuugucggg uaaguuccga ccugcacgaa uggcguaaug    1980
auggccaggc ugucuccacc cgagacucag ugaaauugaa cucgcuguga agaugcagug    2040
uacccgcggc aagacggaaa gaccccguga accuuuacua uagcuugaca cugaacauug    2100
agccuugaug uguaggauag gugggaggcu uugaagugug gacgccaguc ugcauggagc    2160
cgaccuugaa auaccacccu uuaauguuug auguucuaac guugacccgu aauccggguu    2220
gcggacagug ucuggggggu aguugacug gggcggucuc cuccuaaaga guaacggagg    2280
agcacgaagg uuggcuaauc cuggucggac aucaggaggu uagugcaaug gcauaagcca    2340
gcuugacugc gagcgugacg gcgcgagcag gugcgaaagc aggucauagu gauccggugg    2400
uucugaaugg aagggccauc gcucaacgga uaaaagguac uccggggaua acaggcugau    2460
accgcccaag aguucauauc gacggcgguu uuggcaccu cgaugucggc ucaucacauc    2520
cuggggcuga aguaggucc aagggauagg cuguuccgcca uuuaaagugg uacgcgagcu    2580
ggguuuagaa cgucgugaga caguucgguc ccuaucugcc guggggcgcug gagaacugag    2640
```

-continued

```
gggggcugcu ccuaguacga gaggaccgga guggacgcau cacuggguguu cgguugguca   2700 ugccaauggc acugcccggu agcuaaaugc ggaagagaua agugcugaaa gcaucuaagc   2760
acgaaacuug ccccgagaug aguucucccu gacccuuuaa ggguccugaa ggaacguuga   2820
agacgacgac guugauaggc cgggugugua agcgagcga ugcguugagc uaaccgguac   2880
uaaugaaccg ugaggcuuaa ccuuaagucu gagcgugaua cccgcucacu gaagauggcc   2940
cgguagggcc gaaacuuacu agcauaaccc cuuggggccu cuaaacgggu cuugaggggu   3000
uuuuug                                                              3006
```

<210> SEQ ID NO 22
<211> LENGTH: 4377
<212> TYPE: DNA
<213> ORGANISM: Artificial Sequence
<220> FEATURE:
<223> OTHER INFORMATION: p16S-HDV DNA

<400> SEQUENCE: 22

```
taatacgact cactataggg agattgaaga gtttgatcat ggctcagatt gaacgctggc     60
ggcaggccta acacatgcaa gtcgaacggt aacaggaaga agcttgcttc tttgctgacg   120
agtggcggac gggtgagtaa tgtctgggaa actgcctgat ggaggggat aactactgga   180 aacggtagct aataccgcat aacgtcgcaa gaccaaagag ggggaccttc gggcctcttg   240
ccatcggatg tgcccagatg ggattagcta gtaggtgggg taacggctca cctaggcgac   300
gatccctagc tggtctgaga ggatgaccag ccacactgga actgagacac ggtccagact   360
cctacgggag gcagcagtgg ggaatattgc acaatgggcg caagcctgat gcagccatgc   420
cgcgtgtatg aagaaggcct tcgggttgta aagtactttc agcggggagg aagggagtaa   480
agttaatacc tttgctcatt gacgttaccc gcagaagaag caccggctaa ctccgtgcca   540
gcagccgcgg taatacgag ggtgcaagcg ttaatcggaa ttactgggcg taaagcgcac   600
gcaggcggtt tgttaagtca gatgtgaaat ccccgggctc aacctgggaa ctgcatctga   660
tactggcaag cttgagtctc gtagaggggg gtagaattcc aggtgtagcg gtgaaatgcg   720
tagagatctg gaggaatacc ggtggcgaag gcggcccct ggacgaagac tgacgctcag   780
gtgcgaaagc gtggggagca aacaggatta gataccctgg tagtccacgc cgtaaacgat   840
gtcgacttgg aggttgtgcc cttgaggcgt ggcttccgga gctaacgcgt taagtcgacc   900
gcctggggag tacggccgca aggttaaaac tcaaatgaat tgacggggc ccgcacaagc   960 ggtggagcat gtggtttaat tcgatgcaac gcgaagaacc ttacctggtc ttgacatcca  1020
cggaagtttt cagagatgag aatgtgcctt cgggaaccgt gagacaggtg ctgcatggct  1080
gtcgtcagct cgtgttgtga atgttgggt taagtcccgc aacgagcgca acccttatcc  1140
tttgttgcca gcggtccggc cgggaactca aaggagactg ccagtgataa actggaggaa  1200
ggtggggatg acgtcaagtc atcatggccc ttacgaccag gctacacac gtgctacaat  1260 ggcgcataca aagagaagcg acctcgcgag agcaagcgga cctcataaag tgcgtcgtag  1320
tccggattgg agtctgcaac tcgactccat gaagtcggaa tcgctagtaa tcgtggatca  1380
gaatgccacg gtgaatacgt tcccgggcct tgtacacacc gcccgtcaca ccatgggagt  1440
gggttgcaaa agaagtaggt agcttaacct tcgggagggc gcttaccact tgtgattca   1500 tgactgggt gaagtcgtaa caaggtaacc gtagggggaac ctgcggttgg atcacctcct  1560
taggtggccg gcatggtccc agcctcctcg ctggcgccgg ctgggcaaca ttccgagggg  1620
```

```
accgtcccct cggtaatggc gaatgggacc cactagcata acccottggg gcctctaaac    1680
gggtcttgag gggtttttg tctagagtcg acctgcaggc atgcaagctt ggcgtaatca    1740
tggtcatagc tgtttcctgt gtgaaattgt tatccgctca caattccaca acatacga    1800
gccggaagca taaagtgtaa agcctggggt gcctaatgag tgagctaact cacattaatt    1860
gcgttgcgct cactgcccgc tttccagtcg ggaaacctgt cgtgccagct gcattaatga    1920
atcggccaac gcgcgggag aggcggtttg cgtattgggc gctcttccgc ttcctcgctc    1980
actgactcgc tgcgctcggt cgttcggctg cggcgagcgg tatcagctca ctcaaaggcg    2040
gtaatacggt tatccacaga atcagggat aacgcaggaa agaacatgtg agcaaaaggc    2100
cagcaaaagg ccaggaaccg taaaaaggcc gcgttgctgg cgttttcca taggctccgc    2160
cccctgacg agcatcacaa aaatcgacgc tcaagtcaga ggtggcgaaa cccgacagga    2220
ctataaagat accaggcgtt ccccctgga agctccctcg tgcgctctcc tgttccgacc    2280
ctgccgctta ccggatacct gtccgccttt ctcccttcgg gaagcgtggc gctttctcat    2340
agctcacgct gtaggtatct cagttcggtg taggtcgttc gctccaagct gggctgtgtg    2400
cacgaacccc ccgttcagcc cgaccgctgc gccttatccg gtaactatcg tcttgagtcc    2460
aacccggtaa gacacgactt atcgccactg gcagcagcca ctggtaacag gattagcaga    2520
gcgaggtatg taggcggtgc tacagagttc ttgaagtggt ggcctaacta cggctacact    2580
agaagaacag tatttggtat ctgcgctctg ctgaagccag ttaccttcgg aaaaagagtt    2640
ggtagctctt gatccggcaa acaaaccacc gctggtagcg tggttttttt gtttgcaag    2700
cagcagatta cgcgcagaaa aaaggatct caagaagatc ctttgatctt ttctacgggg    2760
tctgacgctc agtggaacga aaactcacgt taagggattt tggtcatgag attatcaaaa    2820
aggatcttca cctagatcct tttaaattaa aaatgaagtt ttaaatcaat ctaaagtata    2880
tatgagtaaa cttggtctga cagttaccaa tgcttaatca gtgaggcacc tatctcagcg    2940
atctgtctat ttcgttcatc catagttgcc tgactcccg tcgtgtagat aactacgata    3000
cgggagggct taccatctgg ccccagtgct gcaatgatac cgcgagaccc acgctcaccg    3060
gctccagatt tatcagcaat aaaccagcca gccggaaggg ccgagcgcag aagtggtcct    3120
gcaactttat ccgcctccat ccagtctatt aattgttgcc gggaagctag agtaagtagt    3180
tcgccagtta atagtttgcg caacgttgtt gccattgcta caggcatcgt ggtgtcacgc    3240
tcgtcgtttg gtatggcttc attcagctcc ggttcccaac gatcaaggcg agttacatga    3300
tcccccatgt tgtgcaaaaa agcggttagc tccttcggtc ctccgatcgt tgtcagaagt    3360
aagttggccg cagtgttatc actcatggtt atggcagcac tgcataattc tcttactgtc    3420
atgccatccg taagatgctt ttctgtgact ggtgagtact caaccaagtc attctgagaa    3480
tagtgtatgc ggcgaccgag ttgctcttgc ccggcgtcaa tacgggataa taccgcgcca    3540
catagcagaa ctttaaaagt gctcatcatt ggaaaacgtt cttcggggcg aaaactctca    3600
aggatcttac cgctgttgag atccagttcg atgtaaccca ctcgtgcacc caactgatct    3660
tcagcatctt ttactttcac cagcgtttct gggtgagcaa aaacaggaag gcaaaatgcc    3720
gcaaaaaagg gaataaggc gacacggaaa tgttgaatac tcatactctt cctttttcaa    3780
tattattgaa gcatttatca gggttattgt ctcatgagcg gatacatatt tgaatgtatt    3840
tagaaaaata aacaaatagg ggttccgcgc acatttcccc gaaaagtgcc acctgacgtc    3900
taagaaacca ttattatcat gacattaacc tataaaaata ggcgtatcac gaggcccttt    3960
cgtctcgcgc gtttcggtga tgacggtgaa aacctctgac acatgcagct cccggagacg    4020
```

-continued

```
gtcacagctt gtctgtaagc ggatgccggg agcagacaag cccgtcaggg cgcgtcagcg   4080
ggtgttggcg ggtgtcgggg ctggcttaac tatgcggcat cagagcagat tgtactgaga   4140
gtgcaccata tgcggtgtga aataccgcac agatgcgtaa ggagaaaata ccgcatcagg   4200
cgccattcgc cattcaggct gcgcaactgt tgggaagggc gatcggtgcg ggcctcttcg   4260
ctattacgcc agctggcgaa agggggatgt gctgcaaggc gattaagttg ggtaacgcca   4320
gggttttccc agtcacgacg ttgtaaaacg acggccagtg aattcgagct cggtacc      4377
```

```

<210> SEQ ID NO 23
<211> LENGTH: 1680
<212> TYPE: RNA
<213> ORGANISM: Artificial Sequence
<220> FEATURE:
<223> OTHER INFORMATION: p16S-HDV 16S RNA

<400> SEQUENCE: 23
agauugaaga guuugaucau ggcucagauu gaacgcuggc ggcaggccua acacaugcaa     60
gucgaacggu aacaggaaga agcuugcuuc uuugcugacg aguggcggac gggugaguaa    120
ugucugggaa acugccugau ggagggggau aacuacugga aacgguagcu aauaccgcau    180
aacgucgcaa gaccaaagag ggggaccuuc gggccucuug ccaucggaug ugcccagaug    240
ggauuagcua guaggugggg uaacggcuca ccuaggcgac gaucccuagc uggucugaga    300
ggaugaccag ccacacugga acugagacac gguccagacu ccuacgggag gcagcagugg    360
ggaauauugc acaaugggcg caagccugau gcagccaugc cgcguguaug aagaaggccu    420
ucggguugua aaguacuuuc agcggggagg aagggaguaa aguuaauacc uuugcucauu    480
gacguuaccc gcagaagaag caccggcuaa cuccgugcca gcagccgcgg uaauacggag    540
ggugcaagcg uuaaucggaa uuacugggcg uaaagcgcac gcaggcgguu uguuaaguca    600
gaugugaaau ccccgggcuc aaccugggaa cugcaucuga uacuggcaag cuugagucuc    660
guagaggggg guagaauucc agguguagcg gugaaaugcg uagagaucug gaggaauacc    720
gguggcgaag gcggcccccu ggacgaagac ugacgcucag gugcgaaagc guggggagca    780
aacaggauua gauacccugg uaguccacgc cguaaacgau gucgacuugg agguugugcc    840
cuugaggcgu ggcuuccgga gcuaacgcgu uaagucgacc gccuggggag uacggccgca    900
agguuaaaac ucaaaugaau ugacgggggc ccgcacaagc gguggagcau gugguuuaau    960
ucgaugcaac gcgaagaacc uuaccugguc uugacaucca cggaaguuuu cagagaugag   1020
aaugugccuu cgggaaccgu gagacaggug cugcauggcu gucgucagcu cguguuguga   1080
aauguugggu uaagucccgc aacgagcgca acccuuaucc uuuguugcca gcgguccggc   1140
cgggaacuca aaggagacug ccagugauaa acuggaggaa gguggggaug acgucaaguc   1200
aucauggccc uuacgaccag ggcuacacac gugcuacaau ggcgcauaca aagagaagcg   1260
accucgcgag agcaagcgga ccucauaaag ugcgucguag uccggauugg agucugcaac   1320
ucgacuccau gaagucggaa ucgcuaguaa ucguggauca gaaugccacg gugaauacgu   1380
ucccgggccu uguacacacc gcccgucaca ccaugggagu ggguugcaaa agaaguaggu   1440
agcuuaaccu ucgggagggc gcuuaccacu uugugauuca ugacuggggu gaagucguaa   1500
caagguaacc guaggggaac cugcgguugg aucaccuccu uagguggccg gcauggucce   1560
agccuccucg cuggcgccgg cugggcaaca uuccgagggg accguccccu cgguaauggc   1620
gaaugggacc cacuagcaua accccuuggg gccucuaaac gggucuugag ggguuuuuug   1680
```

<210> SEQ ID NO 24
<211> LENGTH: 5728
<212> TYPE: DNA
<213> ORGANISM: Artificial Sequence
<220> FEATURE:
<223> OTHER INFORMATION: p23S-HDV DNA

<400> SEQUENCE: 24

```
taatacgact cactataggt taagcgacta agcgtacacg gtggatgccc tggcagtcag      60
aggcgatgaa ggacgtgcta atctgcgata agcgtcggta aggtgatatg aaccgttata     120
accggcgatt tccgaatggg gaaacccagt gtgtttcgac acactatcat taactgaatc     180
cataggttaa tgaggcgaac cggggggaact gaaacatcta agtaccccga ggaaaagaaa    240
tcaaccgaga ttcccccagt agcggcgagc gaacggggag cagcccagag cctgaatcag     300
tgtgtgtgtt agtggaagcg tctggaaagg cgcgcgatac agggtgacag ccccgtacac     360
aaaaatgcac atgctgtgag ctcgatgagt agggcgggac acgtggtatc ctgtctgaat     420
atgggggggac catcctccaa ggctaaatac tcctgactga ccgatagtga accagtaccg    480
tgagggaaag gcgaaaagaa ccccggcgag gggagtgaaa agaacctga aaccgtgtac      540
gtacaagcag tgggagcacg cttaggcgtg tgactgcgta ccttttgtat aatgggtcag     600
cgacttatat tctgtagcaa ggttaaccga ataggggagc cgaagggaaa ccgagtctta     660
actgggcgtt aagttgcagg gtatagaccc gaaacccgt gatctagcca tgggcaggtt      720
gaaggttggg taacactaac tggaggaccg aaccgactaa tgttgaaaaa ttagcggatg     780
acttgtggct gggggtgaaa ggccaatcaa accgggagat agctggttct ccccgaaagc     840
tatttaggta gcgcctcgtg aattcatctc cggggtaga gcactgtttc ggcaagggg      900
tcatcccgac ttaccaaccc gatgcaaact gcgaataccg gagaatgtta tcacgggaga    960
cacacggcgg gtgctaacgt ccgtcgtgaa gagggaaaca acccagaccg ccagctaagg    1020
tcccaaagtc atggttaagt gggaaacgat gtgggaaggc ccagacagcc aggatgttgg    1080
cttagaagca gccatcattt aaagaaagcg taatagctca ctggtcgagt cggcctgcgc    1140
ggaagatgta acgggctaa accatgcacc gaagctgcgg cagcgacgct tatgcgttgt     1200
tgggtagggg agcgttctgt aagcctgcga aggtgtgctg tgaggcatgc tggaggtatc    1260
agaagtgcga atgctgacat aagtaacgat aaagcgggtg aaaagcccgc tcgccggaag    1320
accaagggtt cctgtccaac gttaatcggg gcagggtgag tcgacccta aggcgaggcc     1380
gaaaggcgta gtcgatggga aacaggttaa tattcctgta cttggtgtta ctgcgaaggg    1440
gggacggaga aggctatgtt ggccgggcga cggttgtccc ggtttaagcg tgtaggctgg    1500
ttttccaggc aaatccggaa atcaaggct gaggcgtgat gacgaggcac tacggtgctg     1560
aagcaacaaa tgccctgctt ccaggaaaag cctctaagca tcaggtaaca tcaaatcgta    1620
ccccaaaccg acacaggtgg tcaggtagag aataccaagg cgcttgagag aactcgggtg    1680
aaggaactag gcaaaatggt gccgtaactt cgggagaagg cacgctgata tgtaggtgag    1740
gtccctcgcg gatggagctg aaatcagtcg aagataccag ctggctgcaa ctgtttatta    1800
aaaacacagc actgtgcaaa cacgaaagtg gacgtatacg gtgtgacgcc tgcccggtgc    1860
cggaaggtta attgatgggg ttagcgcaag cgaagctctt gatcgaagcc ccggtaaacg    1920
gcggccgtaa ctataacggt cctaaggtag cgaaattcct tgtcgggtaa gttccgacct    1980
gcacgaatgg cgtaatgatg gccaggctgt ctccacccga gactcagtga aattgaactc    2040
gctgtgaaga tgcagtgtac ccgcggcaag acggaaagac cccgtgaacc tttactatag    2100
```

```
cttgacactg aacattgagc cttgatgtgt aggataggtg ggaggctttg aagtgtggac    2160
gccagtctgc atggagccga ccttgaaata ccacccttta atgtttgatg ttctaacgtt    2220
gacccgtaat ccgggttgcg gacagtgtct ggtgggtagt ttgactgggg cggtctcctc    2280
ctaaagagta acggaggagc acgaaggttg gctaatcctg gtcggacatc aggaggttag    2340
tgcaatggca taagccagct tgactgcgag cgtgacggcg cgagcaggtg cgaaagcagg    2400
tcatagtgat ccggtggttc tgaatggaag ggccatcgct caacggataa aaggtactcc    2460
ggggataaca ggctgatacc gcccaagagt tcatatcgac ggcggtgttt ggcacctcga    2520
tgtcggctca tcacatcctg gggctgaagt aggtcccaag ggtatggctg ttcgccattt    2580
aaagtggtac gcgagctggg tttagaacgt cgtgagacag ttcggtccct atctgccgtg    2640
ggcgctggag aactgagggg ggctgctcct agtacgagag gaccggagtg gacgcatcac    2700
tggtgttcgg gttgtcatgc caatggcact gcccggtagc taaatgcgga agagataagt    2760
gctgaaagca tctaagcacg aaacttgccc cgagatgagt tctccctgac cctttaaggg    2820
tcctgaagga acgttgaaga cgacgacgtt gataggccgg gtgtgtaagc gcagcgatgc    2880
gttgagctaa ccggtactaa tgaaccgtga ggcttaacct taagtggccg gcatggtccc    2940
agcctcctcg ctggcgccgg ctgggcaaca ttccgagggg accgtcccct cggtaatggc    3000
gaatgggacc cactagcata accccttggg gcctctaaac gggtcttgag gggttttttg    3060
aagctgcagg catgcaagct tggcgtaatc atggtcatag ctgtttcctg tgtgaaattg    3120
ttatccgctc acaattccac acaacatacg agccggaagc ataaagtgta aagcctgggg    3180
tgcctaatga gtgagctaac tcacattaat tgcgttgcgc tcactgcccg ctttccagtc    3240
gggaaacctg tcgtgccagc tgcattaatg aatcggccaa cgcgcgggga gaggcggttt    3300
gcgtattggg cgctcttccg cttcctcgct cactgactcg ctgcgctcgg tcgttcggct    3360
gcggcgagcg gtatcagctc actcaaaggc ggtaatacgg ttatccacag aatcaggggA    3420
taacgcagga aagaacatgt gagcaaaagg ccagcaaaag gccaggaacc gtaaaaaggc    3480
cgcgttgctg gcgttttttcc ataggctccg ccccccctgac gagcatcaca aaaatcgacg    3540
ctcaagtcag aggtggcgaa acccgacagg actataaaga taccaggcgt tccccctgg    3600
aagctccctc gtgcgctctc ctgttccgac cctgccgctt accggatacc tgtccgcctt    3660
tctcccttcg ggaagcgtgg cgctttctca tagctcacgc tgtaggtatc tcagttcggt    3720
gtaggtcgtt cgctccaagc tgggctgtgt gcacgaaccc cccgttcagc ccgaccgctg    3780
cgccttatcc ggtaactatc gtcttgagtc caacccggta agacacgact tatcgccact    3840
ggcagcagcc actggtaaca ggattagcag agcgaggtat gtaggcggtg ctacagagtt    3900
cttgaagtgg tggcctaact acggctacac tagaagaaca gtatttggta tctgcgctct    3960
gctgaagcca gttaccttcg aaaaagagt tggtagctct tgatccggca aacaaaccac    4020
cgctggtagc ggtggttttt ttgtttgcaa gcagcagatt acgcgcagaa aaaaaggatc    4080
tcaagaagat cctttgatct tttctacggg gtctgacgct cagtggaacg aaaactcacg    4140
ttaagggatt ttggtcatga gattatcaaa aaggatcttc acctagatcc ttttaaatta    4200
aaaatgaagt tttaaatcaa tctaaagtat atatgagtaa acttggtctg acagttacca    4260
atgcttaatc agtgaggcac ctatctcagc gatctgtcta tttcgttcat ccatagttgc    4320
ctgactcccc gtcgtgtaga taactacgat acgggagggc ttaccatctg gccccagtgc    4380
tgcaatgata ccgcgagacc cacgctcacc ggctccagat ttatcagcaa taaaccagcc    4440
```

| | |
|---|---|
| agccggaagg gccgagcgca gaagtggtcc tgcaacttta tccgcctcca tccagtctat | 4500 |
| taattgttgc cgggaagcta gagtaagtag ttcgccagtt aatagtttgc gcaacgttgt | 4560 |
| tgccattgct acaggcatcg tggtgtcacg ctcgtcgttt ggtatggctt cattcagctc | 4620 |
| cggttcccaa cgatcaaggc gagttacatg atcccccatg ttgtgcaaaa aagcggttag | 4680 |
| ctccttcggt cctccgatcg ttgtcagaag taagttggcc gcagtgttat cactcatggt | 4740 |
| tatggcagca ctgcataatt ctcttactgt catgccatcc gtaagatgct tttctgtgac | 4800 |
| tggtgagtac tcaaccaagt cattctgaga atagtgtatg cggcgaccga gttgctcttg | 4860 |
| cccggcgtca atacgggata ataccgcgcc acatagcaga actttaaaag tgctcatcat | 4920 |
| tggaaaacgt tcttcggggc gaaaactctc aaggatctta ccgctgttga gatccagttc | 4980 |
| gatgtaaccc actcgtgcac ccaactgatc ttcagcatct tttactttca ccagcgtttc | 5040 |
| tgggtgagca aaaacaggaa ggcaaaatgc cgcaaaaaag gaataagggc gacacggaa | 5100 |
| atgttgaata ctcatactct ccttttttca atattattga agcatttatc agggttattg | 5160 |
| tctcatgagc ggatacatat ttgaatgtat ttagaaaaat aaacaaatag gggttccgcg | 5220 |
| cacatttccc cgaaaagtgc cacctgacgt ctaagaaacc attattatca tgacattaac | 5280 |
| ctataaaaat aggcgtatca cgaggccctt tcgtctcgcg cgtttcggtg atgacggtga | 5340 |
| aaacctctga cacatgcagc tcccggagac ggtcacagct tgtctgtaag cggatgccgg | 5400 |
| gagcagacaa gcccgtcagg gcgcgtcagc gggtgttggc gggtgtcggg gctggcttaa | 5460 |
| ctatgcggca tcagagcaga ttgtactgag agtgcaccat atgcggtgtg aaataccgca | 5520 |
| cagatgcgta aggagaaaat accgcatcag gcgccattcg ccattcaggc tgcgcaactg | 5580 |
| ttgggaaggg cgatcggtgc gggcctcttc gctattacgc cagctggcga aggggggatg | 5640 |
| tgctgcaagg cgattaagtt gggtaacgcc agggttttcc cagtcacgac gttgtaaaac | 5700 |
| gacggccagt gaattcgagc tcggtacc | 5728 |

<210> SEQ ID NO 25
<211> LENGTH: 3043
<212> TYPE: RNA
<213> ORGANISM: Artificial Sequence
<220> FEATURE:
<223> OTHER INFORMATION: p23S-HDV 23S RNA

<400> SEQUENCE: 25

| | |
|---|---|
| gguuaagcga cuaagcguac acgguggaug cccuggcagu cagaggcgau gaaggacgug | 60 |
| cuaaucugcg auaagcgucg guaaggugau augaaccguu auaaccggcg auuuccgaau | 120 |
| ggggaaaccc agugguguuc gacacacuau cauuaacuga auccauaggu uaaugaggcg | 180 |
| aaccggggga acugaaacau cuaaguaccc cgaggaaaag aaaucaaccg agauucccc | 240 |
| aguagcggcg agcgaacggg gagcagccca gagccugaau cagugugugu guuaguggaa | 300 |
| gcgucuggaa aggcgcgcga uacagggugu cagccccgua cacaaaaaug cacaugcugu | 360 |
| gagcucgaug aguagggcgg gacacguggu auccugucug aauauggggg gaccauccuc | 420 |
| caaggcuaaa uacuccugac ugaccgauag ugaaccagua ccgugaggga aaggcgaaaa | 480 |
| gaaccccggc gagggggagug aaaaagaacc ugaaaccgug uacguacaag caguggggagc | 540 |
| acgcuuaggc gugugacugc guaccuuuug uauaaugggu cagcgacuua uaucuguag | 600 |
| caagguuaac cgaauagggg agccgaaggg aaaccgaguc uuaacugggc guuaaguugc | 660 |
| agggauauaga cccgaaaccc ggugaucuag ccaugggcag guugaagguu gguaacacu | 720 |
| aacuggagga ccgaaccgac uaauguugaa aaauuagcgg augacuugug gcuggggug | 780 |

-continued

```
aaaggccaau caaaccggga gauagcuggu ucuccccgaa agcuauuuag guagcgccuc    840
gugaauucau cuccggggu agagcacugu uucggcaagg gggucauccc gacuuaccaa    900
cccgaugcaa acugcgaaua ccggagaaug uuaucacggg agacacacgg cgggugcuaa    960
cguccgucgu gaagagggaa acaacccaga ccgccagcua agguccccaaa gucaugguua   1020
aguggggaaac gaugugggaa ggcccagaca gccaggaugu uggcuuagaa gcagccauca   1080
uuuaaagaaa gcguaauagc ucacggucg agucggccug cgcggaagau guaacggggc    1140
uaaaccaugc accgaagcug cggcagcgac gcuuaugcgu uguuggguag gggagcguuc    1200
uguaagccug cgaaggugug cuguaggca ugcuggaggu aucagaagug cgaaugcuga    1260
cauaaguaac gauaaagcgg gugaaaagcc cgcucgccgg aagaccaagg guuccugucc    1320
aacguuaauc ggggcagggu gagucgaccc cuaaggcgag gccgaaaggc guagucgaug    1380
ggaaacaggu uaauauuccu guacuuggug uuacugcgaa gggggggacgg agaaggcuau   1440
guuggccggg cgacgguugu cccgguuaa gcguguaggc ugguuuucca ggcaaauccg    1500
gaaaaucaag gcugaggcgu gaugacgagg cacuacggug cugaagcaac aaaugcccug    1560
cuuccaggaa aagccucuaa gcaucaggua acaucaaauc guaccccaaa ccgacacagg    1620
uggucaggua gagaauacca aggcgcuuga gagaacucgg gugaaggaac uaggcaaaau    1680
ggugccguaa cuucgggaga aggcacgcug auauguaggu gaggcccuc gcggaugag     1740
cugaaaucag ucgaagauac cagcuggcug caacuguuua uuaaaaacac agcacugugc    1800
aaacacgaaa guggacguau acggugugac gccugcccgg ugccggaagg uuaauugaug    1860
ggguuagcgc aagcgaagcu cuugaucgaa gccccgguaa acggcggccg uaacuauaac    1920
gguccuaagg uagcgaaauu ccuugucggg uaaguuccga ccugcacgaa uggcguaaug    1980
auggccaggc ugucuccacc cgagacucag ugaaauugaa cucgcuguga agaugcagug    2040
uacccgcggc aagacggaaa gaccccguga accuuuacua uagcuugaca cugaacauug    2100
agccuugaug uguaggauag gugggaggcu uugaagugug gacgccaguc ugcauggagc    2160
cgaccuugaa auaccacccu uuaauguuug auguucuaac guugacccgu aauccggguu    2220
gcggacagug ucugguggu aguuugacug gggcggucuc cuccaaaga guaacggagg     2280
agcacgaagg uuggcuaauc cuggucggac aucaggaggu uagugcaaug gcauaagcca    2340
gcuugacugc gagcgugacg gcgcgagcag gugcgaaagc aggucauagu gauccggugg    2400
uucugaaugg aagggccauc gcucaacgga uaaaagguac uccggggaua acaggcugau    2460
accgccaag aguucauauc gacgcggug uuuggcaccu cgaugucggc ucaucacauc     2520
cuggggcuga aguaggucccc aaggguaugg cuguucgcca uuuaaagugg uacgcgagcu    2580
ggguuuagaa cgucgugaga caguuccguc ccuaucugcc guggcgcug gagaaacugag    2640
gggggcugcu ccuaguacga gggaccggga guggacgcau cacuggugu cggguuguca     2700
ugccaauggc acugcccggu agcuaaaugc ggaagagaua agugcugaaa gcaucuaagc    2760
acgaaacuug ccccgagaug aguucucccu gacccuuuaa ggguccugaa ggaacguuga    2820
agacgacgac guugauaggc cggugugua agcgcagcga ugcguugagc uaaccgguac    2880
uaaugaaccg ugaggcuuaa ccuuaagugg ccggcauggu cccagccucc ucgcuggcgc    2940
cggcugggca acauuccgag gggaccgucc ccucgguaau ggcgaauggg acccacuagc    3000
auaaccccuu ggggccucua aacgggucuu gaggggguuuu uug                    3043
```

<210> SEQ ID NO 26

<211> LENGTH: 7311
<212> TYPE: DNA
<213> ORGANISM: Artificial Sequence
<220> FEATURE:
<223> OTHER INFORMATION: pT7rrnB DNA

<400> SEQUENCE: 26

| | | | | | |
|---|---|---|---|---|---|
| ttaatacgac | tcactatagg | ggccgctgag | aaaaagcgaa | gcggcactgc | tctttaacaa | 60 |
| tttatcagac | aatctgtgtg | ggcactcgaa | gatacggatt | cttaacgtcg | caagacgaaa | 120 |
| aatgaatacc | aagtctcaag | agtgaacacg | taattcatta | cgaagtttaa | ttctttgagc | 180 |
| gtcaaacttt | taaattgaag | agtttgatca | tggctcagat | tgaacgctgg | cggcaggcct | 240 |
| aacacatgca | agtcgaacgg | taacaggaag | aagcttgctt | ctttgctgac | gagtggcgga | 300 |
| cgggtgagta | atgtctggga | aactgcctga | tggaggggga | taactactgg | aaacggtagc | 360 |
| taataccgca | taacgtcgca | agaccaaaga | gggggacctt | cgggcctctt | gccatcggat | 420 |
| gtgcccagat | gggattagct | agtaggtggg | gtaacggctc | acctaggcga | cgatccctag | 480 |
| ctggtctgag | aggatgacca | gccacactgg | aactgagaca | cggtccagac | tcctacggga | 540 |
| ggcagcagtg | gggaatattg | cacaatgggc | gcaagcctga | tgcagccatg | ccgcgtgtat | 600 |
| gaagaaggcc | ttcgggttgt | aaagtacttt | cagcggggag | gaagggagta | agttaatac | 660 |
| ctttgctcat | tgacgttacc | cgcagaagaa | gcaccggcta | actccgtgcc | agcagccgcg | 720 |
| gtaatacgga | gggtgcaagc | gttaatcgga | attactgggc | gtaaagcgca | cgcaggcggt | 780 |
| ttgttaagtc | agatgtgaaa | tccccgggct | caacctggga | actgcatctg | atactggcaa | 840 |
| gcttgagtct | cgtagagggg | ggtagaattc | caggtgtagc | ggtgaaatgc | gtagagatct | 900 |
| ggaggaatac | cggtggcgaa | ggcggcccc | tggacgaaga | ctgacgctca | ggtgcgaaag | 960 |
| cgtggggagc | aaacaggatt | agataccctg | gtagtccacg | ccgtaaacga | tgtcgacttg | 1020 |
| gaggttgtgc | ccttgaggcg | tggcttccgg | agctaacgcg | ttaagtcgac | cgcctgggga | 1080 |
| gtacggccgc | aaggttaaaa | ctcaaatgaa | ttgacggggg | cccgcacaag | cggtggagca | 1140 |
| tgtggtttaa | ttcgatgcaa | cgcgaagaac | cttacctggt | cttgacatcc | acggaagttt | 1200 |
| tcagagatga | gaatgtgcct | tcgggaaccg | tgagacaggt | gctgcatggc | tgtcgtcagc | 1260 |
| tcgtgttgtg | aaatgttggg | ttaagtcccg | caacgagcgc | aacccttatc | ctttgttgcc | 1320 |
| agcggtccgg | ccgggaactc | aaaggagact | gccagtgata | aactggagga | aggtggggat | 1380 |
| gacgtcaagt | catcatggcc | cttacgacca | gggctacaca | cgtgctacaa | tggcgcatac | 1440 |
| aaagagaagc | gacctcgcga | gagcaagcgg | acctcataaa | gtgcgtcgta | gtccggattg | 1500 |
| gagtctgcaa | ctcgactcca | tgaagtcgga | atcgctagta | atcgtggatc | agaatgccac | 1560 |
| ggtgaatacg | ttcccgggcc | ttgtacacac | cgcccgtcac | accatgggag | tgggttgcaa | 1620 |
| aagaagtagg | tagcttaacc | ttcgggaggg | cgcttaccac | tttgtgattc | atgactgggg | 1680 |
| tgaagtcgta | acaaggtaac | cgtagggaa | cctgcggttg | gatcacctcc | ttaccttaaa | 1740 |
| gaagcgtact | ttgtagtgct | cacacagatt | gtctgataga | aagtgaaaag | caaggcgttt | 1800 |
| acgcgttggg | agtgaggctg | aagagaataa | ggccgttcgc | tttctattaa | tgaaagctca | 1860 |
| ccctacacga | aaatatacg | caacgcgtga | taagcaattt | tcgtgtcccc | ttcgtctaga | 1920 |
| ggcccaggac | accgcccttt | cacggcggta | acaggggttc | gaatccccta | ggggacgcca | 1980 |
| cttgctggtt | tgtgagtgaa | agtcgccgac | cttaatatct | caaaactcat | cttcgggtga | 2040 |
| tgtttgagat | atttgctctt | taaaaatctg | gatcaagctg | aaaattgaaa | cactgaacaa | 2100 |
| cgagagttgt | tcgtgagtct | ctcaaatttt | cgcaacacga | tgatgaatcg | aaagaaacat | 2160 |

```
cttcgggttg tgaggttaag cgactaagcg tacacggtgg atgccctggc agtcagaggc   2220
gatgaaggac gtgctaatct gcgataagcg tcggtaaggt gatatgaacc gttataaccg   2280
gcgatttccg aatggggaaa cccagtgtgt ttcgacacac tatcattaac tgaatccata   2340
ggttaatgag gcgaaccggg ggaactgaaa catctaagta ccccgaggaa aagaaatcaa   2400
ccgagattcc cccagtagcg gcgagcgaac ggggagcagc ccagagcctg aatcagtgtg   2460
tgtgttagtg gaagcgtctg gaaaggcgcg cgatacaggg tgacagcccc gtacacaaaa   2520
atgcacatgc tgtgagctcg atgagtaggg cgggacacgt ggtatcctgt ctgaatatgg   2580
ggggaccatc ctccaaggct aaatactcct gactgaccga tagtgaacca gtaccgtgag   2640
ggaaaggcga aagaaccccg gcgaggggga gtgaaaaaga acctgaaacc gtgtacgtac   2700
aagcagtggg agcacgctta ggcgtgtgac tgcgtacctt ttgtataatg ggtcagcgac   2760
ttatattctg tagcaaggtt aaccgaatag gggagccgaa gggaaaccga gtcttaactg   2820
ggcgttaagt tgcagggtat agacccgaaa cccggtgatc tagccatggg caggttgaag   2880
gttgggtaac actaactgga ggaccgaacc gactaatgtt gaaaaattag cggatgactt   2940
gtggctgggg gtgaaaggcc aatcaaaccg ggagatagct ggttctcccc gaaagctatt   3000
taggtagcgc ctcgtgaatt catctccggg ggtagagcac tgtttcggca aggggggtcat   3060 cccgacttac caacccgatg caaactgcga ataccggaga atgttatcac gggagacaca   3120
cggcgggtgc taacgtccgt cgtgaagagg gaaacaaccc agaccgccag ctaaggtccc   3180
aaagtcatgg ttaagtggga acgatgtgg gaaggcccag acagccagga tgttggctta   3240
gaagcagcca tcatttaaag aaagcgtaat agctcactgg tcgagtcggc ctgcgcggaa   3300
gatgtaacgg ggctaaacca tgcaccgaag ctgcggcagc gacgcttatg cgttgttggg   3360
taggggagcg ttctgtaagc ctgcgaaggt gtgctgtgag gcatgctgga ggtatcagaa   3420
gtgcgaatgc tgacataagt aacgataaag cgggtgaaaa gcccgctcgc cggaagacca   3480
agggttcctg tccaacgtta atcggggcag ggtgagtcga cccctaaggc gaggccgaaa   3540
ggcgtagtcg atgggaaaca ggttaatatt cctgtacttg gtgttactgc gaagggggga   3600
cggagaaggc tatgttggcc gggcgacggt tgtcccggtt taagcgtgta ggctggtttt   3660
ccaggcaaat ccggaaaatc aaggctgagg cgtgatgacg aggcactacg gtgctgaagc   3720
aacaaatgcc ctgcttccag gaaaagcctc taagcatcag gtaacatcaa atcgtacccc   3780
aaaccgacac aggtggtcag gtagagaata ccaaggcgct tgagagaact cgggtgaagg   3840
aactaggcaa aatggtgccg taacttcggg agaaggcacg ctgatatgta ggtgaggtcc   3900
ctcgcggatg gagctgaaat cagtcgaaga taccagctgg ctgcaactgt ttattaaaaa   3960
cacagcactg tgcaaacacg aaagtggacg tatacggtgt gacgcctgcc cggtgccgga   4020
aggttaattg atggggttag cgcaagcgaa gctcttgatc gaagccccgg taaacggcgg   4080
ccgtaactat aacggtccta aggtagcgaa attccttgtc gggtaagttc cgacctgcac   4140
gaatggcgta atgatggcca ggctgtctcc acccgagact cagtgaaatt gaactcgctg   4200
tgaagatgca gtgtacccgc ggcaagacgg aaagaccccg tgaaccttta ctatagcttg   4260
acactgaaca ttgagccttg atgtgtagga taggtgggag gctttgaagt gtggacgcca   4320
gtctgcatgg agccgacctt gaaataccac cctttaatgt ttgatgttct aacgttgacc   4380
cgtaatccgg gttgcggaca gtgtctggtg ggtagtttga ctggggcggt ctcctcctaa   4440
agagtaacgg aggagcacga aggttggcta atcctggtcg gacatcagga ggttagtgca   4500
```

```
atggcataag ccagcttgac tgcgagcgtg acggcgcgag caggtgcgaa agcaggtcat    4560
agtgatccgg tggttctgaa tggaagggcc atcgctcaac ggataaaagg tactccgggg    4620
ataacaggct gataccgccc aagagttcat atcgacggcg gtgtttggca cctcgatgtc    4680
ggctcatcac atcctggggc tgaagtaggt cccaagggta tggctgttcg ccatttaaag    4740
tggtacgcga gctgggttta aacgtcgtg agacagttcg gtccctatct gccgtgggcg     4800
ctggagaact gagggggggct gctcctagta cgagaggacc ggagtggacg catcactggt    4860
gttcgggttg tcatgccaat ggcactgccc ggtagctaaa tgcggaagag ataagtgctg    4920
aaagcatcta agcacgaaac ttgccccgag atgagttctc cctgacccct taagggtcct    4980
gaaggaacgt tgaagacgac gacgttgata ggccgggtgt gtaagcgcag cgatgcgttg    5040
agctaaccgg tactaatgaa ccgtgaggct taaccttaca acgccgaagc tgttttggcg    5100
gatgagagaa gattttcagc ctgatacaga ttaaatcaga acgcagaagc ggtctgataa    5160
aacagaattt gcctgcggc agtagcgcgg tggtcccacc tgaccccatg ccgaactcag     5220
aagtgaaacg ccgtagcgcc gatggtagtg tggggtctcc ccatgcgaga gtagggaact    5280
gccaggcatc aaataaaacg aaaggctcag tcgaaagact gggcctttcg ttttatctgt    5340
tgtttgtcgg tgaacgctct cctgagtagg acaaatccgc cgggagcgga tttgaacgtt    5400
gcgaagcaac ggcccggagg gtggcgggca ggacgcccgc cataaactgc caggcatcaa    5460
attaagcaga aggccatcct gacgatggc cttttgcgt ttctacaaac tcttcctgtc       5520
gtcatatcta caagccggcg cgccaaattg acaattactc atccggctcg aataatgtgt    5580
ggaacttaaa cacacacagg aggaaaacat atgtctatcc agcacttccg tgttgcgctg    5640
atcccgttct tcgcggcgtt ctgcctgccg gttttcgcgc acccggaaac cctggttaaa    5700
gttaaagacg cggaagacca gctgggtgcg cgtgttggtt acatcgaact ggacctgaac    5760
tctggtaaaa tcctggaatc tttccgtccg gaagaacgtt cccgatgat gtctaccttc     5820 aaagttctgc tgtgcggtgc ggttctgtct cgtgttgacg cgggtcagga acagctgggt    5880
cgtcgtatcc actactctca gaacgacctg gttgaatact ctcccgttac cgaaaaacac    5940
ctgaccgacg gtatgaccgt tcgtgaactg tgctctgcgg cgatcaccat gtctgacaac    6000
accgcagcga acctgctgct gaccaccatc ggtggtccga agaactgac cgcgttcctg    6060 cacaacatgg cgaccacgt tacccgtctg accgttggg aaccggaact gaacgaagcg       6120
atcccgaacg acgaacgtga caccaccatg cctgcggcga tggcgaccac cctgcgtaaa    6180
ctgctgaccg tgaactgct gaccctggca tctcgtcagc agctgatcga ctggatggaa     6240
gcggacaaag ttgcgggtcc gctgctgcgt tctgcgctgc ctgcgggttg gttcatcgcg    6300
gacaaatctg gtgcgggtga acgtggttct cgtggtatca tcgcggcgct gggtccggac    6360
ggtaaaccgt ctcgtatcgt tgttatctac accaccggtt ctcaggcgac catggacgaa    6420
cgtaaccgtc agatcgcgga aatcggtgcg tctctgatta acactggta aactcactcc      6480 tagcccgcct aataagcggg cttttttct gcagaccaag tttactcata tactttag       6540 attgatttaa aacttcattt ttaatttaaa aggatctagg tgaagatcct ttttgataat    6600
ctcatgacca aaatccctta acgtgagttt cgttccact gagcgtcaga ccccgtagaa      6660
aagatcaaag gatcttcttg agatcctttt tttctgcgcg taatctgctg cttgcaaaca    6720
aaaaaaccac cgctaccagc ggtggtttgt ttgccggatc aagagctacc aactcttttt    6780
ccgaaggtaa ctggcttcag cagagcgcag ataccaaata ctgtccttct agtgtagccg    6840
tagttaggcc accacttcaa gaactctgta gcaccgccta catacctcgc tctgctaatc    6900
```

| | | | |
|---|---|---|---|
| ctgttaccag | tggctgctgc | cagtggcgat aagtcgtgtc ttaccgggtt ggactcaaga | 6960 |
| cgatagttac | cggataaggc | gcagcggtcg ggctgaacgg ggggttcgtg cacacagccc | 7020 |
| agcttggagc | gaacgaccta | caccgaactg agatacctac agcgtgagct atgagaaagc | 7080 |
| gccacgcttc | ccgaagggag | aaaggcggac aggtatccgg taagcggcag ggtcggaaca | 7140 |
| ggagagcgca | cgagggagct | tccaggggga acgcctggt atctttatag tcctgtcggg | 7200 |
| tttcgccacc | tctgacttga | gcgtcgattt ttgtgatgct cgtcaggggg gcggagccta | 7260 |
| tggaaaaacg | ccagcaacgc | ggccttttta cggttcctgg ccttttgctg g | 7311 |

<210> SEQ ID NO 27
<211> LENGTH: 5478
<212> TYPE: RNA
<213> ORGANISM: Artificial Sequence
<220> FEATURE:
<223> OTHER INFORMATION: pT7rrnB RNA

<400> SEQUENCE: 27

| | | | |
|---|---|---|---|
| gggccgcuga | gaaaaagcga | agcggcacug cucuuuaaca auuuaucaga caaucugugu | 60 |
| gggcacucga | agauacggau | ucuuaacguc gcaagacgaa aaaugaauac caagucucaa | 120 |
| gagugaacac | guaauucauu | acgaaguuua auucuuugag cgucaaacuu uuaaauugaa | 180 |
| gaguuugauc | auggcucaga | uugaacgcug gcggcaggcc uaacacaugc aagucgaacg | 240 |
| guaacaggaa | gaagcuugcu | ucuuugcuga cgaguggcgg acggugagu aaugucuggg | 300 |
| aaacugccug | auggaggggg | auaacuacug gaaacgguag cuaauaccgc auaacgucgc | 360 |
| aagaccaaag | aggggggaccu | ucgggccucu ugccaucgga ugugcccaga ugggauuagc | 420 |
| uaguaggugg | gguaacggcu | caccuaggcg acgaucccua gcugucuga gaggaugacc | 480 |
| agccacacug | gaacugagac | acgguccaga cuccuacggg aggcagcagu ggggaauauu | 540 |
| gcacaauggg | cgcaagccug | augcagccau gccgcguguua ugaagaaggc cuucggguug | 600 |
| uaaaguacuu | ucagcgggga | ggaagggagu aaaguuaaua ccuuugcuca uugacguuac | 660 |
| ccgcagaaga | agcaccggcu | aacuccgugc cagcagccgc gguaauacgg agggugcaag | 720 |
| cguuaaucgg | aauuacuggg | cguaaagcgc acgcaggcgg uuuguuaagu cagaugugaa | 780 |
| auccccgggc | ucaaccuggg | aacugcaucu gauacuggca agcuugaguc ucguagaggg | 840 |
| gggauagaauu | ccagguguag | cggugaaaug cguagagauc uggaggaaua ccgguggcga | 900 |
| aggcggcccc | cuggacgaag | acugacgcuc aggugcgaaa gcgugggag caaacaggau | 960 |
| uagauacccu | gguaguccac | gccguaaacg augucgacuu ggagguugug cccuugaggc | 1020 |
| guggcuuccg | gagcuaacgc | guuaagucga ccgccugggg aguacggccg caagguuaaa | 1080 |
| acucaaauga | auugacgggg | gcccgcacaa gcgguggagc augugguuua auucgaugca | 1140 |
| acgcgaagaa | ccuuaccugg | ucuugacauc cacggaaguu ucagagaug agaaugugcc | 1200 |
| uucgggaacc | gugagacagg | ugcugcaugg cugucgucag cucguguguu gaaaugauugg | 1260 |
| guuaaguccc | gcaacgagcg | caacccuuau ccuuuguugc cagcgguccg gccgggaacu | 1320 |
| caaaggagac | ugccagugau | aaacuggagg aaguggggga ugacgucaag ucaucauggc | 1380 |
| ccuuacgacc | agggcuacac | acgugcuaca augggcgcaua caaagagaag cgaccucgcg | 1440 |
| agagcaagcg | gaccucauaa | agugcgucgu aguccggauu ggagucugca acucgacucc | 1500 |
| augaagucgg | aaucgcuagu | aaucguggau cagaaugcca cggugaauac guucccgggc | 1560 |
| cuuguacaca | ccgcccguca | caccauggga guggguugca aaagaaguag guagcuuaac | 1620 |

```
cuucgggagg gcgcuuacca cuuugugauu caugacuggg gugaagucgu aacaagguaa   1680
ccguagggga accugcgguu ggaucaccuc cuuaccuuaa agaagcguac uuuguagugc   1740
ucacacagau ugucugauag aaagugaaaa gcaaggcguu uacgcguugg gagugaggcu   1800
gaagagaaua aggccguucg cuuucuauua augaaagcuc acccuacacg aaaauaucac   1860
gcaacgcgug auaagcaauu uucgugnccc cuucgucuag aggcccagga caccgcccuu   1920
ucacggcggu aacaggdgguu cgaaucccc aggggacgcc acuugcuggu uugugaguga   1980
aagucgccga ccuuaauauc ucaaaacuca ucuucgggug auguuugaga uauuugcucu   2040
uuaaaaaucu ggaucaagcu gaaaauugaa acacugaaca acgagaguug uucgugaguc   2100
ucucaaauuu ucgcaacacg augaugaauc gaaagaaaca cuucggguu gugagguuaa   2160 gcgacuaagc guacacgug gaugcccugg cagucagagg cgaugaagga cgugcuaauc   2220
ugcgauaagc gucgguaagg ugauaugaac cguuauaacc ggcgauuucc gaaugggaa   2280 acccagugug uuucgacaca cuaucauuaa cugaauccau agguuaauga ggcgaaccgg   2340
gggaacugaa acaucuaagu accccgagga aaagaaauca accgagauuc ccccaguagc   2400
ggcgagcgaa cggggagcag cccagagccu gaaucagugu guguguuagu ggaagcgucu   2460
ggaaaggcgc gcgauacagg gugacagccc cguacacaaa aaugcacaug cuguga gcuc   2520 gaugaguagg gcgggacacg ugguauccug ucugaauaug gggggaccau ccuccaaggc   2580
uaaauacucc ugacugaccg auagugaacc aguaccguga gggaaaggcg aaaagaaccc   2640
cggcgagggg agugaaaaag aaccugaaac cgugacgua caagcagugg gagcacgcuu   2700
aggcguguga cugcguaccu uuuguauaau ggucagcga cuuauauucu guagcaaggu   2760
uaaccgaaua ggggagccga agggaaaccg agucuuaacu ggcgguuaag uugcagggua   2820 uagcccgaa acccgugau cuagccaugg gcagguugaa gguugggua acuaacugg   2880 aggaccgaac cgacuaaugu gaaaaauua gcggaugacu uguggcuggg ggugaaaggc   2940
caaucaaacc gggagauagc ugguucuccc cgaaagcuau uuaggguagcg ccucgugaau   3000 ucaucuccgg ggguagagca cuguucggc aagggguca ucccgacuua ccaacccgau   3060
gcaaacugcg aauaccggag aauguuauca cgggagacac acggcgggug cuaacguccg   3120
ucgugaagag ggaaacaacc cagaccgcca gcuaaggucc caaagucaug guuaagugggg   3180 aaacgaugug ggaaggccca gacagccagg auguugggcuu agaagcagcc aucauuaaa   3240 gaaagcguaa uagcucacug gucgagucgg ccugcgcgga agauguaacg ggggcuaaacc   3300 augcaccgaa gcugcggcag cgacgcuuau gcguuguug guagggggagc guucuguaag   3360 ccugcgaagg ugugcuguga ggcaugcugg agguaucaga agugcgaaug cugacauaag   3420
uaacgauaaa gcgggugaaa agcccgcucg ccggaagacc aaggguuccu guccaacguu   3480
aaucggggca gggugagucg accccuaagg cgaggccgaa aggcguaguc gaugggaaac   3540
agguuaauau uccuguacuu gguguuacug cgaggggggg acgagaaggg cuauguuggc   3600
cgggcgacgg uugucccggu uuaagcgugu aggcugguuu ccaggcaaa uccggaaaau   3660 caaggcugag gcgugaugac gaggcacuac ggugcugaag caacaaaugc ccugcuucca   3720
ggaaaagccu cuaagcauca gguaacauca aaucguaccc caaaccgaca cagguguca   3780 gguagagaau accaaggcgc uugagagaac ucggugaag gaacuaggca aaauggugcc   3840
guaacuucgg gagaaggcac gcugauaugu aggugaggu ccucgcggau ggagcugaaa   3900
ucagucgaag auaccagcug gcugcaacug uuuauuaaaa acacagcacu gugcaaacac   3960
gaaaguggac guauacgggu ugacgccugc ccggugccgg aagguuaauu gauggggu ua   4020
```

```
gcgcaagcga agcucuugau cgaagccccg guaaacggcg ccguaacua uaacgguccu    4080
aaggguagcga aauccuugu cggguaaguu ccgaccugca cgaauggcgu aaugauggcc    4140
aggcugucuc cacccgagac ucagugaaau ugaacucgcu gugaagaugc aguguacccg    4200
cggcaagacg gaaagacccc gugaaccuuu acuauagcuu gacacugaac auugagccuu    4260
gaugaguagg auaggugga ggcuuugaag uggacgcc agucugcaug gagccgaccu    4320
ugaaauacca cccuuuaaug uuugauguuc uaacguugac ccguaauccg gguugcggac    4380
agugucuggu ggguaguuug acuggggcgg ucuccuccua aagaguaacg gaggagcacg    4440
aagguuggcu aauccuggu ggacaucagg agguuagugc aauggcauaa gccagcuuga    4500
cugcgagcgu gacggcgcga gcaggugcga aagcaggguca uagugauccg gugguucuga    4560
auggaagggc caucgcucaa cggauaaaag guacuccggg gauaacaggc ugauaccgcc    4620
caagaguuca uaucgacggc ggguguuggc accucgaugu cggcucauca cauccugggg    4680
cugaaguagg ucccaagggu auggcuguuc gccauuuaaa gugguacgcg agcuggguuu    4740
agaacgucgu gagacaguuc ggucccuauc ugccguggc gcuggagaac ugagggggc    4800
ugcuccuagu acgagaggac cggagugggac gcaucacugg uguucggguu gucaugccaa    4860
uggcacugcc cgguagcuaa augcggaaga gauaagugcu gaaagcaucu aagcacgaaa    4920
cuugccccga gaugauucu cccugacccu uuaagggucc ugaaggaacg uugaagacga    4980
cgacguugau aggccgggug uguaagcgca gcgaugcguu gagcuaaccg guacuaauga    5040
accgugaggc uuaaccuuac aacgccgaag cuguuggc ggaugagaga agauuucag    5100
ccugauacag auuaaaucag aacgcagaag cggucugaua aaacagaauu ugccggcgg    5160
caguagcgcg guggucccac cugaccccau gccgaacuca aagugaaac gccguagcgc    5220
cgauggauagu guggggucuc cccaugcgag aguagggaac ugccaggcau caaauaaaac    5280
gaaaggcuca gucgaaagac uggccuuuc guuuuaucug uuguuugucg gugaacgcuc    5340
uccugaguag gacaaauccg ccgggagcgg auuugaacgu ugcgaagcaa cggcccggag    5400
gguggcgggc aggacgcccg ccauaaacug ccaggcauca aauuaagcag aaggccaucc    5460
ugacggaugg ccuuuuug                                                  5478
```

<210> SEQ ID NO 28
<211> LENGTH: 7311
<212> TYPE: DNA
<213> ORGANISM: Artificial Sequence
<220> FEATURE:
<223> OTHER INFORMATION: pT7rrnB-CR DNA

<400> SEQUENCE: 28

```
ttaatacgac tcactatagg ggccgctgag aaaaagcgaa gcggcactgc tctttaacaa      60
tttatcagac aatctgtgtg ggcactcgaa gatacggatt cttaacgtcg caagacgaaa     120
aatgaatacc aagtctcaag agtgaacacg taattcatta cgaagtttaa ttctttgagc     180
gtcaaacttt taaattgaag agtttgatca tggctcagat tgaacgctgg cggcaggcct     240
aacacatgca agtcgaacgg taacaggaag aagcttgctt ctttgctgac gagtggcgga     300
cgggtgagta atgtctggga aactgcctga tggaggggga taactactgg aaacggtagc     360
taataccgca taacgtcgca agaccaaaga ggggaccctt cgggcctctt gccatcggat     420
gtgcccagat gggattagct agtaggtggg gtaacggctc acctaggcga cgatccctag     480
ctggtctgag aggatgacca gccacactgg aactgagaca cggtccagac tcctacggga     540
```

```
ggcagcagtg gggaatattg cacaatgggc gcaagcctga tgcagccatg ccgcgtgtat    600
gaagaaggcc ttcgggttgt aaagtacttt cagcggggag gaagggagta aagttaatac    660
ctttgctcat tgacgttacc cgcagaagaa gcaccggcta actccgtgcc agcagccgcg    720
gtaatacgga gggtgcaagc gttaatcgga attactgggc gtaaagcgca cgcaggcggt    780
ttgttaagtc agatgtgaaa tccccgggct caacctggga actgcatctg atactggcaa    840
gcttgagtct cgtagagggg ggtagaattc caggtgtagc ggtgaaatgc gtagagatct    900
ggaggaatac cggtggcgaa ggcggcccc tggacgaaga ctgacgctca ggtgcgaaag    960
cgtggggagc aaacaggatt agatacctg gtagtccacg ccgtaaacga tgtcgacttg   1020
gaggttgtgc ccttgaggcg tggcttccgg agctaacgcg ttaagtcgac cgcctgggga   1080
gtacggccgc aaggttaaaa ctcaaatgaa ttgacggggg cccgcacaag cggtggagca   1140
tgtggtttaa ttcgatgcaa cgcgaagaac cttacctggt cttgacatcc acggaagttt   1200
tcagagatga gaatgtgcct tcgggaaccg tgagacaggt gctgcatggc tgtcgtcagc   1260
tcgtgttgtg aaatgttggg ttaagtcccg caacgagcgc aacccttatc ctttgttgcc   1320
agcggtccgg ccgggaactc aaaggagact gccagtgata aactggagga aggtggggat   1380
gacgtcaagt catcatggcc cttacgacca gggctacaca cgtgctacaa tggcgcatac   1440
aaagagaagc gacctcgcga gagcaagcgg acctcataaa gtgcgtcgta gtccggattg   1500
gagtctgcaa ctcgactcca tgaagtcgga atcgctagta atcgtggatc agaatgccac   1560
ggtgaatacg ttcccgggcc ttgtacacac cgcccgtcac accatgggag tgggttgcaa   1620
aagaagtagg tagcttaacc ttcgggaggg cgcttaccac tttgtgattc atgactgggg   1680
tgaagtcgta acaaggtaac cgtagggaa cctgcggttg gatcacctcc ttaccttaaa   1740
gaagcgtact ttgtagtgct cacacagatt gtctgataga aagtgaaaag caaggcgttt   1800
acgcgttggg agtgaggctg aagagaataa ggccgttcgc tttctattaa tgaaagctca   1860
ccctacacga aaatatcacg caacgcgtga taagcaattt tcgtgtcccc ttcgtctaga   1920
ggcccaggac accgcccttt cacggcggta acaggggttc gaatcccta ggggacgcca   1980
cttgctggtt tgtgagtgaa agtcgccgac cttaatatct caaaactcat cttcgggtga   2040
tgtttgagat atttgctctt taaaaatctg gatcaagctg aaaattgaaa cactgaacaa   2100
cgagagttgt tcgtgagtct ctcaaatttt cgcaacacga tgatgaatcg aaagaaacat   2160
cttcgggttg tgaggttaag cgactaagcg tacacggtgg atgccctggc agtcagaggc   2220
gatgaaggac gtgctaatct gcgataagcg tcggtaaggt gatatgaacc gttataaccg   2280
gcgatttccg aatggggaaa cccagtgtgt ttcgacacac tatcattaac tgaatccata   2340
ggttaatgag gcgaaccggg ggaactgaaa catctaagta ccccgaggaa aagaaatcaa   2400
ccgagattcc cccagtagcg gcgagcgaac ggggagcagc ccagagcctg aatcagtgtg   2460
tgtgttagtg gaagcgtctg gaaaggcgcg cgatacaggg tgacagcccc gtacacaaaa   2520
atgcacatgc tgtgagctcg atgagtaggg cgggacacgt ggtatcctgt ctgaatatgg   2580
ggggaccatc ctccaaggct aaatactcct gactgaccga tagtgaacca gtaccgtgag   2640
ggaaaggcga aaagaacccc ggcgagggga gtgaaaaaga acctgaaacc gtgtacgtac   2700
aagcagtggg agcacgctta ggcgtgtgac tgcgtacctt ttgtataatg ggtcagcgac   2760
ttatattctg tagcaaggtt aaccgaatag gggagccgaa gggaaaccga gtcttaactg   2820
ggcgttaagt tgcagggtat agacccgaaa cccggtgatc tagccatggg caggttgaag   2880
gttgggtaac actaactgga ggaccgaacc gactaatgtt gaaaaattag cggatgactt   2940
```

```
gtggctgggg gtgaaaggcc aatcaaaccg ggagatagct ggttctcccc gaaagctatt    3000
taggtagcgc ctcgtgaatt catctccggg ggtagagcac tgtttcggca aggggggtcat   3060 cccgacttac caacccgatg caaactgcga ataccggaga atgttatcac gggagacaca    3120
cggcgggtgc taacgtccgt cgtgaagagg gaaacaaccc agaccgccag ctaaggtccc    3180
aaagtcatgg ttaagtggga aacgatgtgg gaaggcccag acagccagga tgttggctta    3240
gaagcagcca tcatttaaag aaagcgtaat agctcactgg tcgagtcggc ctgcgcggaa    3300
gatgtaacgg ggctaaacca tgcaccgaag ctgcggcagc gacgcttatg cgttgttggg    3360
taggggagcg ttctgtaagc ctgcgaaggt gtgctgtgag gcatgctgga ggtatcagaa    3420
gtgcgaatgc tgacataagt aacgataaag cgggtgaaaa gcccgctcgc cggaagacca    3480
agggttcctg tccaacgtta atcggggcag ggtgagtcga cccctaaggc gaggccgaaa    3540
ggcgtagtcg atgggaaaca ggttaatatt cctgtacttg gtgttactgc gaaggggggga   3600 cggagaaggc tatgttggcc gggcgacggt tgtcccggtt taagcgtgta ggctggtttt    3660
ccaggcaaat ccggaaaatc aaggctgagg cgtgatgacg aggcactacg gtgctgaagc    3720
aacaaatgcc ctgcttccag gaaaagcctc taagcatcag gtaacatcaa atcgtacccc    3780
aaaccgacac aggtggtcag gtagagaata ccaaggcgct tgagagaact cgggtgaagg    3840
aactaggcaa aatggtgccg taacttcggg agaaggcacg ctgatatgta ggtgaggtcc    3900
ctcgcggatg gagctgaaat cagtcgaaga taccagctgg ctgcaactgt ttattaaaaa    3960
cacagcactg tgcaaacacg aaagtggacg tatacggtgt gacgcctgcc cggtgccgga    4020
aggttaattg atggggttag cgcaagcgaa gctcttgatc gaagccccgg taaacggcgg    4080
ccgtaactat aacggtccta aggtagcgaa attccttgtc gggtaagttc cgacctgcac    4140
gaatggcgta atgatggcca ggctgtctcc acccgagact cagtgaaatt gaactcgctg    4200
tgaagatgca gtgtacccgc ggcaagacgg taagacccg tgaacccttta ctatagcttg    4260 acactgaaca ttgagccttg atgtgtagga taggtgggag gctttgaagt gtggacgcca    4320
gtctgcatgg agccgacctt gaaataccac cctttaatgt ttgatgttct aacgttgacc    4380
cgtaatccgg gttgcggaca gtgtctggtg ggtagtttga ctggggcggt ctcctcctaa    4440
agagtaacgg aggagcacga aggttggcta atcctggtcg gacatcagga ggttagtgca    4500
atggcataag ccagcttgac tgcgagcgtg acggcgcgag caggtgcgaa agcaggtcat    4560
agtgatccgg tggttctgaa tggaagggcc atcgctcaac ggataaaagg tactccgggg    4620
ataacaggct gataccgccc aagagttcat atcgacggcg gtgtttggca cctcgatgtc    4680
ggctcatcac atcctggggc tgaagtaggt cccaagggta tggctgttcg ccatttaaag    4740
tggtacgcga gctggttta aacgtcgtg agacagttcg gtccctatct gccgtgggcg    4800
ctggagaact gagggggct gctcctagta cgagaggacc ggagtggacg catcactggt    4860
gttcgggttg tcatgccaat ggcactgccc ggtagctaaa tgcggaagag ataagtgctg    4920
aaagcatcta agcacgaaac ttgccccgag atgagttctc cctgacccttt aagggtcct    4980 gaaggaacgt tgaagacgac gacgttgata ggccgggtgt gtaagcgcag cgatgcgttg    5040
agctaaccgg tactaatgaa ccgtgaggct taaccttaca acgccgaagc tgttttggcg    5100
gatgagagaa gattttcagc ctgatacaga ttaaatcaga acgcagaagc ggtctgataa    5160
aacagaattt gcctgcggc agtagcgcgg tggtcccacc tgaccccatg ccgaactcag    5220
aagtgaaacg ccgtagcgcc gatggtagtg tggggtctcc ccatgcgaga gtagggaact    5280
```

```
gccaggcatc aaataaaacg aaaggctcag tcgaaagact gggcctttcg tttatctgt    5340 tgtttgtcgg tgaacgctct cctgagtagg acaaatccgc cgggagcgga tttgaacgtt    5400
gcgaagcaac ggcccggagg gtggcgggca ggacgcccgc cataaactgc caggcatcaa    5460
attaagcaga aggccatcct gacgatggc cttttgcgt ttctacaaac tcttcctgtc      5520
gtcatatcta aagccggcg cgccaaattg acaattactc atccggctcg aataatgtgt    5580
ggaacttaaa cacacacagg aggaaaacat atgtctatcc agcacttccg tgttgcgctg    5640
atcccgttct tcgcggcgtt ctgcctgccg gttttcgcgc acccggaaac cctggttaaa    5700
gttaaagacg cggaagacca gctgggtgcg cgtgttggtt acatcgaact ggacctgaac    5760
tctggtaaaa tcctggaatc tttccgtccg gaagaacgtt tcccgatgat gtctaccttc    5820
aaagttctgc tgtgcggtgc ggttctgtct cgtgttgacg cgggtcagga acagctgggt    5880
cgtcgtatcc actactctca gaacgacctg gttgaatact ctcccgttac cgaaaaacac    5940
ctgaccgacg gtatgaccgt tcgtgaactg tgctctgcgg cgatcaccat gtctgacaac    6000
accgcagcga acctgctgct gaccaccatc ggtggtccga agaactgac cgcgttcctg     6060 cacaacatgg cgaccacgt tacccgtctg gaccgttggg aaccggaact gaacgaagcg    6120
atcccgaacg acgaacgtga caccaccatg cctgcgcgca tggcgaccac cctgcgtaaa    6180
ctgctgaccg gtgaactgct gacctggca tctcgtcagc agctgatcga ctggatggaa    6240
gcggacaaag ttgcgggtcc gctgctgcgt ctgcgctgc ctgcggggttg gttcatcgcg   6300 gacaaatctg gtgcgggtga acgtggttct cgtggtatca tcgcggcgct gggtccggac    6360
ggtaaaccgt ctcgtatcgt tgttatctac accaccggtt ctcaggcgac catggacgaa    6420
cgtaaccgtc agatcgcgga aatcggtgcg tctctgatta acactggta aactcactcc     6480 tagcccgcct aataagcggg cttttttct gcagaccaag tttactcata tactttag       6540 attgatttaa aacttcattt taatttaaa aggatctagg tgaagatcct ttttgataat     6600
ctcatgacca aaatccctta acgtgagttt tcgttccact gagcgtcaga ccccgtagaa    6660
aagatcaaag gatcttcttg agatcctttt tttctgcgcg taatctgctg cttgcaaaca    6720
aaaaaaccac cgctaccagc ggtggtttgt ttgccggatc aagagctacc aactcttttt    6780
ccgaaggtaa ctggcttcag cagagcgcag ataccaaata ctgtccttct agtgtagccg    6840
tagttaggcc accacttcaa gaactctgta gcaccgccta catacctcgc tctgctaatc    6900
ctgttaccag tggctgctgc cagtggcgat aagtcgtgtc ttaccgggtt ggactcaaga    6960
cgatagttac cggataaggc gcagcggtcg ggctgaacgg ggggttcgtg cacacagccc    7020
agcttggagc gaacgaccta caccgaactg agatacctac agcgtgagct atgagaaagc    7080
gccacgcttc ccgaagggag aaaggcggac aggtatccgg taagcggcag gtcggaaca    7140 ggagagcgca cgagggagct ccaggggga aacgcctggt atctttatag tcctgtcggg    7200
tttcgccacc tctgacttga gcgtcgattt ttgtgatgct cgtcaggggg cggagccta     7260 tggaaaaacg ccagcaacgc ggccttttta cggttcctgg ccttttgctg g             7311
```

<210> SEQ ID NO 29
<211> LENGTH: 5478
<212> TYPE: RNA
<213> ORGANISM: Artificial Sequence
<220> FEATURE:
<223> OTHER INFORMATION: pT7rrnB-CR RNA

<400> SEQUENCE: 29

```
gggccgcuga gaaaagcga agcggcacug cucuuuaaca auuuaucaga caaucugugu    60
```

```
gggcacucga agauacggau ucuuaacguc gcaagacgaa aaaugaauac caagcucaa     120 gagugaacac guaauucauu acgaaguuua auucuuugag cgucaaacuu uuaaauugaa    180
gaguuugauc auggcucaga uugaacgcug gcggcaggcc uaacacaugc aagucgaacg    240
guaacaggaa gaagcuugcu ucuuugcuga cgaguggcgg acggugagua augucuggg     300 aaacugccug auggagggg auaacuacug gaaacgguag cuaauaccgc auaacgucgc     360
aagaccaaag aggggaccu ucgggccucu ugccaucgga ugugcccaga ugggauuagc     420
uaguaggugg gguaacggcu caccuaggcg acgauccua gcuggucuga gaggaugacc      480
agccacacug gaacugagac acgguccaga cuccuacggg aggcagcagu ggggaauauu    540
gcacaauggg cgcaagccug augcagccau gccgcgugua ugaagaaggc cuucgggug     600 uaaaguacuu ucagcgggga ggaagggagu aaaguuaaua ccuuugcuca uugacguuac    660
ccgcagaaga agcaccggcu aacuccgugc cagcagccgc gguauacgg agggugcaag    720 cguuaaucgg aauuacuggg cguaaagcgc acgcaggcgg uuuguuaagu cagaugugaa    780
auccccgggc ucaaccuggg aacugcaucu gauacuggca agcuugaguc ucguagaggg    840
ggguagaauu ccaggugag cggugaaaug cguagagauc uggaggaaua ccgguggcga    900
aggcggcccc cuggacgaag acugacgcuc aggugcgaaa gcgugggag caaacaggau    960 uagauacccu gguaguccac gccguaaacg augucgacuu ggagguugug cccuugaggc    1020
guggcuuccg gagcuaacgc guuaagucga ccgccugggg aguacggccg caagguuaaa    1080
acucaaauga auugacgggg gcccgcacaa gcgguggagc augugguuua auucgaugca    1140
acgcgaagaa ccuuaccugg ucuugacauc cacggaaguu ucagagaug agaaugugcc    1200 uucgggaacc gugagacagg ugcugcaugg cugucucag cucguguugu gaaaugsuugg    1260 guuaagucc gcaacgagcg caacccuuau ccuuuguugc cagcggsuccg gccgggaacu    1320 caaaggagac ugccagugau aaacuggagg aagggugga ugacgucaag ucaucauggc    1380
ccuuacgacc agggcuacac acgugcuaca auggcgcaua caaagagaag cgaccucgcg    1440
agagcaagcg gaccucauaa agucgcugu aguccggauu ggagucugca acucgacucc    1500
augaagucgg aaucgcuagu aaucguggau cagaaugcca cggugaauac guucccgggc    1560
cuuguacaca ccgcccguca caccauggga gugguuugca aaagaaguag guagcuuaac    1620
cuucgggagg gcgcuuacca cuuugugauu caugacuggg gugaagucgu aacaagguaa    1680 ccguaggga accugcgguu ggaucaccuc cuuaccuuaa agaagcguac uuuguagugc    1740
ucacacagau ugucugauag aaagugaaaa gcaaggcguu uacgcguugg gagugaggcu    1800 gaagagaauaa aggccguucg cuuucuauua augaaagcuc acccuacacg aaaauaucac    1860
gcaacgcgug auaagcaauu ucgugucccc cuucgucuag aggccccagga caccgcccuu    1920 ucacggcggu aacaggggu cgaauccccu aggggacgcc acuugcuggu uugugaguga    1980
aagucgccga ccuuaauauc ucaaacucua cuucggugug auguugaga uauugcucu     2040 uuaaaaucu ggaucaagcu gaaaauugaa acacugaaca acgagaguug uucgugaguc    2100
ucucaaauuu ucgcaacacg augaugaauc gaaagaaaca ucuucggguu gugagguuaa    2160
gcgacuaagc guacacggug gaugcccugg cagcagagg cgaugaagga cgugcuaauc    2220
ugcgauaagc gucgguaagg ugauaugaac cguuauaacc ggcgauuucc gaaugggaa    2280 acccagugug uuucgacaca cuaucauuaa cugaauccau agguuaauga ggcgaaccgg    2340
gggaacugaa acaucuaagu accccgagga aaagaaauca accgagauuc ccccaguagc    2400
```

```
ggcgagcgaa cggggagcag cccagagccu gaaucagugu gugguuagu ggaagcgucu    2460 ggaaaggcgc gcgauacagg gugacagccc cguacacaaa aaugcacaug cugugagcuc    2520
gaugaguagg gcgggacacg ugguauccug ucugaauaug ggggggaccau ccuccaaggc    2580 uaaauacucc ugacugaccg auagugaacc aguaccguga gggaaaggcg aaaagaaccc    2640
cggcgagggg agugaaaaag aaccugaaac cguguacgua caagcagugg gagcacgcuu    2700
aggcguguga cugcguaccu uuuguauaau ggucagcga cuuauauucu guagcaaggu    2760
uaaccgaaua ggggagccga agggaaaccg agucuuaacu gggcguuaag uugcagggua    2820
uagacccgaa acccgugau cuagccaugg gcagguugaa gguuggguaa cacuaacugg    2880
aggaccgaac cgacuaaugu ugaaaaauua gcggaugacu uguggcuggg ggugaaaggc    2940
caaucaaacc gggagauagc ugguucuccc cgaaagcuau uuagguagcg ccucugaauu    3000
ucaucuccgg ggguagagca cuguuucggc aaggggguca ucccgacuua ccaacccgau    3060
gcaaacugcg aauaccggag aauguuauca cgggagacac acggcggug cuaacguccg    3120 ucgugaagag ggaaacaacc cagaccgcca gcuaaggucc caaagucaug guuaaguggg    3180
aaacgaugug ggaaggccca gacagccagg auguuggcuu agaagcagcc aucauuuaaa    3240
gaaagcguaa uagcucacug gucgagucgg ccugcgcgga agauguaacg gggcuaaacc    3300
augcaccgaa gcugcggcag cgacgcuuau gcguguugg guaggggagc guucuguaag    3360
ccugcgaagg ugugcuguga ggcaugcugg agguaucaga agugcgaaug cugacauaag    3420
uaacgauaaa gcgggugaaa agcccgcucg ccggaagacc aagggguuccu guccaacguu    3480 aaucggggca gggugagucg accccuaagg cgaggccgaa aggcguaguc gauggaaaac    3540
agguuaauau uccuguacuu ggugguuacug cgaaggggg acggagaagg cuauguuggc    3600
cgggcgacgu uugucccggu uuaagcgugu aggcuggguu uccaggcaaa uccgaaaaau    3660
caaggcugag gcgugaugac gaggcacuac ggugcugaag caacaaaugc ccugcuucca    3720
ggaaaagccu cuaagcauca gguaacauca aaucguaccc caaaccgaca cagguggguca    3780 gguagagaau accaaggcgc uugagagaac ucggugugag gaacuaggca aaauggugcc    3840
guaacuucgg gagaaggcac gcugauaugu aggugaagguc ccucgcggau ggagcugaaa    3900
ucagucgaag auaccagcug gcugcaacug uuuauuaaaa acacagcacu gugcaaacac    3960
gaaaguggac guaucgggug ugacgccugc ccggugccgg aagguuaauu gaugggguua    4020
gcgcaagcga agcucuugau cgaagccccg guaaacggcg gccguaacua uaacgguccu    4080
aagguagcga aauccuugu cgggguaaguu ccgaccugca cgaauggcgu aaugauggcc    4140
aggcugucuc caccccgagac ucagugaaau ugaacucgcu gugaagaugc aguguaccg    4200 cggcaagacg guaagacccc gugaaccuuu acuauagcu gacacugaac auugagccuu    4260 gaugguagg auagugggga ggcuuugaag uguggacgcc agucugcaug gagccgaccu    4320
ugaaauacca cccuuuaug uuugauguuc uaacguugac ccguaauccg gguugcggac    4380
agugucuggu gggguaguuug acugggggcgg ucucccuccua aagaguaacg gaggagcacg    4440
aagguuggcu aauccuggc ggacaucagg agguuagugc aauggcauaa gccagcuuga    4500
cugcgagcgu gacggcgcga gcaggugcga aagcaggguca uagugauccg gugguucuga    4560
augaaggggc caucgcucaa cggauaaaag guacuccggg gauaacaggc ugauaccgcc    4620
caagaguuca uaucgacggc ggguguuggc accucgaugu cggcucauca cauccgguggg    4680 cugaaguagu ucccaagggu auggcuguuc gccauuaaaa guggguacgcg agcuggguuu    4740 agaacgucgu gagacaguuc gguccuauc ugccgugggc gcuggagaac ugagggggc    4800
```

```
ugcuccuagu acgagaggac cggaguggac gcaucacugg uguucggguu gucaugccaa    4860
uggcacugcc cgguagcuaa augcggaaga gauaagugcu gaaagcaucu aagcacgaaa    4920
cuugccccga gaugaguucu cccugacccu uuaagggucc ugaaggaacg uugaagacga    4980
cgacguugau aggccggguug uguaagcgca gcgaugcguu gagcuaaccg guacuaauga    5040
accgugaggc uuaaccuuac aacgccgaag cuguuuuggc ggaugagaga agauuuucag    5100
ccugauacag auuaaaucag aacgcagaag cggucugaua aaacgaauu ugccuggcgg    5160 caguagcgcg ugguucccac cugaccccau gccgaacuca aagugaaac gccguagcgc    5220 cgaugguagu ugugggucuc cccaugcgag aguagggaac ugccaggcau caaauaaaac    5280
gaaaggcuca gucgaaagac ugggccuuuc guuuuaucug uuguuugucg gugaacgcuc    5340
uccugaguag gacaaauccg ccgggagcgg auuugaacgu ugcgaagcaa cggcccggag    5400
gguggcgggc aggacgcccg ccauaaacug ccaggcauca aauuaagcag aaggccaucc    5460
ugacggaugg ccuuuuug                                                  5478

<210> SEQ ID NO 30
<211> LENGTH: 7311
<212> TYPE: DNA
<213> ORGANISM: Artificial Sequence
<220> FEATURE:
<223> OTHER INFORMATION: pT7rrnB-NF DNA

<400> SEQUENCE: 30
ttaatacgac tcactatagg ggccgctgag aaaaagcgaa gcggcactgc tctttaacaa      60
tttatcagac aatctgtgtg gcactcgaa gatacggatt cttaacgtcg caagacgaaa     120
aatgaatacc aagtctcaag agtgaacacg taattcatta cgaagtttaa ttctttgagc    180
gtcaaacttt taaattgaag agtttgatca tggctcagat tgaacgctgg cggcaggcct    240
aacacatgca agtcgaacgg taacaggaag aagcttgctt ctttgctgac gagtggcgga    300
cgggtgagta atgtctggga aactgcctga tgagggggga taactactgg aaacggtagc    360
taataccgca taacgtcgca agaccaaaga gggggacctt cgggcctctt gccatcggat    420
gtgcccagat gggattagct agtaggtggg gtaacggctc acctaggcga cgatccctag    480
ctggtctgag aggatgacca gccacactgg aactgagaca cggtccagac tcctacggga    540
ggcagcagtg gggaatattg cacaatgggc gcaagcctga tgcagccatg ccgcgtgtat    600
gaagaaggcc ttcgggttgt aaagtacttt cagcggggag gaagggagta agttaatac    660 ctttgctcat tgacgttacc cgcagaagaa gcaccggcta actccgtgcc agcagccgcg    720
gtaatacgga gggtgcaagc gttaatcgga attactgggc gtaaagcgca cgcaggcgt    780 ttgttaagtc agatgtgaaa tccccgggct caacctggga actgcatctg atactggcaa    840
gcttgagtct cgtagagggg ggtagaattc caggtgtagc ggtgaaatgc gtagagatct    900
ggaggaatac cggtggcgaa ggcggccccc tggacgaaga ctgacgctca ggtgcgaaag    960 cgtgggagc aaacaggatt agataccctg gtagtccacg ccgtaaacga tgtcgacttg    1020
gaggttgtgc ccttgaggcg tggcttccgg agctaacgcg ttaagtcgac cgcctgggga   1080
gtacggccgc aaggttaaaa ctcaaatgaa ttgacggggg cccgcacaag cggtggagca   1140
tgtggtttaa ttcgatgcaa cgcgaagaac cttacctggt cttgacatcc acggaagttt   1200
tcagagatga gaatgtgcct tcgggaaccg tgagacaggt gctgcatggc tgtcgtcagc   1260
tcgtgttgtg aaatgttggg ttaagtcccg caacgagcgc aacccttatc ctttgttgcc   1320
```

```
agcggtccgg ccgggaactc aaaggagact gccagtgata aactggagga aggtggggat   1380
gacgtcaagt catcatggcc cttacgacca gggctacaca cgtgctacaa tggcgcatac   1440
aaagagaagc gacctcgcga gagcaagcgg acctcataaa gtgcgtcgta gtccggattg   1500
gagtctgcaa ctcgactcca tgaagtcgga atcgctagta atcgtggatc agaatgccac   1560
ggtgaatacg ttcccgggcc ttgtacacac cgcccgtcac accatgggag tgggttgcaa   1620
aagaagtagg tagcttaacc ttcgggaggg cgcttaccac tttgtgattc atgactgggg   1680
tgaagtcgta acaaggtaac cgtaggggaa cctgcggttg gatcacctcc ttaccttaaa   1740
gaagcgtact ttgtagtgct cacacagatt gtctgataga agtgaaaaag caaggcgttt   1800
acgcgttggg agtgaggctg aagagaataa ggccgttcgc tttctattaa tgaaagctca   1860
ccctacacga aaatatcacg caacgcgtga taagcaattt tcgtgtcccc ttcgtctaga   1920
ggcccaggac accgcccttt cacggcggta acaggggttc gaatcccta ggggacgcca   1980
cttgctggtt tgtgagtgaa agtcgccgac cttaatatct caaaactcat cttcgggtga   2040
tgtttgagat atttgctctt taaaaatctg atcaagctg aaaattgaaa cactgaacaa    2100
cgagagttgt tcgtgagtct ctcaaatttt cgcaacacga tgatgaatcg aaagaaacat   2160
cttcggggttg tgaggttaag cgactaagcg tacacggtgg atgccctggc agtcagaggc   2220
gatgaaggac gtgctaatct gcgataagcg tcggtaaggt gatatgaacc gttataaccg   2280
gcgatttccg aatggggaaa cccagtgtgt ttcgacacac tatcattaac tgaatccata   2340
ggttaatgag gcgaaccggg ggaactgaaa catctaagta ccccgaggaa aagaaatcaa   2400
ccgagattcc cccagtagcg gcgagcgaac ggggagcagc ccagagcctg aatcagtgtg   2460
tgtgttagtg gaagcgtctg gaaaggcgcg cgatacaggg tgacagcccc gtacacaaaa   2520
atgcacatgc tgtgagctcg atgagtaggg cgggacacgg gtatcctgt ctgaatatgg    2580
ggggaccatc ctccaaggct aaatactcct gactgaccga tagtgaacca gtaccgtgag   2640
ggaaaggcga aaagaacccc ggcgagggga gtgaaaaaga acctgaaacc gtgtacgtac   2700
aagcagtggg agcacgctta ggcgtgtgac tgcgtacctt ttgtataatg ggtcagcgac   2760
ttatattctg tagcaaggtt aaccgaatag gggagccgaa gggaaaccga gtcttaactg   2820
ggcgttaagt tgcagggtat agacccgaaa cccggtgatc tagccatggg caggttgaag   2880
gttgggtaac actaactgga ggaccgaacc gactaatgtt gaaaaattag cggatgactt   2940
gtggctgggg gtgaaaggcc aatcaaaccg ggagatagct ggttctcccc gaaagctatt   3000
taggtagcgc ctcgtgaatt catctccggg ggtagagcac tgtttcggca aggggggtcat  3060
cccgacttac caacccgatg caaactgcga ataccggaga atgttatcac gggagacaca   3120
cggcgggtgc taacgtccgt cgtgaagagg gaaacaaccc agaccgccag ctaaggtccc   3180
aaagtcatgg ttaagtggga acgatgtgg gaaggcccag acagcagga tgttggctta    3240
gaagcagcca tcatttaaag aaagcgtaat agctcactgg tcgagtcggc ctgcgcggaa   3300
gatgtaacgg ggctaaacca tgcaccgaag ctgcggcagc gacgcttatg cgttgttggg   3360
taggggagcg ttctgtaagc ctgcgaaggt gtgctgtgag catgctgga ggtatcagaa    3420
gtgcgaatgc tgacataagt aacgataaag cgggtgaaaa gcccgctcgc cggaagacca   3480
agggttcctg tccaacgtta atcggggcag ggtgagtcga cccctaaggc gaggccgaaa   3540
ggcgtagtcg atgggaaaca ggttaatatt cctgtacttg gtgttactgc aagggggga    3600
cggagaaggc tatgttggcc gggcgacggt tgtcccggtt taagcgtgta ggctggtttt   3660
ccaggcaaat ccggaaaatc aaggctgagg cgtgatgacg aggcactacg gtgctgaagc   3720
```

```
aacaaatgcc ctgcttccag gaaaagcctc taagcatcag gtaacatcaa atcgtacccc    3780
aaaccgacac aggtggtcag gtagagaata ccaaggcgct tgagagaact cgggtgaagg    3840
aactaggcaa aatggtgccg taacttcggg agaaggcacg ctgatatgta ggtgaggtcc    3900
ctcgcggatg gagctgaaat cagtcgaaga taccagctgg ctgcaactgt ttattaaaaa    3960
cacagcactg tgcaaacacg aaagtggacg tatacggtgt gacgcctgcc cggtgccgga    4020
aggttaattg atggggttag cgcaagcgaa gctcttgatc gaagcccgg taaacgcgg     4080 ccgtaactat aacggtccta aggtagcgaa attccttgtc gggtaagttc cgacctgcac    4140
gaatggcgta atgatggcca ggctgtctcc acccgagact cagtgaaatt gaactcgctg    4200
tgaagatgca gtgtacccgc ggcaagacgg aaagaccccg tgaacctta ctatagcttg    4260 acactgaaca ttgagccttg atgtgtagga taggtgggag gctttgaagt gtggacgcca    4320
gtctgcatgg agccgacctt gaaataccac cctttaatgt ttgatgttct aacgttgacc    4380
cgtaatccgg gttgcggaca gtgtctggtg ggtagtttga ctggggcggt ctcctcctaa    4440
agagtaacgg aggagcacga aggttggcta atcctggtcg gacatcagga ggttagtgca    4500
atggcataag ccagcttgac tgcgagcgtg acggcgcgag caggtgcgaa agcaggtcat    4560
agtgatccgg tggttctgaa tggaagggcc atcgctcaac ggataaaagg tactccgggg    4620
ataacaggct gataccgccc aagagttcat atcgacggcg gtgtttggca cctcgatgtc    4680
ggctcatcac atcctggggc tgaagtaggt cccaagggta tggctgttcg ccatttaaag    4740
tggtacgcga gctgggtcta gaacgtcgtg agacagttcg gtccctatct gccgtgggcg    4800
ctggagaact gaggggggct gctcctagta cgagaggacc ggagtggacg catcactggt    4860
gttcgggttg tcatgccaat ggcactgccc ggtagctaaa tgcggaagag ataagtgctg    4920
aaagcatcta agcacgaaac ttgccccgag atgagttctc cctgaccctt taagggtcct    4980
gaaggaacgt tgaagacgac gacgttgata ggccgggtgt gtaagcgcag cgatgcgttg    5040
agctaaccgg tactaatgaa ccgtgaggct taaccttaca acgccgaagc tgttttggcg    5100
gatgagagaa gattttcagc ctgatacaga ttaaatcaga acgcagaagc ggtctgataa    5160
aacagaattt gcctggcggc agtagcgcgg tggtcccacc tgaccccatg ccgaactcag    5220
aagtgaaacg ccgtagcgcc gatggtagtg tggggtctcc ccatgcgaga gtagggaact    5280
gccaggcatc aaataaaacg aaaggctcag tcgaaagact gggcctttcg ttttatctgt    5340
tgtttgtcgg tgaacgctct cctgagtagg acaaatccgc cgggagcgga tttgaacgtt    5400
gcgaagcaac ggcccggagg gtggcgggca ggacgcccgc cataaactgc caggcatcaa    5460
attaagcaga aggccatcct gacggatggc cttttttgcgt ttctacaaac tcttcctgtc    5520
gtcatatcta caagccggcg cgccaaattg acaattactc atccggctcg aataatgtgt    5580
ggaacttaaa cacacacagg aggaaaacat atgtctatcc agcacttccg tgttgcgctg    5640
atcccgttct tcgcggcgtt ctgcctgccg gttttcgcgc acccggaaac cctggttaaa    5700
gttaaagacg cggaagacca gctgggtgcg cgtgttggtt acatcgaact ggacctgaac    5760
tctggtaaaa tcctggaatc tttccgtccg gaagaacgtt tcccgatgat gtctaccttc    5820
aaagttctgc tgtgcggtgc ggttctgtct cgtgttgacg cgggtcagga acagctgggt    5880
cgtcgtatcc actactctca gaacgacctg gttgaatact ctcccgttac cgaaaaacac    5940
ctgaccgacg gtatgaccgt tcgtgaactg tgctctgcgg cgatcaccat gtctgacaac    6000
accgcagcga acctgctgct gaccaccatc ggtggtccga agaactgac cgcgttcctg    6060
```

| | | | |
|---|---|---|---|
| cacaacatgg | gcgaccacgt tacccgtctg gaccgttggg aaccggaact | gaacgaagcg | 6120 |
| atcccgaacg | acgaacgtga caccaccatg cctgcggcga tggcgaccac | cctgcgtaaa | 6180 |
| ctgctgaccg | gtgaactgct gaccctggca tctcgtcagc agctgatcga | ctggatggaa | 6240 |
| gcggacaaag | ttgcgggtcc gctgctgcgt tctgcgctgc ctgcgggttg | gttcatcgcg | 6300 |
| gacaaatctg | gtgcgggtga acgtggttct cgtggtatca tcgcggcgct | gggtccggac | 6360 |
| ggtaaaccgt | ctcgtatcgt tgttatctac accaccggtt ctcaggcgac | catggacgaa | 6420 |
| cgtaaccgtc | agatcgcgga atcggtgcg tctctgatta aacactggta | aactcactcc | 6480 |
| tagcccgcct | aataagcggg ctttttttct gcagaccaag tttactcata | tactttag | 6540 |
| attgatttaa | aacttcattt ttaatttaaa aggatctagg tgaagatcct | ttttgataat | 6600 |
| ctcatgacca | aaatccctta acgtgagttt tcgttccact gagcgtcaga | ccccgtagaa | 6660 |
| aagatcaaag | gatcttcttg agatcctttt tttctgcgcg taatctgctg | cttgcaaaca | 6720 |
| aaaaaccac | cgctaccagc ggtggtttgt ttgccggatc aagagctacc | aactctttt | 6780 |
| ccgaaggtaa | ctggcttcag cagagcgcag ataccaaata ctgtccttct | agtgtagccg | 6840 |
| tagttaggcc | accacttcaa gaactctgta gcaccgccta catacctcgc | tctgctaatc | 6900 |
| ctgttaccag | tggctgctgc cagtggcgat aagtcgtgtc ttaccgggtt | ggactcaaga | 6960 |
| cgatagttac | cggataaggc gcagcggtcg ggctgaacgg ggggttcgtg | cacacagccc | 7020 |
| agcttggagc | gaacgaccta caccgaactg agatacctac agcgtgagct | atgagaaagc | 7080 |
| gccacgcttc | ccgaagggag aaaggcggac aggtatccgg taagcggcag | ggtcggaaca | 7140 |
| ggagagcgca | cgagggagct tccaggggga aacgcctggt atctttatag | tcctgtcggg | 7200 |
| tttcgccacc | tctgacttga gcgtcgattt ttgtgatgct cgtcaggggg | gcggagccta | 7260 |
| tggaaaaacg | ccagcaacgc ggccttttta cggttcctgg ccttttgctg | g | 7311 |

```
<210> SEQ ID NO 31
<211> LENGTH: 5479
<212> TYPE: RNA
<213> ORGANISM: Artificial Sequence
<220> FEATURE:
<223> OTHER INFORMATION: pT7rrnB-NF RNA

<400> SEQUENCE: 31
```

| | | |
|---|---|---|
| ggggccgcug agaaaaagcg aagcggcacu gcucuuuaac aauuuaucag acaaucugug | | 60 |
| ugggcacucg aagauacgga uucuuaacgu cgcaagacga aaaugaaua ccaagucuca | | 120 |
| agagugaaca cguaauucau uacgaaguuu aauucuuuga gcucaaacu uuuaaauuga | | 180 |
| agaguuugau cauggcucag auugaacgcu ggcggcaggc cuaacacaug caagucgaac | | 240 |
| gguaacagga gaagcuugc uucuuugcug acgagugcg gacgggugag uaaugucugg | | 300 |
| gaaacugccu gaugagggg gauaacuacu ggaaacggua gcuauaccg cauaacgucg | | 360 |
| caagaccaaa gaggggggacc uucgggccuc uugccaucgg augugcccag augggauuag | | 420 |
| cuaguaggug gggguaacggc ucaccuaggc gacgauccu agcuggucug agaggaugac | | 480 |
| cagccacacu ggaacugaga cacgguccag acuccuacgg gaggcagcag ugggaauau | | 540 |
| ugcacaaugg gcgcaagccu gaugcagcca ugccgcgugu augaagaagg ccuucggguu | | 600 |
| guaaaguacu uucagcgggg aggaagggag uaaaguuaau accuugcuc auugacguua | | 660 |
| cccgcagaag aagcaccggc uaacuccgug ccagcagccg cgguaauacg gagggugcaa | | 720 |
| gcguuaaucg gaauuacugg gcguaaagcg cacgcaggcg guuguuaag ucagaugugaa | | 780 |
| aaucccggg cucaaccugg gaacugcauc ugauacuggc aagcuugagu cucguagagg | | 840 |

-continued

```
gggguagaau uccaggugua gcggugaaau gcguagagau cuggaggaau accgguggcg      900
aaggcggccc ccuggacgaa gacugacgcu caggugcgaa agcgugggga gcaaacagga      960
uuagauaccc ugguagucca cgccguaaac gaugucgacu uggagguugu gcccuugagg     1020
cguggcuucc ggagcuaacg cguuaagucg accgccuggg gaguacggcc gcaagguuaa     1080
aacucaaaug aauugacggg ggcccgcaca agcgguggag caugugguuu aauucgaugc     1140
aacgcgaaga accuuaccug gucuugacau ccacggaagu uuucagagau gagaaugugc     1200
cuucgggaac cgugagacag gugcugcaug gcugucguca gcucguguug ugaaauguug     1260
gguuaaguuc cgcaacgagc gcaacccuua uccuuuguug ccagcggucc ggccgggaac     1320
ucaaaggaga cugccaguga uaaacuggag gaagugggg augacgucaa gucaucaugg     1380
cccuuacgac cagggcuaca cacgugcuac aauggcgcau acaaagagaa gcgaccucgc     1440
gagagcaagc ggaccucaua aagugcgucg uaguccggau uggagucugc aacucgacuc     1500
caugaagucg gaaucgcuag uaaucgugga ucagaaugcc acggaauua cguuccggg      1560 ccuuguacac accgcccguc acaccauggg aguggguugc aaaagaagua gguagcuuaa     1620
ccuucgggag ggcgcuuacc acuuugugau ucaugacugg ggugaagucg uaacaaggua     1680
accguagggg aaccugcggu uggaucaccu ccuuaccuua aagaagcgua cuuuguagug     1740
cucacacaga uugucugaua gaaagugaaa agcaaggcgu uuacgcguug ggagugaggc     1800
ugaagagaau aaggccguuc gcuuucuauu aaugaaagcu cacccuacac gaaaauauca     1860
cgcaacgcgu gauaagcaau uuucgugucc ccuucgucua gaggcccagg acaccgcccu     1920
uucacggcgg uaacaggggu ucgaauccc uaggggacgc cacuugcugg uuugugagug     1980
aaagucgccg accuuaauau cucaaaacuc aucuucgggu gauguuugag auauuugcuc     2040
uuuaaaaauc uggaucaagc ugaaaauuga aacacugaac aacgagaguu guucgugagu     2100
cucucaaauu uucgcaacac gaugaugaau cgaaagaaac aucuucgggu gugagguua     2160 agcgacuaag cguacacggu ggaugcccug gcagucagag gcgaugaagg acgugcuaau     2220
cugcgauaag cgucgguaag gugauaugaa ccguuauaac cggcgauuuc cgauggggga     2280
aacccagugu guuucgacac acuaucauua acugaaucca uagguuaaug aggcgaaccg     2340
ggggaacuga acaucuaag uaccccgagg aaagaaauc aaccgagauu cccccaguag      2400
cggcgagcga acgggagca gcccagagcc ugaaucagug gugugguuag uggaagcguc     2460
uggaaaggcg cgcgauacag ggugacagcc ccguacacaa aaaugcacau gcugugagcu     2520
cgaugaguag ggcgggacac guggguaucc gucugaauau gggggaccca uccuccaagg     2580
cuaaauacuc cugacugacc gauagugaac caguaccgug agggaaaggc gaaaagaacc     2640
ccggcgaggg gagugaaaaa gaaccugaaa ccguguacgu acaagcagug ggagcacgcu     2700
uaggcgugug acugcguacc uuuuguauaa uggggucagcg acuuauauuc uguagcaagg     2760
uuaaccgaau aggggagccg aagggaaacc gagucuuaac ugggcguuaa guugcagggu     2820
auagaccgca aacccgguga ucuagccaug ggcagguuga aagguugggua acacuaacug     2880 gaggaccgaa ccgacuaaug uugaaaaauu agcggaugac uuguggcugg ggugaaagg      2940 ccaaucaaac cggagauag cugguucucc ccgaaagcua uuuaggugc gccucgugaa       3000 uucaucuccg gggguagagc acuguucgg caagggggggu auccccgacuu accaacccga    3060 ugcaaacugc gaauaccgga gaauguuauc acgggagaca cacggcgggu gcuaacgucc     3120
gucgugaaga gggaaacaac ccagaccgcc agcuaaagguc ccaaagucau gguuaaggugg    3180
```

```
gaaacgaugu gggaaggccc agacagccag gauguuggcu uagaagcagc caucauuuaa    3240
agaaagcgua auagcucacu ggucgagucg gccugcgcgg aagauguaac ggggcuaaac    3300
caugcaccga agcugcggca gcgacgcuua ugcguuguug gguagggag cguucuguaa    3360
gccugcgaag gugugcugug aggcaugcug gagguaucag aagugcgaau gcugacauaa    3420
guaacgauaa agcggguaa aagcccgcuc gccggaagac caagggulcc uguccaacgu    3480
uaaucgggc agggugaguc gaccccuaag gcgaggccga aaggcguagu cgaugggaaa    3540
cagguuaaua uuccuguacu uggguuacu gcgaaggggg gacggagaag gcuauguugg    3600
ccgggcgacg guugucccgg uuuaagcgug uaggcugguu uccaggcaa auccggaaaa    3660
ucaaggcuga ggcgugauga cgaggcacua cggugcugaa gcaacaaaug cccugcuucc    3720
aggaaaagcc ucuaagcauc agguaacauc aaaucguacc ccaaaccgac acagguggu    3780
agguagagaa uaccaaggcg cuugagagaa ucucggguaa ggaacuaggc aaaauggugc    3840
cguaacuucg ggagaaggca cgcugauaug uaggugaggu cccucgcgga uggagcugaa    3900
aucagucgaa gauaccagcu ggcugcaacu guuuauuaaa aacacagcac ugugcaaaca    3960
cgaaagugga cguauacggu gugacgccuc cccggugccg gaagguuaau ugaugggguu    4020
agcgcaagcg aagcucuuga ucgaagcccc gguaaacgge ggccguaacu auaacgguc    4080
uaaggguagcg aaauuccuug ucggguaagu uccgaccuge acgaauggcg uauagauggc    4140
caggcugucu ccacccgaga cucagugaaa uugaaccggc ugugaagaug caguucaccc    4200
gcggcaagac ggaaagaccc cgugaaaccuu uacuauagcu ugacacugaa cauugagccu    4260
ugauguguag gauaagguggg aagcuuugaa gugggacgc cagucugcau ggagccgacc    4320
uugaaauacc acccuuuaau guugauguu cuaacguuga cccguaaucc ggguuugcgga    4380
cagugucugg ugggguagguu gacugggggcg gucuccuccu aaagaguaac ggaggacgac    4440
gaagguuggc uaauccuggu cggacaucag gagguuguug caauggcaua agccagcuug    4500
acugcgagcg ugacgcgcg agcaggugcg aaagcagguc auagauaucc ggugguucug    4560
aauggaaggg ccaucgcuca acggauaaaa gguacuccgg ggauaacagg cugauaccgc    4620
ccaagagguuc auaucgacgg cgguguuuugg caccugaug ucggcucauc acauccuggg    4680
gcugaaguag gucccaaggg uauggcuguu cgccauuuaa agguguacgc gagcugggu    4740
uagaacgucg ugacagaguu cgguccuau cugccguggg cgcuggaggaa cugagggggg    4800
cugcuccuag uacgagagga ccggagugga cgcaucacug uguucggu ugucaugcca    4860
augcacugc ccgguagcua aaugcggaag agauaagugc ugaaagcauc uaagcacgaa    4920
acuugccccg agaugaguuc ucccugaccc uuuaagggug cugaaggaac guugaagacg    4980
acgacguuga uaggcgggu guguaagcgc agcgaugcgu ugagcuaacc gguacuaaug    5040
aaccgugagg cuuaaccuua caacgccgaa gcuguuuugg cggaugagag aagauuuuca    5100
gccugauaca gauuaaauca gaacgcagaa gcggucugau aaaacagaau uugccuggcg    5160
gcaguagcgc ggugguccca ccugaccccca ugccgaacuc agaagugaaa cgccguagcg    5220
ccgauggguag uggggucu ccccaugcga gaguagggaa cugccaggca ucaaauaaaa    5280
cgaaaggcuc agucgaaaga cugggccuuu cguuuuaucu guuguuugu ggugaacgcu    5340
cuccugaguaa ggacaaauucc gccggagcg gauuugaacg uugcgaagca acggcccgga    5400
ggguggcggg caggacgccc gccauaaacu gccaggcauc aaauuaagca gaaggccauc    5460
cugacggaug gccuuuuug                                                  5479
```

METHODS FOR MAKING RIBOSOMES

CROSS-REFERENCE TO RELATED APPLICATIONS

This application is a U.S. national stage application of International Application No. PCT/US2014/035376, filed Apr. 24, 2014, which claims benefit of priority to U.S. provisional application No. 61/815,631, filed on Apr. 24, 2013, both of which are incorporated by reference in their entirety.

STATEMENT OF GOVERNMENT SUPPORT

This invention was made with government support under GM081450 awarded by the National Institutes of Health, MCB0943383 awarded by the National Science Foundation, and N00014-11-1-0363 awarded by the Office of Naval Research. The government has certain rights in this invention.

FIELD OF THE INVENTION

This invention pertains to translation platforms and methods for preparing a sequence defined biopolymer in vitro.

BACKGROUND OF THE INVENTION

*Escherichia coli* 70S ribosomes are complex macromolecular machines consisting of 3 ribosomal RNA (rRNA) molecules and 54 ribosomal proteins (r-proteins). 70S ribosomes are capable of sequence-defined polymerization of 20 amino acid monomers into proteins with a wide variety of biological functions. In vitro ribosome studies have elucidated ribosome structure, r-protein assembly, and translational mechanisms.

In vitro assembly, or reconstitution, of *Escherichia coli* ribosomes from purified native ribosomal components into functionally active small (30S) and large (50S) ribosomal subunits was first achieved in pioneering works ~40 years ago (Nierhaus K H & Dohme F, "Total reconstitution of functionally active 50S ribosomal subunits from *Escherichia coli*." *Proc. Natl. Acad. Sci., U.S.A.* 71, 4713-4717 (1974); Traub P & Nomura M, "Structure and function of *E. coli* ribosomes. V. Reconstitution of functionally active 30S ribosomal particles from RNA and proteins," *Proc. Natl. Acad. Sci., U.S.A.* 59, 777-784 (1968)). The conventional 30S subunit reconstitution protocol involves a one-step incubation at 20 mM $Mg^{2+}$ and 40° C. (see, for example, (Traub & Nomura (1968); Church, G M & Jewett, M C, U.S. Patent Application Publication US20120171720A1, published Jul. 5, 2012 and entitled "Method of Making Ribosomes"), and can be facilitated at lower temperatures by chaperones (Maki J A & Culver G M, "Recent developments in factor-facilitated ribosome assembly." *Methods* 36, 313-320 (2005)). The conventional 50S subunit reconstitution protocol involves a non-physiological two-step high-temperature incubation, first at 4 mM $Mg^{2+}$ and 44° C., then at 20 mM $Mg^{2+}$ and 50° C. (Nierhaus & Dohme (1974); Church & Jewett (2012)).

Studies using the conventional reconstitution approach have revealed many important insights into ribosome assembly (Nierhaus K H, *Reconstitution of ribosomes, in Ribosomes and Protein Synthesis, A Practical Approach*, Oxford: Oxford University Press, (1990). Yet inefficiencies in reconstitution make the construction and analysis of engineered variants difficult (Semrad K & Green R, "Osmolytes stimulate the reconstitution of functional 50S ribosomes from in vitro transcripts of *Escherichia coli* 23S rRNA," *RNA*, 8, 401-411 (2002)). For example, conventionally reconstituted 50S subunits made with in vitro-transcribed 23S rRNA (lacking the naturally occurring post-transcriptional modifications) are up to 10,000 times less efficient in reconstitution than those using mature 23S rRNA as measured by the fragment reaction, where single peptide bonds are formed on isolated 50S subunits (Semrad & Green (2002)). Furthermore, the non-physiological two-step conditions for 50S assembly preclude coupling of ribosome synthesis and assembly in a single, integrated system.

Ribosome biogenesis is still not fully defined, as some RNases involved in rRNA processing are unidentified, while in vitro ribosome reconstitution studies using purified rRNA may not accurately reflect the simultaneous in vivo processes of rRNA synthesis and ribosome assembly (Wilson D N & Nierhaus K H, "The weird and wonderful world of bacterial ribosome regulation," *Critical reviews in biochemistry and molecular biology* 42, 187-219 (2007)). In addition, attempts at engineering the ribosome to introduce new functionalities are severely limited by cell viability constraints. Orthogonal ribosomes provide one route, but they must be separated from native ribosomes required for cell growth and may still be toxic to cells (Barrett, O P & Chin, J W, "Evolved orthogonal ribosome purification for in vitro characterization," *Nucleic Acids Res*, 38, 2682-2691 (2010); Cochella L & Green R, "Isolation of antibiotic resistance mutations in the rRNA by using an in vitro selection system," *Proc. Natl. Acad. Sci., U.S.A.* 101, 3786-3791 (2004)). Meanwhile, attempts to assemble ribosomes from in vitro transcribed and purified rRNA using classical reconstitution methods has proven unsuccessful, likely due to the need for post-transcriptional modification of the 23S rRNA (Traub & Nomura (1968); Nierhaus & Dohme (1974); Green R & Noller H F "In vitro complementation analysis localizes 23S rRNA posttranscriptional modifications that are required for *Escherichia coli* 50S ribosomal subunit assembly and function," *RNA*, 2, 1011-1021 (1996)); Semrad & Green (2002)). The direct study of ribosome biogenesis in vitro necessitates removal of the complication of cell viability.

The integrated synthesis, assembly, and translation (iSAT) technology was developed for in vitro 70S ribosome biogenesis to circumvent several of the limitations to previous in vitro translation systems using reconstituted ribosomes (Church and Jewett, (2012); Jewett M C et al., "In vitro integration of ribosomal RNA synthesis, ribosome assembly, and translation," *Mol Syst Biol.* 9:678 (2013)). This technology allows for synthesis of rRNA from individual plasmids, assembly with purified total protein of 70S ribosomes (TP70), and translation of a reporter protein such as luciferase or superfolder GFP (sfGFP) as a measure of ribosome activity (FIG. 1) (Jewett et al. (2013)). These processes all occur simultaneously in vitro at 37° C. A near-physiological salt conditions of this technology allow these biological processes to be active at 37° C. without magnesium shifts previously required for ribosome constitution from purified components (see, for example, Jewett et al. (2013)).

However, iSAT technology as previously reported showed limitations in efficiency leading to low ribosomal activity (Jewett et al. (2013)). Full 70S iSAT ribosomes showed 8-fold lower activity than ribosomes assembled in the same system from purified total rRNA of 70S ribosomes (TR70) and TP70, suggesting a discrepancy between in vitro synthesized rRNA and purified native rRNA. Previous iSAT methods focused on individual subunit assembly to improve reporter signal in translation assays. Yet present iSAT systems maintain bottlenecks that limit the iSAT process and bar increased ribosome activity.

BRIEF SUMMARY OF THE INVENTION

In a first aspect, a platform for preparing a sequence defined biopolymer in vitro is disclosed. The platform includes a ribosome-depleted cellular extract, ribosomal RNAs prepared by in vitro transcription, and purified ribosomal proteins depleted of ribosomal RNAs.

In a second aspect, a method of synthesizing and assembling ribosomes in vitro is disclosed. The method includes three steps. The first step is preparing a ribosome-depleted cellular extract. The second step is transcribing ribosomal RNAs in vitro from at least one transcription template. The third step is adding the transcribed ribosomal RNAs and purified ribosomal proteins depleted of ribosomal RNAs from the ribosome-depleted cellular extract.

In a third aspect, a method for preparing a sequence defined biopolymer in vitro is disclosed. The method includes four steps. The first step is providing a ribosome-depleted cellular extract. The second step is generating ribosomal RNA prepared by in vitro transcription. The third step is adding purified ribosomal proteins depleted of ribosomal RNA to the generated ribosomal RNA in the presence of the ribosome-depleted extract to provide a translation platform mixture. The fourth step is providing an RNA transcription template encoding the sequence defined biopolymer to the translational platform mixture to prepare the sequence defined biopolymer in vitro.

DETAILED DESCRIPTION OF THE INVENTION

Figure 1:
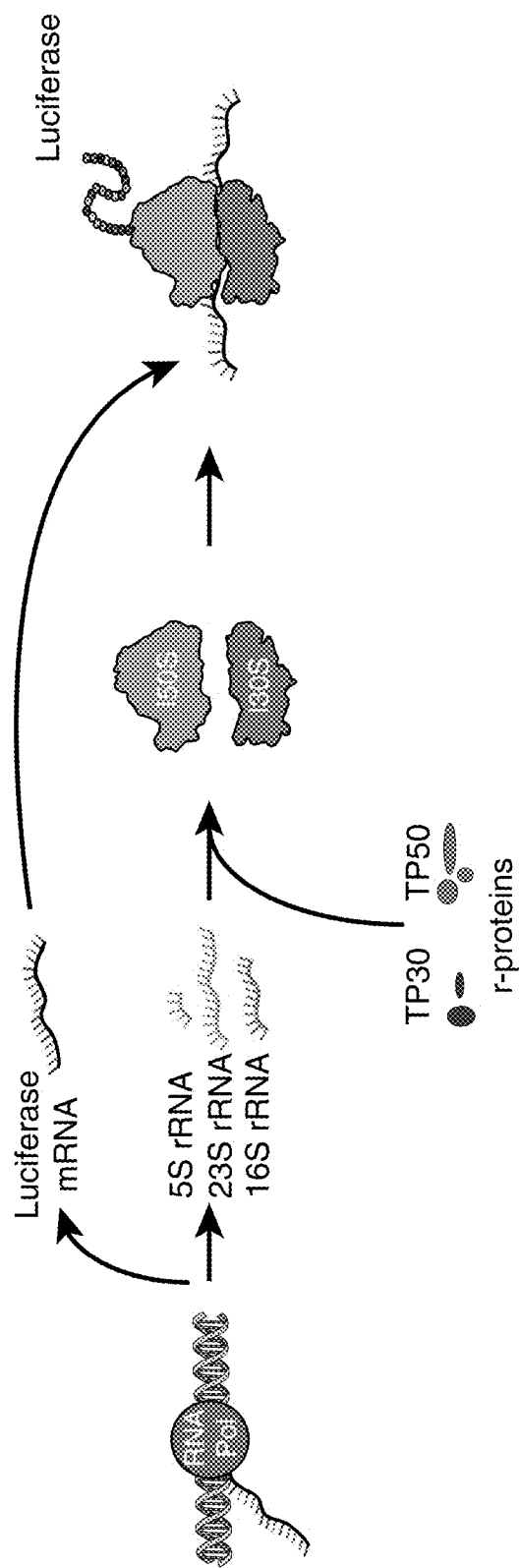
FIG. 1 depicts the principle of iSAT: an integrated method for the assembly of ribosomes from in vitro-transcribed rRNA from ribosomal proteins ("r-proteins") purified from isolated 30S ribosomal subunit ("TP30") and 50S ribosomal subunit ("TP70") and subsequent translation by these ribosomes in the same compartment. The rRNAs and mRNA are depicted being transcribed from DNA transcription template(s) (one DNA is shown for simplicity).

Improvements in the integrated synthesis, assembly, and translation (iSAT) technology is disclosed that provide three orders of magnitude increases over the translational efficiency of prior iSAT technologies. The disclosed iSAT technology pertains to four areas of improved design and methodology. First, cell culturing conditions are optimized to provide a highly active S150 extract for use in iSAT. Second, a novel operon that expresses ribosomal RNA subunits to provide stoichiometrically balanced rRNA transcription and post-transcriptional processing in vitro is presented. Third, conditions and methods for assembling ribosomes from ribosomal RNA prepared from transcription in vitro with purified ribosomal proteins are described. Finally, an optimized conditions for in vitro ribosomal RNA transcription system with exogenous RNA polymerases is disclosed. The combination of these features provides for robust translational capabilities from iSAT technology previously unattainable from prior art systems.

Definitions

To aid in understanding the invention, several terms are defined below.

Unless defined otherwise, all technical and scientific terms used herein have the same meaning as commonly understood by one of skill in the art. Although any methods and materials similar to or equivalent to those described herein can be used in the practice or testing of the claims, the exemplary methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "about" means within a statistically meaningful range of a value or values such as a stated concentration, length, molecular weight, pH, time frame, temperature, pressure or volume. Such a value or range can be within an order of magnitude, typically within 20%, more typically within 10%, and even more typically within 5% of a given value or range. The allowable variation encompassed by "about" will depend upon the particular system under study.

The terms "comprising," "having," "including," and "containing" are to be construed as open-ended terms (i.e., meaning "including, but not limited to") unless otherwise noted.

Recitation of ranges of values herein are merely intended to serve as a shorthand method of referring individually to each separate value falling within the range, and includes the endpoint boundaries defining the range, unless otherwise indicated herein, and each separate value is incorporated into the specification as if it were individually recited herein.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter), termination of RNA transcription (for example, a ribozyme), or translation of protein. The region of the primer that is sufficiently complementary to the template to hybridize is referred to herein as the hybridizing region.

The term "promoter" refers to a cis-acting DNA sequence that directs RNA polymerase and other trans-acting transcription factors to initiate RNA transcription from the DNA template that includes the cis-acting DNA sequence.

The terms "target, "target sequence", "target region", and "target nucleic acid," as used herein, are synonymous and refer to a region or sequence of a nucleic acid which is to be amplified, sequenced or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, *Biochemistry*, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The term "natural polymer" refers to any polymer comprising natural monomers found in biology. For example, polypeptides are natural polymers made from natural amino acids, where the term "amino acid" includes organic compounds containing both a basic amino group and an acidic carboxyl group. Natural protein occurring amino acids, which make up natural polymers, include alanine, arginine, asparagine, aspartic acid, cysteine, glutamic acid, glutamine, glycine, histidine, isoleucine, leucine, lysine, methionine, phenylalanine, serine, threonine, tyrosine, tryptophan, proline, and valine.

The term "non-natural polymer" refers to any polymer comprising natural and non-natural monomers found in biology. For example, a ribosome can be designed to produce a non-naturally occurring biopolymer based on amino acids where naturally occurring and/or synthetic versions of naturally occurring components are used. For example, non-natural polymers could be made that comprise both natural and unnatural amino acids. These unnatural amino acids could comprise modified and unusual amino acids (e.g., D-amino acids and β-amino acids), as well as amino acids which are known to occur biologically in free or combined form but usually do not occur in proteins. Natural non-protein amino acids include arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5,-triiodothyronine, and 3,3',5,5'-tetraiodothyronine. Modified or unusual amino acids include D-amino acids, hydroxylysine, 4-hydroxyproline, N-Cbz-protected amino acids, 2,4-diaminobutyric acid, homoarginine, norleucine, N-methylaminobutyric acid, naphthylalanine, phenylglycine, α-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, "expression template" refers to a nucleic acid that serves as substrate for transcribing at least one RNA that can be translated into a polypeptide or protein. Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product of transcription from an expression template that can be used by ribosomes to synthesize polypeptide or protein.

Certain plasmid name variations disclosed herein have the same meaning and encode the same nucleic acid information. For example, "pLuc" and "pK7Luc" are used interchangeably and refer to the nucleic acid identified by SEQ ID NO: 1.

Optimized Cell Culturing Conditions for Robust S150 Extract Preparation

Figure 17:
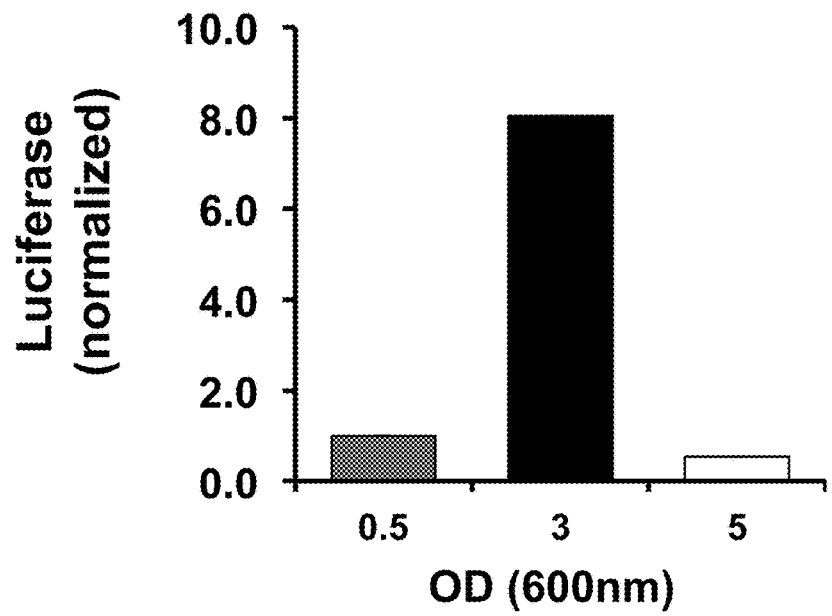
FIG. 17A illustrates the iSAT assays of luciferase acivity as a function of S150 extracts prepared from bacterial cultures harvested at different growth phases.
FIG. 17B illustrates the iSAT assays of luciferase acivity as a function of S150 extracts prepared with different dialysis buffers, wherein rRNA alone, r-protein alone and 70S ribosomes assembled from rRNA and r-protein ("A70S") are shown.
FIG. 17C illustrates the iSAT assays of luciferase acivity as a function of S150 extract protein concentration.
Figure 17:
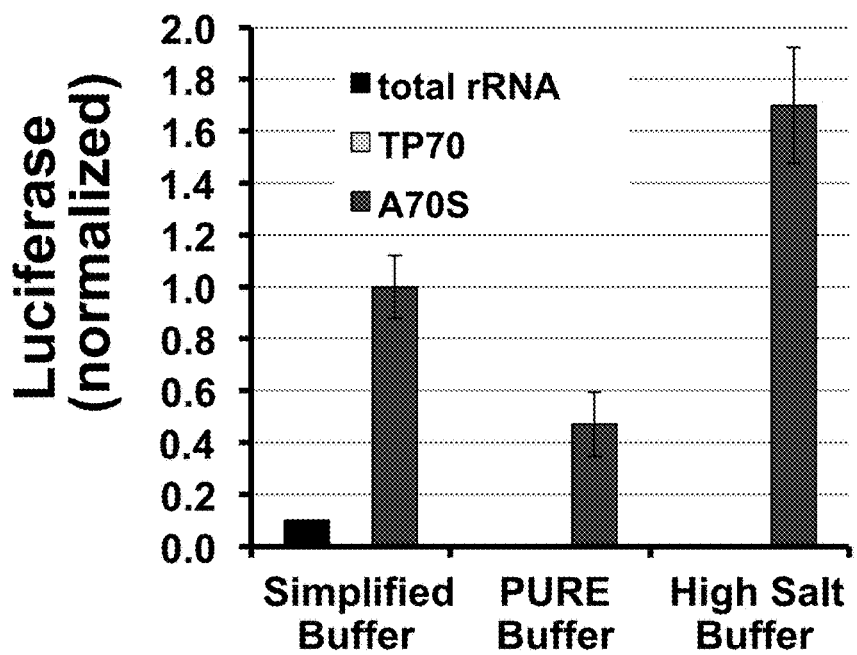
Figure 17:
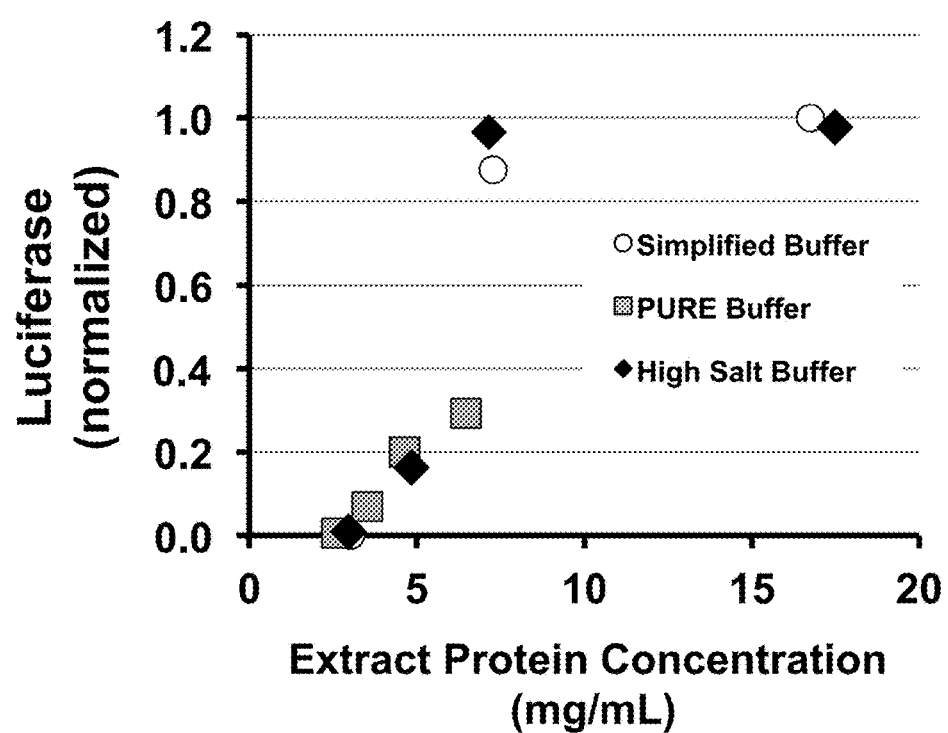

Bacterial cultures used for prior iSAT S150 extracts are harvested during early exponential growth phase ($OD_{600}$=0.50). Different iSAT S150 extracts were evaluated from bacterial cultures harvested at early-, mid- and late-exponential growth phase. Surprisingly, S150 extracts prepared from cultures harvested at $OD_{600}$=3.0 supported the highest iSAT activity of all culture extracts evaluated (FIG. 17A).

The impact of extract dialysis buffer on S150 extract activity can also affect the activity quality of the S150 extract. Three extracts were prepared as originally described, except the cells were grown in a 10 L fermentor to $OD_{600}$=3.0, and one of three dialysis buffers was used as provided in Table 1.

TABLE 1

Different S150 extract dialysis buffer compositions.

| Buffer | Composition |
| --- | --- |
| Simplified | 10 mM TrisOAc, pH 7.5 at 4° C., 10 mM Mg(OAc)$_2$, 2 mM DTT |
| PURE ™ | 50 mM HEPES-KOH pH 7.6, 100 mM KGlu, 13 mM Mg (OAc)$_2$, 2 mM spermidine, 1 mM DTT |
| High Salt | 10 mM TrisOAc, pH 7.5 at 4° C., 10 mM Mg (OAc)$_2$, 20 mM NH$_4$OAc, 30 mM KOAc, 200 mM KGlu, 1 mM spermidine, 1 mM putrescine, 1 mM DTT |

The High Salt Buffer enables the highest yields of luciferase following an assembly and translation reaction (FIG. 17B).

The S150 extract can preferably include a polyamine. Exemplary polyamines include spermine, spermidine and putrescine, among others, as well as combinations thereof. The polyamine concentration in an S150 extract can range from about 0 mM to about 10 mM final concentrations. The S150 extract can preferably include a reducing agent. Exemplary reducing agents include dithiothreatol (DTT), β-mercaptoethanol (BME), tris(2-carboxyethyl)phosphine hydrochloride (TCEP), dithiobutylamine (DTBA), and glutathione, among others, as well as combinations thereof. The reducing agent concentration in an S150 extract can range from about 0 mM to about 20 mM final concentrations (or alternatively, from about 0% (w/v) to about 10% (w/v)). The S150 extract can preferably include a macromolecular crowding agent. Exemplary macromolecular crowding agents include polyethylene glycol (PEG) of three different molecular weights (3350, 6000, or 8000 Da), Ficoll® 400 and glycerol, among others, as well as combinations thereof. A macromolecular crowding agent concentration in an S150 extract can range from about 1% (w/v) to about 4% (w/v). A greater concentration of macromolecular crowding agent in an S150 extract is limited by the amount of volume that can be added to the reaction mixture while maintaining greatest S150 extract activity without precipitation of S150 extract components.

The protein synthesis activities from extracts condensed to different concentrations, and dialyzed with different buffers as indicated, were assessed. S150 extracts having protein concentration of about 10 mg/mL provided maximum luciferase synthesis in iSAT reactions (FIG. 17C).

The disclosed S150 extract used for iSAT platforms are depleted of ribosomes during preparation. As further explained in the examples, the bacterial cultures harvested for S150 extract preparation also provide a source of purified ribosomes. The purified ribosomes can be resolved into separated fractions, wherein a first fraction includes native ribosomal protein subunits devoid of rRNA and a second fraction includes rRNA subunits devoid of ribosomal protein. The isolated ribosomal proteins are used for reconstituting ribosomes in iSAT reactions using rRNA subunits transcribed in vitro from DNA transcription templates.

Transcription Templates for Expressing Stoichiometrically Balanced Complement of Ribosomal RNAs for Efficient Ribosome Assembly in iSAT Platforms Improvement of 70S iSAT activity can be achieved by modifying the plasmids that encode 16S and 23S rRNA. Previous iSAT rRNA plasmids (for example, pWK1 [SEQ ID NO: 10] and pCW1 [SEQ ID NO: 12]) were designed as linearized templates for run-off in vitro transcription by a phage-specific RNA polymerase (for example, T7 RNAP). Because S150 extract contains endonucleases that degrade linear DNA templates, it is preferable to use circular DNA templates. Yet excess transcription beyond the rRNA genes without termination can consume substrates and lowers transcriptional efficiency. The additional 3' bases found in rRNA run-off transcripts may interfere with rRNA activity.

Accordingly, the 3' end of rRNA genes can be modified preferably to improve rRNA processing and transcriptional efficiency in the iSAT platform. Where a phage-specific promoter sequence is used to direct transcription of rRNA genes, the corresponding phage-specific termination sequence can be used to direct termination of rRNA transcription from circular transcription templates. Examples of suitable phage-specific promoter and termination sequences include those from phages T3, T7 and SP6. A set of highly preferred promoter and termination sequences for controlling rRNA transcription units are those from phage T7.

In addition to the inclusion of phage-specific termination sequences, ribozyme-mediated cleavage motifs can be included at the 3'-ends of the rRNA genes to enable efficient 3'-end formation of rRNA transcripts. Placement of the ribozyme-mediated cleavage motifs upstream of a phage-specific termination sequence enables removal of extraneous 3'-RNA sequences from rRNA transcripts that result from inefficient transcription termination. Though cis- and trans-mediated ribozyme-mediated cleavage motifs can be included for directed 3'-end formation, the use of cis-acting, self-cleaving ribozyme motifs in the rRNA transcription units is preferred for kinetic reasons. Cis-acting, self-cleaving ribozyme motifs are short sequences that can fold into the appropriate active structure during rRNA transcription to promote self-cleavege within the folded ribozyme structure. Examples of cis-acting, self-cleavage ribozyme motifs include the Hepatitis delta virus (HDV) ribozyme and hammerhead ribozyme(s), among others known in the art.

Where the rRNA genes are expressed from different transcription templates in a given reaction mixture, it is desirable to provide appropriate amounts of the individual transcription templates that yield stoichiometric amounts of each rRNA transcript. T7 RNAP can provide different amounts of transcripts from different transcription templates, even within a single reaction mixture. Accordingly, it is desirable to adjust the concentrations of each transcription template and T7 RNAP present in a given reaction to transcribe rRNAs in stoichiometric yields. The amounts of rRNA transcripts produced in reactions can be monitored in a number of ways, such as gel electrophoresis, quantitative RT-PCR, among others that are known in the art.

The natural rrnB operon encodes all three ribosomal RNA subunits (5S, 16S and 23S rRNAs) under the control of a common promoter. The rRNA precursor is post-transcriptionally processed to form the individual subunit rRNAs. We discovered that the S150 extracts disclosed herein provide the requested enzymes for achieving appropriate post-transcriptional processing of an rrnB rRNA precursor transcript. Accordingly, a T7 RNAP-promoted rRNA operon was designed wherein the rrnB operon located on a plasmid was altered to replace a native promoter with the T7 promoter. A T7 terminator can be inserted downstream of the rrnB operon to address concerns of excess transcription. Optionally, a ribozyme self-cleaving motif can be incorporated 3' of the rrnB operon to provide efficient cleavage of extraneous sequences. This approach provides inherent stoichiometric balance in rRNA subunit production, as complete rrnB operon transcription generates one molecule each of 5S, 16S, and 23S rRNA.

Additional modifications can be included in the rRNA genes that result in conferring specific antibiotic resistance to the resultant rRNA transcripts. These modifications can be introduced into the corresponding rRNA subunit genes on separate DNA transcription templates or into an rrnB operon on a single DNA transcription template. Such modifications typically alter the genotype of the underlying ribosomal RNA gene sequence encoding one or more of the 5S, 16S or 23s rRNA subunits and can be accomplished by conventional site-directed mutagenesis or random mutagenesis procedures known to those having ordinary skill in the art. Post-transcriptional modifications can also be introduced into the ribosomal RNA subunits in a site-directed or sequence specific manner, as such procedures are well understood and practiced in the art. The resultant modified rRNA gnes encode rRNA mutations for assembly of ribosomes with altered function. The use of so-marked ribosomes provide for the ability to monitor assembly and activity of specific ribosomes in iSAT platforms as well as provide for tunable iSAT platforms that are responsive to specific antibiotic compounds.

For example, nucleic acids and methods are disclosed herein for assembling clindamycin-resistant ribosomes for use in iSAT assays that include a 23S rRNA gene variant encoding a A→U transversion mutation at position 2058 in the 23S rRNA coding sequence (SEQ ID NOS: 28 (DNA) and 29 (RNA)). One of ordinary skill in the art can readily prepare other variant rRNA sequences conferring a variety of antibiotic resistant phenotypes for use in iSAT assays based upon known examples of such rRNA mutations in the art and using routine site-directed mutagenesis and recombinant DNA procedures. Exemplary rRNA subunit modifications and the corresponding antibiotic resistances that are known in the art are illustrated in Table 2.

TABLE 2 rRNA subunit modifications for conferring antibiotic resistant ribosomes

| rRNA subunit modification | Antibiotic Resistance |
| --- | --- |
| 23S rRNA-A2058U | Clindamycin |
| 16S rRNA - C1066U | Spectinomycin |
| 16S rRNA - C1192U | Spectinomycin |
| 16S rRNA - G1058C | Tetracycline |

Optimizing iSAT Reactions for Efficient S150 Extract-based Transcription/Translation Assays The iSAT reactions can preferably include a polyamine. Exemplary polyamines include spermine, spermidine and putrescine, among others, as well as combinations thereof. Polyamine concentrations in the iSAT reactions range from about 0 mM to about 10 mM final concentrations. The iSAT reactions can preferably include a reducing agent. Exemplary reducing agents include dithiothreatol (DTT), β-mercaptoethanol (BME), tris(2-carboxyethyl)phosphine hydrochloride (TCEP), dithiobutylamine (DTBA), and glutathione, among others, as well as combinations thereof. Reducing agent concentrations in the iSAT reactions can range from about 0 mM to about 20 mM final concentrations (or alternatively, from about 0% (w/v) to about 10% (w/v)). The iSAT reactions can preferably include a macromolecular crowding agent. Exemplary macromolecular crowding agents include polyethylene glycol (PEG) of three different molecular weights (3350, 6000, or 8000 Da), Ficoll® 400 and glycerol, among others, as well as combinations thereof. Macromolecular crowding agent concentrations in the iSAT reactions can range from about 1% (w/v) to about 4% (w/v). Higher concentrations of macromolecular crowding agent in the iSAT reaction is limited by the amount of volume that can be added to the reaction mixture while maintaining greatest iSAT activity without precipitation of iSAT reaction components. Preferred iSAT reactions supporting highly active iSAT protein synthesis acivity include PEG8000 and DDT at a final concentration of 2% (w/v) and 2 mM, respectively.

Protein synthesis in iSAT reactions slows over time, wherein protein yields plateau. An analysis of substrate consumption in iSAT reactions revealed that the protein synthesis activity of iSAT reactions becomes limited once primary energy (NTPs) and secondary energy (phosphoenolpyruvate (PEP), magnesium glutamate) sources are depleted. End-point protein synthesis of iSAT reactions can be increased by replenishing one or more of the depleted substrates at mid-point in the reaction. A preferred source of replenished substrates is the combination of PEP and magnesium glutamate in the appropriate concentration ratios. For example, lucerferase protein yield at the end of iSAT reaction can be increased by 3.5-fold by adding a final concentration of 30 mM PEP and 8 mM magnesium glutamate to the iSAT reaction at the mid-point of reaction. Magnesium glutamate can be added to help lessen the effect of accumulating inorganic phosphate, which accumulates to toxic levels once liberated from PEP.

iSAT Platforms

A platform for preparing a sequence defined biopolymer in vitro is provided herein. The platform preferably includes three components. The first component includes a ribosome-depleted cellular extract. The second component includes ribosomal RNAs prepared by in vitro transcription. The third component includes purified ribosomal proteins depleted of ribosomal RNAs. The ribosome-depleted cellular extract preferably includes an S150 extract. The ribosome-depleted extract is prepared preferably from mid- to late-exponential growth phase cell cultures, such as cultures harvested at about an O.D.$_{600}$~3.0. The ribosome-depleted extract is prepared preferably with one or more polyamines, such as spermine, spermidine and putrescine or combinations thereof. The ribosome-depleted extract is prepared preferably with a concentration of salts from about 50 mM to about 300 mM.

The platform preferably includes additional components. A first component can include at least one exogenous DNA template encoding ribosomal RNAs. A second component can include at least one exogenous DNA template encoding a mRNA for the sequence defined biopolymer. The platform includes preferably both the first and second components.

The platform can include the ribosomal RNAs prepared from different isolated nucleic acid sources. In one aspect of the platform, the ribosomal RNAs are prepared from an isolated nucleic acid comprising SEQ ID NO: 26 or variants thereof. In another aspect of the platform, the ribosomal RNAs are produced from one or more isolated nucleic acids comprising SEQ ID NOS: 14, 16, 18, 20, 22 and/or 24.

The platform can include ribosomal RNA having synthetic 3' gene modifications to enable highly efficient termination of rRNA-encoding plasmids (e.g., SEQ ID NOS: 14, 16, 18, 20, 22 and/or 24). In other aspects, the platform can include ribosomal RNA (rRNA) having a native operon structure and RNA processing sites to enhance synthesis and stoichiometric balancing of the rRNA produced therefrom (e.g., SEQ ID NO: 26).

The platform provides conditions to enable ribosomes assembly from ribosomal RNA and ribosomal proteins that are competent to produce a biopolymer from a provided mRNA. In one aspect of the platform, the sequence defined polymer is a natural biopolymer. In another aspect of the platform, the sequence defined polymer is a non-natural biopolymer.

In one aspect, the platform is configured for fed-batch operation or continuous operation. In a further respect of this aspect, at least one substrate is replenished in the platform during operation.

In another aspect, the platform includes a DNA-dependent RNA polymerase. The DNA-dependent DNA polymerase is especially useful for promoting transcription of rRNAs and/or mRNAs from appropriate DNA transcription templates that may be included in the platform.

In another aspect, the platform preferably includes at least one macromolecular crowding agent. In one respect of this aspect, platforms that include DNA transcription templates and a DNA-dependent RNA polymerase preferably include at least one macromolecular crowding agent.

In another aspect, the platform preferably includes at least one reducing agent. In one respect of this aspect, platforms that include DNA transcription templates and a DNA-dependent RNA polymerase preferably include at least one reducing agent.

Methods of Making Ribosomes In Vitro

A method of synthesizing and assembling ribosomes in vitro is disclosed. The method includes three steps. The first step includes the step of preparing a ribosome-depleted cellular extract. The second step is transcribing ribosomal RNAs in vitro from at least one transcription template. The third step is adding the transcribed ribosomal RNAs and purified ribosomal proteins depleted of ribosomal RNAs from the ribosome-depleted cellular extract. In one aspect of the method, the ribosome-depleted cellular extract comprises an S150 extract. In one aspect of the method, the the ribosome-depleted extract is prepared from mid- to late-exponential growth phase cell cultures, such as cultures harvested at about an $O.D._{600}$~3.0.

The method can include the ribosomal RNAs prepared from different isolated nucleic acid sources. In one aspect of the method, the ribosomal RNAs are transcribed from an isolated nucleic acid comprising SEQ ID NO: 26 or variants thereof. In another aspect of the method, the ribosomal RNAs are transcribed from plurality of nucleic acids encoding ribosomal RNAs comprising SEQ ID NOS: 14, 16, 18, 20, 22 and/or 24

Methods of Preparing a Sequence Defined Biopolymer In Vitro

A method for preparing a sequence defined biopolymer in vitro is disclosed. The method includes four steps. The first step includes providing a ribosome-depleted cellular extract. The second step includes generating ribosomal RNA prepared by in vitro transcription. The third step includes adding purified ribosomal proteins depleted of ribosomal RNA to the generated ribosomal RNA in the presence of the ribosome-depleted extract to provide a translation platform mixture. The fourth step includes providing an RNA transcription template encoding the sequence defined biopolymer to the translational platform mixture to prepare the sequence defined biopolymer in vitro.

In one aspect of the method, the ribosome-depleted cellular extract includes an S150 extract. In one aspect of the method, the ribosome-depleted extract is prepared from mid- to late-exponential growth phase cell cultures, such as cultures harvested at about an $O.D._{600}$~3.0. In one aspect of the method, the ribosome-depleted extract is prepared with one or more polyamines, such as spermine, spermidine and putrescine, or combinations thereof. In one aspect of the method, the ribosome-depleted extract is prepared with a concentration of salts from about 50 mM to about 300 mM.

In one aspect of the method, one of the first and/or second steps includes adding one exogenous DNA template encoding ribosomal RNAs. In one aspect of the method, one of any of the steps includes adding at least one exogenous DNA template encoding a mRNA for the sequence defined biopolymer.

The method can include the ribosomal RNAs prepared from different isolated nucleic acid sources. In one aspect of the method, the ribosomal RNA (rRNA) uses native operon structure and RNA processing sites to enhance synthesis and stoichiometric balancing of the rRNA. In one aspect of the method, the ribosomal RNAs are prepared from an isolated nucleic acid comprising SEQ ID NO: 26, or variants thereof. In another aspect of the method, the ribosomal RNAs comprise transcripts produced from one or more isolated nucleic acids. In one aspect of the method, the ribosomal RNA uses synthetic 3' gene modifications to enable highly efficient termination of rRNA-encoding plasmids.

In one aspect of the method, ribosomes assemble from ribosomal RNA and ribosomal proteins to produce biopolymers. In one aspect of the method, the sequence defined polymer is a natural biopolymer. In another aspect of the method, the sequence defined polymer is a non-natural biopolymer.

In one aspect, the method is configured for fed-batch operation or continuous operation. In another aspect of the method, at least one substrate is replenished during operation.

In one aspect of the method, at least one step includes a DNA-dependent RNA polymerase. In one aspect of the method, at least one macromolecular crowding agent is included in one of the steps. In one aspect of the method, at least one reducing agent (e.g., dithiothreitol, tris(2-carboxyethyl)phosphine hydrochloride, etc.) is included in one of the steps

EXAMPLES

Example 1

Strains and Reagents

*E. coli* strains MRE600 and DH5α were used. All chemicals were purchased from Sigma-Aldrich (St. Louis, Mo.) unless otherwise noted. DNA polymerase, T4 polynucleotide kinase, T4 DNA ligase, and restriction endonucleases were purchased from New England Biolabs (Ipswich, Mass.).

T7 polymerase was prepared in lab (following the protocol developed by Swartz J R et al., "Cell-free protein synthesis with prokaryotic combined transcription-translation," *Methods in Molecular Biology* (Clifton, N.J.) 267, 169-182 (2004)). T7 RNAP was dialyzed in a midi-size Tube-O-Dialyzer with 1000 MWCO, overnight at 4° C., against 100 volumes of the same simplified high salt buffer used for TP70 preparation (see below). T7 RNAP was then concentrated in 1000 MWCO MicroCon concentrator by spinning at 10,000×g for 15-45 min intervals. T7 RNAP was concentrated to 1.5 mg/mL, as determined by Bradford assay.

Plasmids were extracted using Omega Kits (Omega Bio-Tek, Norcross, Ga.). All DNA oligonucleotides were purchased from Integrated DNA Technologies, Inc. (Coralville, Iowa).

Example 2

Nucleic Acid Manipulations

The nucleic acid sequences used to construct the ribosomal RNA expression plasmids are presented in Table 6 at the end of the Examples section. The 3' modifications to rRNA-encoding plasmids pWK1 ([SEQ ID NO: 10]; encoding 16S rRNA [SEQ ID NO: 11]) or pCW1 ([SEQ ID NO: 12; encoding 23S rRNA [SEQ ID NO: 13]) were introduced through inverse PCR and blunt end ligation of the linear product. Upon transformation and plasmid purification, the resulting constructs were DNA sequenced by the Northwestern University Genomics Core to confirm proper modifications. For constructs including ribozymes, the terminated constructs p16S-T [SEQ ID NO: 14] and p23S-T [SEQ ID NO: 16] were first created and the ribozyme sequences were inserted between the rRNA gene and terminator sequence using a similar method. Likewise, inverse PCR and blunt end ligation was used for insertion of the T7 promoter sequence into pAM552A, a derivative of the pLK35 plasmid encoding the rrnB operon, to create pT7rrnB [SEQ ID NO: 26]. The A2058U clindamycin resistance mutation was introduced into the 23S rRNA gene sequence of pT7rrnB as previously described (PT7rrnB-CR [SEQ ID NO: 28]) (Jewett et al. (2013)).

The gene encoding the red fluorescent protein variant mRFP1 was purchased as an IDT gBlock® containing the cut sites for NdeI and SalI restriction enzymes. The pY71 expression vector contains T7 promoter and termination sequences. Both the gene and the host pY71 plasmid were digested with restriction enzymes and the appropriate DNA fragments were isolated through agarose gel extraction. The fragments were ligated and transformed into heat-shock competent *E. coli* DH5α cells. Cells were grown up and plasmid was recovered using Omega Bio-Tek's E.Z.N.A. Plasmid Mini Kit I. The structure and sequence of the desired plasmid encoding mRFP1 under the transcriptional control of the T7 RNAP promoter and termination sequences (pY71mRFP1 [SEQ ID NO: 7]) was confirmed by restriction enzyme mapping and DNA sequencing.

Example 3

Component Purification and Preparation from *E. coli*

70S Ribosome Purification

Native 70S ribosomes were recovered from MRE600 *E. coli* cells grown to 3.0 $OD_{600}$ in a 10 L fermentor (Sartorius), pelleted, and flash-frozen. Cell pellets were resuspended in 20 mM Tris-HCl (pH 7.2 at 4° C.), 100 mM $NH_4Cl$, 10 mM $MgCl_2$, 0.5 mM EDTA, 2 mM DTT at a ratio of 5 mL buffer per gram of cells. 200 µL, Halt Protease Inhibitor Cocktail (Thermo Fisher Scientific Inc.) and 75 µL, RNase Inhibitor (Qiagen) was added for every 4 grams of cells in the suspension. The cells were lysed at approximately 20,000 psi with an EmulsiFlex-C3 homogenizer (Avestin). An equivalent dose of RNase Inhibitor and 3 µL, 1M DTT per mL was added to lysate prior to two clarification spins at 30,000 g and 4° C. for 30 min. Supernatant equivalent to S30 crude extract was recovered and gently layered into Ti45 ultracentrifuge tubes on top of an equivalent volume of resuspension buffer supplemented with 37.7% sucrose. Samples were centrifuged at 90,000 g (33,900 rpm in Ti45 rotor) and 4° C. for 20 hours. Supernatant was recovered for S150 extract, and the remaining ribosome pellet was resuspended in Buffer C: 10 mM Tris-OAc (pH 7.5 at 4° C.), 60 mM $NH_4Cl$, 7.5 mM $Mg(OAc)_2$, 0.5 mM EDTA, 2 mM DTT. Ribosome resuspension was aliquoted and flash frozen for use as purified 70S ribosomes.

S150 Extract Preparation

Supernatant collected from 70S ribosome pellet was spun at 90,000 g and 4° C. for an additional 3 hours. The top two-thirds of the supernatant were recovered and dialyzed in reconstituted Spectra/Por® 3 dialysis membrane tubing (3500 dalton MWCO) against a high salt buffer of 10 mM Tris-OAc (pH 7.5 at 4° C.), 10 mM $Mg(OAc)_2$, 20 mM $NH_4OAC$, 30 mM KOAc, 200 mM KGlu, 1 mM spermidine, 1 mM putrescine, 1 mM DTT. Dialysis buffer volume was 50-fold greater than sample volume and exchanged after 2 hours for 3 dialysis steps. A fourth dialysis was performed overnight for 15 hours. Extract was clarified at 4,000 g for 10 min and concentrated 6-8 fold to account for dilution through preparation. Final protein concentration of S150 extract was ~7 mg/mL.

Total Protein of 70S Ribosomes (TP70) Preparation

Purified ribosomes were diluted 5-fold in Buffer C and passed over a second sucrose cushion as in the initial purification. The resulting pellet was resuspended in the Buffer C and spermine and spermidine were added to final concentrations of 0.2 mM and 2 mM, respectively. One-tenth of the sample volume of 1M $Mg(OAc)_2$ was added, and two volumes of glacial acetic acid were added to precipitate rRNA. Sample was vortexed at 4° C. for 45 minutes and then centrifuged at 16,000 g for 30 min. Supernatant containing r-proteins was collected and mixed with 5 volumes of chilled acetone and stored overnight at −20° C. Precipitated protein was then collected by centrifugation at 10,000 g for 30 min, dried, and resuspended in simplified high salt buffer with urea: 10 mM Tris-OAc (pH=7.5 at 4° C.), 10 mM $Mg(OAc)_2$, 200 mM KGlu, 1 mM DTT, 6 M urea (buffer was mixed with 1 g/L bentonite for 1 hour at 4° C. and bentonite was filtered out prior to use). Sample was transferred to midi-size Tube-O-Dialyzer with 1000 MWCO and dialyzed overnight against 100 volumes of simplified high salt buffer with urea. Sample was then dialyzed against 100 volumes of simplified high salt buffer without urea 3 times for 90 minutes each. Sample was clarified at 4,000 g for 10 minutes, and concentration was determined to be 6.4 µM based on A230 NanoDrop readings ($\epsilon$=4.17E+06 $M^{-1}$ $cm^{-1}$).

Total RNA of 70S Ribosomes (TR70) Preparation

Purified ribosomes were diluted below 250 $A_{260}$/mL with Buffer C and mixed with 0.1 volume 10% w/v SDS, 0.05 volume 2% w/v bentonite, and 1.0 volume 70% v/v phenol. Sample was vortexed for 8 minutes at 4° C. then centrifuged at 12,500 g for 15 minutes. The aqueous phase was collected, mixed with 1.0 volume 70% v/v phenol, shaken for 5 min at 4° C., centrifuged at 12,500 g for 15 minutes and collected again. 2 volumes of chilled ethanol were added, and the sample was stored at −20° C. overnight to precipitate rRNA. Precipitant was collected by centrifugation at 15,000 g for 45 min, washed with 0.5 volumes ethanol, and dried. TR70 pellet was then resuspended in Buffer J (10 mM Tris-OAc (pH=7.5 at 4° C.) and 7.5 mM $Mg(OAc)_2$) and concentration was determined to be 5.9 µM based on A260 NanoDrop readings ($\epsilon$=4.17E+07 $M^{-1}$ $cm^{-1}$).

Example 4

Set-up and Analysis of iSAT Reactions iSAT Cell-free Protein Synthesis Batch Reaction Cell-free reactions were set-up as previously described (Jewett et al. (2013)). Reagents are listed in Table 3 showing concentration ranges used for optimizations. Reagents were premixed and added to S150 extract with purified ribosomal components (TP70, TR70, or 70S ribosomes) to a final volume of 15 µL. Tubes were then incubated at 37° C. The final optimized reaction conditions for the separate plasmid and operon-based iSAT systems are also shown in Table 3.

TABLE 3

Reagents and concentrations used in 70S iSAT reactions.

| Reagents | Reagent concentration range | Concentrations for separate plasmid iSAT reactions | Concentrations for operon-based iSAT reactions |
|---|---|---|---|
| Salts (in addition to component buffers): | | | |
| Magnesium glutamate ($Mg(Glu)_2$) | 0-15 mM | 7.5 mM | 7.5 mM |
| Ammonium glutamate ($NH_4(Glu)$) | 0-25 mM | 0 mM | 0 mM |
| Potassium glutamate (KGlu) | 0-500 mM | 167 mM | 167 mM |

TABLE 3-continued

Reagents and concentrations used in 70S iSAT reactions.

| Reagents | Reagent concentration range | Concentrations for separate plasmid iSAT reactions | Concentrations for operon-based iSAT reactions |
|---|---|---|---|
| Polyamines (in addition to component buffers): | | | |
| Spermidine | 0.0-5.0 mM | 1.5 mM | 1.5 mM |
| Putrescine | 0.0-5.0 mM | 1.0 mM | 1.0 mM |
| Transcriptional master mix, consisting of: | | | |
| ATP | 1.20 mM | 1.20 mM | 1.20 mM |
| GTP | 0.85 mM | 0.85 mM | 0.85 mM |
| UTP | 0.85 mM | 0.85 mM | 0.85 mM |
| CTP | 0.85 mM | 0.85 mM | 0.85 mM |
| Folinic acid | 34.0 µg/mL | 34.0 µg/mL | 34.0 µg/mL |
| tRNA | 171 µg/mL | 171 µg/mL | 171 µg/mL |
| Transcriptional and translational components: | | | |
| rRNA plasmid(s):  p16S constructs | 0-4 nM each | 2.0 nM | — |
| p23S constructs | 0-20 nM each | 20.0 nM | — |
| pT7rrnB | 1-10 nM each | — | 4.0 nM |
| Reporter plasmid: pK7Luc, pY71sfGFP, pY71mRFP1 | 0-10 nM | 4.0 nM | 4.0 nM |
| T7 RNA polymerase | 30-120 µg/mL | 30 µg/mL | 30 µg/mL |
| Purified 70S ribosomes | 100 nM | 100 nM | 100 nM |
| Total protein of 70S ribosomes (TP70) | 0-300 nM | 200 nM | 200 nM |
| Total rRNA of 70S ribosomes (TR70) | 100 nM | 100 nM | 100 nM |
| Other components - substrates, cofactors, buffers: | | | |
| 20 amino acids | 2.00 mM | 2.00 mM | 2.00 mM |
| NAD | 0.33 mM | 0.33 mM | 0.33 mM |
| CoA | 0.27 mM | 0.27 mM | 0.27 mM |
| HEPES-KOH, pH 7.6 | 57.00 mM | 57.00 mM | 57.00 mM |
| Oxalic acid | 4.00 mM | 4.00 mM | 4.00 mM |
| PEP | 42.00 mM | 42.00 mM | 42.00 mM |

Luciferase Quantification

When producing luciferase as a reporter protein from the plasmid pK7Luc, iSAT reactions were performed in 1.5 mL microtubes and incubated in heat blocks within an incubator for a set period of time (typically 4 hours). Microtubes were placed on ice to stop the reactions. Luciferase concentration in each reaction was determined by mixing 1 or 10 µL of sample with 30 µL ONE-Glo™ (Promega) in a white half-area 96-well plate. Resulting luminescence was read at 26° C. in a BioTek Synergy2 plate reader over 20 min. The maximum values for each reaction was converted to molar concentrations using a standard curve generated from a dilution series of QuantiLum® recombinant luciferase (Promega).

sfGFP Quantification

When producing sfGFP as a reporter protein from the plasmid pY71sfGFP [SEQ ID NO: 4], iSAT reactions were performed in flat-capped PCR tubes and incubated in a CFX96™ real-time thermal cycler (Bio-Rad). sfGFP production was monitored by measuring fluorescence at 5 min intervals (excitation: 450-490 nm, emission: 510-530 nm). Arbitrary fluorescence units were converted to molar concentrations using a standard curve generated from a dilution series of purified recombinant sfGFP [SEQ ID NO: 6].

mRFP1 Quantification

The pY71mRFP1 plasmid [SEQ ID NO: 7] was used as a reporter plasmid in iSAT reactions. When producing mRFP1 [SEQ ID NO: 9], iSAT reactions were performed in flat-capped PCR tubes and incubated in a CFX96™ real-time thermal cycler (Bio-Rad). mRFP1 production was monitored by measuring fluorescence at 5 or 30 min intervals (excitation: 560-590 nm, emission: 610-650 nm). Control reactions were performed with pT7rrnB plasmid containing a T2585C mutation of the 23S rRNA gene (pT7rrnB-NF; [SEQ ID NO: 30]); this mutation prevents formation of functional large ribosomal subunits. Residual protein synthesis production of control reactions was subtracted from iSAT production values.

RNA Denaturing Gel

Agarose gels were prepared with 1.0% agarose, 2.2 M formaldehyde, 1× MOPS buffer (20 mM MOPS, 2 mM NaOAc, 1 mM EDTA, adjusted to pH 7.0 with NaOH), and 1× GelRed™ dye (Biotium). Samples were prepared by RNA purification of standard iSAT reactions without reporter plasmid, using Bio-Rad's Aurum™ Total RNA Mini kit. The kit's bacteria protocol was followed with the exception of initial lysozyme treatment, as no cell lysis was required. Controls included purified rRNA from subunits or ribosomes and prepared as previously reported (Jewett (2013)). Ladder was 0.5-10 kb RNA ladder from Life Technologies. Samples, ladders, and controls were denatured in 1× blue loading dye (New England BioLabs), 1× MOPS buffer, 40% formamide, and 8% formaldehyde at 70° C. for 10 min, then placed on ice for 5 min. Gels were pre-run at 100 V for 10 min. Gels were then loaded with RNA and run at 50 V for 3 hours. Upon completion, gels were imaged in a Bio-Rad Gel Doc™ XR+ station. Images were inverted and contrast was adjusted to improve band visibility, and band intensities were approximated with Image Lab™ software.

Product Determination

Luciferase synthesis was assayed using 1 µL of final reaction mixed with 30 µL of OneGlo assay buffer and luminescence measured using Biota. Synergy 2 plate reader. Reactions for sfGFP synthesis were run at 37° C. on BIO-RAD CFX96 Real-Time System and fluorescence measurements taken by the machine every 15 minutes throughout reaction cycle.

ISAT Cell-Free Protein Synthesis Fed Batch Reactions

For fed batch reactions, 15 μL iSAT cell-free protein synthesis batch reactions were prepared and performed as described above. At t=45 minutes, reactions were fed with 30 mM PEP and varying concentrations of magnesium glutamate. Reactions were assayed for reporter synthesis as described above.

Nucleotide, Phosphenolpyruvate, and Amino Acid Concentration Measurement

High-Performance liquid chromatography (HPLC) analysis was used to measure nucleotide and amino acid concentrations. For both assays, 5% (v/v) trichloroacetic acid (TCA) was added to the cell-free reaction mixture in a 1:1 volumetric ratio. Samples were centrifuged at 23,000×g for 5 minutes at 4° C. The supernant was collected and samples analyzed using an Agilent 1200 series HPLC system (Agilent, Santa Clara, Calif.).

For amino acid analysis, a ZORBAX Eclipse Plus (4,6× 100 mm, 1.8 μm particle size) (Aglient, Santa Clara, Calif.) was performed in a Rapid Resolution HT derivitization method using o-phthalaldehyde (OPA) and fluorenyl-methoxy chloroformate (FMOC), Separation was carried out at a flow rate of 1.0 mL/min for 20 minutes. Mobile phase A contained 10 mM sodium borate, 10 mM sodium phosphate dibasic, and 5 mM sodium azide (pH 8.2 with HCl) and mobile phase B contained acetonitrile, methanol, and water in a 45:45:10 volumetric ratio. The gradient of the buffers is described in Table 4. Amino acids were detected at 262 nm and 338 nm. Amino acid concentrations were determined by comparison to a standard calibration.

TABLE 4

Gradient conditions for amino acid HPLC analysis.

| Time (min) | % B |
| --- | --- |
| 0 | 2 |
| 0.35 | 2 |
| 16.4 | 57 |
| 16.5 | 100 |
| 17.7 | 100 |
| 17.8 | 2 |
| 20 | end |

For nucleotide and phosphenolpyruvate (PEP) analysis, a BioBasic AX column (4.6×150 mm 5 μm particle size) (Thermo Scientific, West Palm Beach, Fla.) was used for analysis. Separation was carried out at a flow rate of 0.75 mL/min. Nucleotide monophosphates (NMPs) and nucleotide diphosphates (NDPs) were analyzed with one method, and nucleotide triphosphates (NTPs) were analyzed separately. PEP analysis was performed using the NTP separation method. Both methods started with a mobile phase of 100% 5 mM $Na_2HPO_4$ (mobile phase A) and 0% 750 mM $Na_2HPO_4$ (mobile phase B), both adjusted to pH 3.2 with phosphoric acid. The gradients of both methods are listed in Table 5. Nucleotides were detected at 254 nm and PEP was detected at 210 nm. Nucleotide and PEP concentrations were determined by comparison to a standard calibration.

TABLE 5

Gradient conditions for energy substrate HPLC analysis.

| NMP and NDP Analysis | | NTP and PEP analysis | |
| --- | --- | --- | --- |
| Time | % B | Time | % B |
| 0 | 0 | 0 | 0 |
| 45 | 45 | 10 | 40 |
| 47 | 100 | 40 | 80 |
| 51 | 100 | 45 | 100 |
| 53 | 0 | 47 | 0 |
| 55 | end | 50 | end |

Figure 2A:
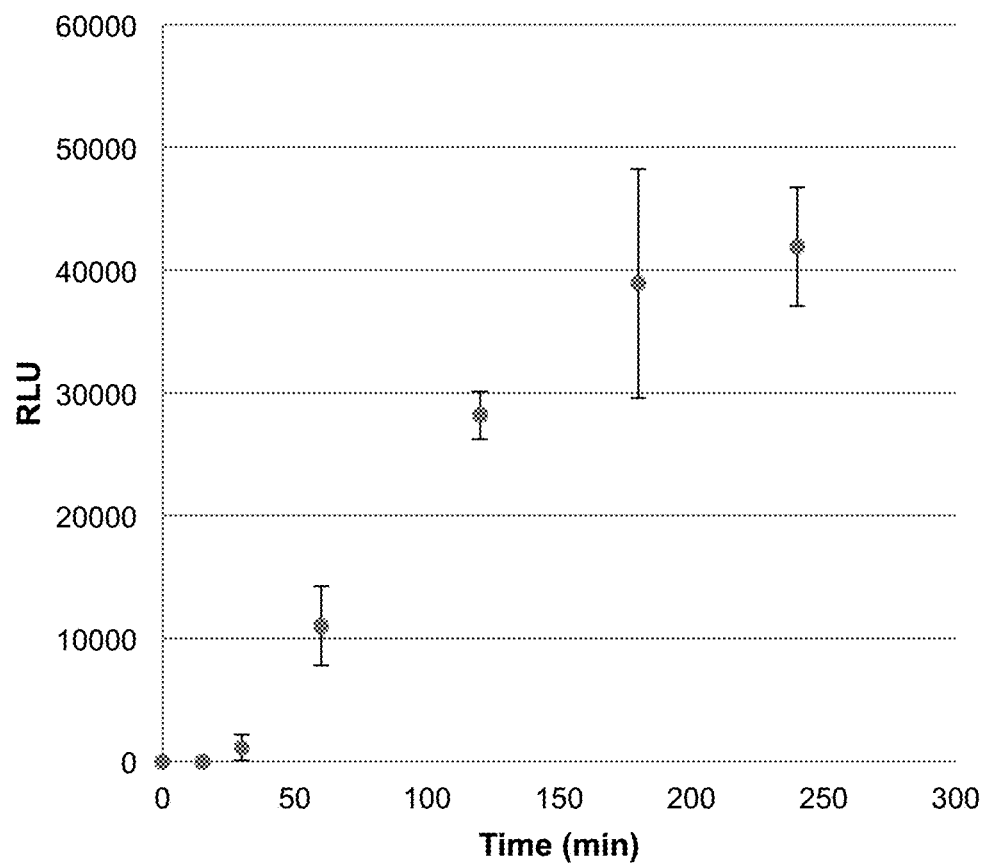
FIG. 2A Illustrates expression kinetics for iSAT production of luciferase.
Figure 2B:
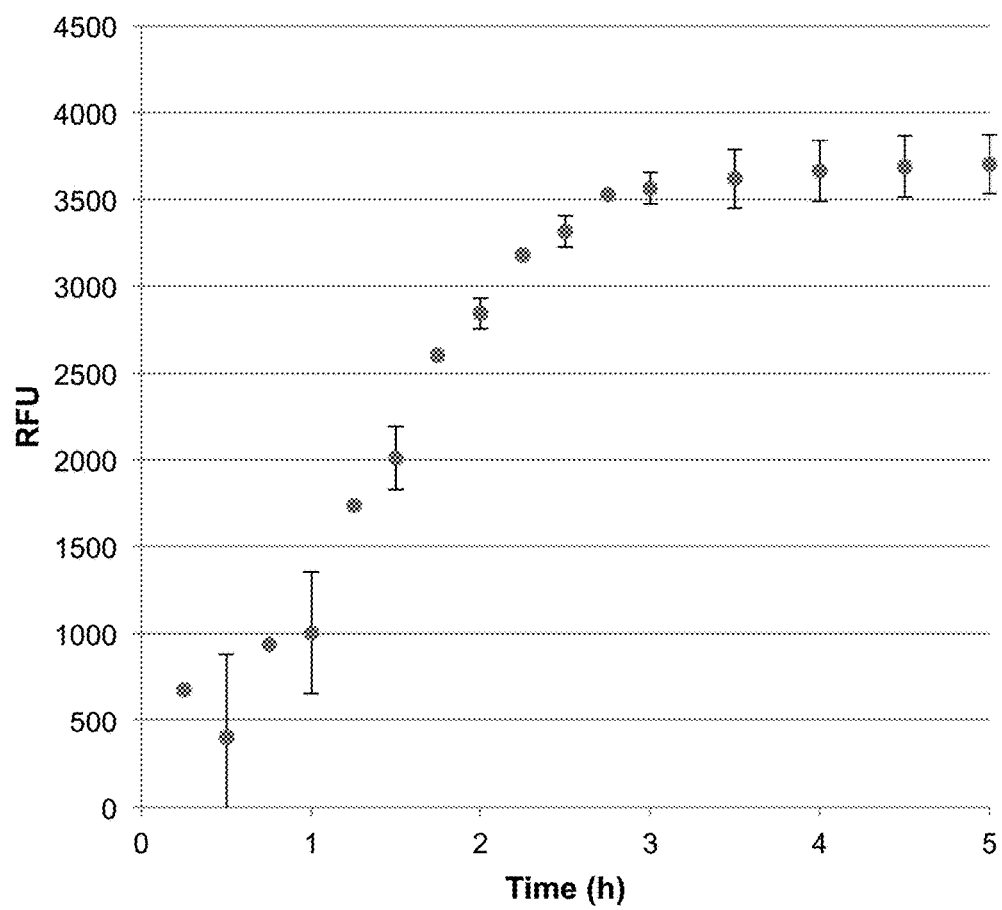
FIG. 2B Illustrates expression kinetics for iSAT production of superfolder GFP.

FIG. 2 Illustrates expression kinetics for iSAT. iSAT uses phosophoenolpyruvate (PEP) as its energy source to generate ATP for protein synthesis reactions. Batch reactions (15 μL) measuring luciferase [SEQ ID NO: 3] (FIG. 2A) and sfGFP [SEQ ID NO: 6] (FIG. 2B) reporter synthesis over time at 37° C. Error bars represent standard deviation for 2-3 separate experiments. Rate of protein synthesis in iSAT for both reporters plateaus around t=180 minutes (3 hours).

Figure 3:
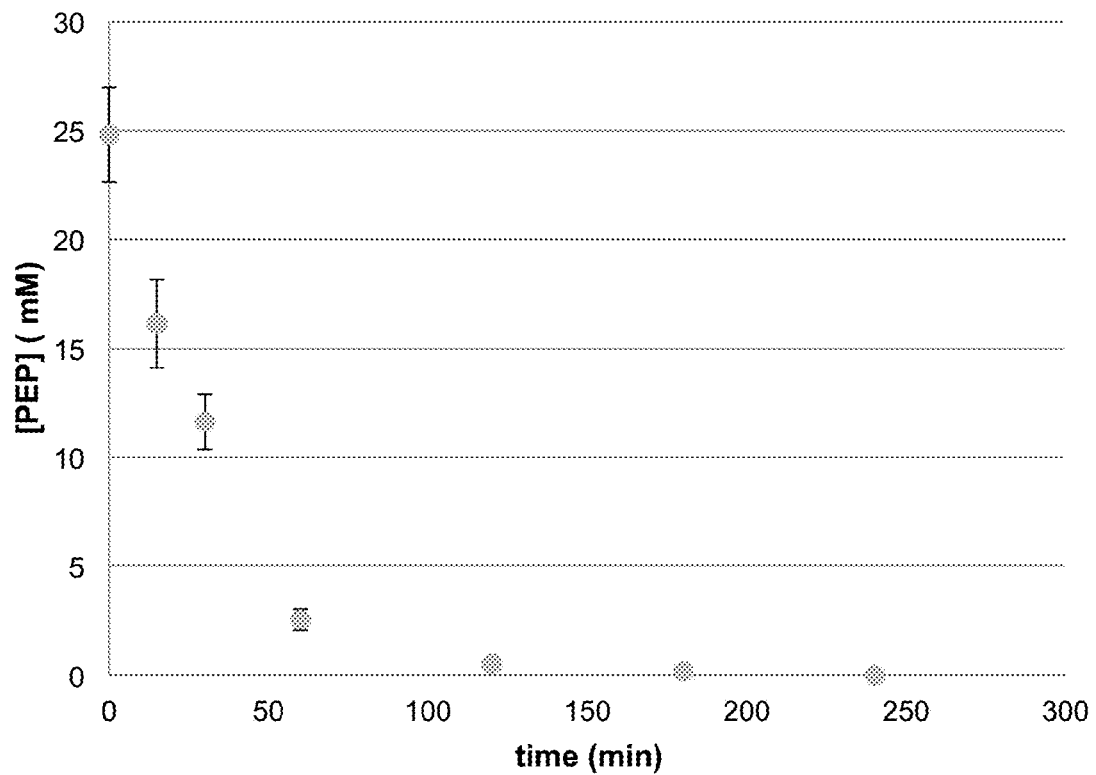
FIG. 3 illustrates secondary energy source depletes over time.

FIG. 3 illustrates secondary energy source depletes over time. iSAT uses phosophoenolpyruphate (PEP) as its energy source to generate ATP for protein synthesis reactions. Measurement of PEP concentration over time using Agilent HPLC system. [PEP] is depleted more than 5-fold after t=60 minutes, and is entirely consumed by iSAT by t=120 minutes.

Figure 4:
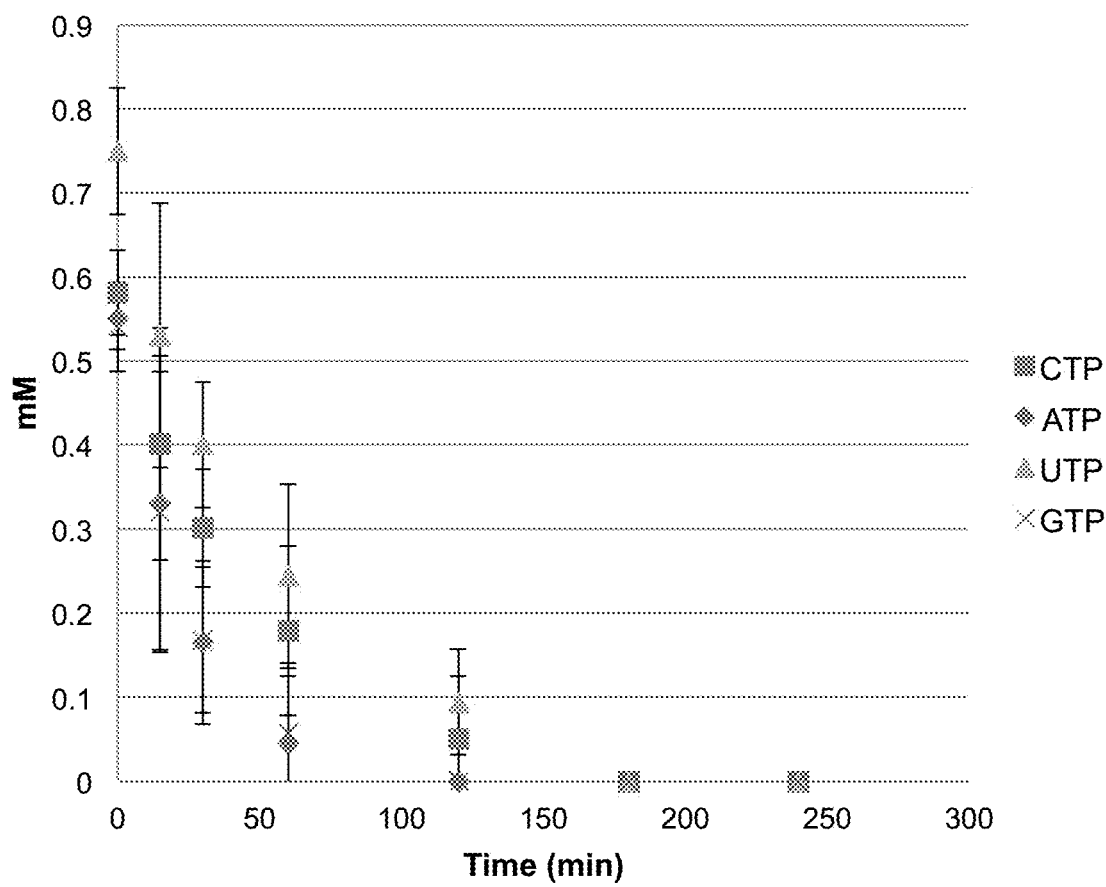
FIG. 4 illustrates the nucleotide profile analysis.

FIG. 4 illustrates the nucleotide profile analysis. NTP concentrations of iSAT reactions over time were measured using Agilent HPLC system. By reaction t=120, [ATP] and [GTP] are almost depleted. By t=120 minutes, most nucleotides have been consumed in the reaction. Combined, FIGS. 3 and 4 show that the iSAT reaction is limited by loss of energy substrates required for protein synthesis.

Figure 5:
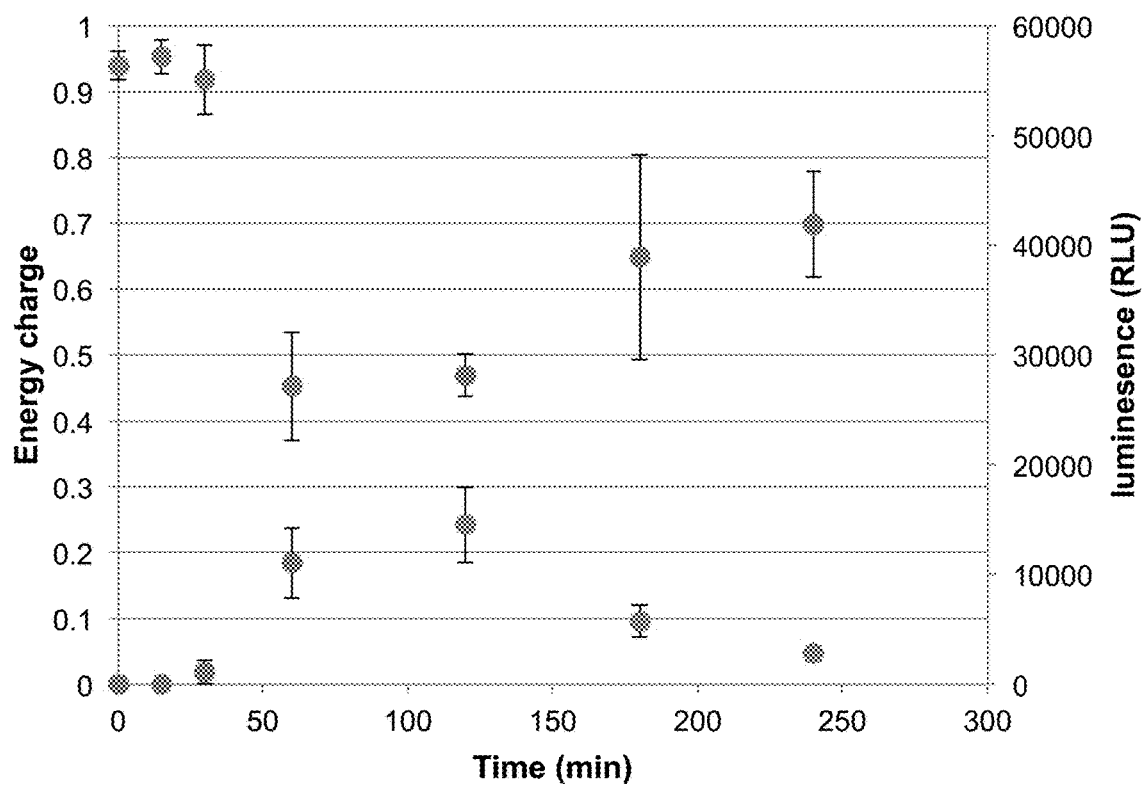
FIG. 5 illustrates the profile of energy charge versus rate of protein synthesis.

FIG. 5 illustrates the profile of energy charge versus rate of protein synthesis. Energy charge (blue) is a measurement of the energy status in a reaction using concentrations of ATP, ADP, and AMP. Energy charges less than 0.8 are inhibitory to the reaction. Over time, energy charge decreases, reaching 0.1 at t=180 minutes. Synthesis of luciferase reporter (red) increases as energy charge decreases, and synthesis plateaus when energy charge is completely depleted. Through the above experiments we discovered that the iSAT reaction is limited by energy.

Figure 6:
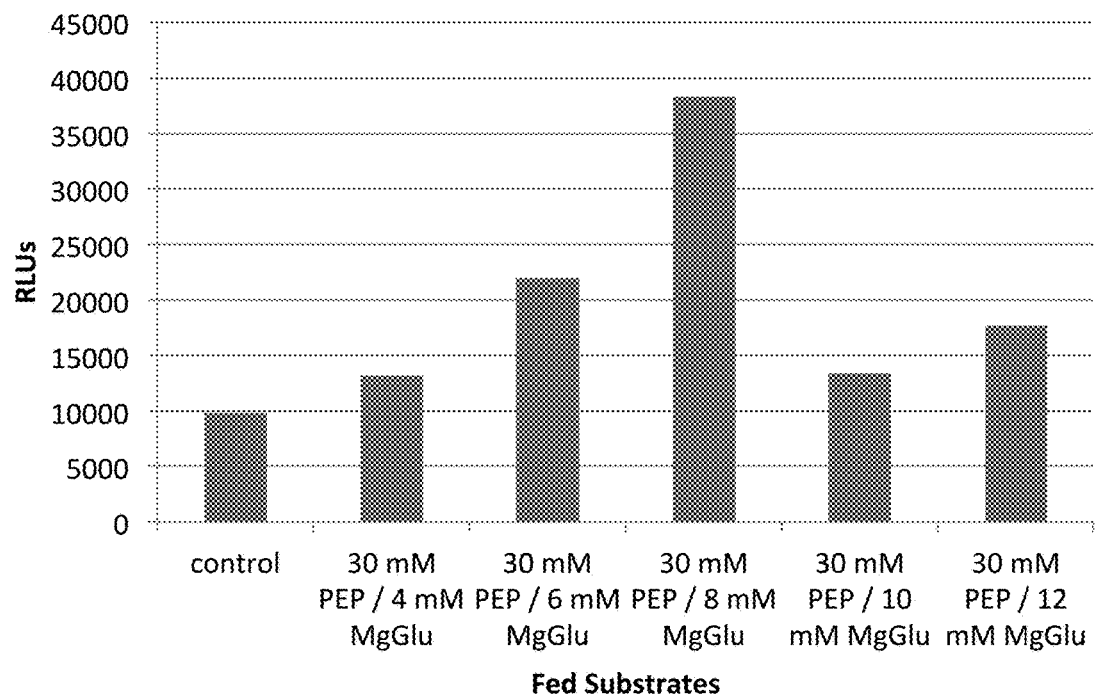
FIG. 6 illustrates that substrate feeding mid-reaction improves end-point protein synthesis yields in iSAT.

FIG. 6 illustrates that substrate feeding mid-reaction improves end-point protein synthesis yields in iSAT. Batch reactions for luciferase reporter synthesis were carried out at 37° C. for 4 hours. Luciferase synthesis measured as a function of luminescence (RLU) using OneGlo assay. Reactions were fed at t=45 minutes with 30 mM PEP and varying magnesium glutamate (MgGlu) concentrations, or $H_2O$ (control). Of the fed batch substrates, an optimal concentration of 30 mM PEP and 8 mM MgGlu improves luciferase synthesis over 3.5-fold compared to the control.

These data show that substrate limitations can be alleviated by feeding PEP and magnesium in an optimized ratio.

Example 5

3' Modifications of rRNA Gene Constructs Impact 70S iSAT Activity

Further improvement of 70S iSAT activity was sought through modification of the plasmids encoding 16S and 23S rRNA. Previous iSAT rRNA plasmids pWK1 and pCW1 were to be linearized for run-off in vitro transcription by T7 RNA polymerase (T7 RNAP). However, S150 extract contains endonucleases that degrade linear DNA templates, so pWK1 and pCW1 were used as circular DNA with no defined 3' termination. Without termination, excess transcription beyond the rRNA genes consumes substrates and lowers transcriptional efficiency. In addition, the additional 3' bases may interfere with rRNA activity. Therefore, modifications were introduced at the 3' end of rRNA genes to assess if 70S iSAT activity could increase through improved rRNA processing and transcriptional efficiency.

Figure 7:
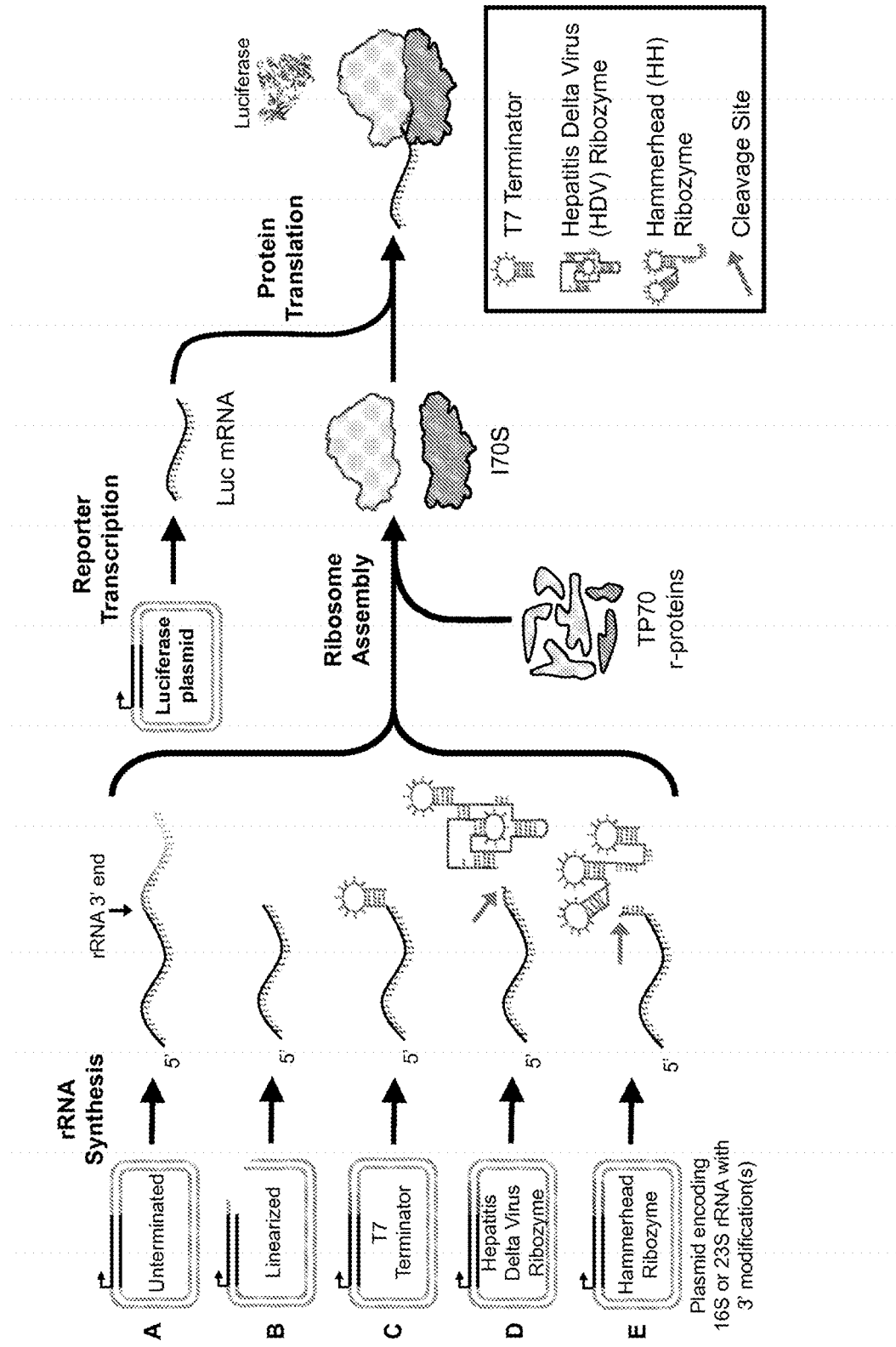
FIG. 7A illustrates a schematic of unterminated plasmids (pWK1 [SEQ ID NO: 10] and pCW1 [SEQ ID NO: 12] encoding 16S rRNA [SEQ ID NO: 11] and 23S rRNA [SEQ ID NO: 13], respectively) in an iSAT assay.
FIG. 7B illustrates a schematic of 3' linearization by digestion with Bsu36I (pWK1) or Afl11 (pCW1) to allow for run-off transcription in an iSAT assay.
FIG. 7C illustrates a schematic of a 48-nt T7 terminator following the 16S or 23S gene in an iSAT assay.
FIG. 7D illustrates a schematic of a Hepatitis Delta Virus (HDV) ribozyme following the 16S or 23S gene in an iSAT assay. The ribozymes are intended to perform rRNA cleavage, denoted by red arrows, to minimize number of additional bases included beyond native 16S or 23S rRNA 3' end. Ribozyme-modified genes are inserted before the T7 terminator sequence to limit superfluous transcription.
FIG. 7E illustrates a schematic of a hammerhead ribozyme following the 16S or 23S gene in an iSAT assay. The ribozymes are intended to perform rRNA cleavage, denoted by red arrows, to minimize number of additional bases included beyond native 16S or 23S rRNA 3' end. Ribozyme-modified genes are inserted before the T7 terminator sequence to limit superfluous transcription.

Modifications to the rRNA-encoding plasmids included linearization of pWK1 [SEQ ID NO: 10] and pCW1 [SEQ ID NO: 12] by Bsu36I and AflII, respectively, termination with a T7 RNAP termination sequence, and addition of the self-cleaving ribozymes hepatitis delta virus (HDV) or hammerhead (HH) followed by termination (FIG. 7). These modifications were introduced for both the 16S and 23S rRNA genes and 70S iSAT reactions were performed to assess impact on luciferase synthesis after 4 hours (FIG. 8A) and sfGFP production from 0 to 6 hours (FIG. 8B). In addition, iSAT reactions without reporter plasmids were incubated for 4 hours and total RNA was purified from each reaction. The purified RNA was run on a denaturing gel to assess size and quality of rRNA transcribed within the iSAT reaction (FIG. 8C). Similar reactions were performed with 16S or 23S rRNA plasmids only (FIG. 11F) in order to identify bands in FIG. 8C as being 16S and 23S rRNA.

Figure 8:
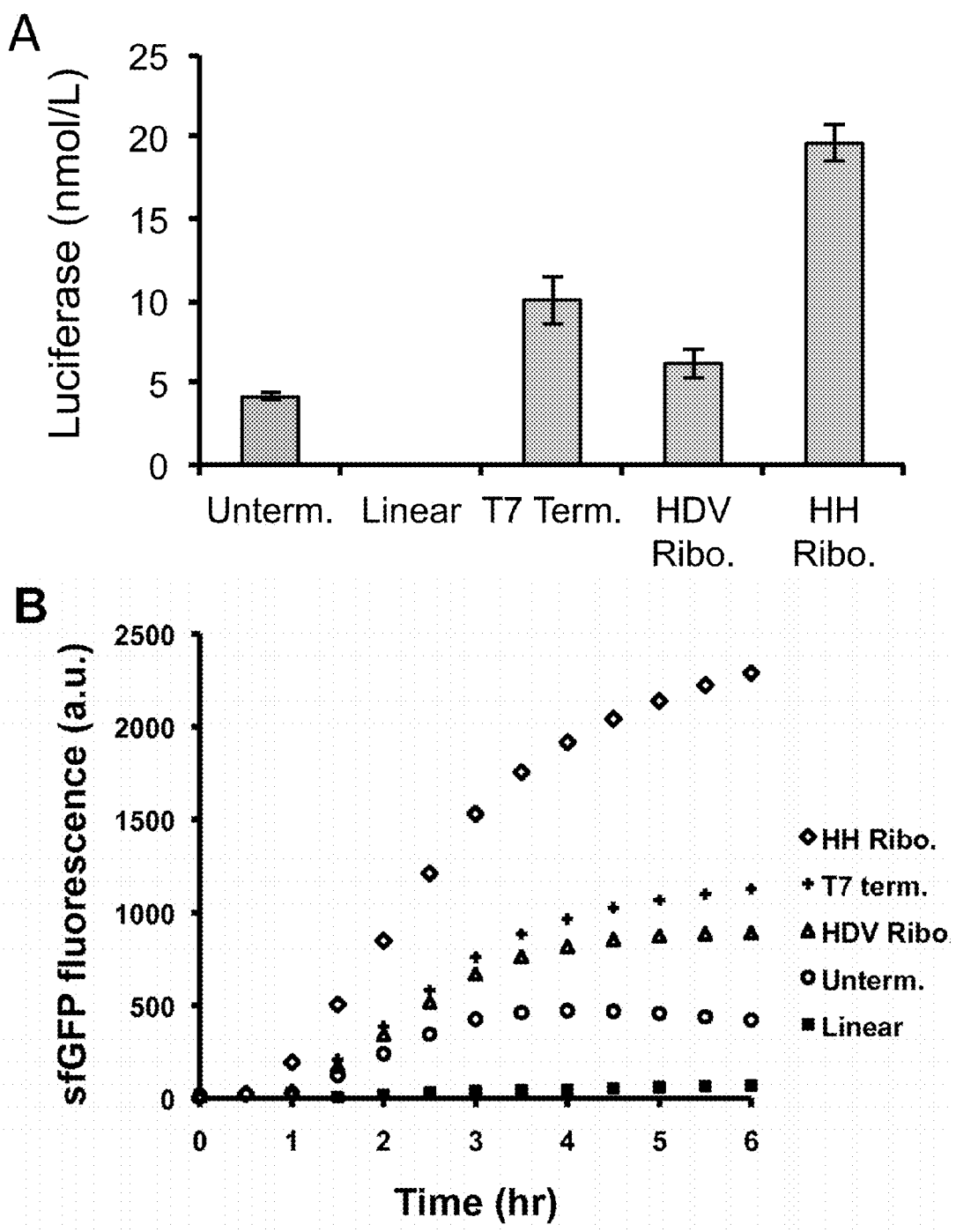
FIG. 8A depicts luciferase protein yields in iSAT reactions as a function of using different ribosomal DNA transcription templates being a circular template without a termination sequence ("Unterm."), a linear template ("Linear"), a circular template with a T7 termination sequence ("T7 Term"), a circular template with a hammerhead ribozyme 3'-rRNA gene modification ("HH Ribo") and a circular template with a HDV ribozyme 3'-rRNA gene modification ("HDV Ribo").
FIG. 8B depicts superfolder GFP (sfGFP) fluorescence in iSAT reactions as a function of using different ribosomal DNA transcription templates being a circular template without a termination sequence ("Unterm."), a linear template ("Linear"), a circular template with a T7 termination sequence ("T7 Term"), a circular template with a hammerhead ribozyme 3'-rRNA gene modification ("HH Ribo") and a circular template with a HDV ribozyme 3'-rRNA gene modification ("HDV Ribo").
FIG. 8C depicts RNA gel assays of iSAT reactions containing different types of 16S and 23S ribosomal RNAs produced from different DNA transcription templates, wherein native 16S and 23S RNAs alone, S150 extract alone, and iSAT reactions containing different 16S and 23S ribosomal DNA transcription templates [circular templates without a termination sequence ("Unterm."), linear templates ("Linear"), circular templates with a T7 termination sequence ("T7 Term"), circular templates with a hammerhead ribozyme 3'-rRNA gene modification ("HH Ribo") and circular templates with a HDV ribozyme 3'-rRNA gene modification ("HDV Ribo")] are illustrated.
Figure 8:
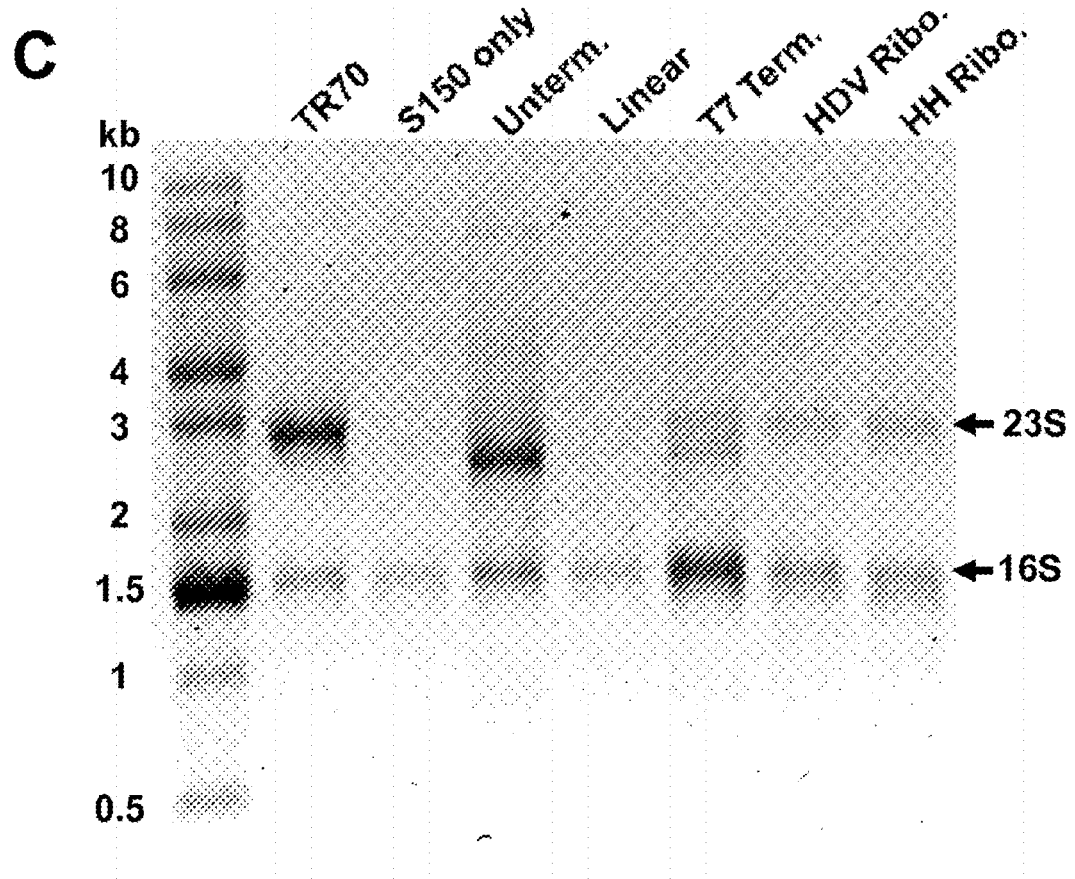
Figure 9:
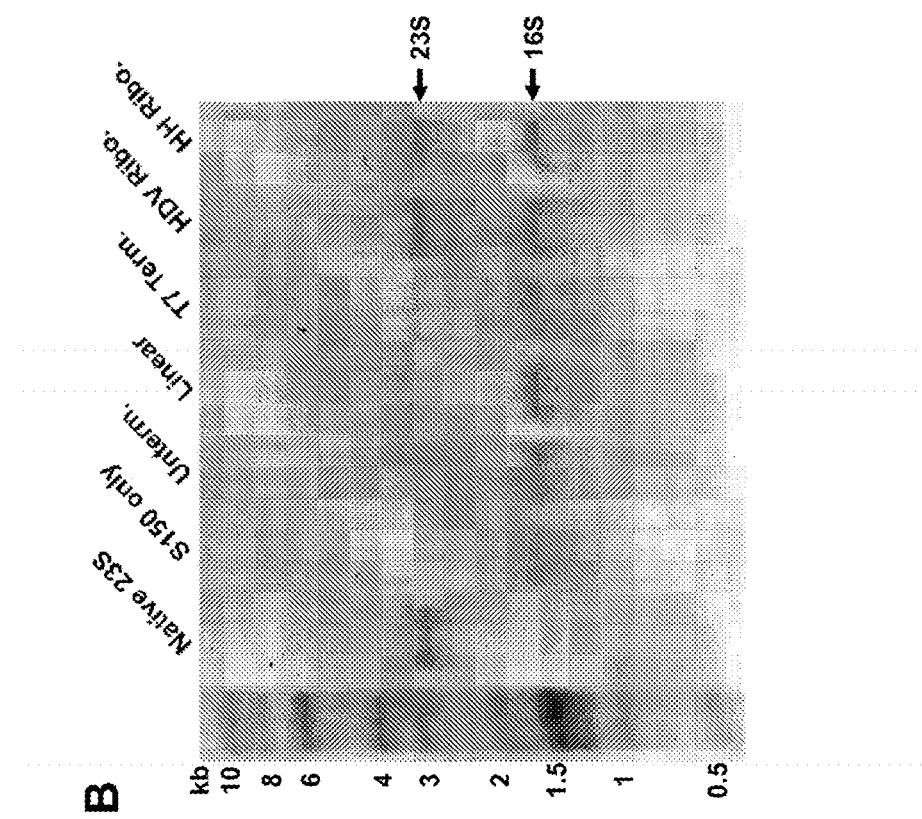
FIG. 9A depicts RNA gel assays of iSAT reactions containing different types of 16S ribosomal RNA produced from different DNA transcription templates, wherein native 16S RNA alone, S150 extract alone, and iSAT reactions containing different 16S ribosomal DNA transcription templates [a circular template without a termination sequence ("Unterm."), a linear template ("Linear"), a circular template with a T7 termination sequence ("T7 Term"), a circular template with a hammerhead ribozyme 3'-rRNA gene modification ("HH Ribo") and a circular template with a HDV ribozyme 3'-rRNA gene modification ("HDV Ribo")] is illustrated.
FIG. 9B depicts RNA gel assays of iSAT reactions containing different types of 23S ribosomal RNA produced from different DNA transcription templates, wherein native 23S RNA alone, S150 extract alone, and iSAT reactions containing different 23S ribosomal DNA transcription templates [a circular template without a termination sequence ("Unterm."), a linear template ("Linear"), a circular template with a T7 termination sequence ("T7 Term"), a circular template with a hammerhead ribozyme 3'-rRNA gene modification ("HH Ribo") and a circular template with a HDV ribozyme 3'-rRNA gene modification ("HDV Ribo")] is illustrated.
Figure 9:
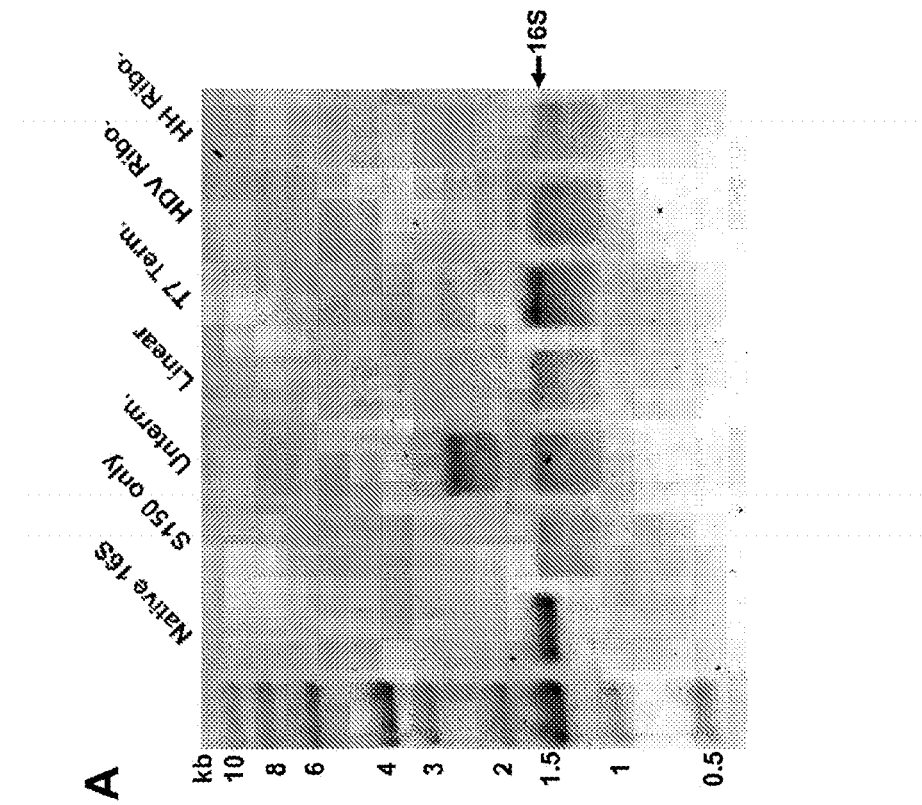

These experiments demonstrate the impact of 3' gene modifications on iSAT activity and specifically on rRNA transcription within the reactions. As expected, linearized plasmids are not viable in iSAT reactions, as protein production remained near background levels and no rRNA production was observed on the gel. Other modifications, however, showed improvement over the original unterminated constructs. Addition of T7 terminators improved luciferase production by 2.4-fold, and the RNA gel indicates a decrease of over-transcribed bands and more RNA near the correct 16S and 23S sizes (1.5 and 2.9 kb, respectively; see FIGS. 8C and 11F). Meanwhile, inclusion of 3' HDV or HH ribozymes also resulted in increased luciferase production: 1.5-fold and 4.8-fold (FIG. 8A). The RNA gel shows that iSAT using the ribozyme constructs lack a band appearing near 2.7 kb that appears for iSAT with unterminated and T7 terminated constructs (see FIGS. 8C and 11F). This band appears to be over-transcribed 16S rRNA (FIG. 9A). This band is decreased for the terminated construct, indicating that the T7 terminator is not capable of halting all 16S transcription (FIGS. 8C and 9A). The reactions using ribozyme constructs, however, lack this band and now show additional bands around 1.3 kb (FIG. 9A). This result implies that the ribozymes are able to cleave over-transcribed rRNA to the correct size, as intended. However, the HDV ribozyme constructs are out-performed by the T7 terminator constructs (FIG. 8). This may be the result of poor cleavage efficiency or slow kinetics. The resulting 3' end with uncleaved HDV ribozyme may be detrimental to ribosome activity. Meanwhile, the HH ribozyme constructs clearly out-perform the T7-terminated constructs (FIGS. 8 and 9), suggest superior cleavage efficiency or kinetics associated with this ribozyme. This result is consistent with literature regarding the kinetics of the two ribozymes.

Example 6

Concentration Optimization of Transcriptional Components Improves 70S iSAT Activity RNA gels of iSAT reactions show that 16S and 23S rRNA transcription are not stoichiometrically balanced (FIG. 8C). The relative sizes suggest that 23S rRNA should be 1.9-fold more intense than an equimolar amount of 16S rRNA. In addition, iSAT reactions use T7 RNAP for transcription of both rRNA and reporter mRNA. Therefore, we asked if 70S iSAT activity could be further improved through balancing transcription of rRNA and mRNA by adjusting plasmid and RNAP concentrations.

Figure 10:
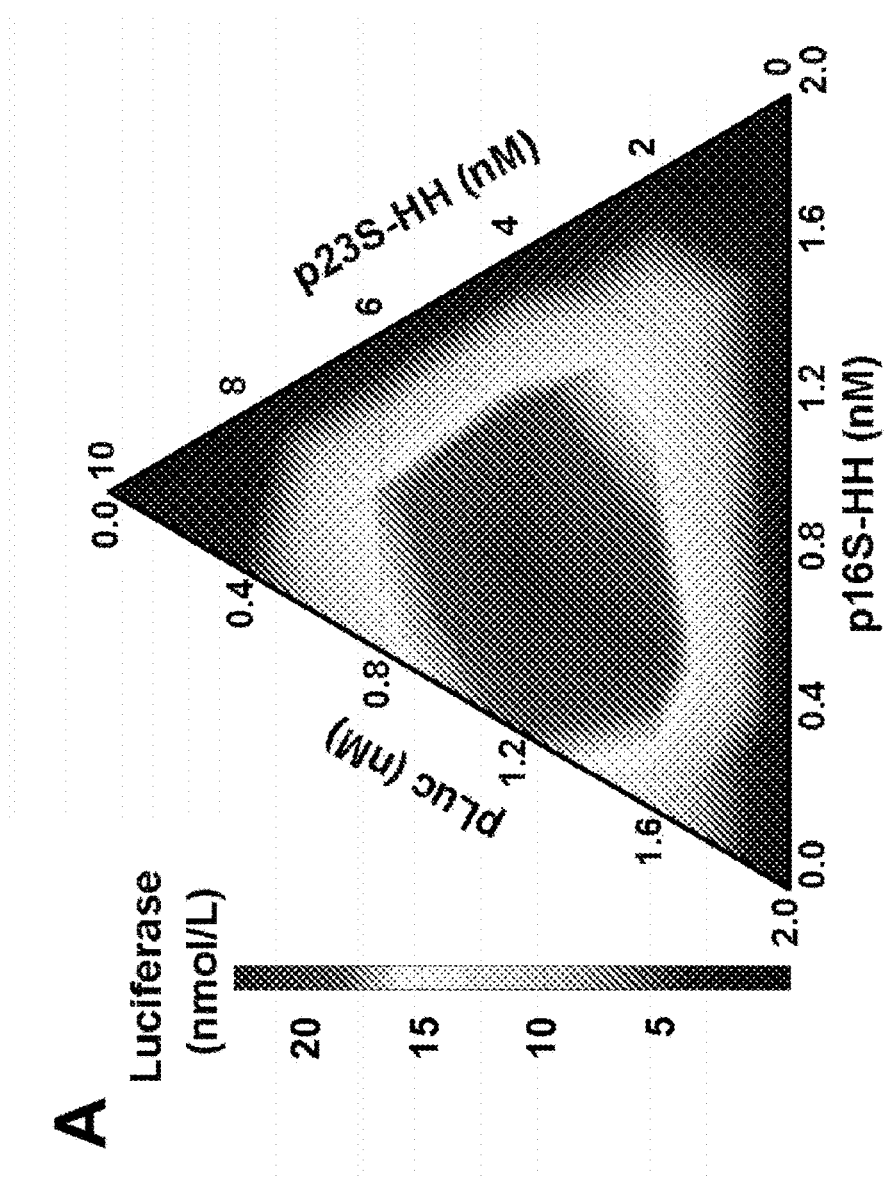
FIG. 10A depicts variations in luceriferase activity as a function of varying three different DNA transcription templates that encode luciferase mRNA (pK7Luc [SEQ ID NO: 1]), 16S rRNA (p16S-HH) [SEQ ID NO: 18]), and 23S rRNA (p23S-HH [SEQ ID NO: 20]).
FIG. 10B depicts variations in luceriferase activity as a function of varying T7 RNAP concentration and total DNA transcription template concentration.
FIG. 10C depicts variation in luciferase activity in iSAT activity assays using assembled ribosomes constructed from rRNAs transcribed from DNA transcription templates encoding 16S rRNA (p16S-HH) [SEQ ID NO: 18]), and 23S rRNA (p23S-HH [SEQ ID NO: 20]), wherein the TP70 concentration is varied from 0 to 300 nmol/L.
FIG. 10D depicts three different iSAT activity assays for luciferase expression using iSAT ribosomes constructed from DNA transcription templates encoding 16S rRNA (p16S-HH) [SEQ ID NO: 18]), and 23S rRNA (p23S-HH [SEQ ID NO: 20]), wherein the original conditions ("Initial Conditions"), conditions optimized for DNA template concentration ("Plasmid Ratio Opt.") and conditions optimized for both DNA template concentration and T7 RNAP concentration ("[T7 RNAP]/[Plasmid] Opt.").
Figure 10:
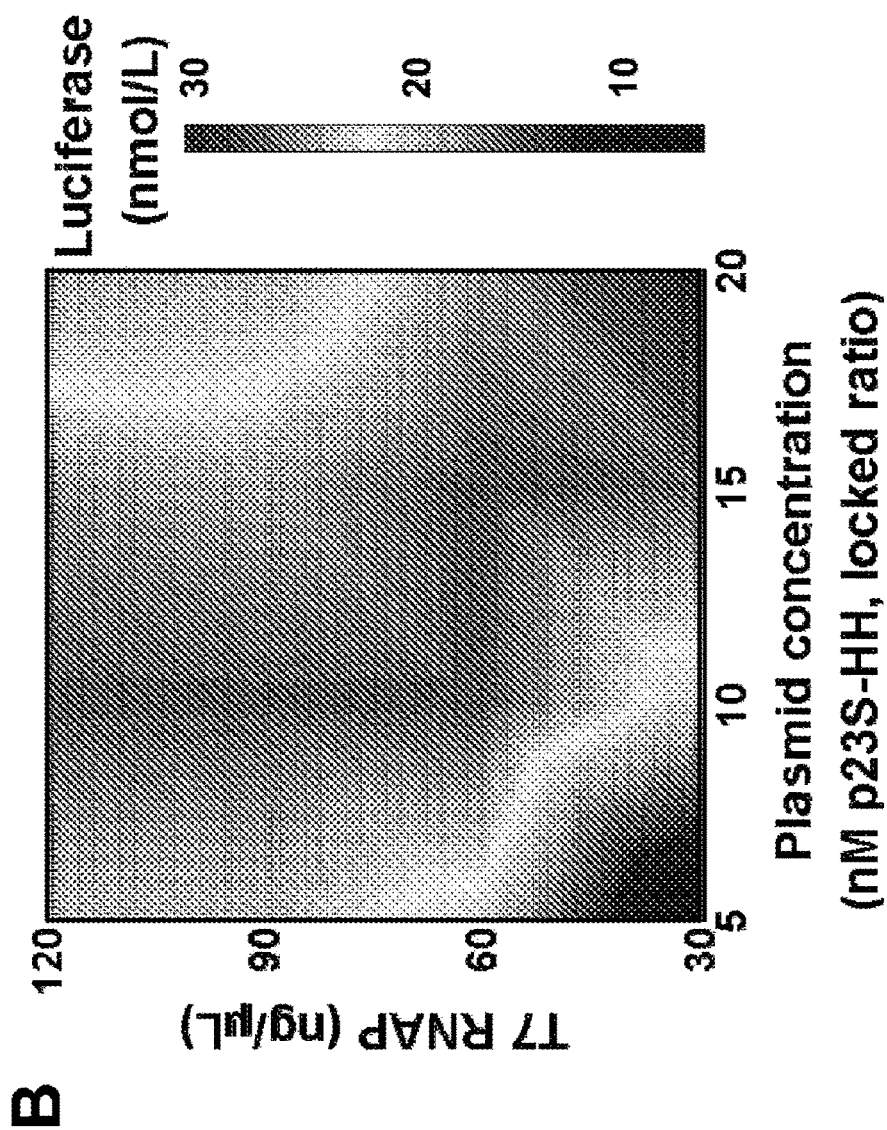

Using the hammerhead ribozyme constructs encoding 16S and 23S rRNA, 70S iSAT reactions were performed with various concentrations of pK7Luc, p16S-HH [SEQ ID NO: 18], and p23S-HH [SEQ ID NO: 20] (FIG. 10A). Experiment was performed with a simplex lattice design to determine the optimal ratio of the three plasmids. Based on FIG. 8C indicating low levels of 23S rRNA transcription, p23S-HH concentration ranged from 0 to 10 nM, while pK7Luc and p16S-HH concentrations ranged from 0 to 2 nM. From this experiment, the concentration ratio of pK7Luc to p16S-HH to p23S-HH was set at 2:1:10. Based on this ratio, plasmid and T7 RNAP concentrations were varied combinatorial to determine optimal concentrations for 70S iSAT activity (FIG. 10B). Activity was highest for plasmid mix at 20 nM p23S-HH and 30 ng/µL T7 RNAP, though FIG. 10B shows inversely varying these concentrations also results in high reaction activity. This suggests that transcriptional rate in iSAT reactions must be balanced for optimal luciferase synthesis over 4 hours.

Figure 10C:
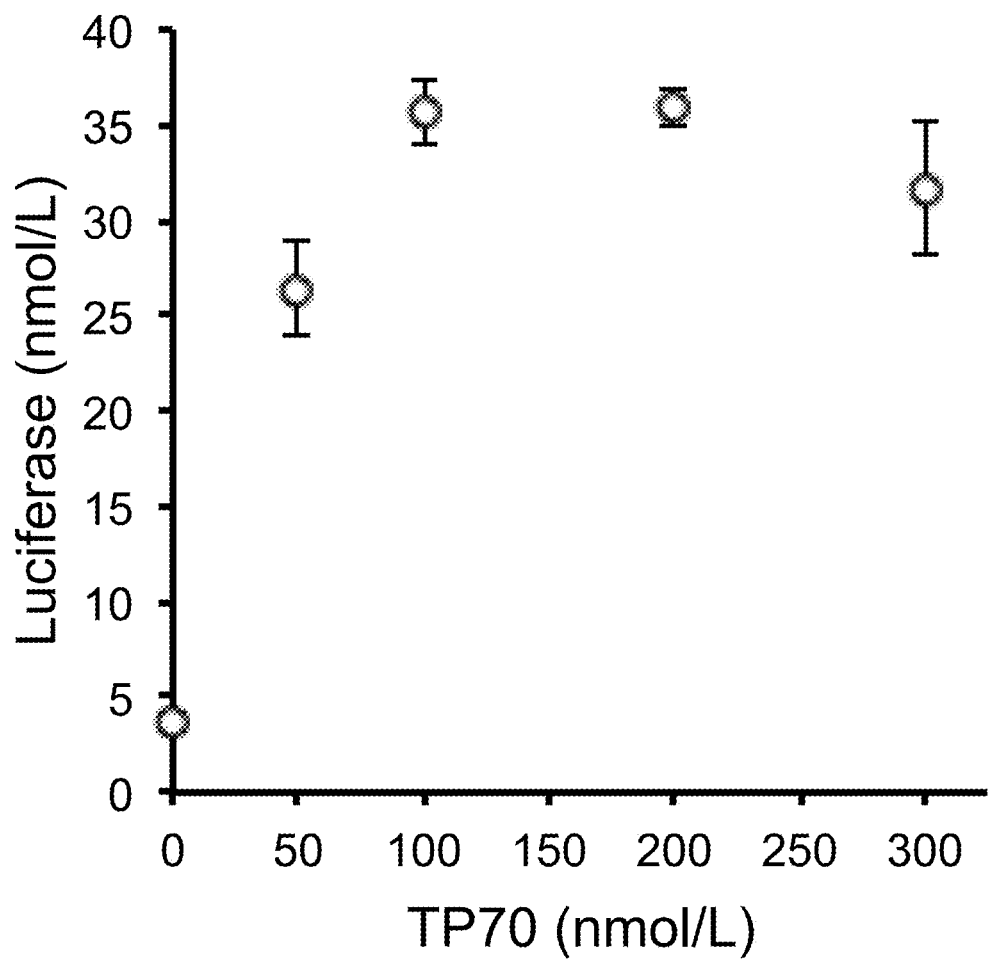
Figure 10D:
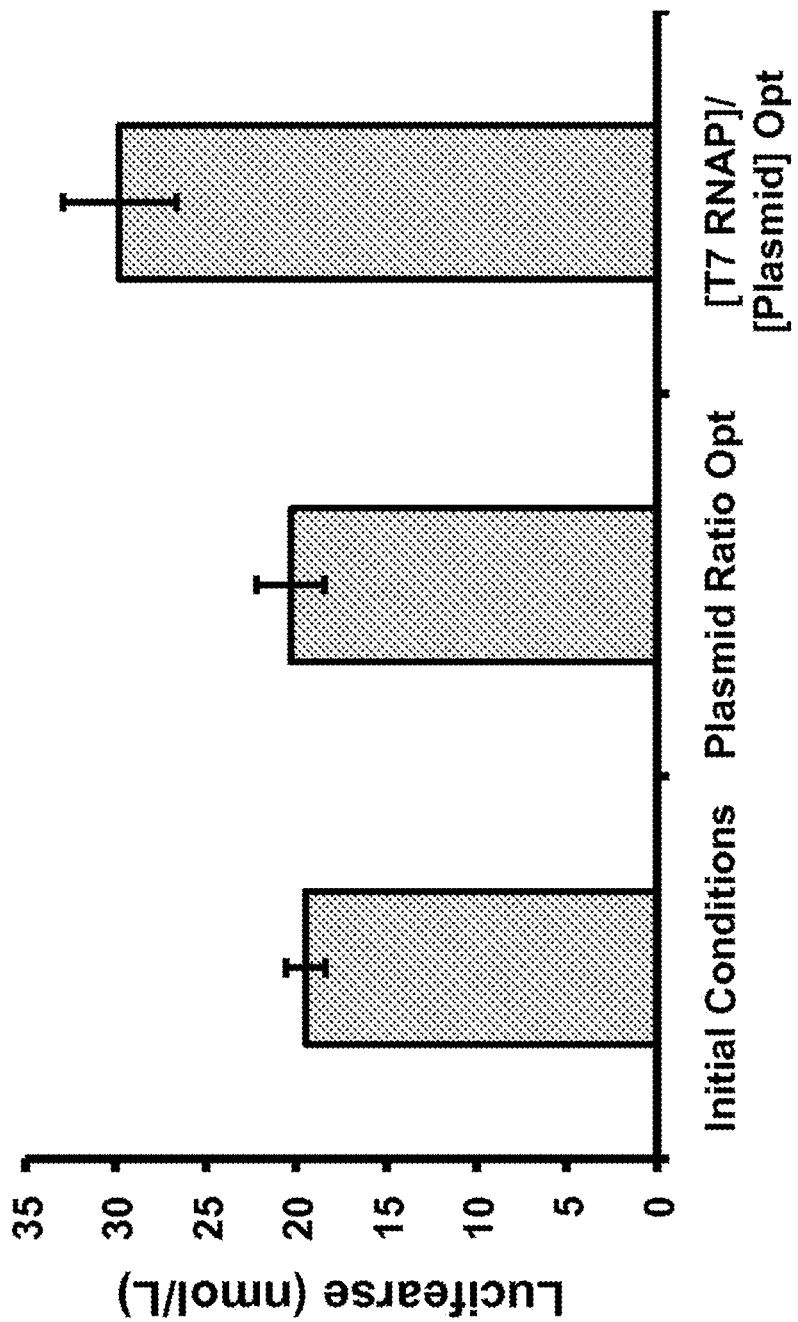

To follow up these results, TP70 concentration was varied to determine if more ribosomes could now be assembled with improved transcriptional balance (FIG. 10C). However, in setting up the reactions, it was observed that addition of TP70 to S150 extract beyond the final reaction concentration of 0.1 uM resulted in precipitation. S150 and TP70 use similar storage buffers, so this result would seem to suggest some aggregation that occurs upon mixing. The peak shown in FIG. 10C at 0.1 uM suggests that it is not possible to assemble more than 0.1 uM ribosomal equivalents in the current reaction. FIG. 10D shows a 53% overall improvement in 70S iSAT activity from the balancing of transcriptional component concentrations.

Example 7

T7-promoted Native rRNA Operon can be Utilized in iSAT Reaction

Figure 11:
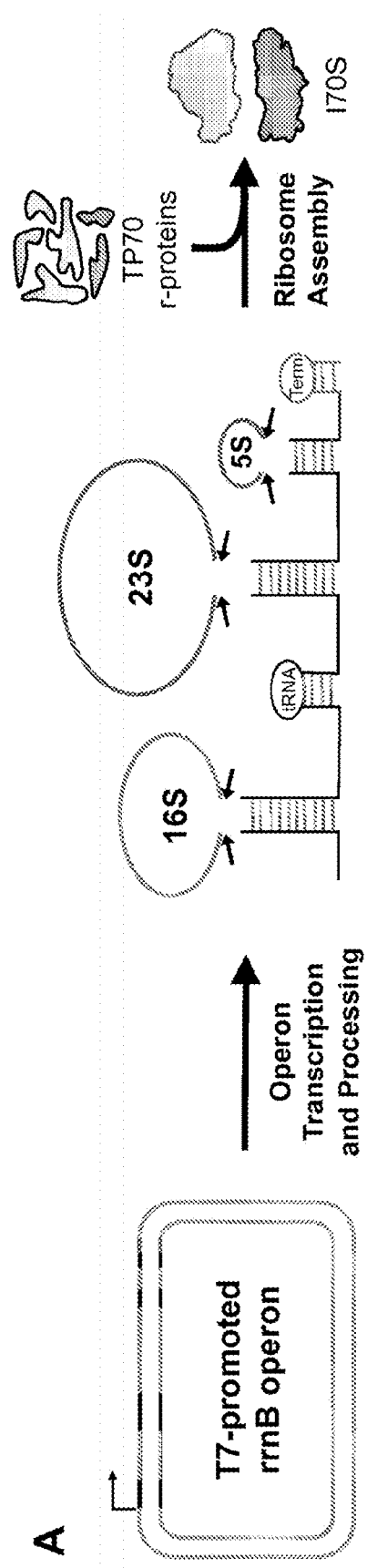
FIG. 11A depicts an rrnB operon under the transcriptional control of T7 RNAP promoter and termination sequences.
FIG. 11B depicts results of iSAT reactions of luceriferase expression under various conditions wherein DNA expression templates encoding the luciferase mRNA ("pK7Luc" [SEQ ID NO: 1]) and the ribosomal RNA operon ("pT7rrnB" [SEQ ID NO: 26]) were varied.
FIG. 11C depicts results of iSAT reactions of luciferase expression under various conditions wherein total DNA expression template concentration and T7 RNAP concentration were varied.
FIG. 11D depicts different iSAT activity assays for luciferase expression using iSAT ribosomes constructed from the ribosomal RNA operon ("pT7rrnB" [SEQ ID NO: 26]), wherein TP70 concentration is varied from 0 to 300 nmol/L.
FIG. 11E depicts the luciferase expression in iSAT activity assays using assembled ribosomes from rRNAs encoded by either separate rDNA transcription templates ("p16S-HH/p23S-HH") or a transcription template encoding the rrnB operon ("pT7rrnB").
FIG. 11F depicts an RNA gel showing the quality of rRNAs produced from iSAT reactions containing the rDNA expression template, pT7rrnB [SEQ ID NO: 26]) compared with constituted ribosomes containing native rRNAs.
Figure 11:
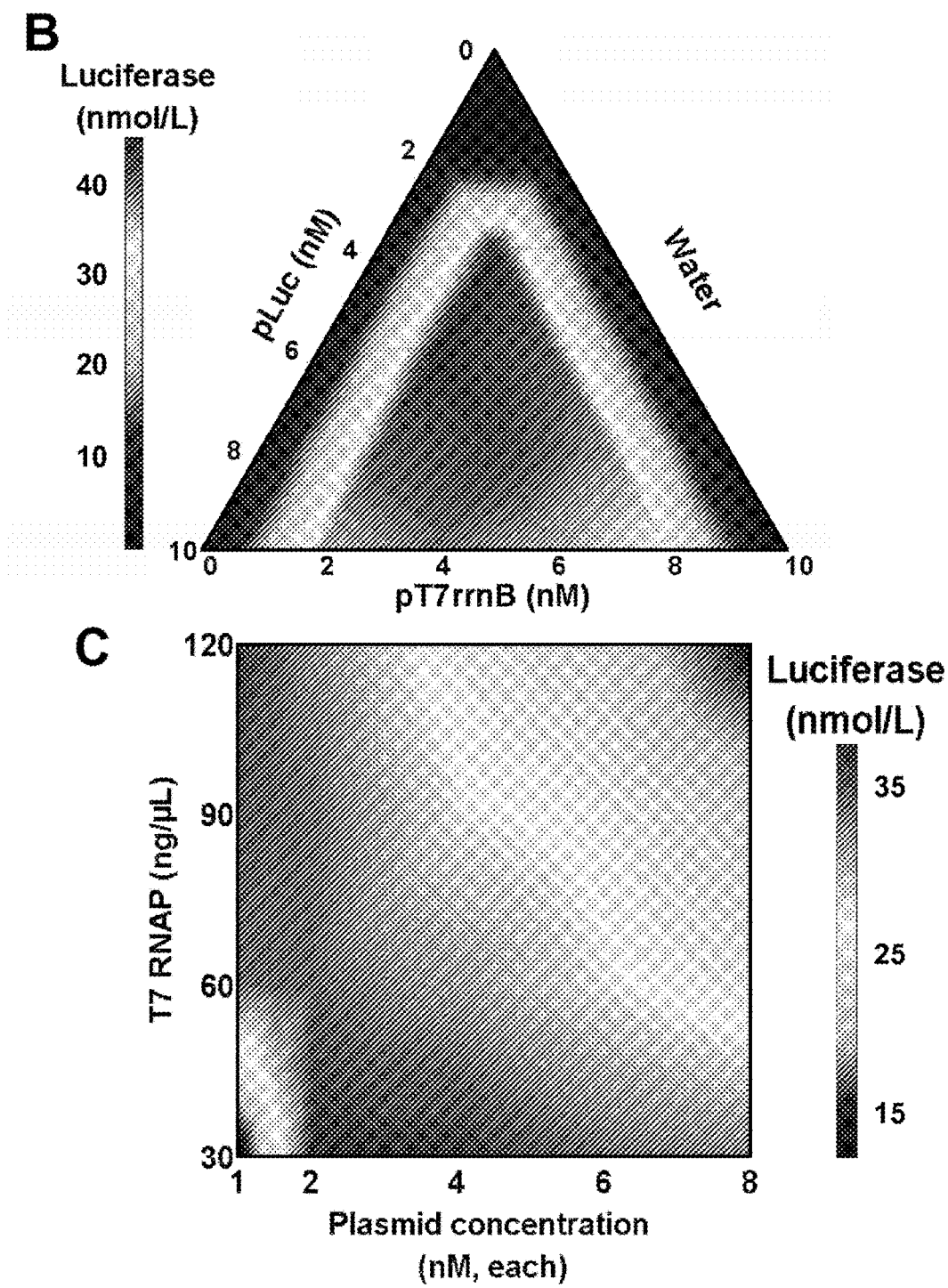
Figure 11:
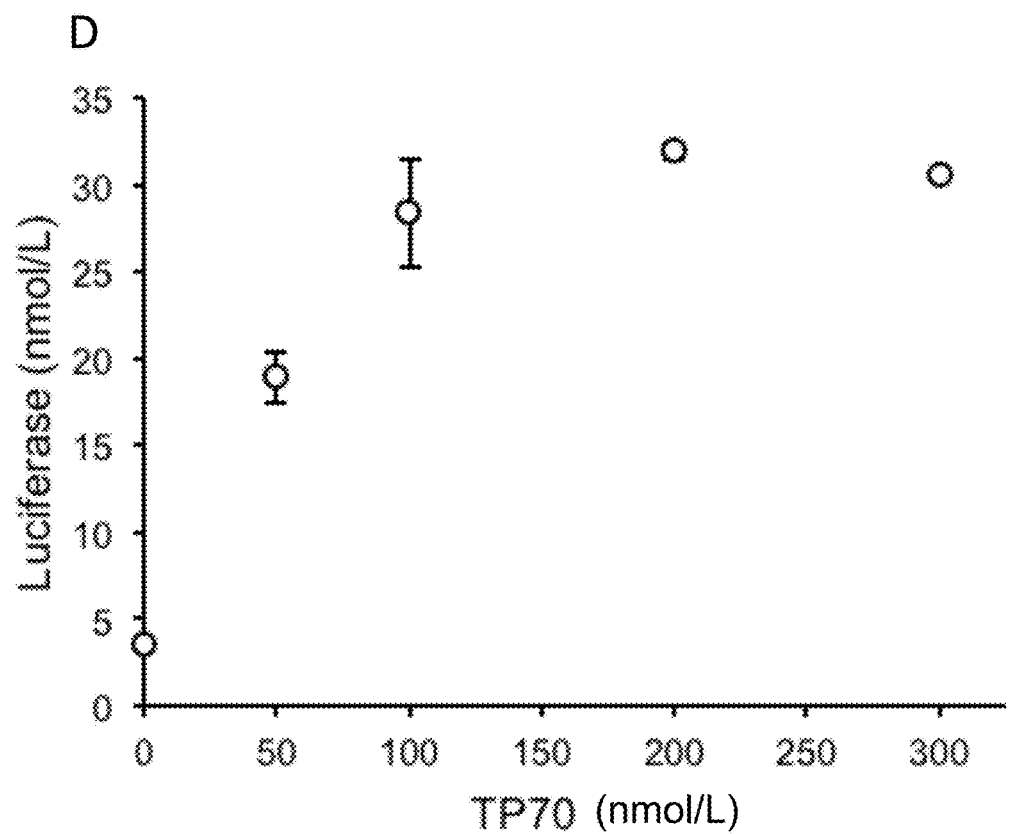
Figure 11:
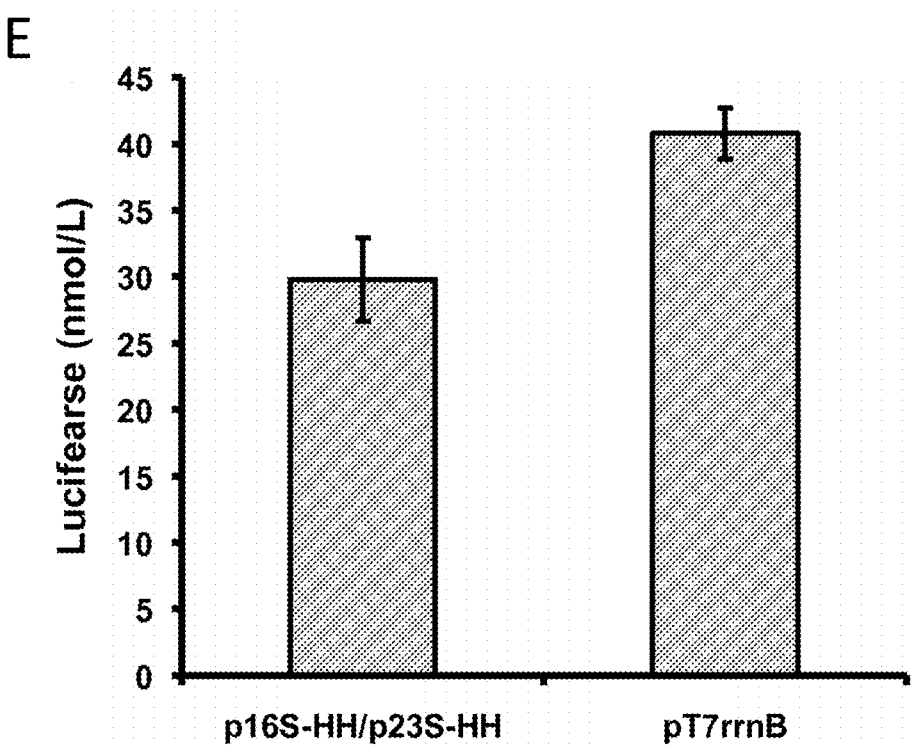
Figure 11:
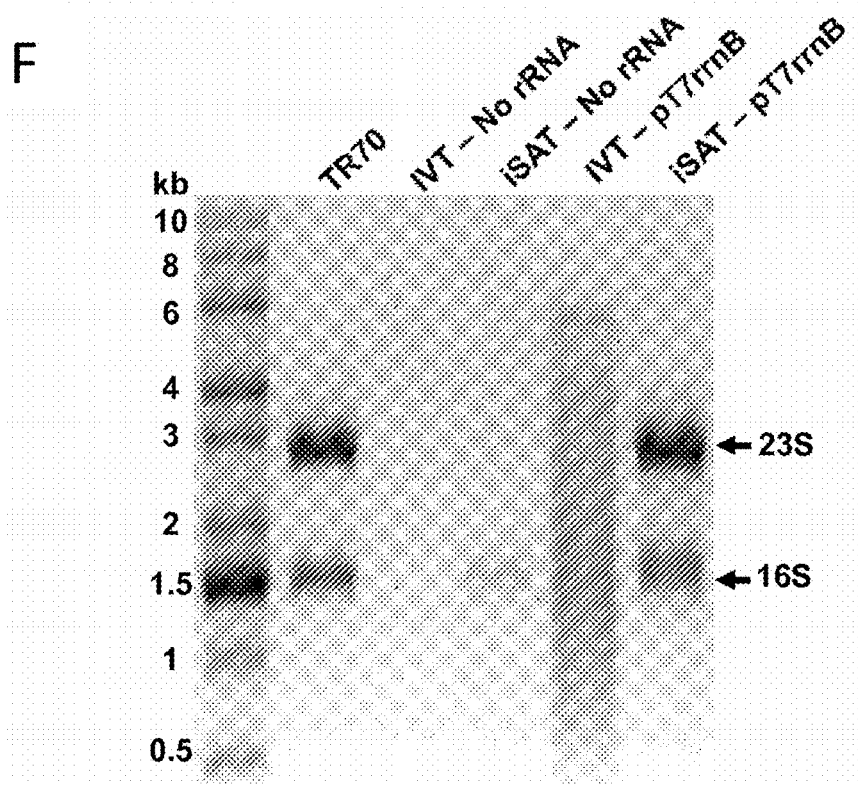

Since in vivo ribosome biogenesis utilizes operon co-transcription of the 3 rRNA molecules, we asked if a T7-promoted rRNA operon would be active in an iSAT reaction. The rrnB operon located on a plasmid was altered to replace a native promoter with the T7 promoter. A T7 terminator follows the operon to address concerns of excess transcription. The resulting construct, pT7rrnB [SEQ ID NO: 26], was used in iSAT reactions in place of individual plasmids encoding 16S and 23S rRNA (FIG. 11A). This approach immediately addresses concerns of stoichiometric balance, as complete operon transcription generates one molecule each of 5S, 16S, and 23S rRNA. However, this approach depends on the presence and activity of RNases in S150 extract that are required for processing of the operon into the individual rRNA molecules based on the folding of intergenic regions into stem loops.

Initial 70S iSAT reactions using the pT7rrnB construct [SEQ ID NO: 26] resulted in luceriferase protein expression. From this result, component concentrations were optimized for operon-based iSAT reactions as for the p16S-HH/p23S-HH iSAT system. Optimization of the plasmid ratio showed a 1:1 ratio of pK7Luc to pT7rrnB resulted in the highest activity levels (FIG. 11B). Optimization of the plasmid and T7 RNAP concentrations (FIG. 11C) showed a trend similar to that seen for individual plasmids (FIG. 10B); high plasmid concentrations should be balanced by low T7 RNAP concentration, and vice versa. Optimization of TP70 concentration for operon-based iSAT reactions showed insignificant difference between 0.1 and 0.2 µM TP70 (FIG. 11D), likely due to protein stability limitations from mixing TP70 with S150 extract. The overall activity improvement of the optimized operon-based iSAT system is approximately 39% compared to the optimized iSAT system using p16S-HH and p23S-HH (FIG. 11E)

To assess if operon rRNA was processed into individual rRNA molecules, iSAT reactions were incubated without reporter plasmid and the RNA was purified for gel electrophoresis (FIG. 11F). Parallel reactions using S150 extract buffer in place of extract were performed in order to attribute any RNA processing to S150 enzymes or RNA self-cleavage. The resulting gel shows a defined IVT band at 5.5 kb, or approximately the size of the full, unprocessed operon, while the iSAT reaction shows strong bands at 16S and 23S rRNA size. The 16S rRNA band notably includes smearing larger than the 16S band of the control, suggesting the possible presence of precursor 16S rRNA resulting from insufficient processing. The 23S rRNA band from the iSAT reaction more closely matches its corresponding control band, both in size and intensity. The intensity of the rRNA bands more closely resemble a stoichiometric balance, as expected for transcription from the rrnB operon.

Figure 12:
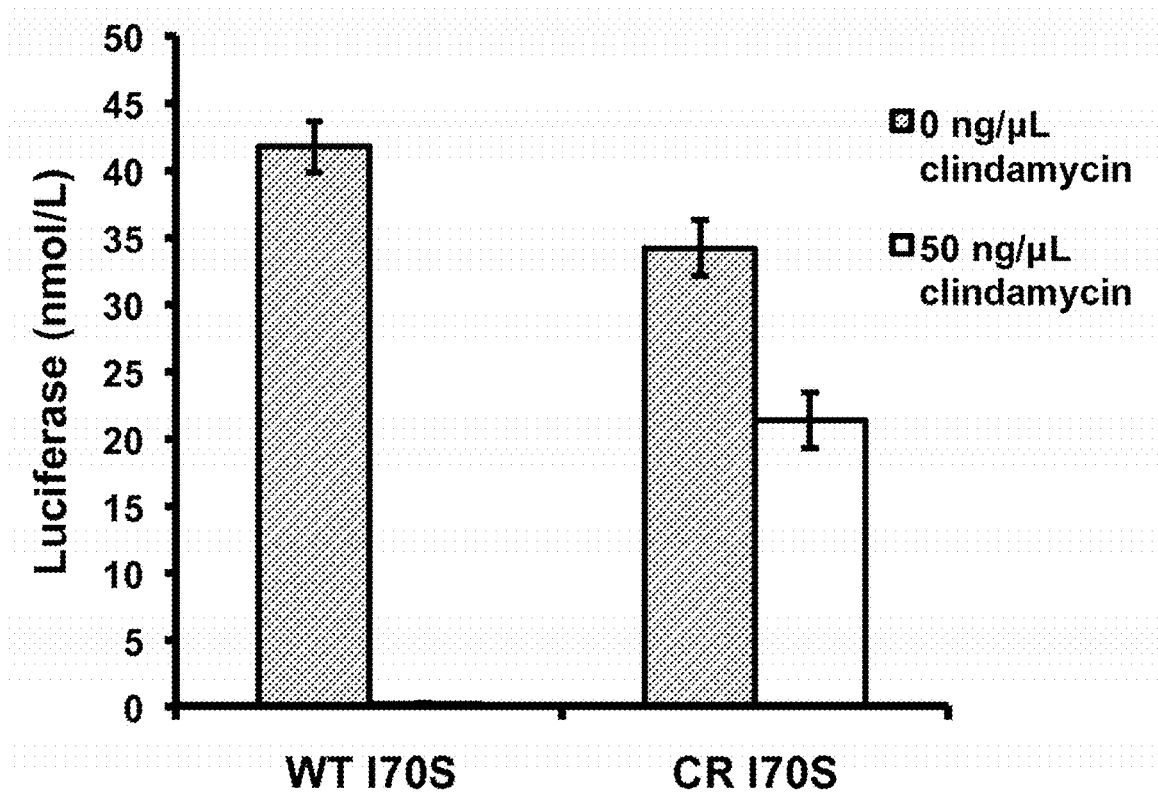
FIG. 12 depicts results of iSAT assays of luciferase expression as a function of added antibiotic (clindamycin), wherein the iSAT reactions were programmed with DNA transcription templates that encode a wild-type rRNA operon (clindamycin-sensitive) or a clindamycin-resistant, variant rRNA operon (A2058U mutation in the 23S rRNA coding sequence [SEQ ID NO: 28]).

The iSAT technology can be used to introduce rRNA mutations for assembly of ribosomes with altered function. This approach was used to introduce resistance to the antibiotic clindamycin through the 23S rRNA mutation A2058U. The same approach was applied to introduce the A2058U mutation into the 23S rRNA gene of pT7rrnB. The construct conveying clindamycin resistance, pT7rrnB-CR [SEQ ID NO: 28], was used in 70S iSAT reactions with and without clindamycin. At 50 ng/µL clindamycin, ribosomes derived from transcription of pT7rrnB-CR retained 51.3% activity, where as ribosomes derived from transcription of pT7rrnB retained 0.5% activity (FIG. 12). This result confirms that ribosome activity in iSAT reactions can be attributed to newly-assembled 50S subunits, and demonstrates the potential for ribosomes engineering by mutating the pT7rrnB construct.

Example 8

Comparison of 70S iSAT Ribosomes to Assembled or Purified 70S Ribosomes

Figure 13:
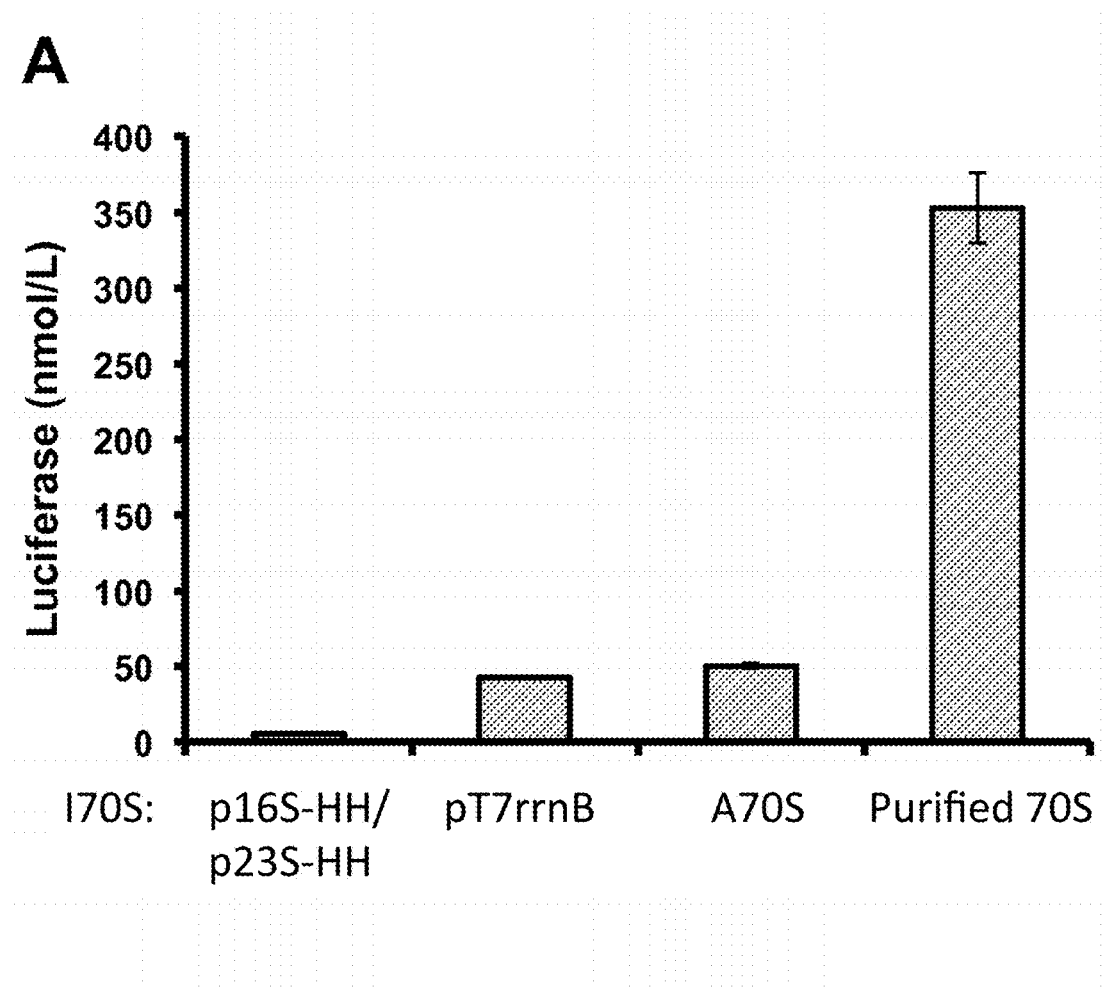
FIG. 13A depicts luciferase protein synthesis in iSAT reactions that contain ribosomes assembled from 16S and 23S rRNAs transcribed in vitro from either separate transcription templates ("p16S-HH/p23S-HH") or a single transcription template encoding a modified rrnB operon ("pT7rrnB") or iSAT reactions that contain either reassembled ribosomes from purified rRNAs and r-proteins ("A70S") or purified native ribosomes ("Purified 70S").
FIG. 13B depicts superfolder GFP (sfGFP) fluorescence from iSAT reactions that contain ribosomes assembled from 16S and 23S rRNAs transcribed in vitro from a single transcription template encoding a modified rrnB operon ("pT7rrnB") or iSAT reactions that contain either reassembled ribosomes from purified rRNAs and r-proteins ("A70S") or purified native ribosomes ("Purified 70S").
Figure 13:
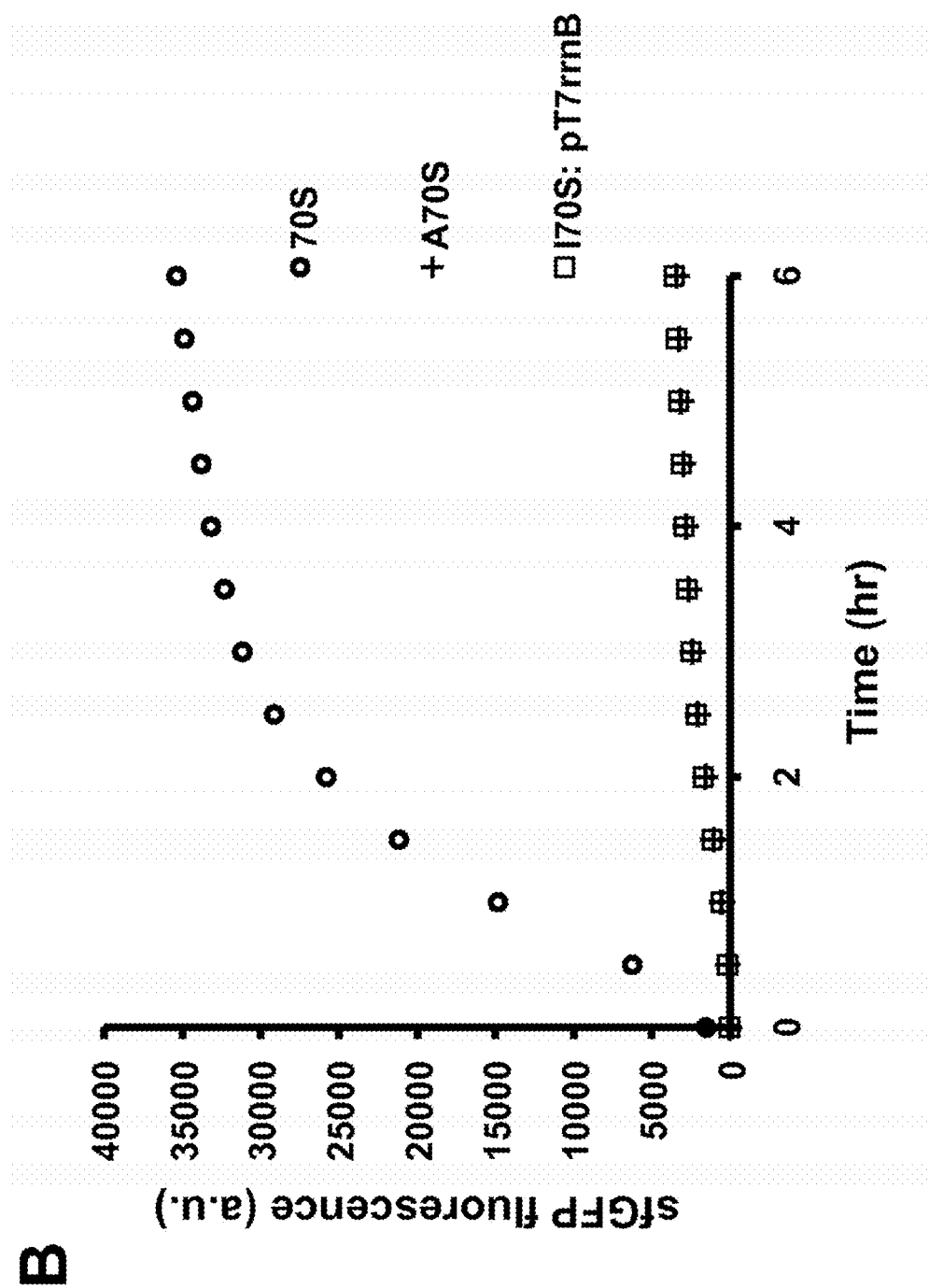

Activity of ribosomes created in 70S iSAT reactions depends on both transcriptional and translational activity. To separate the limitations associated with each of these two activities, 70S iSAT ribosomes (I70S) were compared against ribosomes assembled in S150 extract from TP70 and purified native total rRNA of 70S ribosomes (TR70) (A70S) and purified intact native 70S ribosomes. To maintain equivalent mRNA transcript levels, pT7rrnB was included in A70S and purified 70S reactions, as pilot studies showed no effect from excess rRNA. Luciferase synthesis by I70S and A70S were 42.7 and 51.1 nmol/L (FIG. 13A), suggesting transcribed rRNA and purified rRNA are of similar quality. Purified 70S ribosomes, meanwhile, resulted in luciferase synthesis of 353 nmol/L. These trends are reflected in sfGFP production (FIG. 13B). The 8- to 10-fold difference in activity between I70S and purified 70S ribosomes suggests that 70S iSAT reactions are limited by low efficiency of ribosome assembly rather than transcriptional efficiency.

Example 9

Addition of Macromolecular Crowding and Reducing Agents to iSAT Reactions

The effects of macromolecular crowding and reducing agents on iSAT protein synthesis activity were assessed by addition of the necessary components to the premix solution used in iSAT reactions. All reaction volumes were maintained at 15 µL, by altering the volume of water used in each reaction. For macromolecular crowding agents, polyethylene glycol (PEG) of three different molecular weights (3350, 6000, or 8000 Da), Ficoll® 400, and glycerol were tested at reaction concentrations of 1, 2, and 4% w/v to determine the concentrations of greatest iSAT activity. Concentrations were capped at 4% due to solubility and volume restrictions. Similarly, the reducing agents β-mercaptoethonal (BME) and dithiothreitol (DTT) were tested in iSAT reactions: BME at 3, 6, and 9 mM and DTT at 1, 2, 5, and 10% w/v. Finally, optimum PEG8000 and DTT concentrations were combined in the same reaction to assess any synergistic effect of the two additives on iSAT activity. Effect of all additives in iSAT reactions were assessed by mRFP1 production over time as described above. All additives were purchased from Sigma.

Figure 14:
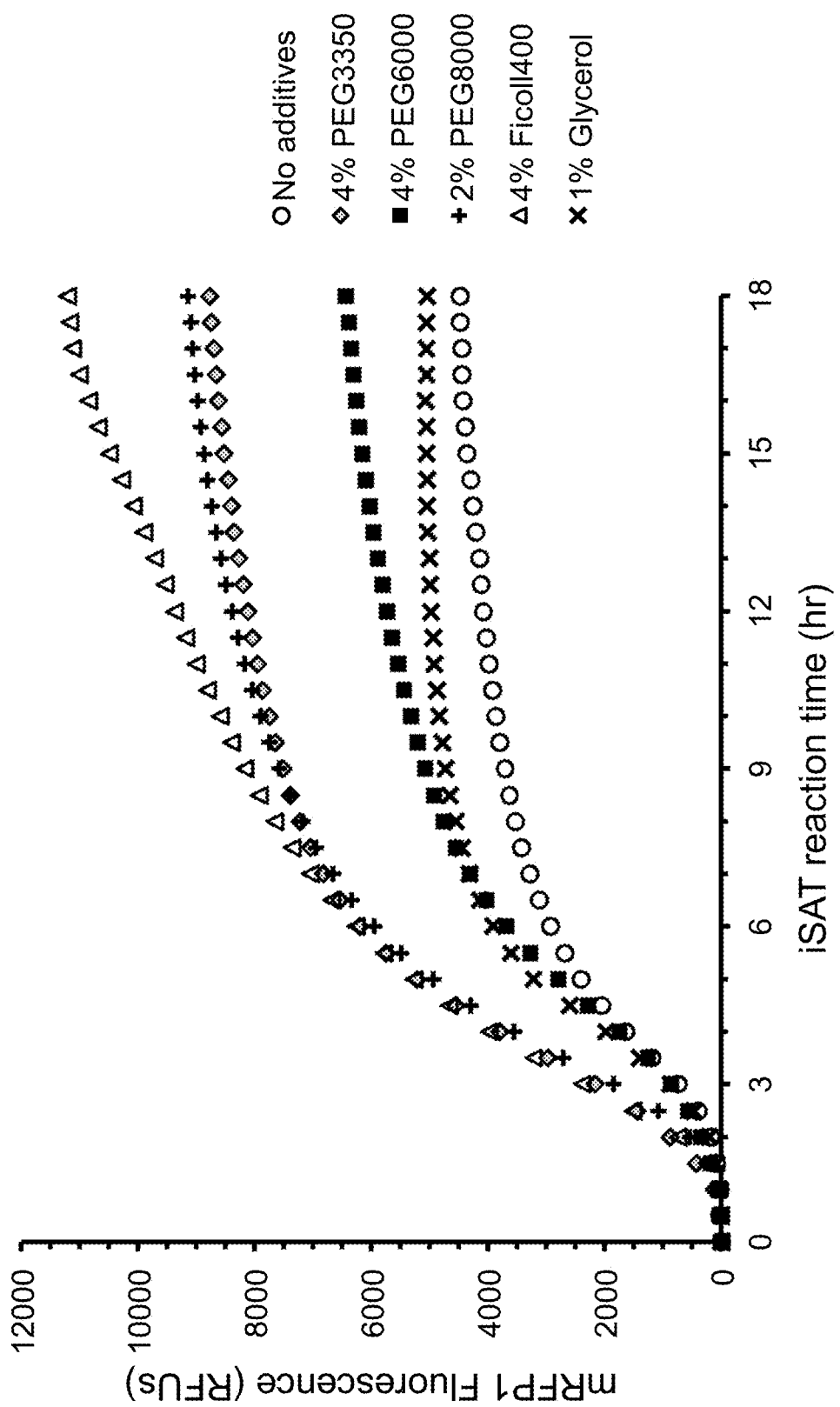
FIG. 14 illustrates the effect of molecular crowding agents on iSAT protein synthesis activity over time.

FIG. 14 illustrates the effect of macromolecular crowding agents on iSAT protein synthesis activity over time. The iSAT reactions were prepared with the indicated final concentrations of crowding agents PEG3350, 6000, or 8000; Ficoll® 400; or glycerol. Shown are the reactions of greatest activity found by varying the concentration of each crowding agent. Although readings were taken at 5 min intervals from 0-8 hours, only 30 min time points are shown for clarity. All five crowding agents resulted in increases in iSAT protein synthesis activity.

Figure 15:
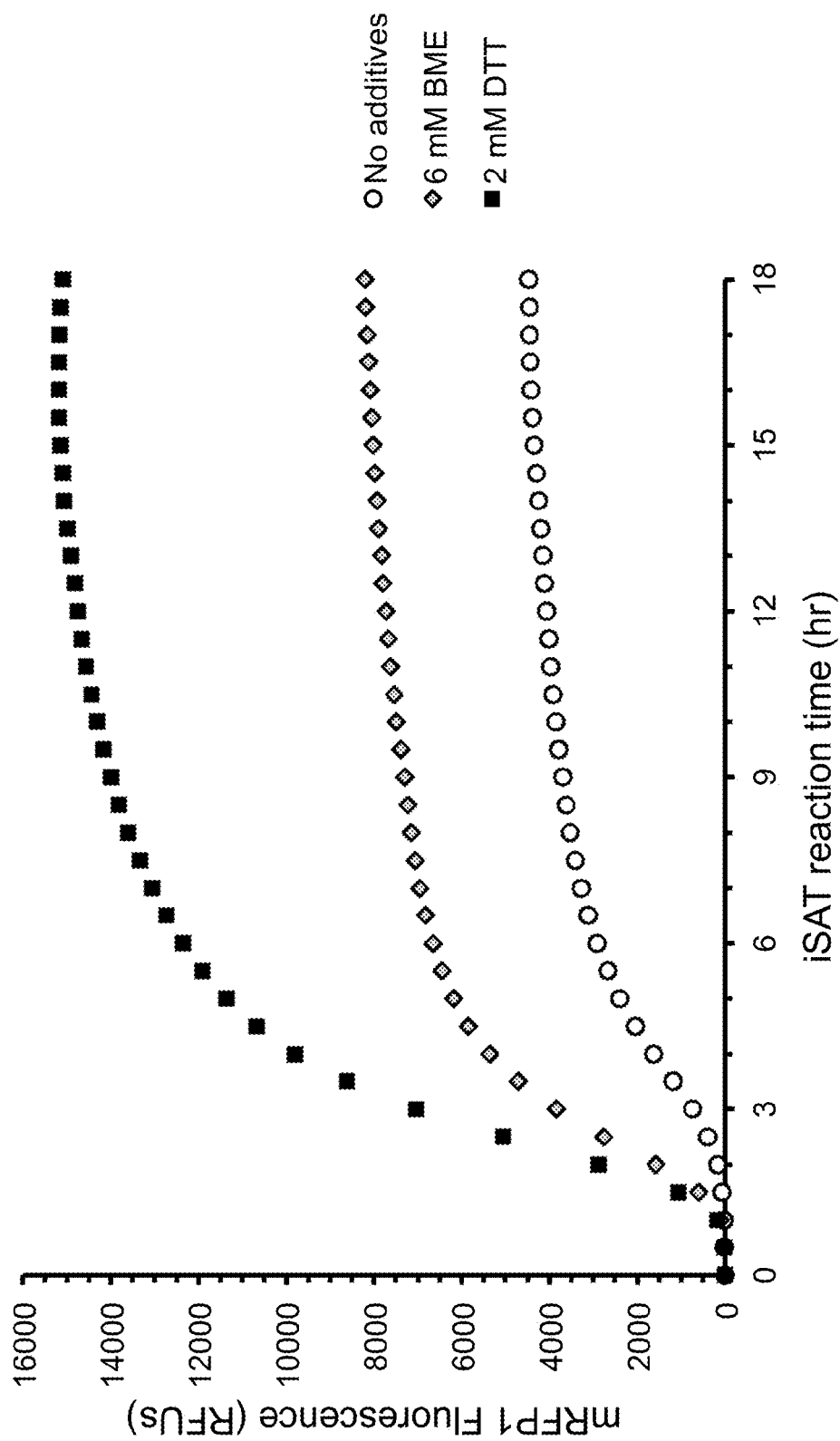
FIG. 15 illustrates the effect of reducing agents on iSAT protein synthesis activity over time.

FIG. 15 illustrates the effect of reducing agents on iSAT protein synthesis activity over time. The iSAT reactions were prepared with the indicated final concentrations of reducing agents BME or DTT. Shown are the reactions of greatest activity found by varying the concentration of each reducing agent. Although readings were taken at 5 min intervals from 0-8 hours, only 30 min time points are shown for clarity. Both reducing agents resulted in increases in iSAT protein synthesis activity.

Figure 16:
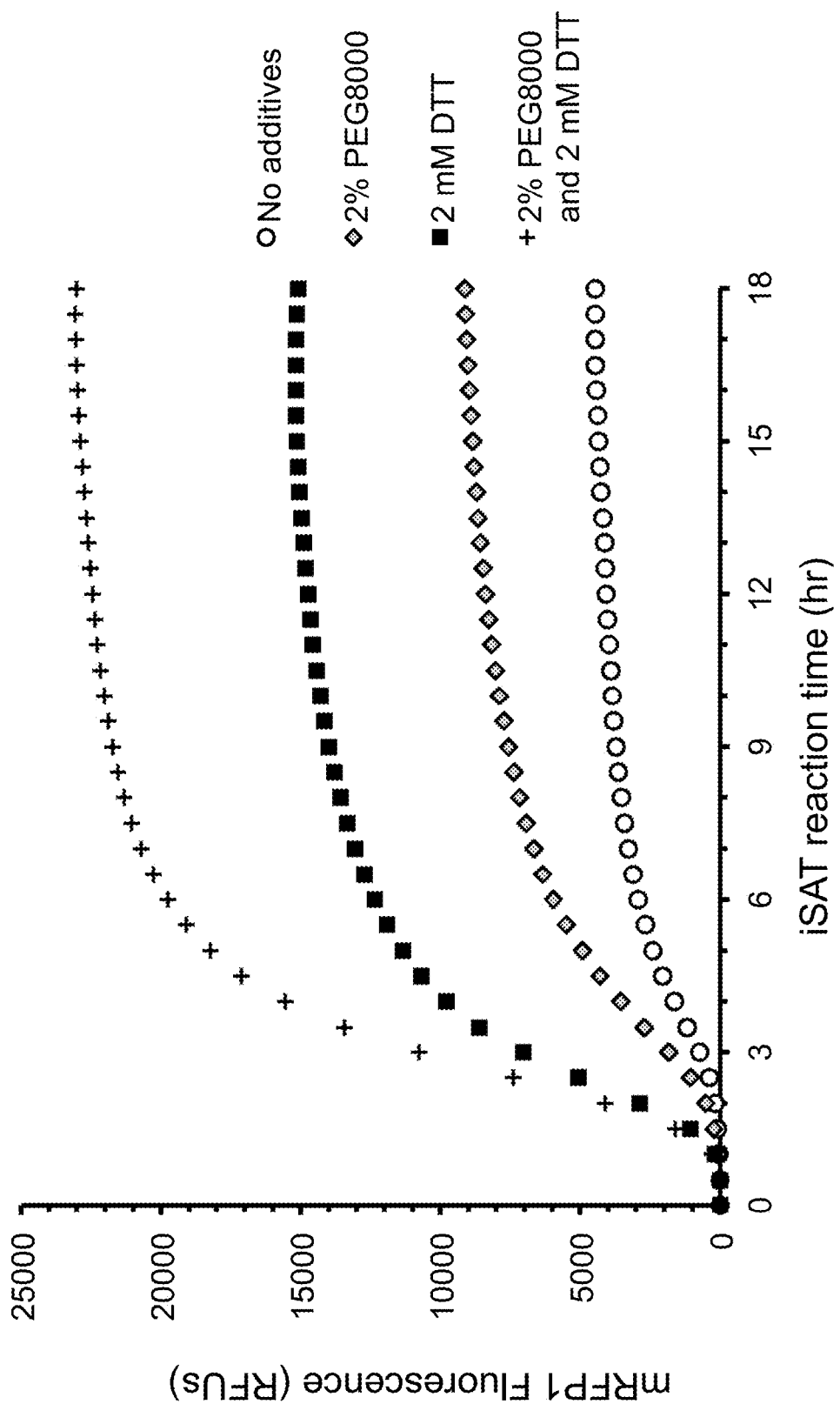
FIG. 16 illustrates the effect of PEG8000 and/or DTT on iSAT protein synthesis activity over time.

FIG. 16 illustrates the effect of PEG8000 and/or DTT on iSAT protein synthesis activity over time. The iSAT reactions were prepared with the indicated final concentrations of PEG8000 and DTT. Although readings were taken at 5 min intervals from 0-8 hours, only 30 min time points are shown for clarity. The combination of PEG8000 and DTT showed further improvement in iSAT protein synthesis activity versus either component individually, suggesting different mechanisms of action for these components on the iSAT reaction.

TABLE 6

Sequences used in this disclosure.

| Sequence Description [SEQ ID NO: __] | Nucleotide or Amino Acid Sequence |
|---|---|
| pK7Luc DNA [SEQ ID NO: 1] | TCGACGGATCGTTCCACTGAGCGTCAGACCCCGTAGAAAAGATCA<br>AAGGATCTTCTTGAGATCCTTTTTTTCTGCGCGTAATCTGCTGCTTG<br>CAAACAAAAAAACCACCGCTACCAGCGGTGGTTTGTTTGCCGGAT<br>CAAGAGCTACCAACTCTTTTTCCGAAGGTAACTGGCTTCAGCAGAG<br>CGCAGATACCAAATACTGTCCTTCTAGTGTAGCCGTAGTTAGGCCA<br>CCACTTCAAGAACTCTGTAGCACCGCCTACATACCTCGCTCTGCTA<br>TCCTGTTACCAGTGGCTGCTGCCAGTGGCGATAAGTCGTGTCTT<br>ACCGGGTTGGACTCAAGACGATAGTTACCGGATAAGGCGCAGCG<br>GTCGGGCTGAACGGGGGGTTCGTGCACACAGCCCAGCTTGGAGC<br>GAACGACCTACACCGAACTGAGATACCTACAGCGTGAGCATTGAG<br>AAAGCGCCACGCTTCCCGAAGGGAGAAAGGCGGACAGGTATCCG<br>GTAAGCGGCAGGGTCGGAACAGGAGAGCGCACGAGGGAGCTTCC<br>AGGGGGAAACGCCTGGTATCTTTATAGTCCTGTCGGGTTTCGCCA<br>CCTCTGACTTGAGCGTCGATTTTTGTGATGCTCGTCAGGGGGGCG<br>GAGCCTATGGAAAAACGCCAGCAACGCGGCCTTTTTACGGTTCCT<br>GGCCTTTTGCTGGCCTTTTGCTCACATGTTCTTTCCTGCGTTATCC<br>CCTGATTCTGTGGATAACCGTATTACCGCCTTTGAGTGAGCTGATA<br>CCGCTCGCCGCAGCCGAACGACCGAGCGCAGCGAGTCAGTGAGC<br>GAGGAAGCGGAAGAAGCTCGCACGCCAATACGCAAACCGCCTCT<br>CCCCGCGCGTTGGCCGATTCATTAATGCAGCTGGCACGACAGGTT<br>TCCCGACTGGAAAGCGGGCAGTGAGCGCAACGCAATTAATGTGAG<br>TTAGCTCACTCATTAGGCACCCCAGGCTTTACACTTTATGCTTCCG<br>GCTCGTATGTTGTGTGGAATTGTGAGCGGATAACAATTTCACACAG<br>GAAACAGCTATGACCATGATTACGAATTCAGATCTCGATCCCGCGA<br>AATTAATACGACTCACTATAGGGAGACCACAACGGTTTCCCTCTAG<br>AAATAATTTTGTTTAACTTTAAGAAGGAGATATACATATGGAAGACG<br>CCAAAAACATAAAGAAAGGCCCGGCGCCATTCTATCCGCTAGAGG<br>ATGGAACCGCTGGAGAGCAACTGCATAAGGCTATGAAGAGATACG<br>CCCTGGTTCCTGGAACAATTGCTTTTACAGATGCACATATCGAGGT<br>GAACATCACGTACGCGGAATACTTCGAAATGTCCGTTCGGTTGGC<br>AGAAGCTATGAAACGATATGGGCTGAATACAAATCACAGAATCGTC<br>GTATGCAGTGAAAACTCTCTTCAATTCTTTATGCCGGTGTTGGGCG<br>CGTTATTTATCGGAGTTGCAGTTGCGCCCGCGAACGACATTTATAA<br>TGAACGTGAATTGCTCAACAGTATGAACATTTCGCAGCCTACCGTA<br>GTGTTTGTTTCCAAAAAGGGGTTGCAAAAAATTTTGAACGTGCAAA<br>AAAAATTACCAATAATCCAGAAAATTATTATCATGGATTCTAAAACG<br>GATTACCAGGGATTTCAGTCGATGTACACGTTCGTCACATCTCATC<br>TACCTCCCGGTTTTAATGAATACGATTTTGTACCAGAGTCCTTTGAT<br>CGTGACAAAACAATTGCACTGATAATGAACTCCTCTGGATCTACTG<br>GGTTACCTAAGGGTGTGGCCCTTCCGCATAGAACTGCCTGCGTCA<br>GATTCTCGCATGCCAGAGATCCTATTTTTGGCAATCAAATCATTCC<br>GGATACTGCGATTTTAAGTGTTGTTCCATTCCATCACGGTTTTGGA<br>ATGTTTACTACACTCGGATATTTGATATGTGGATTTCGAGTCGTCTT<br>AATGTATAGATTTGAAGAAGAGCTGTTTTTACGATCCCTTCAGGATT<br>ACAAAATTCAAAGTGCGTTGCTAGTACCAACCCTATTTTCATTCTTC<br>GCCAAAAGCACTCTGATTGACAAATACGATTTATCTAATTTACACGA<br>AATTGCTTCTGGGGGCGCACCTCTTTCGAAAGAAGTCGGGGAAGC<br>GGTTGCAAAACGCTTCCATCTTCCAGGGATACGACAAGGATATGG<br>GCTCACTGAGACTACATCAGCTATTCTGATTACACCCGAGGGGGA<br>TGATAAACCGGGCGCGGTCGGTAAAGTTGTTCCATTTTTTGAAGCG<br>AAGGTTGTGGATCTGGATACCGGGAAAACGCTGGGCGTTAATCAG<br>AGAGGCGAATTATGTGTCAGAGGACCTATGATTATGTCCGGTTATG<br>TAAACAATCCGGAAGCGACCAACGCCTTGATTGACAAGGATGGAT<br>GGCTACATTCTGGAGACATAGCTTACTGGGACGAAGACGAACACT<br>TCTTCATAGTTGACCGCTTGAAGTCTTTAATTAAATACAAAGGATAC<br>CAGGTGGCCCCCGCTGAATTGGAGTCGATATTGTTACAACACCCC<br>AACATCTTCGACGCGGGCGTGGCAGGTCTTCCCGACGATGACGC<br>CGGTGAACTTCCCGCCGCCGTTGTTGTTTGGAGCACGGAAAGAC<br>GATGACGGAAAAAGAGATCGTGGATTACGTCGCCAGTCAAGTAAC<br>AACCGCCAAAAAGTTGCGCGGAGGAGTTGTGTTTGTGGACGAAGT<br>ACCGAAAGGTCTTACCGGAAAACTCGACGCAAGAAAAATCAGAGA<br>GATCCTCATAAAGGCCAAGAAGGGCGGAAAGTCCAAATTGTAAGT<br>CGACCGGCTGCTAACAAAGCCCGAAAGGAAGCTGAGTTGGCTGCT<br>GCCACCGCTGAGCAATAACTAGCATAACCCCTTGGGGCCTCTAAA<br>CGGGTCTTGAGGGGTTTTTTGCTGAAAGGAGGAACTATATCCGGA<br>TAACCTCGAGCTGCAGGGCATGCAAGCTTGGCACTGGCCGTCGTT<br>TTACAACGTCGTGACTGGGAAAACCCTGGCGTTACCCAACTTAATC<br>GCCTTGCAGCACATCCCCCTTTCGCCAGCTGGCGTAATAGCGAAG<br>AGGCCCGCACCGATCGCCCTTCCCAACAGTTGCGCAGCCTGAATG<br>GCGAATGCGATTTATTCAACAAAGCCGCCGTCCCGTCAAGTCAGC<br>GTAATGCTCTGCCAGTGTTACAACCAATTAACCAATTCTGATTAGAA<br>AAACTCATCGAGCATCAAATGAAACTGCAATTTATTCATATCAGGAT<br>TATCAATACCATATTTTTGAAAAAGCCGTTTCTGTAATGAAGGAGAA<br>AACTCACCGAGGCAGTTCCATAGGATGGCAAGATCCTGGTATCGG |

TABLE 6-continued

Sequences used in this disclosure.

| Sequence Description [SEQ ID NO: __] | Nucleotide or Amino Acid Sequence |
|---|---|
| | TCTGCGATTCCGACTCGTCCAACATCAATACAACCTATTAATTTCCC CTCGTCAAAAATAAGGTTATCAAGTGAGAAATCACCATGAGTGACG ACTGAATCCGGTGAGAATGGCAAAAGCTTATGCATTTCTTTCCAGA CTTGTTCAACAGGCCAGCCATTACGCTCGTCATCAAAATCACTCGC ATCAACCAAACCGTTATTCATTCGTGATTGCGCCTGAGCGAGACGA AATACGCGATCGCTGTTAAAAGGACAATTACAAACAGGAATCGAAT GCAACCGGCGCAGGAACACTGCCAGCGCATCAACAATATTTTCAC CTGAATCAGGATATTCTTCTAATACCTGGAATGCTGTTTTCCCGGG GATCGCAGTGGTGAGTAACCATGCATCATCAGGAGTACGGATAAA ATGCTTGATGGTCGGAAGAGGCATAAATTCCGTCAGCCAGTTTAGT CTGACCATCTCATCTGTAACATCATTGGCAACGCTACCTTTGCCAT GTTTCAGAAACAACTCTGGCGCATCGGGCTTCCCATACAATCGATA GATTGTCGCACCTGATTGCCCGACATTATCGCGAGCCCATTTATAC CCATATAAATCAGCATCCATGTTGGAATTTAATCGCGGCTTCGAGC AAGACGTTTCCCGTTGAATATGGCTCATAACACCCCTTGTATTACT GTTTATGTAAGCAGACAGTTTTATTGTTCATGATGATATATTTTTATC TTGTGCAATGTAACATCAGAGATTTTGAGACACAACGTGGCTTTGT TGAATAAATCGAACTTTTGCTGAGTTGAAGGATCAGATCACGCATC TTCCCGACAACGCAGACCGTTCCGTGGCAAAGCAAAAGTTCAAAA TCACCAACTGGCCCACCTACAACAAAGCTCTCATCAACCGTGGCT CCCTCACTTTCTGGCTGGATGATGGGCGATTCAGGCCTGGTATG AGTCAGCAACACCTTCTTCACGAGGCAGACCTC |
| Luciferase mRNA [SEQ ID NO: 2] | GGGAGACCACAACGGUUUCCCUCUAGAAAUAAUUUUGUUUAACU UUAAGAAGGAGAUAUACAUAUGGAAGACGCCAAAAACAUAAAGAA AGGCCCGGCGCCAUUCUAUCCGCUAGAGGAUGGAACCGCUGGA GAGCAACUGCAUAAGGCUAUGAAGAGAUACGCCCUGGUUCCUGG AACAAUUGCUUUUACAGAUGCACAUAUCGAGGUGAACAUCACGU ACGCGGAAUACUUCGAAAUGUCCGUUCGGUUGGCAGAAGCUAU GAAACGAUAUGGGCUGAAUACAAAUCACAGAAUCGUCGUAUGCA GUGAAAACUCUCUUCAAUUCUUUAUGCCGGUGUUGGGCGCGUU AUUUAUCGGAGUUGCAGUUGCGCCCGCGAACGACAUUUAUAAUG AACGUGAAUUGCUCAACAGUAUGAACAUUUCGCAGCCUACCGUA GUGUUUGUUCCAAAAAGGGGUUGCAAAAAAUUUUGAACGUGCA AAAAAAAUUACCAAUAAUCCAGAAAAUUAUUAUCAUGGAUUCUAA AACGGAUUACCAGGGAUUUCAGUCGAUGUACACGUUCGUCACAU CUCAUCUACCUCCCGGUUUUAAUGAAUACGAUUUUGUACCAGAG UCCUUUGAUCGUGACAAAACAAUUGCACUGAUAAUGAACUCCUC UGGAUCUACUGGGUUACCUAAGGGUGUGGCCCUUCCGCAUAGA ACUGCCUGCGUCAGAUUCUCGCAUGCCAGAGAUCCUAUUUUUGG CAAUCAAAUCAUUCCGGAUACUGCGAUUUUAAGUGUUGUUCCAU UCCAUCACGGUUUUGGAAUGUUUACUACACUCGGAUAUUUGAUA UGUGGAUUUCGAGUCGUCUUAAUGUAUAGAUUUGAAGAAGAGCU GUUUUUACGAUCCCUUCAGGAUUACAAAAUUCAAAGUGCGUUGC UAGUACCAACCCUAUUUUCAUUCUUCGCCAAAAGCACUCUGAUU GACAAAUACGAUUUAUCUAAUUUACACGAAAUUGCUUCUGGGGG CGCACCUCUUUCGAAAGAAGUCGGGGAAGCGGUUGCAAAACGCU UCCAUCUUCCAGGGAUACGACAAGGAUAUGGGCUCACUGAGACU ACAUCAGCUAUUCUGAUUACACCCGAGGGGGAUGAUAAACCGGG CGCGGUCGGUAAAGUUGUUCCAUUUUUUGAAGCGAAGGUUGUG GAUCUGGAUACCGGGAAAACGCUGGGCGUUAAUCAGAGAGGCG AAUUAUGUGUCAGAGGACCUAUGAUUAUGUCCGGUUAUGUAAAC AAUCCGGAAGCGACCAACGCCUUGAUUGACAAGGAUGGAUGGCU ACAUUCUGGAGACAUAGCUUACUGGGACGAAGACGAACACUUCU UCAUAGUUGACCGCUUGAAGUCUUUAAUUAAAUACAAAGGAUAC CAGGUGGCCCCCGCUGAAUUGGAGUCGAUAUUGUUACAACACCC CAACAUCUUCGACGCGGGCGUGGCAGGUCUUCCCGACGAUGAC GCCGGUGAACUUCCCGCCGCCGUUGUGUUUGGAGCACGGAA AGACGAUGACGGAAAAAGAGAUCGUGGAUUACGUCGCCAGUCAA GUAACAACCGCCAAAAAGUUGCGCGGAGGAGUUGUGUUUGUGG ACGAAGUACCGAAAGGUCUUACCGGAAAACUCGACGCAAGAAAA AUCAGAGAGAUCCUCAUAAAGGCCAAGAAGGGCGGAAAGUCCAA AUUGUAAGUCGACCGGCUGCUAACAAAGCCCGAAAGGAAGCUGA GUUGGCUGCUGCCACCGCUGAGCAAUAACUAGCAUAACCCCUUG GGGCCUCUAAACGGGUCUUGAGGGGUUUUUUG |
| Luciferase Protein [SEQ ID NO: 3] | MEDAKNIKKGPAPFYPLEDGTAGEQLHKAMKRYALVPGTIAFTDAHIE VNITYAEYFEMSVRLAEAMKRYGLNTNHRIVVCSENSLQFFMPVLGAL FIGVAVAPANDIYNERELLNSMNISQPTVVFVSKKGLQKILNVQKKLPII QKIIIMDSKTDYQGFQSMYTFVTSHLPPGFNEYDFVPESFDRDKTIALI MNSSGSTGLPKGVALPHRTACVRFSHARDPIFGNQIIPDTAILSVVPFH HGFGMFTTLGYLICGFRVVLMYRFEEELFLRSLQDYKIQSALLVPTLFS FFAKSTLIDKYDLSNLHEIASGGAPLSKEVGEAVAKRFHLPGIRQGYGL TETTSAILITPEGDDKPGAVGKVVPFFEAKVVDLDTGKTLGVNQRGEL |

TABLE 6-continued

Sequences used in this disclosure.

| Sequence Description [SEQ ID NO: __] | Nucleotide or Amino Acid Sequence |
|---|---|
| | CVRGPMIMSGYVNNPEATNALIDKDGWLHSGDIAYWDEDEHFFIVDR LKSLIKYKGYQVAPAELESILLQHPNIFDAGVAGLPDDDAGELPAAVVV LEHGKTMTEKEIVDYVASQVTTAKKLRGGVVFVDEVPKGLTGKLDAR KIREILIKAKKGGKSKL |
| pY71sfGFP [SEQ ID NO: 4] | GGATCCTGCAGTTGAGATCCTTTTTTTCTGCGCGTAATCTGCTGCT TGCAAACAAAAAAACCACCGCTACCAGCGGTGGTTTGTTTGCCGG ATCAAGAGCTACCAACTCTTTTTCCGAAGGTAACTGGCTTCAGCAG AGCGCAGATACCAAATACTGTCCTTCTAGTGTAGCCGTAGTTAGGC CACCACTTCAAGAACTCTGTAGCACCGCCTACATACCTCGCTCTGC TAATCCTGTTACCAGTGGCTGCTGCCAGTGGCGATAAGTCGTGTC TTACCGGGTTGGACTCAAGACGATAGTTACCGGATAAGGCGCAGC GGTCGGGCTGAACGGGGGGTTCGTGCACACAGCCCAGCTTGGAG CGAACGACCTACACCGAACTGAGATACCTACAGCGTGAGCATTGA GAAAGCGCCACGCTTCCCGAAGGGAGAAAGGCGGACAGGTATCC GGTAAGCGGCAGGGTCGGAACAGGAGAGCGCACGAGGGAGCTTC CAGGGGGAAACGCCTGGTATCTTTATAGTCCTGTCGGGTTTCGCC ACCTCTGACTTGAGCGTCGATTTTTGTGATGCTCGTCAGGGGGGC GGAGCCTATGGAAACGAATTCAGATCTCGATCCCGCGAAATTAATA CGACTCACTATAGGGAGACCACAACGGTTTCCCTCTAGAAATAATT TTGTTTAACTTTAAGAAGGAGATATACATATGAGCAAAGGTGAAGA ACTGTTTACCGGCGTTGTGCCGATTCTGGTGGAACTGGATGGCGA TGTGAACGGTCACAAATTCAGCGTGCGTGGTGAAGGTGAAGGCGA TGCCACGATTGGCAAACTGACGCTGAAATTTATCTGCACCACCGG CAAACTGCCGGTGCCGTGGCCGACGCTGGTGACCACCCTGACCT ATGGCGTTCAGTGTTTTAGTCGCTATCCGGATCACATGAAACGTCA CGATTTCTTTAAATCTGCAATGCCGGAAGGCTATGTGCAGGAACGT ACGATTAGCTTTAAAGATGATGGCAAATATAAAACGCGCGCCGTTG TGAAATTTGAAGGCGATACCCTGGTGAACCGCATTGAACTGAAAG GCACGGATTTTAAAGAAGATGGCAATATCCTGGGCCATAAACTGG AATACAACTTTAATAGCCATAATGTTTATATTACGGCGGATAAACAG AAAAATGGCATCAAAGCGAATTTTACCGTTCGCCATAACGTTGAAG ATGGCAGTGTGCAGCTGGCAGATCATTATCAGCAGAATACCCCGA TTGGTGATGGTCCGGTGCTGCTGCCGGATAATCATTATCTGAGCA CGCAGACCGTTCTGTCTAAAGATCCGAACGAAAAAGGCACCCGGG ACCACATGGTTCTGCACGAATATGTGAATGCGGCAGGTATTACGT GGAGCCATCCGCAGTTCGAAAAATAAGTCGACCGGCTGCTAACAA AGCCCGAAAGGAAGCTGAGTTGGCTGCTGCCACCGCTGAGCAATA ACTAGCATAACCCCTTGGGGCCTCTAAACGGGTCTTGAGGGGTTT TTTGCTGAAAGCCAATTCTGATTAGAAAAACTCATCGAGCATCAAA TGAAACTGCAATTTATTCATATCAGGATTATCAATACCATATTTTTGA AAAAGCCGTTTCTGTAATGAAGGAGAAAACTCACCGAGGCAGTTC CATAGGATGGCAAGATCCTGGTATCGGTCTGCGATTCCGACTCGT CCAACATCAATACAACCTATTAATTTCCCCTCGTCAAAAATAAGGTT ATCAAGTGAGAAATCACCATGAGTGACGACTGAATCCGGTGAGAA TGGCAAAAGCTTATGCATTTCTTTCCAGACTTGTTCAACAGGCCAG CCATTACGCTCGTCATCAAAATCACTCGCATCAACCAAACCGTTAT TCATTCGTGATTGCGCCTGAGCGAGACGAAATACGCGATCGCTGT TAAAAGGACAATTACAAACAGGAATCGAATGCAACCGGCGCAGGA ACACTGCCAGCGCATCAACAATATTTTCACCTGAATCAGGATATTC TTCTAATACCTGGAATGCTGTTTTCCCGGGGATCGCAGTGGTGAGT AACCATGCATCATCAGGAGTACGGATAAAATGCTTGATGGTCGGA AGAGGCATAAATTCCGTCAGCCAGTTTAGTCTGACCATCTCATCTG TAACATCATTGGCAACGCTACCTTTGCCATGTTTCAGAAACAACTC TGGCGCATCGGGCTTCCCATACAATCGATAGATTGTCGCACCTGA TTGCCCGACATTATCGCGAGCCCATTTATACCCATATAAATCAGCA TCCATGTTGGAATTTAATCGCGGCTTCGAGCAAGACGTTTCCCGTT GAATATGGCTCATAACACCCCTTGTATTACTGTTTATGTAAGCAGA CAGTTTTATTGTTCATGATGATATATTTTTATCTTGTGCAATGTAACA TCAGAGATTTTGAGACACAACGT |
| sfGFP mRNA [SEQ ID NO: 5] | GGGAGACCACAACGGUUUCCCUCUAGAAAUAAUUUUGUUUAACU UUAAGAAGGAGAUAUACAUAUGAGCAAAGGUGAAGAACUGUUUA CCGGCGUUGUGCCGAUUCUGGUGGAACUGGAUGGCGAUGUGAA CGGUCACAAAUUCAGCGUGCGUGGUGAAGGUGAAGGCGAUGCC ACGAUUGGCAAACUGACGCUGAAAUUUAUCUGCACCACCGGCAA ACUGCCGGUGCCGUGGCCGACGCUGGUGACCACCCUGACCUAU GGCGUUCAGUGUUUUAGUCGCUAUCCGGAUCACAUGAAACGUCA CGAUUUCUUUAAAUCUGCAAUGCCGGAAGGCUAUGUGCAGGAAC GUACGAUUAGCUUUAAAGAUGAUGGCAAAUAUAAAACGCGCGCC GUUGUGAAAUUUGAAGGCGAUACCCUGGUGAACCGCAUUGAACU GAAAGGCACGGAUUUUAAAGAAGAUGGCAAUAUCCUGGGCCAUA AACUGGAAUACAACUUUAAUAGCCAUAAUGUUUAUAUUACGGCG GAUAAACAGAAAAAUGGCAUCAAAGCGAAUUUUACCGUUCGCCA |

TABLE 6-continued

Sequences used in this disclosure.

| Sequence Description [SEQ ID NO: __] | Nucleotide or Amino Acid Sequence |
| --- | --- |
| | UAACGUUGAAGAUGGCAGUGUGCAGCUGGCAGAUCAUUAUCAGC<br>AGAAUACCCCGAUUGGUGAUGGUCCGGUGCUGCUGCCGGAUAA<br>UCAUUAUCUGAGCACGCAGACCGUUCUGUCUAAAGAUCCGAACG<br>AAAAAGGCACCCGGGACCACAUGGUUCUGCACGAAUAUGUGAAU<br>GCGGCAGGUAUUACGUGGAGCCAUCCGCAGUUCGAAAAAUAAGU<br>CGACCGGCUGCUAACAAAGCCCGAAAGGAAGCUGAGUUGGCUG<br>CUGCCACCGCUGAGCAAUAACUAGCAUAACCCCUUGGGGCCUCU<br>AAACGGGUCUUGAGGGGUUUUUUG |
| sfGFP Protein [SEQ ID NO: 6] | MSKGEELFTGVVPILVELDGDVNGHKFSVRGEGEGDATIGKLTLKFIC<br>TTGKLPVPWPTLVTTLTYGVQCFSRYPDHMKRHDFFKSAMPEGYVQ<br>ERTISFKDDGKYKTRAVVKFEGDTLVNRIELKGTDFKEDGNILGHKLEY<br>NFNSHNVYITADKQKNGIKANFTVRHNVEDGSVQLADHYQQNTPIGD<br>GPVLLPDNHYLSTQTVLSKDPNEKGTRDHMVLHEYVNAAGITWSHPQ<br>FEK |
| pY71mRFP1 DNA [SEQ ID NO: 7] | GGATCCTGCAGTTGAGATCCTTTTTTTCTGCGCGTAATCTGCTGCT<br>TGCAAACAAAAAAACCACCGCTACCAGCGGTGGTTTGTTTGCCGG<br>ATCAAGAGCTACCAACTCTTTTTCCGAAGGTAACTGGCTTCAGCAG<br>AGCGCAGATACCAAATACTGTCCTTCTAGTGTAGCCGTAGTTAGGC<br>CACCACTTCAAGAACTCTGTAGCACCGCCTACATACCTCGCTCTGC<br>TAATCCTGTTACCAGTGGCTGCTGCCAGTGGCGATAAGTCGTGTC<br>TTACCGGGTTGGACTCAAGACGATAGTTACCGGATAAGGCGCAGC<br>GGTCGGGCTGAACGGGGGGTTCGTGCACACAGCCCAGCTTGGAG<br>CGAACGACCTACACCGAACTGAGATACCTACAGCGTGAGCATTGA<br>GAAAGCGCCACGCTTCCCGAAGGGAGAAAGGCGGACAGGTATCC<br>GGTAAGCGGCAGGGTCGGAACAGGAGAGCGCACGAGGGAGCTTC<br>CAGGGGGAAACGCCTGGTATCTTTATAGTCCTGTCGGGTTTCGCC<br>ACCTCTGACTTGAGCGTCGATTTTTGTGATGCTCGTCAGGGGGGC<br>GGAGCCTATGGAAACGAATTCAGATCTCGATCCCGCGAAATTAATA<br>CGACTCACTATAGGGAGACCACAACGGTTTCCCTCTAGAAATAATT<br>TTGTTTAACTTTAAGAAGGAGATATACATATGGCTTCCTCCGAAGA<br>CGTTATCAAAGAGTTCATGCGTTTCAAAGTTCGTATGGAAGGTTCC<br>GTTAACGGTCACGAGTTCGAAATCGAAGGTGAAGGTGAAGGTCGT<br>CCGTACGAAGGTACCCAGACCGCTAAACTGAAAGTTACCAAAGGT<br>GGTCCGCTGCCGTTCGCTTGGGACATCCTGTCCCCGCAGTTCCAG<br>TACGGTTCCAAAGCTTACGTTAAACACCCGGCTGACATCCCGGAC<br>TACCTGAAACTGTCCTTCCCGGAAGGTTTCAAATGGGAACGTGTTA<br>TGAACTTCGAAGACGGTGGTGTTGTTACCGTTACCCAGGACTCCT<br>CCCTGCAAGACGGTGAGTTCATCTACAAAGTTAAACTGCGTGGTAC<br>CAACTTCCCGTCCGACGGTCCGGTTATGCAGAAAAAAACCATGGG<br>TTGGGAAGCTTCCACCGAACGTATGTACCCGGAAGACGGTGCTCT<br>GAAAGGTGAAATCAAAATGCGTCTGAAACTGAAAGACGGTGGTCA<br>CTACGACGCTGAAGTTAAAACCACCTACATGGCTAAAAAACCGGTT<br>CAGCTGCCGGGTGCTTACAAAACCGACATCAAACTGGACATCACC<br>TCCCACAACGAAGACTACACCATCGTTGAACAGTACGAACGTGCT<br>GAAGGTCGTCACTCCACCGGTGCTTAAGTCGACCGGCTGCTAACA<br>AAGCCCGAAAGGAAGCTGAGTTGGCTGCTGCCACCGCTGAGCAAT<br>AACTAGCATAACCCCTTGGGGCCTCTAAACGGGTCTTGAGGGGTT<br>TTTTGCTGAAAGCCAATTCTGATTAGAAAAACTCATCGAGCATCAA<br>ATGAAACTGCAATTTATTCATATCAGGATTATCAATACCATATTTTG<br>AAAAAGCCGTTTCTGTAATGAAGGAGAAAACTCACCGAGGCAGTT<br>CCATAGGATGGCAAGATCCTGGTATCGGTCTGCGATTCCGACTCG<br>TCCAACATCAATACAACCTATTAATTTCCCCTCGTCAAAAATAAGGT<br>TATCAAGTGAGAAATCACCATGAGTGACGACTGAATCCGGTGAGA<br>ATGGCAAAAGCTTATGCATTTCTTTCCAGACTTGTTCAACAGGCCA<br>GCCATTACGCTCGTCATCAAAATCACTCGCATCAACCAAACCGTTA<br>TTCATTCGTGATTGCGCCTGAGCGAGACGAAATACGCGATCGCTG<br>TTAAAAGGACAATTACAAACAGGAATGAATGCAACCGGCGCAGG<br>AACACTGCCAGCGCATCAACAATATTTTCACCTGAATCAGGATATT<br>CTTCTAATACCTGGAATGCTGTTTTCCCGGGGATCGCAGTGGTGA<br>GTAACCATGCATCATCAGGAGTACGGATAAAATGCTTGATGGTCG<br>GAAGAGGCATAAATTCCGTCAGCCAGTTTAGTCTGACCATCTCATC<br>TGTAACATCATTGGCAACGCTACCTTTGCCATGTTTCAGAAACAAC<br>TCTGGCGCATCGGGCTTCCCATACAATCGATAGATTGTCGCACCT<br>GATTGCCCGACATTATCGCGAGCCCATTTATACCCATATAAATCAG<br>CATCCATGTTGGAATTTAATCGCGGCTTCGAGCAAGACGTTTCCCG<br>TTGAATATGGCTCATAACACCCCTTGTATTACTGTTTATGTAAGCAG<br>ACAGTTTTATTGTTCATGATGATATATTTTTATCTTGTGCAATGTAAC<br>ATCAGAGATTTTGAGACACAACGT |
| mRFP1 mRNA [SEQ ID NO: 8] | GGGAGACCACAACGGUUUCCCUCUAGAAAUAAUUUUGUUUAACU<br>UUAAGAAGGAGAUAUACAUAUGGCUUCCUCCGAAGACGUUAUCA<br>AAGAGUUCAUGCGUUUCAAAGUUCGUAUGGAAGGUUCCGUUAAC |

TABLE 6-continued

Sequences used in this disclosure.

| Sequence Description [SEQ ID NO: __] | Nucleotide or Amino Acid Sequence |
|---|---|
| | GGUCACGAGUUCGAAAUCGAAGGUGAAGGUGAAGGUCGUCCGU
ACGAAGGUACCCAGACCGCUAAACUGAAAGUUACCAAAGGUGGU
CCGCUGCCGUUCGCUUGGGACAUCCUGUCCCCGCAGUUCCAGU
ACGGUUCCAAAGCUUACGUUAAACACCCGGCUGACAUCCCGGAC
UACCUGAAACUGUCCUUCCCGGAAGGUUUCAAAUGGGAACGUGU
UAUGAACUUCGAAGACGGUGGUGUUGUUACCGUUACCCAGGAC
UCCUCCCUGCAAGACGGUGAGUUCAUCUACAAAGUUAAACUGCG
UGGUACCAACUUCCCGUCCGACGGUCCGGUUAUGCAGAAAAAA
CCAUGGGUUGGGAAGCUUCCACCGAACGUAUGUACCCGGAAGA
CGGUGCUCUGAAAGGUGAAAUCAAAAUGCGUCUGAAACUGAAAG
ACGGUGGUCACUACGACGCUGAAGUUAAAACCACCUACAUGGCU
AAAAAACCGGUUCAGCUGCCGGGUGCUUACAAAACCGACAUCAA
ACUGGACAUCACCUCCCACAACGAAGACUACACCAUCGUUGAAC
AGUACGAACGUGCUGAAGGUCGUCACUCCACCGGUGCUUAAGU
CGACCGGCUGCUAACAAAGCCCGAAAGGAAGCUGAGUUGGCUG
CUGCCACCGCUGAGCAAUAACUAGCAUAACCCCUUGGGGCCUCU
AAACGGGUCUUGAGGGGUUUUUUG |
| mRFP1 Protein [SEQ ID NO: 9] | MASSEDVIKEFMRFKVRMEGSVNGHEFEIEGEGEGRPYEGTQTAKLK
VTKGGPLPFAWDILSPQFQYGSKAYVKHPADIPDYLKLSFPEGFKWE
RVMNFEDGGVVTVTQDSSLQDGEFIYKVKLRGTNFPSDGPVMQKKT
MGWEASTERMYPEDGALKGEIKMRLKLKDGGHYDAEVKTTYMAKKP
VQLPGAYKTDIKLDITSHNEDYTIVEQYERAEGRHSTGA |
| pWK1 DNA [SEQ ID NO: 10] | TCGCGCGTTTCGGTGATGACGGTGAAAACCTCTGACACATGCAGCT
CCCGGAGACGGTCACAGCTTGTCTGTAAGCGGATGCCGGGAGCAG
ACAAGCCCGTCAGGGCGCGTCAGCGGGTGTTGGCGGGTGTCGGG
GCTGGCTTAACTATGCGGCATCAGAGCAGATTGTACTGAGAGTGCA
CCATATGCGGTGTGAAATACCGCACAGATGCGTAAGGAGAAAATAC
CGCATCAGGCGCCATTCGCCATTCAGGCTGCGCAACTGTTGGGAAG
GGCGATCGGTGCGGGCCTCTTCGCTATTACGCCAGCTGGCGAAAG
GGGGATGTGCTGCAAGGCGATTAAGTTGGGTAACGCCAGGGTTTC
CCAGTCACGACGTTGTAAAACGACGGCCAGTGAATTCGAGCTCGGT
ACCTAATACGACTCACTATAGGGAGATTGAAGAGTTTGATCATGGCT
CAGATTGAACGCTGGCGGCAGGCCTAACACATGCAAGTCGAACGGT
AACAGGAAGAAGCTTGCTTCTTTGCTGACGAGTGGCGGACGGGTGA
GTAATGTCTGGGAAACTGCCTGATGGAGGGGGATAACTACTGGAAA
CGGTAGCTAATACCGCATAACGTCGCAAGACCAAAGAGGGGGACCT
TCGGGCCTCTTGCCATCGGATGTGCCCAGATGGGATTAGCTAGTAG
GTGGGGTAACGGCTCACCTAGGCGACGATCCCTAGCTGGTCTGAG
AGGATGACCAGCCACACTGGAACTGAGACACGGTCCAGACTCCTAC
GGGAGGCAGCAGTGGGGAATATTGCACAATGGGCGCAAGCCTGAT
GCAGCCATGCCGCGTGTATGAAGAAGGCCTTCGGGTTGTAAAGTAC
TTTCAGCGGGGAGGAAGGGAGTAAAGTTAATACCTTTGCTCATTGA
CGTTACCCGCAGAAGAAGCACCGGCTAACTCCGTGCCAGCAGCCG
CGGTAATACGGAGGGTGCAAGCGTTAATCGGAATTACTGGGCGTAA
AGCGCACGCAGGCGGTTTGTTAAGTCAGATGTGAAATCCCCGGGCT
CAACCTGGGAACTGCATCTGATACTGGCAAGCTTGAGTCTCGTAGA
GGGGGGTAGAATTCCAGGTGTAGCGGTGAAATGCGTAGAGATCTG
GAGGAATACCGGTGGCGAAGGCGGCCCCCTGGACGAAGACTGACG
CTCAGGTGCGAAAGCGTGGGGAGCAAACAGGATTAGATACCCTGGT
AGTCCACGCCGTAAACGATGTCGACTTGGAGGTTGTGCCCTTGAGG
CGTGGCTTCCGGAGCTAACGCGTTAAGTCGACCGCCTGGGGAGTA
CGGCCGCAAGGTTAAAACTCAAATGAATTGACGGGGGCCCGCACAA
GCGGTGGAGCATGTGGTTTAATTCGATGCAACGCGAAGAACCTTAC
CTGGTCTTGACATCCACGGAAGTTTTCAGAGATGAGAATGTGCCTTC
GGGAACCGTGAGACAGGTGCTGCATGGCTGTCGTCAGCTCGTGTT
GTGAAATGTTGGGTTAAGTCCCGCAACGAGCGCAACCCTTATCCTTT
GTTGCCAGCGGTCCGGCCGGGAACTCAAAGGAGACTGCCAGTGAT
AAACTGGAGGAAGGTGGGGATGACGTCAAGTCATCATGGCCCTTAC
GACCAGGGCTACACACGTGCTACAATGGCGCATACAAAGAGAAGCG
ACCTCGCGAGAGCAAGCGGACCTCATAAAGTGCGTCGTAGTCCGG
ATTGGAGTCTGCAACTCGACTCCATGAAGTCGGAATCGCTAGTAATC
GTGGATCAGAATGCCACGGTGAATACGTTCCCGGGCCTTGTACACA
CCGCCCGTCACACCATGGGAGTGGGTTGCAAAAGAAGTAGGTAGCT
TAACCTTCGGGAGGGCGCTTACCACTTTGTGATTCATGACTGGGGT
GAAGTCGTAACAAGGTAACCGTAGGGGAACCTGCGGTTGGATCACC
TCCTTAGGTCTAGAGTCGACCTGCAGGCATGCAAGCTTGGCGTAAT
CATGGTCATAGCTGTTTCCTGTGTGAAATTGTTATCCGCTCACAATT
CCACACAACATACGAGCCGGAAGCATAAAGTGTAAAGCCTGGGGTG
CCTAATGAGTGAGCTAACTCACATTAATTGCGTTGCGCTCACTGCCC
GCTTTCCAGTCGGGAAACCTGTCGTGCCAGCTGCATTAATGAATCG
GCCAACGCGCGGGGAGAGGCGGTTTGCGTATTGGGCGCTCTTCCG
CTTCCTCGCTCACTGACTCGCTGCGCTCGGTCGTTCGGCTGCGGC |

TABLE 6-continued

Sequences used in this disclosure.

| Sequence Description [SEQ ID NO: __] | Nucleotide or Amino Acid Sequence |
|---|---|
| | GAGCGGTATCAGCTCACTCAAAGGCGGTAATACGGTTATCCACAGA<br>ATCAGGGGATAACGCAGGAAAGAACATGTGAGCAAAAGGCCAGCAA<br>AAGGCCAGGAACCGTAAAAAGGCCGCGTTGCTGGCGTTTTTCCATA<br>GGCTCCGCCCCCTGACGAGCATCACAAAAATCGACGCTCAAGTCA<br>GAGGTGGCGAAACCCGACAGGACTATAAAGATACCAGGCGTTTCCC<br>CCTGGAAGCTCCCTCGTGCGCTCTCCTGTTCCGACCCTGCCGCTTA<br>CCGGATACCTGTCCGCCTTTCTCCCTTCGGGAAGCGTGGCGCTTTC<br>TCATAGCTCACGCTGTAGGTATCTCAGTTCGGTGTAGGTCGTTCGCT<br>CCAAGCTGGGCTGTGTGCACGAACCCCCCGTTCAGCCCGACCGCT<br>GCGCCTTATCCGGTAACTATCGTCTTGAGTCCAACCCGGTAAGACA<br>CGACTTATCGCCACTGGCAGCAGCCACTGGTAACAGGATTAGCAGA<br>GCGAGGTATGTAGGCGGTGCTACAGAGTTCTTGAAGTGGTGGCCTA<br>ACTACGGCTACACTAGAAGAACAGTATTTGGTATCTGCGCTCTGCTG<br>AAGCCAGTTACCTTCGGAAAAAGAGTTGGTAGCTCTTGATCCGGCA<br>AACAAACCACCGCTGGTAGCGGTGGTTTTTTTGTTTGCAAGCAGCA<br>GATTACGCGCAGAAAAAAAGGATCTCAAGAAGATCCTTTGATCTTTT<br>CTACGGGGTCTGACGCTCAGTGGAACGAAAACTCACGTTAAGGGAT<br>TTTGGTCATGAGATTATCAAAAAGGATCTTCACCTAGATCCTTTTAAA<br>TTAAAAATGAAGTTTTAAATCAATCTAAAGTATATATGAGTAAACTTG<br>GTCTGACAGTTACCAATGCTTAATCAGTGAGGCACCTATCTCAGCGA<br>TCTGTCTATTTCGTTCATCCATAGTTGCCTGACTCCCCGTCGTGTAG<br>ATAACTACGATACGGGAGGGCTTACCATCTGGCCCCAGTGCTGCAA<br>TGATACCGCGAGACCCACGCTCACCGGCTCCAGATTTATCAGCAAT<br>AAACCAGCCAGCCGGAAGGGCCGAGCGCAGAAGTGGTCCTGCAAC<br>TTTATCCGCCTCCATCCAGTCTATTAATTGTTGCCGGGAAGCTAGAG<br>TAAGTAGTTCGCCAGTTAATAGTTTGCGCAACGTTGTTGCCATTGCT<br>ACAGGCATCGTGGTGTCACGCTCGTCGTTTGGTATGGCTTCATTCA<br>GCTCCGGTTCCCAACGATCAAGGCGAGTTACATGATCCCCCATGTT<br>GTGCAAAAAAGCGGTTAGCTCCTTCGGTCCTCCGATCGTTGTCAGA<br>AGTAAGTTGGCCGCAGTGTTATCACTCATGGTTATGGCAGCACTGC<br>ATAATTCTCTTACTGTCATGCCATCCGTAAGATGCTTTTCTGTGACTG<br>GTGAGTACTCAACCAAGTCATTCTGAGAATAGTGTATGCGGCGACC<br>GAGTTGCTCTTGCCCGGCGTCAATACGGGATAATACCGCGCCACAT<br>AGCAGAACTTTAAAAGTGCTCATCATTGGAAAACGTTCTTCGGGGCG<br>AAAACTCTCAAGGATCTTACCGCTGTTGAGATCCAGTTCGATGTAAC<br>CCACTCGTGCACCCAACTGATCTTCAGCATCTTTTACTTTCACCAGC<br>GTTTCTGGGTGAGCAAAAACAGGAAGGCAAAATGCCGCAAAAAAGG<br>GAATAAGGGCGACACGGAAATGTTGAATACTCATACTCTTCCTTTTT<br>CAATATTATTGAAGCATTTATCAGGGTTATTGTCTCATGAGCGGATA<br>CATATTTGAATGTATTTAGAAAAATAAACAAATAGGGGTTCCGCGCA<br>CATTTCCCCGAAAAGTGCCACCTGACGTCTAAGAAACCATTATTATC<br>ATGACATTAACCTATAAAAATAGGCGTATCACGAGGCCCTTTCGTC |
| pWK1 16S RNA<br>[SEQ ID NO: 11] | AGAUUGAAGAGUUUGAUCAUGGCUCAGAUUGAACGCUGGCGGC<br>AGGCCUAACACAUGCAAGUCGAACGGUAACAGGAAGAAGCUUGC<br>UUCUUUGCUGACGAGUGGCGGACGGGUGAGUAAUGUCUGGGAA<br>ACUGCCUGAUGGAGGGGGAUAACUACUGGAAACGGUAGCUAAUA<br>CCGCAUAACGUCGCAAGACCAAAGAGGGGGACCUUCGGGCCUC<br>UUGCCAUCGGAUGUGCCCAGAUGGGAUUAGCUAGUAGGUGGGG<br>UAACGGCUCACCUAGGCGACGAUCCCUAGCUGGUCUGAGAGGA<br>UGACCAGCCACACUGGAACUGAGACACGGUCCAGACUCCUACGG<br>GAGGCAGCAGUGGGGAAUAUUGCACAAUGGGCGCAAGCCUGAU<br>GCAGCCAUGCCGCGUGUAUGAAGAAGGCCUUCGGGUUGUAAAG<br>UACUUUCAGCGGGGAGGAAGGGAGUAAAGUUAAUACCUUUGCUC<br>AUUGACGUUACCCGCAGAAGAAGCACCGGCUAACUCCGUGCCAG<br>CAGCCGCGGUAAUACGGAGGGUGCAAGCGUUAAUCGGAAUUAC<br>UGGGCGUAAAGCGCACGCAGGCGGUUUGUUAAGUCAGAUGUGA<br>AAUCCCCGGGCUCAACCUGGGAACUGCAUCUGAUACUGGCAAGC<br>UUGAGUCUCGUAGAGGGGGGUAGAAUUCCAGGUGUAGCGGUGA<br>AAUGCGUAGAGAUCUGGAGGAAUACCGGUGGCGAAGGCGGCCC<br>CCUGGACGAAGACUGACGCUCAGGUGCGAAAGCGUGGGGAGCA<br>AACAGGAUUAGAUACCCUGGUAGUCCACGCCGUAAACGAUGUCG<br>ACUUGGAGGUUGUGCCCUUGAGGCGUGGCUUCCGGAGCUAACG<br>CGUUAAGUCGACCGCCUGGGGAGUACGGCCGCAAGGUUAAAAC<br>UCAAAUGAAUUGACGGGGGCCCGCACAAGCGGUGGAGCAUGUG<br>GUUUAAUUCGAUGCAACGCGAAGAACCUUACCUGGUCUUGACAU<br>CCACGGAAGUUUUCAGAGAUGAGAAUGUGCCUUCGGGAACCGU<br>GAGACAGGUGCUGCAUGGCUGUCGUCAGCUCGUGUUGUGAAAU<br>GUUGGGUUAAGUCCCGCAACGAGCGCAACCCUUAUCCUUUGUU<br>GCCAGCGGUCCGGCCGGGAACUCAAAGGAGACUGCCAGUGAUA<br>AACUGGAGGAAGGUGGGGAUGACGUCAAGUCAUCAUGGCCCUU<br>ACGACCAGGGCUACACACGUGCUACAAUGGCGCAUACAAAGAGA<br>AGCGACCUCGCGAGAGCAAGCGGACCUCAUAAAGUGCGUCGUA<br>GUCCGGAUUGGAGUCUGCAACUCGACUCCAUGAAGUCGGAAUC |

TABLE 6-continued

Sequences used in this disclosure.

| Sequence Description [SEQ ID NO: __] | Nucleotide or Amino Acid Sequence |
|---|---|
| | GCUAGUAAUCGUGGAUCAGAAUGCCACGGUGAAUACGUUCCCG<br>GGCCUUGUACACACCGCCCGUCACACCAUGGGAGUGGGUUGCA<br>AAAGAAGUAGGUAGCUUAACCUUCGGGAGGGCGCUUACCACUUU<br>GUGAUUCAUGACUGGGGUGAAGUCGUAACAAGGUAACCGUAGG<br>GGAACCUGCGGUUGGAUCACCUCCUUA |
| pCW1 DNA<br>[SEQ ID NO: 12] | TAATACGACTCACTATAGGTTAAGCGACTAAGCGTACACGGTGGAT<br>GCCCTGGCAGTCAGAGGCGATGAAGGACGTGCTAATCTGCGATAA<br>GCGTCGGTAAGGTGATATGAACCGTTATAACCGGCGATTTCCGAAT<br>GGGGAAACCCAGTGTGTTTCGACACACTATCATTAACTGAATCCATA<br>GGTTAATGAGGCGAACCGGGGGAACTGAAACATCTAAGTACCCCGA<br>GGAAAAGAAATCAACCGAGATTCCCCCAGTAGCGGCGAGCGAACG<br>GGGAGCAGCCCAGAGCCTGAATCAGTGTGTGTTAGTGGAAGCG<br>TCTGGAAAGGCGCGCGATACAGGGTGACAGCCCCGTACACAAAAAT<br>GCACATGCTGTGAGCTCGATGAGTAGGGCGGGACACGTGGTATCC<br>TGTCTGAATATGGGGGACCATCCTCCAAGGCTAAATACTCCTGAC<br>TGACCGATAGTGAACCAGTACCGTGAGGGAAAGGCGAAAAGAACCC<br>CGGCGAGGGGAGTGAAAAAGAACCTGAAACCGTGTACGTACAAGC<br>AGTGGGAGCACGCTTAGGCGTGTGACTGCGTACCTTTTGTATAATG<br>GGTCAGCGACTTATATTCTGTAGCAAGGTTAACCGAATAGGGGAGC<br>CGAAGGGAAACCGAGTCTTAACTGGGCGTTAAGTTGCAGGGTATAG<br>ACCCGAAACCCGGTGATCTAGCCATGGGCAGGTTGAAGGTTGGGTA<br>ACACTAACTGGAGGACCGAACCGACTAATGTTGAAAAATTAGCGGA<br>TGACTTGTGGCTGGGGGTGAAAGGCCAATCAAACCGGGAGATAGCT<br>GGTTCTCCCCGAAAGCTATTTAGGTAGCGCCTCGTGAATTCATCTCC<br>GGGGGTAGAGCACTGTTTCGGCAAGGGGGTCATCCCGACTTACCA<br>ACCCGATGCAAACTGCGAATACCGGAGAATGTTATCACGGGAGACA<br>CACGGCGGGTGCTAACGTCCGTCGTGAAGAGGGAAACAACCCAGA<br>CCGCCAGCTAAGGTCCCAAAGTCATGGTTAAGTGGGAAACGATGTG<br>GGAAGGCCCAGACAGCCAGGATGTTGGCTTAGAAGCAGCCATCATT<br>TAAAGAAAGCGTAATAGCTCACTGGTCGAGTCGGCCTGCGCGGAAG<br>ATGTAACGGGGCTAAACCATGCACCGAAGCTGCGGCAGCGACGCT<br>TATGCGTTGTTGGGTAGGGGAGCGTTCTGTAAGCCTGCGAAGGTGT<br>GCTGTGAGGCATGCTGGAGGTATCAGAAGTGCGAATGCTGACATAA<br>GTAACGATAAAGCGGGTGAAAAGCCCGCTCGCCGGAAGACCAAGG<br>GTTCCTGTCCAACGTTAATCGGGGCAGGGTGAGTCGACCCCTAAGG<br>CGAGGCCGAAAGGCGTAGTCGATGGGAAACAGGTTAATATTCCTGT<br>ACTTGGTGTTACTGCGAAGGGGGACGGAGAAGGCTATGTTGGCC<br>GGGCGACGGTTGTCCCGGTTTAAGCGTGTAGGCTGGTTTTCCAGGC<br>AAATCCGGAAAATCAAGGCTGAGGCGTGATGACGAGGCACTACGGT<br>GCTGAAGCAACAAATGCCCTGCTTCCAGGAAAAGCCTCTAAGCATC<br>AGGTAACATCAAATCGTACCCCAAACCGACACAGGTGGTCAGGTAG<br>AGAATACCAAGGCGCTTGAGAGAACTCGGGTGAAGGAACTAGGCAA<br>AATGGTGCCGTAACTTCGGGAGAAGGCACGCTGATATGTAGGTGAG<br>GTCCCTCGCGGATGGAGCTGAAATCAGTCGAAGATACCAGCTGGCT<br>GCAACTGTTTATTAAAAACACAGCACTGTGCAAACACGAAAGTGGAC<br>GTATACGGTGTGACGCCTGCCCGGTGCCGGAAGGTTAATTGATGG<br>GGTTAGCGCAAGCGAAGCTCTTGATCGAAGCCCCGGTAAACGGCG<br>GCCGTAACTATAACGGTCCTAAGGTAGCGAAATTCCTTGTCGGGTA<br>AGTTCCGACCTGCACGAATGGCGTAATGATGGCCAGGCTGTCTCCA<br>CCCGAGACTCAGTGAAATTGAACTCGCTGTGAAGATGCAGTGTACC<br>CGCGGCAAGACGGAAAGACCCCGTGAACCTTTACTATAGCTTGACA<br>CTGAACATTGAGCCTTGATGTGTAGGATAGGTGGGAGGCTTTGAAG<br>TGTGGACGCCAGTCTGCATGGAGCCGACCTTGAAATACCACCCTTT<br>AATGTTTGATGTTCTAACGTTGACCCGTAATCCGGGTTGCGGACAGT<br>GTCTGGTGGGTAGTTTGACTGGGGCGGTCTCCTCCTAAAGAGTAAC<br>GGAGGAGCACGAAGGTTGGCTAATCCTGGTCGGACATCAGGAGGT<br>TAGTGCAATGGCATAAGCCAGCTTGACTGCGAGCGTGACGGCGCG<br>AGCAGGTGCGAAAGCAGGTCATAGTGATCCGGTGGTTCTGAATGGA<br>AGGGCCATCGCTCAACGGATAAAAGGTACTCCGGGGATAACAGGCT<br>GATACCGCCCAAGAGTTCATATCGACGGCGGTGTTTGGCACCTCGA<br>TGTCGGCTCATCACATCCTGGGGCTGAAGTAGGTCCCAAGGGTATG<br>GCTGTTCGCCATTTAAAGTGGTACGCGAGCTGGGTTTAGAACGTCG<br>TGAGACAGTTCGGTCCCTATCTGCCGTGGGCGCTGGAGAACTGAG<br>GGGGGCTGCTCCTAGTACGAGAGGACCGGAGTGGACGCATCACTG<br>GTGTTCGGGTTGTCATGCCAATGGCACTGCCCGGTAGCTAAATGCG<br>GAAGAGATAAGTGCTGAAAGCATCTAAGCACGAAACTTGCCCCGAG<br>ATGAGTTCTCCCTGACCCTTTAAGGGTCCTGAAGGAACGTTGAAGA<br>CGACGACGTTGATAGGCCGGGTGTGTAAGCGCAGCGATGCGTTGA<br>GCTAACCGGTACTAATGAACCGTGAGGCTTAACCTTAAGCTGCAGG<br>CATGCAAGCTTGCGTAATCATGGTCATAGCTGTTTCCTGTGTGAAA<br>TTGTTATCCGCTCACAATTCCACACAACATACGAGCCGGAAGCATAA<br>AGTGTAAAGCCTGGGGTGCCTAATGAGTGAGCTAACTCACATTAATT<br>GCGTTGCGCTCACTGCCCGCTTTCCAGTCGGGAAACCTGTCGTGCC |

TABLE 6-continued

Sequences used in this disclosure.

| Sequence Description [SEQ ID NO: __] | Nucleotide or Amino Acid Sequence |
|---|---|
| | AGCTGCATTAATGAATCGGCCAACGCGCGGGGAGAGGCGGTTTGC<br>GTATTGGGCGCTCTTCCGCTTCCTCGCTCACTGACTCGCTGCGCTC<br>GGTCGTTCGGCTGCGGCGAGCGGTATCAGCTCACTCAAAGGCGGT<br>AATACGGTTATCCACAGAATCAGGGGATAACGCAGGAAAGAACATG<br>TGAGCAAAAGGCCAGCAAAAGGCCAGGAACCGTAAAAAGGCCGCG<br>TTGCTGGCGTTTTTCCATAGGCTCCGCCCCCCTGACGAGCATCACA<br>AAAATCGACGCTCAAGTCAGAGGTGGCGAAACCCGACAGGACTATA<br>AAGATACCAGGCGTTTCCCCCTGGAAGCTCCCTCGTGCGCTCTCCT<br>GTTCCGACCCTGCCGCTTACCGGATACCTGTCCGCCTTTCTCCCTT<br>CGGGAAGCGTGGCGCTTTCTCATAGCTCACGCTGTAGGTATCTCAG<br>TTCGGTGTAGGTCGTTCGCTCCAAGCTGGGCTGTGTGCACGAACCC<br>CCCGTTCAGCCCGACCGCTGCGCCTTATCCGGTAACTATCGTCTTG<br>AGTCCAACCCGGTAAGACACGACTTATCGCCACTGGCAGCAGCCAC<br>TGGTAACAGGATTAGCAGAGCGAGGTATGTAGGCGGTGCTACAGAG<br>TTCTTGAAGTGGTGGCCTAACTACGGCTACACTAGAAGAACAGTATT<br>TGGTATCTGCGCTCTGCTGAAGCCAGTTACCTTCGGAAAAAGAGTT<br>GGTAGCTCTTGATCCGGCAAACAAACCACCGCTGGTAGCGGTGGTT<br>TTTTTGTTTGCAAGCAGCAGATTACGCGCAGAAAAAAAGGATCTCAA<br>GAAGATCCTTTGATCTTTTCTACGGGGTCTGACGCTCAGTGGAACG<br>AAAACTCACGTTAAGGGATTTTGGTCATGAGATTATCAAAAAGGATC<br>TTCACCTAGATCCTTTTAAATTAAAAATGAAGTTTTAAATCAATCTAAA<br>GTATATATGAGTAAACTTGGTCTGACAGTTACCAATGCTTAATCAGT<br>GAGGCACCTATCTCAGCGATCTGTCTATTTCGTTCATCCATAGTTGC<br>CTGACTCCCCGTCGTGTAGATAACTACGATACGGGAGGGCTTACCA<br>TCTGGCCCCAGTGCTGCAATGATACCGCGAGACCCACGCTCACCG<br>GCTCCAGATTTATCAGCAATAAACCAGCCAGCCGGAAGGGCCGAGC<br>GCAGAAGTGGTCCTGCAACTTTATCCGCCTCCATCCAGTCTATTAAT<br>TGTTGCCGGGAAGCTAGAGTAAGTAGTTCGCCAGTTAATAGTTTGC<br>GCAACGTTGTTGCCATTGCTACAGGCATCGTGGTGTCACGCTCGTC<br>GTTTGGTATGGCTTCATTCAGCTCCGGTTCCCAACGATCAAGGCGA<br>GTTACATGATCCCCCATGTTGTGCAAAAAAGCGGTTAGCTCCTTCGG<br>TCCTCCGATCGTTGTCAGAAGTAAGTTGGCCGCAGTGTTATCACTCA<br>TGGTTATGGCAGCACTGCATAATTCTCTTACTGTCATGCCATCCGTA<br>AGATGCTTTTCTGTGACTGGTGAGTACTCAACCAAGTCATTCTGAGA<br>ATAGTGTATGCGGCGACCGAGTTGCTCTTGCCCGGCGTCAATACGG<br>GATAATACCGCGCCACATAGCAGAACTTTAAAAGTGCTCATCATTGG<br>AAAACGTTCTTCGGGGCGAAAACTCTCAAGGATCTTACCGCTGTTGA<br>GATCCAGTTCGATGTAACCCACTCGTGCACCCAACTGATCTTCAGCA<br>TCTTTTACTTTCACCAGCGTTTCTGGGTGAGCAAAAACAGGAAGGCA<br>AAATGCCGCAAAAAAGGGAATAAGGGCGACACGGAAATGTTGAATA<br>CTCATACTCTTCCTTTTTCAATATTATTGAAGCATTTATCAGGGTTATT<br>GTCTCATGAGCGGATACATATTTGAATGTATTTAGAAAAATAAACAAA<br>TAGGGGTTCCGCGCACATTTCCCCGAAAAGTGCCACCTGACGTCTA<br>AGAAACCATTATTATCATGACATTAACCTATAAAAATAGGCGTATCAC<br>GAGGCCCTTTCGTCTCGCGCGTTTCGGTGATGACGGTGAAAACCTC<br>TGACACATGCAGCTCCCGGAGACGGTCACAGCTTGTCTGTAAGCGG<br>ATGCCGGGAGCAGACAAGCCCGTCAGGGCGCGTCAGCGGGTGTTG<br>GCGGGTGTCGGGGCTGGCTTAACTATGCGGCATCAGAGCAGATTG<br>TACTGAGAGTGCACCATATGCGGTGTGAAATACCGCACAGATGCGT<br>AAGGAGAAAATACCGCATCAGGCGCCATTCGCCATTCAGGCTGCGC<br>AACTGTTGGGAAGGGCGATCGGTGCGGGCCTCTTCGCTATTACGCC<br>AGCTGGCGAAAGGGGGATGTGCTGCAAGGCGATTAAGTTGGGTAA<br>CGCCAGGGTTTTCCCAGTCACGACGTTGTAAAACGACGGCCAGTGA<br>ATTCGAGCTCGGTACC |
| pCW1 23S RNA [SEQ ID NO: 13] | GGUUAAGCGACUAAGCGUACACGGUGGAUGCCCUGGCAGUCAG<br>AGGCGAUGAAGGACGUGCUAAUCUGCGAUAAGCGUCGGUAAGG<br>UGAUAUGAACCGUUAUAACCGGCGAUUUCCGAAUGGGGAAACCC<br>AGUGUGUUUCGACACACUAUCAUUAACUGAAUCCAUAGGUUAAU<br>GAGGCGAACCGGGGAACUGAAACAUCUAAGUACCCCGAGGAAA<br>AGAAAUCAACCGAGAUUCCCCCAGUAGCGGCGAGCGAACGGGGA<br>GCAGCCCAGAGCCUGAAUCAGUGUGUGUGUUAGUGGAAGCGUC<br>UGGAAAGGCGCGCGAUACAGGGUGACAGCCCCGUACACAAAAAU<br>GCACAUGCUGUGAGCUCGAUGAGUAGGGCGGGACACGUGGUAU<br>CCUGUCUGAAUAUGGGGGGACCAUCCUCCAAGGCUAAAUACUCC<br>UGACUGACCGAUAGUGAACCAGUACCGUGAGGGAAAGGCGAAAA<br>GAACCCCGGCGAGGGGAGUGAAAAAGAACCUGAAACCGUGUACG<br>UACAAGCAGUGGGAGCACGCUUAGGCGUGUGACUGCGUACCUU<br>UUGUAUAAUGGGUCAGCGACUUAUAUUCUGUAGCAAGGUUAACC<br>GAAUAGGGGAGCCGAAGGGAAACCGAGUCUUAACUGGGCGUUA<br>AGUUGCAGGGUAUAGACCCGAAACCCGGUGAUCUAGCCAUGGG<br>CAGGUUGAAGGUUGGGUAACACUAACUGGAGGACCGAACCGACU<br>AAUGUUGAAAAAUUAGCGGAUGACUUGUGGCUGGGGGUGAAAG<br>GCCAAUCAAACCGGGAGAUAGCUGGUUCUCCCCGAAAGCUAUUU |

TABLE 6-continued

Sequences used in this disclosure.

| Sequence Description [SEQ ID NO: __] | Nucleotide or Amino Acid Sequence |
|---|---|
| | AGGUAGCGCCUCGUGAAUUCAUCUCCGGGGGUAGAGCACUGUU UCGGCAAGGGGGUCAUCCCGACUUACCAACCCGAUGCAAACUGC GAAUACCGGAGAAUGUUAUCACGGGAGACACACGGCGGGUGCU AACGUCCGUCGUGAAGAGGGAAACAACCCAGACCGCCAGCUAAG GUCCCAAAGUCAUGGUUAAGUGGGAAACGAUGUGGGAAGGCCC AGACAGCCAGGAUGUUGGCUUAGAAGCAGCCAUCAUUUAAAGAA AGCGUAAUAGCUCACUGGUCGAGUCGGCCUGCGCGGAAGAUGU AACGGGGCUAAACCAUGCACCGAAGCUGCGGCAGCGACGCUUAU GCGUUGUUGGGUAGGGGAGCGUUCUGUAAGCCUGCGAAGGUGU GCUGUGAGGCAUGCUGGAGGUAUCAGAAGUGCGAAUGCUGACA UAAGUAACGAUAAAGCGGGUGAAAAGCCCGCUCGCCGGAAGACC AAGGGUUCCUGUCCAACGUUAAUCGGGGCAGGGUGAGUCGACC CCUAAGGCGAGGCCGAAAGGCGUAGUCGAUGGGAAACAGGUUA AUAUUCCUGUACUUGGUGUUACUGCGAAGGGGGACGGAGAAG GCUAUGUUGGCCGGGCGACGGUUGUCCCGGUUUAAGCGUGUAG GCUGGUUUUCCAGGCAAAUCCGGAAAAUCAAGGCUGAGGCGUG AUGACGAGGCACUACGGUGCUGAAGCAACAAAUGCCCUGCUUCC AGGAAAAGCCUCUAAGCAUCAGGUAACAUCAAAUCGUACCCCAAA CCGACACAGGUGGUCAGGUAGAGAAUACCAAGGCGCUUGAGAGA ACUCGGGUGAAGGAACUAGGCAAAAUGGUGCCGUAACUUCGGG AGAAGGCACGCUGAUAUGUAGGUGAGGUCCCUCGCGGAUGGAG CUGAAAUCAGUCGAAGAUACCAGCUGGCUGCAACUGUUUAUUAA AAACACAGCACUGUGCAAACACGAAAGUGGACGUAUACGGUGUG ACGCCUGCCCGGUGCCGGAAGGUUAAUUGAUGGGGUUAGCGCA AGCGAAGCUCUUGAUCGAAGCCCCGGUAAACGGCGGCCGUAAC UAUAACGGUCCUAAGGUAGCGAAAUUCCUUGUCGGGUAAGUUCC GACCUGCACGAAUGGCGUAAUGACCCAGGCUGUCUCCACCC GAGACUCAGUGAAAUUGAACUCGCUGUGAAGAUGCAGUGUACCC GCGGCAAGACGAAAGACCCCGUGAACCUUUACUAUAGCUUGAC ACUGAACAUUGAGCCUUGAUGUGUAGGAUAGGUGGGAGGCUUU GAAGUGUGGACGCCAGUCUGCAUGGAGCCGACCUUGAAAUACCA CCCUUUAAUGUUUGAUGUUCUAACGUUGACCCGUAAUCCGGGUU GCGGACAGUGUCUGGUGGGUAGUUUGACUGGGGCGGUCUCCUC CUAAAGAGUAACGGAGGAGCACGAAGGUUGGCUAAUCCUGGUC GGACAUCAGGAGGUUAGUGCAAUGGCAUAAGCCAGCUUGACUG CGAGCGUGACGGCGCGAGCAGGUGCGAAAGCAGGUCAUAGUGA UCCGGUGGUUCUGAAUGGAAGGGCCAUCGCUCAACGGAUAAAA GGUACUCCGGGGAUAACAGGCUGAUACCGCCCAAGAGUUCAUAU CGACGGCGGUGUUUGGCACCUCGAUGUCGGCUCAUCACAUCCU GGGGCUGAAGUAGGUCCCAAGGGUAUGGCUGUUCGCCAUUUAA AGUGGUACGCGAGCUGGGUUUAGAACGUCGUGAGACAGUUCGG UCCCUAUCUGCCGUGGGCGCUGGAGAACUGAGGGGGGCUGCUC CUAGUACGAGAGGACCGGAGUGGACGCAUCACUGGUGUUCGGG UUGUCAUGCCAAUGGCACUGCCCGGUAGCUAAAUGCGGAAGAGA UAAGUGCUGAAAGCAUCUAAGCACGAAACUUGCCCCGAGAUGAG UUCUCCCUGACCCUUUAAGGGUCCUGAAGGAACGUUGAAGACGA CGACGUUGAUAGGCCGGGUGUGUAAGCGCAGCGAUGCGUUGAG CUAACCGGUACUAAUGAACCGUGAGGCUUAACCUU |
| p16S-T DNA [SEQ ID NO: 14] | TAATACGACTCACTATAGGGAGATTGAAGAGTTTGATCATGGCTCAG ATTGAACGCTGGCGGCAGGCCTAACACATGCAAGTCGAACGGTAAC AGGAAGAAGCTTGCTTCTTTGCTGACGAGTGGCGGACGGGTGAGTA ATGTCTGGGAAACTGCCTGATGGAGGGGGATAACTACTGGAAACG TAGCTAATACCGCATAACGTCGCAAGACCAAAGAGGGGGACCTTCG GGCCTCTTGCCATCGGATGTGCCCAGATGGGATTAGCTAGTAGGTG GGGTAACGGCTCACCTAGGCGACGATCCCTAGCTGGTCTGAGAGG ATGACCAGCCACACTGGAACTGAGACACGGTCCAGACTCCTACGGG AGGCAGCAGTGGGGAATATTGCACAATGGGCGCAAGCCTGATGCA GCCATGCCGCGTGTATGAAGAAGGCCTTCGGGTTGTAAAGTACTTT CAGCGGGGAGGAAGGGAGTAAAGTTAATACCTTTGCTCATTGACGT TACCCGCAGAAGAAGCACCGGCTAACTCCGTGCCAGCAGCCGCGG TAATACGGAGGGTGCAAGCGTTAATCGGAATTACTGGGCGTAAAGC GCACGCAGGCGGTTTGTTAAGTCAGATGTGAAATCCCCGGGCTCAA CCTGGGAACTGCATCTGATACTGGCAAGCTTGAGTCTCGTAGAGGG GGGTAGAATTCCAGGTGTAGCGGTGAAATGCGTAGAGATCTGGAGG AATACCGGTGGCGAAGGCGGCCCCCTGGACGAAGACTGACGCTCA GGTGCGAAAGCGTGGGGAGCAAACAGGATTAGATACCCTGGTAGT CCACGCCGTAAACGATGTCGACTTGGAGGTTGTGCCCTTGAGGCGT GGCTTCCGGAGCTAACGCGTTAAGTCGACCGCCTGGGGAGTACGG CCGCAAGGTTAAAACTCAAATGAATTGACGGGGGCCCGCACAAGCG GTGGAGCATGTGGTTTAATTCGATGCAACGCGAAGAACCTTACCTG GTCTTGACATCCACGGAAGTTTTCAGAGATGAGAATGTGCCTTCGG GAACCGTGAGACAGGTGCTGCATGGCTGTCGTCAGCTCGTGTTGTG AAATGTTGGGTTAAGTCCCGCAACGAGCGCAACCCTTATCCTTTGTT |

TABLE 6-continued

Sequences used in this disclosure.

| Sequence Description [SEQ ID NO: __] | Nucleotide or Amino Acid Sequence |
|---|---|
| | GCCAGCGGTCCGGCCGGGAACTCAAAGGAGACTGCCAGTGATAAA<br>CTGGAGGAAGGTGGGGATGACGTCAAGTCATCATGGCCCTTACGAC<br>CAGGGCTACACACGTGCTACAATGGCGCATACAAAGAGAAGCGACC<br>TCGCGAGAGCAAGCGGACCTCATAAAGTGCGTCGTAGTCCGGATTG<br>GAGTCTGCAACTCGACTCCATGAAGTCGGAATCGCTAGTAATCGTG<br>GATCAGAATGCCACGGTGAATACGTTCCCGGGCCTTGTACACACCG<br>CCCGTCACACCATGGGAGTGGGTTGCAAAAGAAGTAGGTAGCTTAA<br>CCTTCGGGAGGGCGCTTACCACTTTGTGATTCATGACTGGGGTGAA<br>GTCGTAACAAGGTAACCGTAGGGGAACCTGCGGTTGGATCACCTCC<br>TTAGGCTAGCATAACCCCTTGGGGCCTCTAAACGGGTCTTGAGGGG<br>TTTTTTGTCTAGAGTCGACCTGCAGGCATGCAAGCTTGGCGTAATCA<br>TGGTCATAGCTGTTTCCTGTGTGAAATTGTTATCCGCTCACAATTCC<br>ACACAACATACGAGCCGGAAGCATAAAGTGTAAAGCCTGGGGTGCC<br>TAATGAGTGAGCTAACTCACATTAATTGCGTTGCGCTCACTGCCCGC<br>TTTCCAGTCGGGAAACCTGTCGTGCCAGCTGCATTAATGAATCGGC<br>CAACGCGCGGGGAGAGGCGGTTTGCGTATTGGGCGCTCTTCCGCT<br>TCCTCGCTCACTGACTCGCTGCGCTCGGTCGTTCGGCTGCGGCGA<br>GCGGTATCAGCTCACTCAAAGGCGGTAATACGGTTATCCACAGAAT<br>CAGGGGATAACGCAGGAAAGAACATGTGAGCAAAAGGCCAGCAAAA<br>GGCCAGGAACCGTAAAAAGGCCGCGTTGCTGGCGTTTTTCCATAGG<br>CTCCGCCCCCTGACGAGCATCACAAAAATCGACGCTCAAGTCAGA<br>GGTGGCGAAACCCGACAGGACTATAAAGATACCAGGCGTTTCCCCC<br>TGGAAGCTCCCTCGTGCGCTCTCCTGTTCCGACCCTGCCGCTTACC<br>GGATACCTGTCCGCCTTTCTCCCTTCGGGAAGCGTGGCGCTTTCTC<br>ATAGCTCACGCTGTAGGTATCTCAGTTCGGTGTAGGTCGTTCGCTC<br>CAAGCTGGGCTGTGTGCACGAACCCCCCGTTCAGCCCGACCGCTG<br>CGCCTTATCCGGTAACTATCGTCTTGAGTCCAACCCGGTAAGACAC<br>GACTTATCGCCACTGGCAGCAGCCACTGGTAACAGGATTAGCAGAG<br>CGAGGTATGTAGGCGGTGCTACAGAGTTCTTGAAGTGGTGGCCTAA<br>CTACGGCTACACTAGAAGAACAGTATTTGGTATCTGCGCTCTGCTGA<br>AGCCAGTTACCTTCGGAAAAAGAGTTGGTAGCTCTTGATCCGGCAA<br>ACAAACCACCGCTGGTAGCGGTGGTTTTTTTGTTTGCAAGCAGCAG<br>ATTACGCGCAGAAAAAAAGGATCTCAAGAAGATCCTTTGATCTTTTC<br>TACGGGGTCTGACGCTCAGTGGAACGAAAACTCACGTTAAGGGATT<br>TTGGTCATGAGATTATCAAAAAGGATCTTCACCTAGATCCTTTTAAAT<br>TAAAAATGAAGTTTTAAATCAATCTAAAGTATATATGAGTAAACTTGG<br>TCTGACAGTTACCAATGCTTAATCAGTGAGGCACCTATCTCAGCGAT<br>CTGTCTATTTCGTTCATCCATAGTTGCCTGACTCCCCGTCGTGTAGA<br>TAACTACGATACGGGAGGGCTTACCATCTGGCCCCAGTGCTGCAAT<br>GATACCGCGAGACCCACGCTCACCGGCTCCAGATTTATCAGCAATA<br>AACCAGCCAGCCGGAAGGGCCGAGCGCAGAAGTGGTCCTGCAACT<br>TTATCCGCCTCCATCCAGTCTATTAATTGTTGCCGGGAAGCTAGAGT<br>AAGTAGTTCGCCAGTTAATAGTTTGCGCAACGTTGTTGCCATTGCTA<br>CAGGCATCGTGGTGTCACGCTCGTCGTTTGGTATGGCTTCATTCAG<br>CTCCGGTTCCCAACGATCAAGGCGAGTTACATGATCCCCCATGTTG<br>TGCAAAAAAGCGGTTAGCTCCTTCGGTCCTCCGATCGTTGTCAGAA<br>GTAAGTTGGCCGCAGTGTTATCACTCATGGTTATGGCAGCACTGCA<br>TAATTCTCTTACTGTCATGCCATCCGTAAGATGCTTTTCTGTGACTG<br>GTGAGTACTCAACCAAGTCATTCTGAGAATAGTGTATGCGGCGACC<br>GAGTTGCTCTTGCCCGGCGTCAATACGGGATAATACCGCGCCACAT<br>AGCAGAACTTTAAAAGTGCTCATCATTGGAAAACGTTCTTCGGGGCG<br>AAAACTCTCAAGGATCTTACCGCTGTTGAGATCCAGTTCGATGTAAC<br>CCACTCGTGCACCCAACTGATCTTCAGCATCTTTTACTTTCACCAGC<br>GTTTCTGGGTGAGCAAAAACAGGAAGGCAAAATGCCGCAAAAAAGG<br>GAATAAGGGCGACACGGAAATGTTGAATACTCATACTCTTCCTTTTT<br>CAATATTATTGAAGCATTTATCAGGGTTATTGTCTCATGAGCGGATA<br>CATATTTGAATGTATTTAGAAAAATAAACAAATAGGGGTTCCGCGCA<br>CATTTCCCCGAAAAGTGCCACCTGACGTCTAAGAAACCATTATTATC<br>ATGACATTAACCTATAAAAATAGGCGTATCACGAGGCCCTTTCGTCT<br>CGCGCGTTTCGGTGATGACGGTGAAAACCTCTGACACATGCAGCTC<br>CCGGAGACGGTCACAGCTTGTCTGTAAGCGGATGCCGGGAGCAGA<br>CAAGCCCGTCAGGGCGCGTCAGCGGGTGTTGGCGGGTGTCGGGG<br>CTGGCTTAACTATGCGGCATCAGAGCAGATTGTACTGAGAGTGCAC<br>CATATGCGGTGTGAAATACCGCACAGATGCGTAAGGAGAAAATACC<br>GCATCAGGCGCCATTCGCCATTCAGGCTGCGCAACTGTTGGGAAG<br>GGCGATCGGTGCGGGCCTCTTCGCTATTACGCCAGCTGGCGAAAG<br>GGGGATGTGCTGCAAGGCGATTAAGTTGGGTAACGCCAGGGTTTTC<br>CCAGTCACGACGTTGTAAAACGACGGCCAGTGAATTCGAGCTCGGT<br>ACC |
| p16S-T 16S RNA [SEQ ID NO: 15] | AGAUUGAAGAGUUUGAUCAUGGCUCAGAUUGAACGCUGGCGGC<br>AGGCCUAACACAUGCAAGUCGAACGGUAACAGGAAGAAGCUUGC<br>UUCUUUGCUGACGAGUGGCGGACGGGUGAGUAAUGUCUGGGAA<br>ACUGCCUGAUGGAGGGGGAUAACUACUGGAAACGGUAGCUAAUA |

TABLE 6-continued

Sequences used in this disclosure.

| Sequence Description [SEQ ID NO: __] | Nucleotide or Amino Acid Sequence |
|---|---|
| | CCGCAUAACGUCGCAAGACCAAAGAGGGGGACCUUCGGGCCUC UUGCCAUCGGAUGUGCCCAGAUGGGAUUAGCUAGUAGGUGGGG UAACGGCUCACCUAGGCGACGAUCCCUAGCUGGUCUGAGAGGA UGACCAGCCACACUGGAACUGAGACACGGUCCAGACUCCUACGG GAGGCAGCAGUGGGGAAUAUUGCACAAUGGGCGCAAGCCUGAU GCAGCCAUGCCGCGUGUAUGAAGAAGGCCUUCGGGUUGUAAAG UACUUUCAGCGGGGAGGAAGGGAGUAAAGUUAAUACCUUUGCUC AUUGACGUUACCCGCAGAAGAAGCACCGGCUAACUCCGUGCCAG CAGCCGCGGUAAUACGGAGGGUGCAAGCGUUAAUCGGAAUUAC UGGGCGUAAAGCGCACGCAGGCGGUUUGUUAAGUCAGAUGUGA AAUCCCCGGGCUCAACCUGGGAACUGCAUCUGAUACUGGCAAGC UUGAGUCUCGUAGAGGGGGGUAGAAUUCCAGGUGUAGCGGUGA AAUGCGUAGAGAUCUGGAGGAAUACCGGUGGCGAAGGCGGCCC CCUGGACGAAGACUGACGCUCAGGUGCGAAAGCGUGGGGAGCA AACAGGAUUAGAUACCCUGGUAGUCCACGCCGUAAACGAUGUCG ACUUGGAGGUUGUGCCCUUGAGGCGUGGCUUCCGGAGCUAACG CGUUAAGUCGACCGCCUGGGGAGUACGGCCGCAAGGUUAAAAC UCAAAUGAAUUGACGGGGGCCCGCACAAGCGGUGGAGCAUGUG GUUUAAUUCGAUGCAACGCGAAGAACCUUACCUGGUCUUGACAU CCACGGAAGUUUUCAGAGAUGAGAAUGUGCCUUCGGGAACCGU GAGACAGGUGCUGCAUGGCUGUCGUCAGCUCGUGUUGUGAAAU GUUGGGUUAAGUCCCGCAACGAGCGCAACCCUUAUCCUUUGUU GCCAGCGGUCCGGCCGGGAACUCAAAGGAGACUGCCAGUGAUA AACUGGAGGAAGGUGGGGAUGACGUCAAGUCAUCAUGGCCCUU ACGACCAGGGCUACACACGUGCUACAAUGGCGCAUACAAAGAGA AGCGACCUCGCGAGAGCAAGCGGACCUCAUAAAGUGCGUCGUA GUCCGGAUUGGAGUCUGCAACUCGACUCCAUGAAGUCGGAAUC GCUAGUAAUCGUGGAUCAGAAUGCCACGGUGAAUACGUUCCCG GGCCUUGUACACACCGCCCGUCACACCAUGGGAGUGGGUUGCA AAAGAAGUAGGUAGCUUAACCUUCGGGAGGGCGCUUACCACUUU GUGAUUCAUGACUGGGGUGAAGUCGUAACAAGGUAACCGUAGG GGAACCUGCGGUUGGAUCACCUCCUUAGGCUAGCAUAACCCCUU GGGGCCUCUAAACGGGUCUUGAGGGGUUUUUUG |
| p23S-T DNA [SEQ ID NO: 16] | TAATACGACTCACTATAGGTTAAGCGACTAAGCGTACACGGTGGAT GCCCTGGCAGTCAGAGGCGATGAAGGACGTGCTAATCTGCGATAA GCGTCGGTAAGGTGATATGAACCGTTATAACCGGCGATTTCCGAAT GGGGAAACCCAGTGTGTTTCGACACACTATCATTAACTGAATCCATA GGTTAATGAGGCGAACCGGGGAACTGAAACATCTAAGTACCCCGA GGAAAAGAAATCAACCGAGATTCCCCCAGTAGCGGCGAGCGAACG GGGAGCAGCCCAGAGCCTGAATCAGTGTGTGTTAGTGGAAGCG TCTGGAAAGGCGCGCGATACAGGGTGACAGCCCCGTACACAAAAT GCACATGCTGTGAGCTCGATGAGTAGGGCGGGACACGTGGTATCC TGTCTGAATATGGGGGGACCATCCTCCAAGGCTAAATACTCCTGAC TGACCGATAGTGAACCAGTACCGTGAGGGAAAGGCGAAAAGAACCC CGGCGAGGGGAGTGAAAAAGAACCTGAAACCGTGTACGTACAAGC AGTGGGAGCACGCTTAGGCGTGTGACTGCGTACCTTTTGTATAATG GGTCAGCGACTTATATTCTGTAGCAAGGTTAACCGAATAGGGGAGC CGAAGGGAAACCGAGTCTTAACTGGGCGTTAAGTTGCAGGGTATAG ACCCGAAACCCGGTGATCTAGCCATGGGCAGGTTGAAGGTTGGGTA ACACTAACTGGAGGACCGAACCGACTAATGTTGAAAAATTAGCGGA TGACTTGTGGCTGGGGGTGAAAGGCCAATCAAACCGGGAGATAGCT GGTTCTCCCCGAAAGCTATTTAGGTAGCGCCTCGTGAATTCATCTCC GGGGGTAGAGCACTGTTTCGGCAAGGGGGTCATCCCGACTTACCA AACCCGATGCAAACTGCGAATACCGGAGAATGTTATCACGGGAGACA CACGGCGGGTGCTAACGTCCGTCGTGAAGAGGGAAACAACCCAGA CCGCCAGCTAAGGTCCCAAAGTCATGGTTAAGTGGGAAACGATGTG GGAAGGCCCAGACAGCCAGGATGTTGGCTTAGAAGCAGCCATCATT TAAAGAAAGCGTAATAGCTCACTGGTCGAGTCGGCCTGCGCGGAAG ATGTAACGGGGCTAAACCATGCACCGAAGCTGCGGCAGCGACGCT TATGCGTTGTTGGGTAGGGGAGCGTTCTGTAAGCCTGCGAAGGTGT GCTGTGAGGCATGCTGGAGGTATCAGAAGTGCGAATGCTGACATAA GTAACGATAAAGCGGGTGAAAAGCCCGCTCGCCGGAAGACCAAGG GTTCCTGTCCAACGTTAATCGGGGCAGGGTGAGTCGACCCCTAAGG CGAGGCCGAAAGGCGTAGTCGATGGGAAACAGGTTAATATTCCTGT ACTTGGTGTTACTGCGAAGGGGGACGGAGAAGGCTATGTTGGCC GGGCGACGGTTGTCCCGGTTTAAGCGTGTAGGCTGGTTTTCCAGGC AAATCCGGAAATCAAGGCTGAGGCGTGATGACGAGGCACTACGGT GCTGAAGCAACAAATGCCCTGCTTCCAGGAAAAGCCTCTAAGCATC AGGTAACATCAAATCGTACCCCAAACCGACACAGGTGGTCAGGTAG AGAATACCAAGGCGCTTGAGAGAACTCGGGTGAAGGAACTAGGCAA AATGGTGCCGTAACTTCGGGAGAAGGCACGCTGATATGTAGGTGAG GTCCCTCGCGGATGGAGCTGAAATCAGTCGAAGATACCAGCTGGCT GCAACTGTTTATTAAAAACACAGCACTGTGCAAACACGAAAGTGGAC |

TABLE 6-continued

Sequences used in this disclosure.

| Sequence Description [SEQ ID NO: __] | Nucleotide or Amino Acid Sequence |
|---|---|
| | GTATACGGTGTGACGCCTGCCCGGTGCCGGAAGGTTAATTGATGG |
| | GGTTAGCGCAAGCGAAGCTCTTGATCGAAGCCCCGGTAAACGGCG |
| | GCCGTAACTATAACGGTCCTAAGGTAGCGAAATTCCTTGTCGGGTA |
| | AGTTCCGACCTGCACGAATGGCGTAATGATGGCCAGGCTGTCTCCA |
| | CCCGAGACTCAGTGAAATTGAACTCGCTGTGAAGATGCAGTGTACC |
| | CGCGGCAAGACGGAAAGACCCCGTGAACCTTTACTATAGCTTGACA |
| | CTGAACATTGAGCCTTGATGTGTAGGATAGGTGGGAGGCTTTGAAG |
| | TGTGGACGCCAGTCTGCATGGAGCCGACCTTGAAATACCACCCTTT |
| | AATGTTTGATGTTCTAACGTTGACCCGTAATCCGGGTTGCGGACAGT |
| | GTCTGGTGGGTAGTTTGACTGGGGCGGTCTCCTCCTAAAGAGTAAC |
| | GGAGGAGCACGAAGGTTGGCTAATCCTGGTCGGACATCAGGAGGT |
| | TAGTGCAATGGCATAAGCCAGCTTGACTGCGAGCGTGACGGCGCG |
| | AGCAGGTGCGAAAGCAGGTCATAGTGATCCGGTGGTTCTGAATGGA |
| | AGGGCCATCGCTCAACGGATAAAAGGTACTCCGGGGATAACAGGCT |
| | GATACCGCCCAAGAGTTCATATCGACGGCGGTGTTTGGCACCTCGA |
| | TGTCGGCTCATCACATCCTGGGGCTGAAGTAGGTCCCAAGGGTATG |
| | GCTGTTCGCCATTTAAAGTGGTACGCGAGCTGGGTTTAGAACGTCG |
| | TGAGACAGTTCGGTCCCTATCTGCCGTGGGCGCTGGAGAACTGAG |
| | GGGGGCTGCTCCTAGTACGAGAGGACCGGAGTGGACGCATCACTG |
| | GTGTTCGGGTTGTCATGCCAATGGCACTGCCCGGTAGCTAAATGCG |
| | GAAGAGATAAGTGCTGAAAGCATCTAAGCACGAAACTTGCCCCGAG |
| | ATGAGTTCTCCCTGACCCTTTAAGGGTCCTGAAGGAACGTTGAAGA |
| | CGACGACGTTGATAGGCCGGGTGTGTAAGCGCAGCGATGCGTTGA |
| | GCTAACCGGTACTAATGAACCGTGAGGCTTAACCTTCTAGCATAACC |
| | CCTTGGGGCCTCTAAACGGGTCTTGAGGGGTTTTTTGAAGCTGCAG |
| | GCATGCAAGCTTGGCGTAATCATGGTCATAGCTGTTTCCTGTGTGAA |
| | ATTGTTATCCGCTCACAATTCCACACAACATACGAGCCGGAAGCATA |
| | AAGTGTAAAGCCTGGGGTGCCTAATGAGTGAGCTAACTCACATTAAT |
| | TGCGTTGCGCTCACTGCCCGCTTTCCAGTCGGGAAACCTGTCGTGC |
| | CAGCTGCATTAATGAATCGGCCAACGCGCGGGGAGAGGCGGTTTG |
| | CGTATTGGGCGCTCTTCCGCTTCCTCGCTCACTGACTCGCTGCGCT |
| | CGGTCGTTCGGCTGCGGCGAGCGGTATCAGCTCACTCAAAGGCGG |
| | TAATACGGTTATCCACAGAATCAGGGGATAACGCAGGAAAGAACAT |
| | GTGAGCAAAAGGCCAGCAAAAGGCCAGGAACCGTAAAAAGGCCGC |
| | GTTGCTGGCGTTTTTCCATAGGCTCCGCCCCCCTGACGAGCATCAC |
| | AAAAATCGACGCTCAAGTCAGAGGTGGCGAAACCCGACAGGACTAT |
| | AAAGATACCAGGCGTTTCCCCCTGGAAGCTCCCTCGTGCGCTCTCC |
| | TGTTCCGACCCTGCCGCTTACCGGATACCTGTCCGCCTTTCTCCCTT |
| | CGGGAAGCGTGGCGCTTTCTCATAGCTCACGCTGTAGGTATCTCAG |
| | TTCGGTGTAGGTCGTTCGCTCCAAGCTGGGCTGTGTGCACGAACCC |
| | CCCGTTCAGCCCGACCGCTGCGCCTTATCCGGTAACTATCGTCTTG |
| | AGTCCAACCCGGTAAGACACGACTTATCGCCACTGGCAGCAGCCAC |
| | TGGTAACAGGATTAGCAGAGCGAGGTATGTAGGCGGTGCTACAGAG |
| | TTCTTGAAGTGGTGGCCTAACTACGGCTACACTAGAAGAACAGTATT |
| | TGGTATCTGCGCTCTGCTGAAGCCAGTTACCTTCGGAAAAAGAGTT |
| | GGTAGCTCTTGATCCGGCAAACAAACCACCGCTGGTAGCGGTGGTT |
| | TTTTTGTTTGCAAGCAGCAGATTACGCGCAGAAAAAAAGGATCTCAA |
| | GAAGATCCTTTGATCTTTTCTACGGGGTCTGACGCTCAGTGGAACG |
| | AAAACTCACGTTAAGGGATTTTGGTCATGAGATTATCAAAAAGGATC |
| | TTCACCTAGATCCTTTTAAATTAAAAATGAAGTTTTAAATCAATCTAAA |
| | GTATATATGAGTAAACTTGGTCTGACAGTTACCAATGCTTAATCAGT |
| | GAGGCACCTATCTCAGCGATCTGTCTATTTCGTTCATCCATAGTTGC |
| | CTGACTCCCCGTCGTGTAGATAACTACGATACGGGAGGGCTTACCA |
| | TCTGGCCCCAGTGCTGCAATGATACCGCGAGACCCACGCTCACCG |
| | GCTCCAGATTTATCAGCAATAAACCAGCCAGCCGGAAGGGCCGAGC |
| | GCAGAAGTGGTCCTGCAACTTTATCCGCCTCCATCCAGTCTATTAAT |
| | TGTTGCCGGGAAGCTAGAGTAAGTAGTTCGCCAGTTAATAGTTTGC |
| | GCAACGTTGTTGCCATTGCTACAGGCATCGTGGTGTCACGCTCGTC |
| | GTTTGGTATGGCTTCATTCAGCTCCGGTTCCCAACGATCAAGGCGA |
| | GTTACATGATCCCCCATGTTGTGCAAAAAAGCGGTTAGCTCCTTCGG |
| | TCCTCCGATCGTTGTCAGAAGTAAGTTGGCCGCAGTGTTATCACTCA |
| | TGGTTATGGCAGCACTGCATAATTCTCTTACTGTCATGCCATCCGTA |
| | AGATGCTTTTCTGTGACTGGTGAGTACTCAACCAAGTCATTCTGAGA |
| | ATAGTGTATGCGGCGACCGAGTTGCTCTTGCCCGGCGTCAATACGG |
| | GATAATACCGCGCCACATAGCAGAACTTTAAAAGTGCTCATCATTGG |
| | AAAACGTTCTTCGGGGCGAAAACTCTCAAGGATCTTACCGCTGTTGA |
| | GATCCAGTTCGATGTAACCCACTCGTGCACCCAACTGATCTTCAGCA |
| | TCTTTTACTTTCACCAGCGTTTCTGGGTGAGCAAAAACAGGAAGGCA |
| | AAATGCCGCAAAAAAGGGAATAAGGGCGACACGGAAATGTTGAATA |
| | CTCATACTCTTCCTTTTTCAATATTATTGAAGCATTTATCAGGGTTATT |
| | GTCTCATGAGCGGATACATATTTGAATGTATTTAGAAAAATAAACAAA |
| | TAGGGGTTCCGCGCACATTTCCCCGAAAAGTGCCACCTGACGTCTA |
| | AGAAACCATTATTATCATGACATTAACCTATAAAAATAGGCGTATCAC |
| | GAGGCCCTTTCGTCTCGCGCGTTTCGGTGATGACGGTGAAAACCTC |

TABLE 6-continued

Sequences used in this disclosure.

| Sequence Description [SEQ ID NO: __] | Nucleotide or Amino Acid Sequence |
|---|---|
| | TGACACATGCAGCTCCCGGAGACGGTCACAGCTTGTCTGTAAGCGG ATGCCGGGAGCAGACAAGCCCGTCAGGGCGCGTCAGCGGGTGTTG GCGGGTGTCGGGGCTGGCTTAACTATGCGGCATCAGAGCAGATTG TACTGAGAGTGCACCATATGCGGTGTGAAATACCGCACAGATGCGT AAGGAGAAAATACCGCATCAGGCGCCATTCGCCATTCAGGCTGCGC AACTGTTGGGAAGGGCGATCGGTGCGGGCCTCTTCGCTATTACGCC AGCTGGCGAAAGGGGGATGTGCTGCAAGGCGATTAAGTTGGGTAA CGCCAGGGTTTTCCCAGTCACGACGTTGTAAAACGACGGCCAGTGA ATTCGAGCTCGGTACC |
| p23S-T 23S RNA [SEQ ID NO: 17] | GGUUAAGCGACUAAGCGUACACGGUGGAUGCCCUGGCAGUCAG AGGCGAUGAAGGACGUGCUAAUCUGCGAUAAGCGUCGGUAAGG UGAUAUGAACCGUUAUAACCGGCGAUUUCCGAAUGGGGAAACCC AGUGUGUUUCGACACACUAUCAUUAACUGAAUCCAUAGGUUAAU GAGGCGAACCGGGGAACUGAAACAUCUAAGUACCCCGAGGAAA AGAAAUCAACCGAGAUUCCCCCAGUAGCGGCGAGCGAACGGGGA GCAGCCCAGAGCCUGAAUCAGUGUGUGUGUUAGUGGAAGCGUC UGGAAAGGCGCGCGAUACAGGGUGACAGCCCCGUACACAAAAAU GCACAUGCUGUGAGCUCGAUGAGUAGGGCGGGACACGUGGUAU CCUGUCUGAAUAUGGGGGGACCAUCCUCCAAGGCUAAAUACUCC UGACUGACCGAUAGUGAACCAGUACCGUGAGGGAAAGGCGAAAA GAACCCCGGCGAGGGGAGUGAAAAAGAACCUGAAACCGUGUACG UACAAGCAGUGGGAGCACGCUUAGGCGUGUGACUGCGUACCUU UUGUAUAAUGGGUCAGCGACUUAUAUUCUGUAGCAAGGUUAACC GAAUAGGGGAGCCGAAGGGAAACCGAGUCUUAACUGGGCGUUA AGUUGCAGGGUAUAGACCCGAAACCCGGUGAUCUAGCCAUGGG CAGGUUGAAGGUUGGGUAACACUAACUGGAGGACCGAACCGACU AAUGUUGAAAAAUUAGCGGAUGACUUGUGGCUGGGGGUGAAAG GCCAAUCAAACCGGGAGAUAGCUGGUUCUCCCCGAAAGCUAUUU AGGUAGCGCCUCGUGAAUUCAUCUCCGGGGGUAGAGCACUGUU UCGGCAAGGGGGUCAUCCCGACUUACCAACCCGAUGCAAACUGC GAAUACCGGAGAAUGUUAUCACGGGAGACACACGGCGGGUGCU AACGUCCGUCGUGAAGAGGGAAACAACCCAGACCGCCAGCUAAG GUCCCAAAGUCAUGGUUAAGUGGGAAACGAUGUGGGAAGGCCC AGACAGCCAGGAUGUUGGCUUAGAAGCAGCCAUCAUUUAAAGAA AGCGUAAUAGCUCACUGGUCGAGUCGGCCUGCGCGGAAGAUGU AACGGGGCUAAACCAUGCACCGAAGCUGCGGCAGCGACGCUUAU GCGUUGUUGGGUAGGGGAGCGUUCUGUAAGCCUGCGAAGGUGU GCUGUGAGGCAUGCUGGAGGUAUCAGAAGUGCGAAUGCUGACA UAAGUAACGAUAAAGCGGGUGAAAAGCCCGCUCGCCGGAAGACC AAGGGUUCCUGUCCAACGUUAAUCGGGGCAGGGUGAGUCGACC CCUAAGGCGAGGCCGAAAGGCGUAGUCGAUGGGAAACAGGUUA AUAUUCCUGUACUUGGUGUUACUGCGAAGGGGGGACGGAGAAG GCUAUGUUGGCCGGGCGACGGUUGUCCCGGUUUAAGCGUGUAG GCUGGUUUUCCAGGCAAAUCCGGAAAAUCAAGGCUGAGGCGUG AUGACGAGGCACUACGGUGCUGAAGCAACAAAUGCCCUGCUUCC AGGAAAAGCCUCUAAGCAUCAGGUAACAUCAAAUCGUACCCCAAA CCGACACAGGUGGUCAGGUAGAGAAUACCAAGGCGCUUGAGAGA ACUCGGGUGAAGGAACUAGGCAAAAUGGUGCCGUAACUUCGGG AGAAGGCACGCUGAUAUGUAGGUGAGGUCCCUCGCGGAUGGAG CUGAAAUCAGUCGAAGAUACCAGCUGGCUGCAACUGUUUAUUAA AAACACAGCACUGUGCAAACACGAAAGUGGACGUAUACGGUGUG ACGCCUGCCCGGUGCCGGAAGGUUAAUUGAUGGGGUUAGCGCA AGCGAAGCUCUUGAUCGAAGCCCCGGUAAACGGCGGCCGUAAC UAUAACGGUCCUAAGGUAGCGAAAUUCCUUGUCGGGUAAGUUCC GACCUGCACGAAUGGCGUAAUGAUGGCCAGGCUGUCUCCACCC GAGACUCAGUGAAAUUGAACUCGCUGUGAAGAUGCAGUGUACCC GCGGCAAGACGGAAAGACCCCGUGAACCUUUACUAUAGCUUGAC ACUGAACAUUGAGCCUUGAUGUGUAGGAUAGGUGGGAGGCUUU GAAGUGUGGACGCCAGUCUGCAUGGAGCCGACCUUGAAAUACCA CCCUUUAAUGUUUGAUGUUCUAACGUUGACCCGUAAUCCGGGUU GCGGACAGUGUCUGGUGGGUAGUUUGACUGGGGCGGUCUCCUC CUAAAGAGUAACGGAGGAGCACAAGGUUGGCUAAUCCUGGUC GGACAUCAGGAGGUUAGUGCAAUGGCAUAAGCCAGCUUGACUG CGAGCGUGACGGCGCGAGCAGGUGCGAAAGCAGGUCAUAGUGA UCCGGUGGUUCUGAAUGGAAGGGCCAUCGCUCAACGGAUAAAA GGUACUCCGGGGAUAACAGGCUGAUACCGCCCAAGAGUUCAUAU CGACGGCGGUGUUUGGCACCUCGAUGUCGGCUCAUCACAUCCU GGGGCUGAAGUAGGUCCCAAGGGUAUGGCUGUUCGCCAUUUAA AGUGGUACGCGAGCUGGGUUUAGAACGUCGUGAGACAGUUCGG UCCCUAUCUGCCGUGGGCGCUGGAGAACUGAGGGGGGCUGCUC CUAGUACGAGAGGACCGGAGUGGACGCAUCACUGGUGUUCGGG UUGUCAUGCCAAUGGCACUGCCCGGUAGCUAAAUGCGGAAGAGA UAAGUGCUGAAAGCAUCUAAGCACGAAACUUGCCCCGAGAUGAG |

TABLE 6-continued

Sequences used in this disclosure.

| Sequence Description [SEQ ID NO: __] | Nucleotide or Amino Acid Sequence |
| --- | --- |
| | UUCUCCCUGACCCUUUAAGGGUCCUGAAGGAACGUUGAAGACGA<br>CGACGUUGAUAGGCCGGGUGUGUAAGCGCAGCGAUGCGUUGAG<br>CUAACCGGUACUAAUGAACCGUGAGGCUUAACCUUCUAGCAUAA<br>CCCCUUGGGGCCUCUAAACGGGUCUUGAGGGGUUUUUUG |
| p16S-HH DNA<br>[SEQ ID NO: 18] | TAATACGACTCACTATAGGGAGATTGAAGAGTTTGATCATGGCTCAG<br>ATTGAACGCTGGCGGCAGGCCTAACACATGCAAGTCGAACGGTAAC<br>AGGAAGAAGCTTGCTTCTTTGCTGACGAGTGGCGGACGGGTGAGTA<br>ATGTCTGGGAAACTGCCTGATGGAGGGGGATAACTACTGGAAACGG<br>TAGCTAATACCGCATAACGTCGCAAGACCAAAGAGGGGGACCTTCG<br>GGCCTCTTGCCATCGGATGTGCCCAGATGGGATTAGCTAGTAGGTG<br>GGGTAACGGCTCACCTAGGCGACGATCCCTAGCTGGTCTGAGAGG<br>ATGACCAGCCACACTGGAACTGAGACACGGTCCAGACTCCTACGGG<br>AGGCAGCAGTGGGGAATATTGCACAATGGGCGCAAGCCTGATGCA<br>GCCATGCCGCGTGTATGAAGAAGGCCTTCGGGTTGTAAAGTACTTT<br>CAGCGGGGAGGAAGGGAGTAAAGTTAATACCTTTGCTCATTGACGT<br>TACCCGCAGAAGAAGCACCGGCTAACTCCGTGCCAGCAGCCGCGG<br>TAATACGGAGGGTGCAAGCGTTAATCGGAATTACTGGGCGTAAAGC<br>GCACGCAGGCGGTTTGTTAAGTCAGATGTGAAATCCCCGGGCTCAA<br>CCTGGGAACTGCATCTGATACTGGCAAGCTTGAGTCTCGTAGAGGG<br>GGGTAGAATTCCAGGTGTAGCGGTGAAATGCGTAGAGATCTGGAGG<br>AATACCGGTGGCGAAGGCGGCCCCCTGGACGAAGACTGACGCTCA<br>GGTGCGAAAGCGTGGGGAGCAAACAGGATTAGATACCCTGGTAGT<br>CCACGCCGTAAACGATGTCGACTTGGAGGTTGTGCCCTTGAGGCGT<br>GGCTTCCGGAGCTAACGCGTTAAGTCGACCGCCTGGGGAGTACGG<br>CCGCAAGGTTAAAACTCAAATGAATTGACGGGGGCCCGCACAAGCG<br>GTGGAGCATGTGGTTTAATTCGATGCAACGCGAAGAACCTTACCTG<br>GTCTTGACATCCACGGAAGTTTTCAGAGATGAGAATGTGCCTTCGG<br>GAACCGTGAGACAGGTGCTGCATGGCTGTCGTCAGCTCGTGTTGTG<br>AAATGTTGGGTTAAGTCCCGCAACGAGCGCAACCCTTATCCTTTGTT<br>GCCAGCGGTCCGGCCGGGAACTCAAAGGAGACTGCCAGTGATAAA<br>CTGGAGGAAGGTGGGGATGACGTCAAGTCATCATGGCCCTTACGAC<br>CAGGGCTACACACGTGCTACAATGGCGCATACAAAGAGAAGCGACC<br>TCGCGAGAGCAAGCGGACCTCATAAAGTGCGTCGTAGTCCGGATTG<br>GAGTCTGCAACTCGACTCCATGAAGTCGGAATCGCTAGTAATCGTG<br>GATCAGAATGCCACGGTGAATACGTTCCCGGGCCTTGTACACACCG<br>CCCGTCACACCATGGGAGTGGGTTGCAAAAGAAGTAGGTAGCTTAA<br>CCTTCGGGAGGGCGCTTACCACTTTGTGATTCATGACTGGGGTGAA<br>GTCGTAACAAGGTAACCGTAGGGGAACCTGCGGTTGGATCACCTCC<br>TTAGGTCTGAGCGTGATACCCGCTCACTGAAGATGGCCCGGTAGGG<br>CCGAAACCTACTAGCATAACCCCTTGGGGCCTCTAAACGGGTCTTG<br>AGGGGTTTTTTGTCTAGAGTCGACCTGCAGGCATGCAAGCTTGGCG<br>TAATCATGGTCATAGCTGTTTCCTGTGTGAAATTGTTATCCGCTCAC<br>AATTCCACACAACATACGAGCCGGAAGCATAAAGTGTAAAGCCTGG<br>GGTGCCTAATGAGTGAGCTAACTCACATTAATTGCGTTGCGCTCACT<br>GCCCGCTTTCCAGTCGGGAAACCTGTCGTGCCAGCTGCATTAATGA<br>ATCGGCCAACGCGCGGGGAGAGGCGGTTTGCGTATTGGGCGCTCT<br>TCCGCTTCCTCGCTCACTGACTCGCTGCGCTCGGTCGTTCGGCTGC<br>GGCGAGCGGTATCAGCTCACTCAAAGGCGGTAATACGGTTATCCAC<br>AGAATCAGGGGATAACGCAGGAAAGAACATGTGAGCAAAAGGCCAG<br>CAAAAGGCCAGGAACCGTAAAAAGGCCGCGTTGCTGGCGTTTTTCC<br>ATAGGCTCCGCCCCCCTGACGAGCATCACAAAAATCGACGCTCAAG<br>TCAGAGGTGGCGAAACCCGACAGGACTATAAAGATACCAGGCGTTT<br>CCCCCTGGAAGCTCCCTCGTGCGCTCTCCTGTTCCGACCCTGCCGC<br>TTACCGGATACCTGTCCGCCTTTCTCCCTTCGGGAAGCGTGGCGCT<br>TTCTCATAGCTCACGCTGTAGGTATCTCAGTTCGGTGTAGGTCGTTC<br>GCTCCAAGCTGGGCTGTGTGCACGAACCCCCCGTTCAGCCCGACC<br>GCTGCGCCTTATCCGGTAACTATCGTCTTGAGTCCAACCCGGTAAG<br>ACACGACTTATCGCCACTGGCAGCAGCCACTGGTAACAGGATTAGC<br>AGAGCGAGGTATGTAGGCGGTGCTACAGAGTTCTTGAAGTGGTGGC<br>CTAACTACGGCTACACTAGAAGAACAGTATTTGGTATCTGCGCTCTG<br>CTGAAGCCAGTTACCTTCGGAAAAAGAGTTGGTAGCTCTTGATCCG<br>GCAAACAAACCACCGCTGGTAGCGGTGGTTTTTTTGTTTGCAAGCA<br>GCAGATTACGCGCAGAAAAAAAGGATCTCAAGAAGATCCTTTGATCT<br>TTTCTACGGGGTCTGACGCTCAGTGGAACGAAAACTCACGTTAAGG<br>GATTTTGGTCATGAGATTATCAAAAAGGATCTTCACCTAGATCCTTTT<br>AAATTAAAAATGAAGTTTTAAATCAATCTAAAGTATATATGAGTAAACT<br>TGGTCTGACAGTTACCAATGCTTAATCAGTGAGGCACCTATCTCAGC<br>GATCTGTCTATTTCGTTCATCCATAGTTGCCTGACTCCCCGTCGTGT<br>AGATAACTACGATACGGGAGGGCTTACCATCTGGCCCCAGTGCTGC<br>AATGATACCGCGAGACCCACGCTCACCGGCTCCAGATTTATCAGCA<br>ATAAACCAGCCAGCCGGAAGGGCCGAGCGCAGAAGTGGTCCTGCA<br>ACTTTATCCGCCTCCATCCAGTCTATTAATTGTTGCCGGGAAGCTAG<br>AGTAAGTAGTTCGCCAGTTAATAGTTTGCGCAACGTTGTTGCCATTG |

TABLE 6-continued

Sequences used in this disclosure.

| Sequence Description [SEQ ID NO: __] | Nucleotide or Amino Acid Sequence |
|---|---|
| | CTACAGGCATCGTGGTGTCACGCTCGTCGTTTGGTATGGCTTCATT<br>CAGCTCCGGTTCCCAACGATCAAGGCGAGTTACATGATCCCCCATG<br>TTGTGCAAAAAAGCGGTTAGCTCCTTCGGTCCTCCGATCGTTGTCA<br>GAAGTAAGTTGGCCGCAGTGTTATCACTCATGGTTATGGCAGCACT<br>GCATAATTCTCTTACTGTCATGCCATCCGTAAGATGCTTTTCTGTGA<br>CTGGTGAGTACTCAACCAAGTCATTCTGAGAATAGTGTATGCGGCG<br>ACCGAGTTGCTCTTGCCCGGCGTCAATACGGGATAATACCGCGCCA<br>CATAGCAGAACTTTAAAAGTGCTCATCATTGGAAAACGTTCTTCGGG<br>GCGAAAACTCTCAAGGATCTTACCGCTGTTGAGATCCAGTTCGATGT<br>AACCCACTCGTGCACCCAACTGATCTTCAGCATCTTTTACTTTCACC<br>AGCGTTTCTGGGTGAGCAAAAACAGGAAGGCAAAATGCCGCAAAAA<br>AGGGAATAAGGGCGACACGGAAATGTTGAATACTCATACTCTTCCTT<br>TTTCAATATTATTGAAGCATTTATCAGGGTTATTGTCTCATGAGCGGA<br>TACATATTTGAATGTATTTAGAAAAATAAACAAATAGGGGTTCCGCG<br>CACATTTCCCCGAAAAGTGCCACCTGACGTCTAAGAAACCATTATTA<br>TCATGACATTAACCTATAAAAATAGGCGTATCACGAGGCCCTTTCGT<br>CTCGCGCGTTTCGGTGATGACGGTGAAAACCTCTGACACATGCAGC<br>TCCCGGAGACGGTCACAGCTTGTCTGTAAGCGGATGCCGGGAGCA<br>GACAAGCCCGTCAGGGCGCGTCAGCGGGTGTTGGCGGGTGTCGG<br>GGCTGGCTTAACTATGCGGCATCAGAGCAGATTGTACTGAGAGTGC<br>ACCATATGCGGTGTGAAATACCGCACAGATGCGTAAGGAGAAAATA<br>CCGCATCAGGCGCCATTCGCCATTCAGGCTGCGCAACTGTTGGGAA<br>GGGCGATCGGTGCGGGCCTCTTCGCTATTACGCCAGCTGGCGAAA<br>GGGGGATGTGCTGCAAGGCGATTAAGTTGGGTAACGCCAGGGTTTT<br>CCCAGTCACGACGTTGTAAAACGACGGCCAGTGAATTCGAGCTCGG<br>TACC |
| p16S-HH 16S RNA [SEQ ID NO: 19] | AGAUUGAAGAGUUUGAUCAUGGCUCAGAUUGAACGCUGGCGGC<br>AGGCCUAACACAUGCAAGUCGAACGGUAACAGGAAGAAGCUUGC<br>UUCUUUGCUGACGAGUGGCGGACGGGUGAGUAAUGUCUGGGAA<br>ACUGCCUGAUGGAGGGGGAUAACUACUGGAAACGGUAGCUAAUA<br>CCGCAUAACGUCGCAAGACCAAAGAGGGGGACCUUCGGGCCUC<br>UUGCCAUCGGAUGUGCCCAGAUGGGAUUAGCUAGUAGGUGGGG<br>UAACGGCUCACCUAGGCGACGAUCCCUAGCUGGUCUGAGAGGA<br>UGACCAGCCACACUGGAACUGAGACACGGUCCAGACUCCUACGG<br>GAGGCAGCAGUGGGGAAUAUUGCACAAUGGGCGCAAGCCUGAU<br>GCAGCCAUGCCGCGUGUAUGAAGAAGGCCUUCGGGUUGUAAAG<br>UACUUUCAGCGGGGAGGAAGGGAGUAAAGUUAAUACCUUUGCUC<br>AUUGACGUUACCCGCAGAAGAAGCACCGGCUAACUCCGUGCCAG<br>CAGCCGCGGUAAUACGGAGGGUGCAAGCGUUAAUCGGAAUUAC<br>UGGGCGUAAAGCGCACGCAGGCGGUUUGUUAAGUCAGAUGUGA<br>AAUCCCCGGGCUCAACCUGGGAACUGCAUCUGAUACUGGCAAGC<br>UUGAGUCUCGUAGAGGGGGGUAGAAUUCCAGGUGUAGCGGUGA<br>AAUGCGUAGAGAUCUGGAGGAAUACCGGUGGCGAAGGCGGCCC<br>CCUGGACGAAGACUGACGCUCAGGUGCGAAAGCGUGGGGAGCA<br>AACAGGAUUAGAUACCCUGGUAGUCCACGCCGUAAACGAUGUCG<br>ACUUGGAGGUUGUGCCCUUGAGGCGUGGCUUCCGGAGCUAACG<br>CGUUAAGUCGACCGCCUGGGGAGUACGGCCGCAAGGUUAAAAC<br>UCAAAUGAAUUGACGGGGGCCCGCACAAGCGGUGGAGCAUGUG<br>GUUUAAUUCGAUGCAACGCGAAGAACCUUACCUGGUCUUGACAU<br>CCACGGAAGUUUUCAGAGAUGAGAAUGUGCCUUCGGGAACCGU<br>GAGACAGGUGCUGCAUGGCUGUCGUCAGCUCGUGUUGUGAAAU<br>GUUGGGUUAAGUCCCGCAACGAGCGCAACCCUUAUCCUUUGUU<br>GCCAGCGGUCCGGCCGGGAACUCAAAGGAGACUGCCAGUGAUA<br>AACUGGAGGAAGGUGGGGAUGACGUCAAGUCAUCAUGGCCCUU<br>ACGACCAGGGCUACACACGUGCUACAAUGGCGCAUACAAAGAGA<br>AGCGACCUCGCGAGAGCAAGCGGACCUCAUAAAGUGCGUCGUA<br>GUCCGGAUUGGAGUCUGCAACUCGACUCCAUGAAGUCGGAAUC<br>GCUAGUAAUCGUGGAUCAGAAUGCCACGGUGAAUACGUUCCCG<br>GGCCUUGUACACACCGCCCGUCACACCAUGGGAGUGGGUUGCA<br>AAAGAAGUAGGUAGCUUAACCUUCGGGAGGGCGCUUACCACUUU<br>GUGAUUCAUGACUGGGGUGAAGUCGUAACAAGGUAACCGUAGG<br>GGAACUGCGGUUGGAUCACCUCCUUAGGUCUGAGCGUGAUAC<br>CCGCUCACUGAAGAUGGCCCGGUAGGGCCGAAACCUACUAGCAU<br>AACCCCUUGGGGCCUCUAAACGGGUCUUGAGGGGUUUUUUG |
| p23S-HH DNA [SEQ ID NO: 20] | TAATACGACTCACTATAGGTTAAGCGACTAAGCGTACACGGTGGAT<br>GCCCTGGCAGTCAGAGGCGATGAAGGACGTGCTAATCTGCGATAA<br>GCGTCGGTAAGGTGATATGAACCGTTATAACCGGCGATTTCCGAAT<br>GGGGAAACCCAGTGTGTTTCGACACACTATCATTAACTGAATCCATA<br>GGTTAATGAGGCGAACCGGGGAACTGAAACATCTAAGTACCCCGA<br>GGAAAAGAAATCAACCGAGATTCCCCCAGTAGCGGCGAGCGAACG<br>GGGAGCAGCCCAGAGCCTGAATCAGTGTGTGTGTTAGTGGAAGCG<br>TCTGGAAAGGCGCGCGATACAGGGTGACAGCCCCGTACACAAAAAT |

TABLE 6-continued

Sequences used in this disclosure.

| Sequence Description [SEQ ID NO: __] | Nucleotide or Amino Acid Sequence |
|---|---|
| | GCACATGCTGTGAGCTCGATGAGTAGGGCGGGACACGTGGTATCC
TGTCTGAATATGGGGGGACCATCCTCCAAGGCTAAATACTCCTGAC
TGACCGATAGTGAACCAGTACCGTGAGGGAAAGGCGAAAAGAACCC
CGGCGAGGGGAGTGAAAAAGAACCTGAAACCGTGTACGTACAAGC
AGTGGGAGCACGCTTAGGCGTGTGACTGCGTACCTTTTGTATAATG
GGTCAGCGACTTATATTCTGTAGCAAGGTTAACCGAATAGGGGAGC
CGAAGGGAAACCGAGTCTTAACTGGGCGTTAAGTTGCAGGGTATAG
ACCCGAAACCCGGTGATCTAGCCATGGGCAGGTTGAAGGTTGGGTA
ACACTAACTGGAGGACCGAACCGACTAATGTTGAAAAATTAGCGGA
TGACTTGTGGCTGGGGGTGAAAGGCCAATCAAACCGGGAGATAGCT
GGTTCTCCCCGAAAGCTATTTAGGTAGCGCCTCGTGAATTCATCTCC
GGGGGTAGAGCACTGTTTCGGCAAGGGGGTCATCCCGACTTACCA
ACCCGATGCAAACTGCGAATACCGGAGAATGTTATCACGGGAGACA
CACGGCGGGTGCTAACGTCCGTCGTGAAGAGGGAAACAACCCAGA
CCGCCAGCTAAGGTCCCAAAGTCATGGTTAAGTGGGAAACGATGTG
GGAAGGCCCAGACAGCCAGGATGTTGGCTTAGAAGCAGCCATCATT
TAAAGAAAGCGTAATAGCTCACTGGTCGAGTCGGCCTGCGCGGAAG
ATGTAACGGGCTAAACCATGCACCGAAGCTGCGGCAGCGACGCT
TATGCGTTGTTGGGTAGGGGAGCGTTCTGTAAGCCTGCGAAGGTGT
GCTGTGAGGCATGCTGGAGGTATCAGAAGTGCGAATGCTGACATAA
GTAACGATAAAGCGGGTGAAAAGCCCGCTCGCCGGAAGACCAAGG
GTTCCTGTCCAACGTTAATCGGGGCAGGGTGAGTCGACCCCTAAGG
CGAGGCCGAAAGGCGTAGTCGATGGGAAACAGGTTAATATTCCTGT
ACTTGGTGTTACTGCGAAGGGGGACGGAGAAGGCTATGTTGGCC
GGGCGACGGTTGTCCCGGTTTAAGCGTGTAGGCTGGTTTTCCAGGC
AAATCCGGAAAATCAAGGCTGAGGCGTGATGACGAGGCACTACGGT
GCTGAAGCAACAAATGCCCTGCTTCCAGGAAAAGCCTCTAAGCATC
AGGTAACATCAAATCGTACCCCAAACCGACACAGGTGGTCAGGTAG
AGAATACCAAGGCGCTTGAGAGAACTCGGGTGAAGGAACTAGGCAA
AATGGTGCCGTAACTTCGGGAGAAGGCACGCTGATATGTAGGTGAG
GTCCCTCGCGGATGGAGCTGAAATCAGTCGAAGATACCAGCTGGCT
GCAACTGTTTATTAAAAACACAGCACTGTGCAAACACGAAAGTGGAC
GTATACGGTGTGACGCCTGCCCGGTGCCGGAAGGTTAATTGATGG
GGTTAGCGCAAGCGAAGCTCTTGATCGAAGCCCCGGTAAACGGCG
GCCGTAACTATAACGGTCCTAAGGTAGCGAAATTCCTTGTCGGGTA
AGTTCCGACCTGCACGAATGGCGTAATGATGGCCAGGCTGTCTCCA
CCCGAGACTCAGTGAAATTGAACTCGCTGTGAAGATGCAGTGTACC
CGCGGCAAGACGGAAAGACCCCGTGAACCTTTACTATAGCTTGACA
CTGAACATTGAGCCTTGATGTGTAGGATAGGTGGGAGGCTTTGAAG
TGTGGACGCCAGTCTGCATGGAGCCGACCTTGAAATACCACCCTTT
AATGTTTGATGTTCTAACGTTGACCCGTAATCCGGGTTGCGGACAGT
GTCTGGTGGGTAGTTTGACTGGGGCGGTCTCCTCCTAAAGAGTAAC
GGAGGAGCACGAAGGTTGGCTAATCCTGGTCGGACATCAGGAGGT
TAGTGCAATGGCATAAGCCAGCTTGACTGCGAGCGTGACGGCGCG
AGCAGGTGCGAAAGCAGGTCATAGTGATCCGGTGGTTCTGAATGGA
AGGGCCATCGCTCAACGGATAAAAGGTACTCCGGGGATAACAGGCT
GATACCGCCCAAGAGTTCATATCGACGGCGGTGTTTGGCACCTCGA
TGTCGGCTCATCACATCCTGGGGCTGAAGTAGGTCCCAAGGGTATG
GCTGTTCGCCATTTAAAGTGGTACGCGAGCTGGGTTTAGAACGTCG
TGAGACAGTTCGGTCCCTATCTGCCGTGGGCGCTGGAGAACTGAG
GGGGGCTGCTCCTAGTACGAGAGGACCGGAGTGGACGCATCACTG
GTGTTCGGGTTGTCATGCCAATGGCACTGCCCGGTAGCTAAATGCG
GAAGAGATAAGTGCTGAAAGCATCTAAGCACGAAACTTGCCCCGAG
ATGAGTTCTCCCTGACCCTTTAAGGGTCCTGAAGGAACGTTGAAGA
CGACGACGTTGATAGGCCGGGTGTGTAAGCGCAGCGATGCGTTGA
GCTAACCGGTACTAATGAACCGTGAGGCTTAACCTTAAGTCTGAGC
GTGATACCCGCTCACTGAAGATGGCCCGGTAGGGCCGAAACTTACT
AGCATAACCCCTTGGGGCCTCTAAACGGGTCTTGAGGGGTTTTTTG
AAGCTGCAGGCATGCAAGCTTGGCGTAATCATGGTCATAGCTGTTT
CCTGTGTGAAATTGTTATCCGCTCACAATTCCACACAACATACGAGC
CGGAAGCATAAAGTGTAAAGCCTGGGGTGCCTAATGAGTGAGCTAA
CTCACATTAATTGCGTTGCGCTCACTGCCCGCTTTCCAGTCGGGAA
ACCTGTCGTGCCAGCTGCATTAATGAATCGGCCAACGCGCGGGGA
GAGGCGGTTTGCGTATTGGGCGCTCTTCCGCTTCCTCGCTCACTGA
CTCGCTGCGCTCGGTCGTTCGGCTGCGGCGAGCGGTATCAGCTCA
CTCAAAGGCGGTAATACGGTTATCCACAGAATCAGGGGATAACGCA
GGAAAGAACATGTGAGCAAAAGGCCAGCAAAAGGCCAGGAACCGT
AAAAAGGCCGCGTTGCTGGCGTTTTTCCATAGGCTCCGCCCCCTG
ACGAGCATCACAAAAATCGACGCTCAAGTCAGAGGTGGCGAAACCC
GACAGGACTATAAAGATACCAGGCGTTTCCCCCTGGAAGCTCCCTC
GTGCGCTCTCCTGTTCCGACCCTGCCGCTTACCGGATACCTGTCCG
CCTTTCTCCCTTCGGGAAGCGTGGCGCTTTCTCATAGCTCACGCTG
TAGGTATCTCAGTTCGGTGTAGGTCGTTCGCTCCAAGCTGGGCTGT
GTGCACGAACCCCCCGTTCAGCCCGACCGCTGCGCCTTATCCGGT |

TABLE 6-continued

Sequences used in this disclosure.

| Sequence Description [SEQ ID NO: __] | Nucleotide or Amino Acid Sequence |
|---|---|
| | AACTATCGTCTTGAGTCCAACCCGGTAAGACACGACTTATCGCCACT GGCAGCAGCCACTGGTAACAGGATTAGCAGAGCGAGGTATGTAGG CGGTGCTACAGAGTTCTTGAAGTGGTGGCCTAACTACGGCTACACT AGAAGAACAGTATTTGGTATCTGCGCTCTGCTGAAGCCAGTTACCTT CGGAAAAAGAGTTGGTAGCTCTTGATCCGGCAAACAAACCACCGCT GGTAGCGGTGGTTTTTTTGTTTGCAAGCAGCAGATTACGCGCAGAA AAAAAGGATCTCAAGAAGATCCTTTGATCTTTTCTACGGGGTCTGAC GCTCAGTGGAACGAAAACTCACGTTAAGGGATTTTGGTCATGAGATT ATCAAAAAGGATCTTCAGCTAGATCCTTTTAAATTAAAAATGAAGTTT TAAATCAATCTAAAGTATATATGAGTAAACTTGGTCTGACAGTTACCA ATGCTTAATCAGTGAGGCACCTATCTCAGCGATCTGTCTATTTCGTT CATCCATAGTTGCCTGACTCCCCGTCGTGTAGATAACTACGATACG GGAGGGCTTACCATCTGGCCCCAGTGCTGCAATGATACCGCGAGA CCCACGCTCACCGGCTCCAGATTTATCAGCAATAAACCAGCCAGCC GGAAGGGCCGAGCGCAGAAGTGGTCCTGCAACTTTATCCGCCTCC ATCCAGTCTATTAATTGTGCCGGGAAGCTAGAGTAAGTAGTTCGCC AGTTAATAGTTTGCGCAACGTTGTTGCCATTGCTACAGGCATCGTGG TGTCACGCTCGTCGTTTGGTATGGCTTCATTCAGCTCCGGTTCCCAA CGATCAAGGCGAGTTACATGATCCCCCATGTTGTGCAAAAAAGCGG TTAGCTCCTTCGGTCCTCCGATCGTTGTCAGAAGTAAGTTGGCCGC AGTGTTATCACTCATGGTTATGGCAGCACTGCATAATTCTCTTACTG TCATGCCATCCGTAAGATGCTTTTCTGTGACTGGTGAGTACTCAACC AAGTCATTCTGAGAATAGTGTATGCGGCGACCGAGTTGCTCTTGCC CGGCGTCAATACGGGATAATACCGCGCCACATAGCAGAACTTTAAA AGTGCTCATCATTGGAAAACGTTCTTCGGGGCGAAAACTCTCAAGG ATCTTACCGCTGTTGAGATCCAGTTCGATGTAACCCACTCGTGCACC CAACTGATCTTCAGCATCTTTTACTTTCACCAGCGTTTCTGGGTGAG CAAAAACAGGAAGGCAAAATGCCGCAAAAAAGGGAATAAGGGCGAC ACGGAAATGTTGAATACTCATACTCTTCCTTTTTCAATATTATTGAAG CATTTATCAGGGTTATTGTCTCATGAGCGGATACATATTTGAATGTAT TTAGAAAAATAAACAAATAGGGGTTCCGCGCACATTTCCCCGAAAAG TGCCACCTGACGTCTAAGAAACCATTATTATCATGACATTAACCTATA AAAATAGGCGTATCACGAGGCCCTTTCGTCTCGCGCGTTTCGGTGA TGACGGTGAAAACCTCTGACACATGCAGCTCCCGGAGACGGTCACA GCTTGTCTGTAAGCGGATGCCGGGAGCAGACAAGCCCGTCAGGGC GCGTCAGCGGGTGTTGGCGGGTGTCGGGGCTGGCTTAACTATGCG GCATCAGAGCAGATTGTACTGAGAGTGCACCATATGCGGTGTGAAA TACCGCACAGATGCGTAAGGAGAAAATACCGCATCAGGCGCCATTC GCCATTCAGGCTGCGCAACTGTTGGGAAGGGCGATCGGTGCGGGC CTCTTCGCTATTACGCCAGCTGGCGAAAGGGGGATGTGCTGCAAGG CGATTAAGTTGGGTAACGCCAGGGTTTTCCCAGTCACGACGTTGTA AAACGACGGCCAGTGAATTCGAGCTCGGTACC |
| p23S-HH 23S RNA [SEQ ID NO: 21] | GGUUAAGCGACUAAGCGUACACGGUGGAUGCCCUGGCAGUCAG AGGCGAUGAAGGACGUGCUAAUCUGCGAUAAGCGUCGGUAAGG UGAUAUGAACCGUUAUAACCGGCGAUUUCCGAAUGGGGAAACCC AGUGUGUUUCGACACACUAUCAUUAACUGAAUCCAUAGGUUAAU GAGGCGAACCGGGGGAACUGAAACAUCUAAGUACCCCGAGGAAA AGAAAUCAACCGAGAUUCCCCCAGUAGCGGCGAGCGAACGGGGA GCAGCCCAGAGCCUGAAUCAGUGUGUGUGUUAGUGGAAGCGUC UGGAAAGGCGCGCGAUACAGGGUGACAGCCCCGUACACAAAAAU GCACAUGCUGUGAGCUCGAUGAGUAGGGCGGGACACGUGGUAU CCUGUCUGAAUAUGGGGGGACCAUCCUCCAAGGCUAAAUACUCC UGACUGACCGAUAGUGAACCAGUACCGUGAGGGAAAGGCGAAAA GAACCCCGGCGAGGGGAGUGAAAAAGAACCUGAAACCGUGUACG UACAAGCAGUGGGAGCACGCUUAGGCGUGUGACUGCGUACCUU UUGUAUAAUGGGUCAGCGACUUAUAUUCUGUAGCAAGGUUAACC GAAUAGGGGAGCCGAAGGGAAACCGAGUCUUAACUGGGCGUUA AGUUGCAGGGUAUAGACCCGAAACCCGGUGAUCUAGCCAUGGG CAGGUUGAAGGUUGGGUAACACUAACUGGAGGACCGAACCGACU AAUGUUGAAAAAUUAGCGGAUGACUUGUGGCUGGGGGUGAAAG GCCAAUCAAACCGGGAGAUAGCUGGUUCUCCCCGAAAGCUAUUU AGGUAGCGCCUCGUGAAUUCAUCUCCGGGGGUAGAGCACUGUU UCGGCAAGGGGGUCAUCCCGACUUACCAACCCGAUGCAAACUGC GAAUACCGGAGAAUGUUAUCACGGGAGACACACGGCGGGUGCU AACGUCCGUCGUGAAGAGGGAAACAACCCAGACCGCCAGCUAAG GUCCCAAAGUCAUGGUUAAGUGGGAAACGAUGUGGGAAGGCCC AGACAGCCAGGAUGUUGGCUUAGAAGCAGCCAUCAUUUAAAGAA AGCGUAAUAGCUCACUGGUCGAGUCGGCCUGCGCGGAAGAUGU AACGGGGCUAAACCAUGCACCGAAGCUGCGGCAGCGACGCUUAU GCGUUGUUGGGUAGGGGAGCGUUCUGUAAGCCUGCGAAGGUGU GCUGUGAGGCAUGCUGGAGGUAUCAGAAGUGCGAAUGCUGACA UAAGUAACGAUAAAGCGGGUGAAAAGCCCGCUCGCCGGAAGACC AAGGGUUCCUGUCCAACGUUAAUCGGGGCAGGGUGAGUCGACC |

TABLE 6-continued

Sequences used in this disclosure.

| Sequence Description [SEQ ID NO: __] | Nucleotide or Amino Acid Sequence |
| --- | --- |
| | CCUAAGGCGAGGCCGAAAGGCGUAGUCGAUGGGAAACAGGUUA<br>AUAUUCCUGUACUUGGUGUUACUGCGAAGGGGGACGGAGAAG<br>GCUAUGUUGGCCGGGCGACGGUUGUCCCGGUUUAAGCGUGUAG<br>GCUGGUUUUCCAGGCAAAUCCGGAAAAUCAAGGCUGAGGCGUG<br>AUGACGAGGCACUACGGUGCUGAAGCAACAAAUGCCCUGCUUCC<br>AGGAAAAGCCUCUAAGCAUCAGGUAACAUCAAAUCGUACCCCAAA<br>CCGACACAGGUGGUCAGGUAGAGAAUACCAAGGCGCUUGAGAGA<br>ACUCGGGUGAAGGAACUAGGCAAAAUGGUGCCGUAACUUCGGG<br>AGAAGGCACGCUGAUAUGUAGGUGAGGUCCCUCGCGGAUGGAG<br>CUGAAAUCAGUCGAAGAUACCAGCUGGCUGCAACUGUUUAUUAA<br>AAACACAGCACUGUGCAAACACGAAAGUGGACGUAUACGGUGUG<br>ACGCCUGCCCGUGCCGGAAGGUUAAUUGAUGGGGUUAGCGCA<br>AGCGAAGCUCUUGAUCGAAGCCCCGGUAAACGGCGGCCGUAAC<br>UAUAACGGUCCUAAGGUAGCGAAAUUCCUUGUCGGGUAAGUUCC<br>GACCUGCACGAAUGGCGUAAUGAUGGCCAGGCUGUCUCCACCC<br>GAGACUCAGUGAAAUUGAACUCGCUGUGAAGAUGCAGUGUACCC<br>GCGGCAAGACGGAAAGACCCCGUGAACCUUUACUAUAGCUUGAC<br>ACUGAACAUUGAGCCUUGAUGUGUAGGAUAGGUGGGAGGCUUU<br>GAAGUGUGGACGCCAGUCUGCAUGGAGCCGACCUUGAAAUACCA<br>CCCUUUAAUGUUUGAUGUUCUAACGUUGACCCGUAAUCCGGGUU<br>GCGGACAGUGUCUGGUGGGUAGUUUGACUGGGGCGGUCUCCUC<br>CUAAAGAGUAACGGAGGAGCACGAAGGUUGGCUAAUCCUGGUC<br>GGACAUCAGGAGGUUAGUGCAAUGGCAUAAGCCAGCUUGACUG<br>CGAGCGUGACGGCGCGAGCAGGUGCGAAAGCAGGUCAUAGUGA<br>UCCGGUGGUUCUGAAUGGAAGGGCCAUCGCUCAACGGAUAAAA<br>GGUACUCCGGGGAUAACAGGCUGAUACCGCCCAAGAGUUCAUAU<br>CGACGGCGGUGUUUGGCACCUCGAUGUCGGCUCAUCACAUCCU<br>GGGGCUGAAGUAGGUCCCAAGGGUAUGGCUGUUCGCCAUUUAA<br>AGUGGUACGCGAGCUGGGUUUAGAACGUCGUGAGACAGUUCGG<br>UCCCUAUCUGCCGUGGGCGCUGGAGAACUGAGGGGGGCUGCUC<br>CUAGUACGAGAGGACCGGAGUGGACGCAUCACUGGUGUUCGGG<br>UUGUCAUGCCAAUGGCACUGCCCGGUAGCUAAAUGCGGAAGAGA<br>UAAGUGCUGAAAGCAUCUAAGCACGAAACUUGCCCCGAGAUGAG<br>UUCUCCCUGACCCUUUAAGGGUCCUGAAGGAACGUUGAAGACGA<br>CGACGUUGAUAGGCCGGGUGUGUAAGCGCAGCGAUGCGUUGAG<br>CUAACCGGUACUAAUGAACCGUGAGGCUUAACCUUAAGUCUGAG<br>CGUGAUACCCGCUCACUGAAGAUGGCCCGGUAGGGCCGAAACU<br>UACUAGCAUAACCCCUUGGGGCCUCUAAACGGGUCUUGAGGGG<br>UUUUUUG |
| p16S-HDV DNA [SEQ ID NO: 22] | TAATACGACTCACTATAGGGAGATTGAAGAGTTTGATCATGGCTCAG<br>ATTGAACGCTGGCGGCAGGCCTAACACATGCAAGTCGAACGGTAAC<br>AGGAAGAAGCTTGCTTCTTTGCTGACGAGTGGCGGACGGGTGAGTA<br>ATGTCTGGGAAACTGCCTGATGGAGGGGGATAACTACTGGAAACGG<br>TAGCTAATACCGCATAACGTCGCAAGACCAAAGAGGGGGACCTTCG<br>GGCCTCTTGCCATCGGATGTGCCCAGATGGGATTAGCTAGTAGGTG<br>GGGTAACGGCTCACCTAGGCGACGATCCCTAGCTGGTCTGAGAGG<br>ATGACCAGCCACACTGGAACTGAGACACGGTCCAGACTCCTACGGG<br>AGGCAGCAGTGGGGAATATTGCACAATGGGCGCAAGCCTGATGCA<br>GCCATGCCGCGTGTATGAAGAAGGCCTTCGGGTTGTAAAGTACTTT<br>CAGCGGGGAGGAAGGGAGTAAAGTTAATACCTTTGCTCATTGACGT<br>TACCCGCAGAAGAAGCACCGGCTAACTCCGTGCCAGCAGCCGCGG<br>TAATACGGAGGGTGCAAGCGTTAATCGGAATTACTGGGCGTAAAGC<br>GCACGCAGGCGGTTTGTTAAGTCAGATGTGAAATCCCCGGGCTCAA<br>CCTGGGAACTGCATCTGATACTGGCAAGCTTGAGTCTCGTAGAGGG<br>GGGTAGAATTCCAGGTGTAGCGGTGAAATGCGTAGAGATCTGGAGG<br>AATACCGGTGGCGAAGGCGGCCCCCTGGACGAAGACTGACGCTCA<br>GGTGCGAAAGCGTGGGGAGCAAACAGGATTAGATACCCTGGTAGT<br>CCACGCCGTAAACGATGTCGACTTGGAGGTTGTGCCCTTGAGGCGT<br>GGCTTCCGGAGCTAACGCGTTAAGTCGACCGCCTGGGGAGTACGG<br>CCGCAAGGTTAAAACTCAAATGAATTGACGGGGGCCCGCACAAGCG<br>GTGGAGCATGTGGTTTAATTCGATGCAACGCGAAGAACCTTACCTG<br>GTCTTGACATCCACGGAAGTTTTCAGAGATGAGAATGTGCCTTCGG<br>GAACCGTGAGACAGGTGCTGCATGGCTGTCGTCAGCTCGTGTTGTG<br>AAATGTTGGGTTAAGTCCCGCAACGAGCGCAACCCTTATCCTTTGTT<br>GCCAGCGGTCCGGCCGGGAACTCAAAGGAGACTGCCAGTGATAAA<br>CTGGAGGAAGGTGGGGATGACGTCAAGTCATCATGGCCCTTACGAC<br>CAGGGCTACACACGTGCTACAATGGCGCATACAAAGAGAAGCGACC<br>TCGCGAGAGCAAGCGGACCTCATAAAGTGCGTCGTAGTCCGGATTG<br>GAGTCTGCAACTCGACTCCATGAAGTCGGAATCGCTAGTAATCGTG<br>GATCAGAATGCCACGGTGAATACGTTCCCGGGCCTTGTACACACCG<br>CCCGTCACACCATGGGAGTGGGTTGCAAAAGAAGTAGGTAGCTTAA<br>CCTTCGGGAGGGCGCTTACCACTTTGTGATTCATGACTGGGGTGAA<br>GTCGTAACAAGGTAACCGTAGGGGAACCTGCGGTTGGATCACCTCC |

| Sequence Description [SEQ ID NO: __] | Nucleotide or Amino Acid Sequence |
|---|---|
| | TTAGGTGGCCGGCATGGTCCCAGCCTCCTCGCTGGCGCCGGCTGG GCAACATTCCGAGGGGACCGTCCCCTCGGTAATGGCGAATGGGAC CCACTAGCATAACCCCTTGGGGCCTCTAAACGGGTCTTGAGGGGTT TTTTGTCTAGAGTCGACCTGCAGGCATGCAAGCTTGGCGTAATCAT GGTCATAGCTGTTTCCTGTGTGAAATTGTTATCCGCTCACAATTCCA CACAACATACGAGCCGGAAGCATAAAGTGTAAAGCCTGGGGTGCCT AATGAGTGAGCTAACTCACATTAATTGCGTTGCGCTCACTGCCCGCT TTCCAGTCGGGAAACCTGTCGTGCCAGCTGCATTAATGAATCGGCC AACGCGCGGGGAGAGGCGGTTTGCGTATTGGGCGCTCTTCCGCTT CCTCGCTCACTGACTCGCTGCGCTCGGTCGTTCGGCTGCGGCGAG CGGTATCAGCTCACTCAAAGGCGGTAATACGGTTATCCACAGAATC AGGGGATAACGCAGGAAAGAACATGTGAGCAAAAGGCCAGCAAAA GGCCAGGAACCGTAAAAAGGCCGCGTTGCTGGCGTTTTTCCATAGG CTCCGCCCCCCTGACGAGCATCACAAAAATCGACGCTCAAGTCAGA GGTGGCGAAACCCGACAGGACTATAAAGATACCAGGCGTTTCCCCC TGGAAGCTCCCTCGTGCGCTCTCCTGTTCCGACCCTGCCGCTTACC GGATACCTGTCCGCCTTTCTCCCTTCGGGAAGCGTGGCGCTTTCTC ATAGCTCACGCTGTAGGTATCTCAGTTCGGTGTAGGTCGTTCGCTC CAAGCTGGGCTGTGTGCACGAACCCCCCGTTCAGCCCGACCGCTG CGCCTTATCCGGTAACTATCGTCTTGAGTCCAACCCGGTAAGACAC GACTTATCGCCACTGGCAGCAGCCACTGGTAACAGGATTAGCAGAG CGAGGTATGTAGGCGGTGCTACAGAGTTCTTGAAGTGGTGGCCTAA CTACGGCTACACTAGAAGAACAGTATTTGGTATCTGCGCTCTGCTGA AGCCAGTTACCTTCGGAAAAAGAGTTGGTAGCTCTTGATCCGGCAA ACAAACCACCGCTGGTAGCGGTGGTTTTTTTGTTTGCAAGCAGCAG ATTACGCGCAGAAAAAAAGGATCTCAAGAAGATCCTTTGATCTTTTC TACGGGGTCTGACGCTCAGTGGAACGAAAACTCACGTTAAGGGATT TTGGTCATGAGATTATCAAAAAGGATCTTCACCTAGATCCTTTTAAAT TAAAAATGAAGTTTTAAATCAATCTAAAGTATATATGAGTAAACTTGG TCTGACAGTTACCAATGCTTAATCAGTGAGGCACCTATCTCAGCGAT CTGTCTATTTCGTTCATCCATAGTTGCCTGACTCCCCGTCGTGTAGA TAACTACGATACGGGAGGGCTTACCATCTGGCCCCAGTGCTGCAAT GATACCGCGAGACCCACGCTCACCGGCTCCAGATTTATCAGCAATA AACCAGCCAGCCGGAAGGGCCGAGCGCAGAAGTGGTCCTGCAACT TTATCCGCCTCCATCCAGTCTATTAATTGTTGCCGGGAAGCTAGAGT AAGTAGTTCGCCAGTTAATAGTTTGCGCAACGTTGTTGCCATTGCTA CAGGCATCGTGGTGTCACGCTCGTCGTTTGGTATGGCTTCATTCAG CTCCGGTTCCCAACGATCAAGGCGAGTTACATGATCCCCCATGTTG TGCAAAAAAGCGGTTAGCTCCTTCGGTCCTCCGATCGTTGTCAGAA GTAAGTTGGCCGCAGTGTTATCACTCATGGTTATGGCAGCACTGCA TAATTCTCTTACTGTCATGCCATCCGTAAGATGCTTTTCTGTGACTG GTGAGTACTCAACCAAGTCATTCTGAGAATAGTGTATGCGGCGACC GAGTTGCTCTTGCCCGGCGTCAATACGGGATAATACCGCGCCACAT AGCAGAACTTTAAAAGTGCTCATCATTGGAAAACGTTCTTCGGGGCG AAAACTCTCAAGGATCTTACCGCTGTTGAGATCCAGTTCGATGTAAC CCACTCGTGCACCCAACTGATCTTCAGCATCTTTTACTTTCACCAGC GTTTCTGGGTGAGCAAAACAGGAAGGCAAAATGCCGCAAAAAAGG GAATAAGGGCGACACGGAAATGTTGAATACTCATACTCTTCCTTTTT CAATATTATTGAAGCATTTATCAGGGTTATTGTCTCATGAGCGGATA CATATTTGAATGTATTTAGAAAAATAAACAAATAGGGGTTCCGCGCA CATTTCCCCGAAAAGTGCCACCTGACGTCTAAGAAACCATTATTATC ATGACATTAACCTATAAAAATAGGCGTATCACGAGGCCCTTTCGTCT CGCGCGTTTCGGTGATGACGGTGAAAACCTCTGACACATGCAGCTC CCGGAGACGGTCACAGCTTGTCTGTAAGCGGATGCCGGGAGCAGA CAAGCCCGTCAGGGCGCGTCAGCGGGTGTTGGCGGGTGTCGGGG CTGGCTTAACTATGCGGCATCAGAGCAGATTGTACTGAGAGTGCAC CATATGCGGTGTGAAATACCGCACAGATGCGTAAGGAGAAAATACC GCATCAGGCGCCATTCGCCATTCAGGCTGCGCAACTGTTGGGAAG GGCGATCGGTGCGGGCCTCTTCGCTATTACGCCAGCTGGCGAAAG GGGGATGTGCTGCAAGGCGATTAAGTTGGGTAACGCCAGGGTTTTC CCAGTCACGACGTTGTAAAACGACGGCCAGTGAATTCGAGCTCGGT ACC |
| p16S-HDV 16S RNA [SEQ ID NO: 23] | AGAUUGAAGAGUUUGAUCAUGGCUCAGAUUGAACGCUGGCGGC AGGCCUAACACAUGCAAGUCGAACGGUAACAGGAAGAAGCUUGC UUCUUUGCUGACGAGUGGCGGACGGGUGAGUAAUGUCUGGGAA ACUGCCUGAUGGAGGGGGAUAACUACUGGAAACGGUAGCUAAUA CCGCAUAACGUCGCAAGACCAAAGAGGGGGACCUUCGGGCCUC UUGCCAUCGGAUGUGCCCAGAUGGGAUUAGCUAGUAGGUGGGG UAACGGCUCACCUAGGCGACGAUCCCUAGCUGGUCUGAGAGGA UGACCAGCCACACUGGAACUGAGACACGGUCCAGACUCCUACGG GAGGCAGCAGUGGGGAAUAUUGCACAAUGGGCGCAAGCCUGAU GCAGCCAUGCCGCGUGUAUGAAGAAGGCCUUCGGGUUGUAAAG UACUUUCAGCGGGGAGGAAGGGAGUAAAGUUAAUACCUUUGCUC |

TABLE 6-continued

Sequences used in this disclosure.

| Sequence Description [SEQ ID NO: __] | Nucleotide or Amino Acid Sequence |
|---|---|
| | AUUGACGUUACCCGCAGAAGAAGCACCGGCUAACUCCGUGCCAG<br>CAGCCGCGGUAAUACGGAGGGUGCAAGCGUUAAUCGGAAUUAC<br>UGGGCGUAAAGCGCACGCAGGCGGUUUGUUAAGUCAGAUGUGA<br>AAUCCCCGGGCUCAACCUGGGAACUGCAUCUGAUACUGGCAAGC<br>UUGAGUCUCGUAGAGGGGGGUAGAAUUCCAGGUGUAGCGGUGA<br>AAUGCGUAGAGAUCUGGAGGAAUACCGGUGGCGAAGGCGGCCC<br>CCUGGACGAAGACUGACGCUCAGGUGCGAAAGCGUGGGGAGCA<br>AACAGGAUUAGAUACCCUGGUAGUCCACGCCGUAAACGAUGUCG<br>ACUUGGAGGUUGUGCCCUUGAGGCGUGGCUUCCGGAGCUAACG<br>CGUUAAGUCGACCGCCUGGGGAGUACGGCCGCAAGGUUAAAAC<br>UCAAAUGAAUUGACGGGGGCCCGCACAAGCGGUGGAGCAUGUG<br>GUUUAAUUCGAUGCAACGCGAAGAACCUUACCUGGUCUUGACAU<br>CCACGGAAGUUUUCAGAGAUGAGAAUGUGCCUUCGGGAACCGU<br>GAGACAGGUGCUGCAUGGCUGUCGUCAGCUCGUGUUGUGAAAU<br>GUUGGGUUAAGUCCCGCAACGAGCGCAACCCUUAUCCUUUGUU<br>GCCAGCGGUCCGGCCGGGAACUCAAAGGAGACUGCCAGUGAUA<br>AACUGGAGGAAGGUGGGGAUGACGUCAAGUCAUCAUGGCCCUU<br>ACGACCAGGGCUACACACGUGCUACAAUGGCGCAUACAAAGAGA<br>AGCGACCUCGCGAGAGCAAGCGGACCUCAUAAAGUGCGUCGUA<br>GUCCGGAUUGGAGUCUGCAACUCGACUCCAUGAAGUCGGAAUC<br>GCUAGUAAUCGUGGAUCAGAAUGCCACGGUGAAUACGUUCCCG<br>GGCCUUGUACACACCGCCCGUCACACCAUGGGAGUGGGUUGCA<br>AAAGAAGUAGGUAGCUUAACCUUCGGGAGGGCGCUUACCACUUU<br>GUGAUUCAUGACUGGGGUGAAGUCGUAACAAGGUAACCGUAGG<br>GGAACCUGCGGUUGGAUCACCUCCUUAGGUGGCCGGCAUGGUC<br>CCAGCCUCCUCGCUGGCGCCGGCUGGGCAACAUUCCGAGGGGA<br>CCGUCCCCUCGGUAAUGGCGAAUGGGACCCACUAGCAUAACCCC<br>UUGGGGCCUCUAAACGGGUCUUGAGGGGUUUUUUG |
| p23S-HDV DNA<br>[SEQ ID NO: 24] | TAATACGACTCACTATAGGTTAAGCGACTAAGCGTACACGGTGGAT<br>GCCCTGGCAGTCAGAGGCGATGAAGGACGTGCTAATCTGCGATAA<br>GCGTCGGTAAGGTGATATGAACCGTTATAACCGGCGATTTCCGAAT<br>GGGGAAACCCAGTGTGTTTCGACACACTATCATTAACTGAATCCATA<br>GGTTAATGAGGCGAACCGGGGGAACTGAAACATCTAAGTACCCCGA<br>GGAAAAGAAATCAACCGAGATTCCCCCAGTAGCGGCGAGCGAACG<br>GGGAGCAGCCCAGAGCCTGAATCAGTGTGTGTTAGTGGAAGCG<br>TCTGGAAAGGCGCGCGATACAGGGTGACAGCCCCGTACACAAAAAT<br>GCACATGCTGTGAGCTCGATGAGTAGGGCGGGACACGTGGTATCC<br>TGTCTGAATATGGGGGACCATCCTCCAAGGCTAAATACTCCTGAC<br>TGACCGATAGTGAACCAGTACCGTGAGGGAAAGGCGAAAAGAACCC<br>CGGCGAGGGGAGTGAAAAAGAACCTGAAACCGTGTACGTACAAGC<br>AGTGGGAGCACGCTTAGGCGTGTGACTGCGTACCTTTTGTATAATG<br>GGTCAGCGACTTATATTCTGTAGCAAGGTTAACCGAATAGGGGAGC<br>CGAAGGGAAACCGAGTCTTAACTGGGCGTTAAGTTGCAGGGTATAG<br>ACCCGAAACCCGGTGATCTAGCCATGGGCAGGTTGAAGGTTGGGTA<br>ACACTAACTGGAGGACCGAACCGACTAATGTTGAAAAATTAGCGGA<br>TGACTTGTGGCTGGGGGTGAAAGGCCAATCAAACCGGGAGATAGCT<br>GGTTCTCCCCGAAAGCTATTTAGGTAGCGCCTCGTGAATTCATCTCC<br>GGGGGTAGAGCACTGTTTCGGCAAGGGGGTCATCCCGACTTACCA<br>ACCCGATGCAAACTGCGAATACCGGAGAATGTTATCACGGGAGACA<br>CACGGCGGGTGCTAACGTCCGTCGTGAAGAGGGAAACAACCCAGA<br>CCGCCAGCTAAGGTCCCAAAGTCATGGTTAAGTGGGAAACGATGTG<br>GGAAGGCCCAGACAGCCAGGATGTTGGCTTAGAAGCAGCCATCATT<br>TAAAGAAAGCGTAATAGCTCACTGGTCGAGTCGGCCTGCGCGGAAG<br>ATGTAACGGGGCTAAACCATGCACCGAAGCTGCGGCAGCGACGCT<br>TATGCGTTGTTGGGTAGGGGAGCGTTCTGTAAGCCTGCGAAGGTGT<br>GCTGTGAGGCATGCTGGAGGTATCAGAAGTGCGAATGCTGACATAA<br>GTAACGATAAAGCGGGTGAAAAGCCCGCTCGCCGGAAGACCAAGG<br>GTTCCTGTCCAACGTTAATCGGGGCAGGGTGAGTCGACCCCTAAGG<br>CGAGGCCGAAAGGCGTAGTCGATGGGAAACAGGTTAATATTCCTGT<br>ACTTGGTGTTACTGCGAAGGGGGACGGAGAAGGCTATGTTGGCC<br>GGGCGACGGTTGTCCCGGTTTAAGCGTGTAGGCTGGTTTTCCAGGC<br>AAATCCGGAAAATCAAGGCTGAGGCGTGATGACGAGGCACTACGGT<br>GCTGAAGCAACAAATGCCCTGCTTCCAGGAAAAGCCTCTAAGCATC<br>AGGTAACATCAAATCGTACCCCAAACCGACACAGGTGGTCAGGTAG<br>AGAATACCAAGGCGCTTGAGAGAACTCGGGTGAAGGAACTAGGCAA<br>AATGGTGCCGTAACTTCGGGAGAAGGCACGCTGATATGTAGGTGAG<br>GTCCCTCGCGGATGGAGCTGAAATCAGTCGAAGATACCAGCTGGCT<br>GCAACTGTTTATTAAAAACACAGCACTGTGCAAACACGAAAGTGGAC<br>GTATACGGTGTGACGCCTGCCCGGTGCCGGAAGGTTAATTGATGG<br>GGTTAGCGCAAGCGAAGCTCTTGATCGAAGCCCCGGTAAACGGCG<br>GCCGTAACTATAACGGTCCTAAGGTAGCGAAATTCCTTGTCGGGTA<br>AGTTCCGACCTGCACGAATGGCGTAATGATGCCAGGCTGTCTCCA<br>CCCGAGACTCAGTGAAATTGAACTCGCTGTGAAGATGCAGTGTACC |

TABLE 6-continued

Sequences used in this disclosure.

| Sequence Description [SEQ ID NO: __] | Nucleotide or Amino Acid Sequence |
|---|---|
| | CGCGGCAAGACGGAAAGACCCCGTGAACCTTTACTATAGCTTGACA<br>CTGAACATTGAGCCTTGATGTGTAGGATAGGTGGGAGGCTTTGAAG<br>TGTGGACGCCAGTCTGCATGGAGCCGACCTTGAAATACCACCCTTT<br>AATGTTTGATGTTCTAACGTTGACCCGTAATCCGGGTTGCGGACAGT<br>GTCTGGTGGGTAGTTTGACTGGGGCGGTCTCCTCCTAAAGAGTAAC<br>GGAGGAGCACGAAGGTTGGCTAATCCTGGTCGGACATCAGGAGGT<br>TAGTGCAATGGCATAAGCCAGCTTGACTGCGAGCGTGACGGCGCG<br>AGCAGGTGCGAAAGCAGGTCATAGTGATCCGGTGGTTCTGAATGGA<br>AGGGCCATCGCTCAACGGATAAAAGGTACTCCGGGGATAACAGGCT<br>GATACCGCCCAAGAGTTCATATCGACGGCGGTGTTTGGCACCTCGA<br>TGTCGGCTCATCACATCCTGGGGCTGAAGTAGGTCCCAAGGGTATG<br>GCTGTTCGCCATTTAAAGTGGTACGCGAGCTGGGTTTAGAACGTCG<br>TGAGACAGTTCGGTCCCTATCTGCCGTGGGCGCTGGAGAACTGAG<br>GGGGGCTGCTCCTAGTACGAGAGGACCGGAGTGGACGCATCACTG<br>GTGTTCGGGTTGTCATGCCAATGGCACTGCCCGGTAGCTAAATGCG<br>GAAGAGATAAGTGCTGAAAGCATCTAAGCACGAAACTTGCCCCGAG<br>ATGAGTTCTCCCTGACCCTTTAAGGGTCCTGAAGGAACGTTGAAGA<br>CGACGACGTTGATAGGCCGGGTGTGTAAGCGCAGCGATGCGTTGA<br>GCTAACCGGTACTAATGAACCGTGAGGCTTAACCTTAAGTGGCCGG<br>CATGGTCCCAGCCTCCTCGCTGGCGCCGGCTGGGCAACATTCCGA<br>GGGGACCGTCCCCTCGGTAATGGCGAATGGGACCCACTAGCATAA<br>CCCCTTGGGGCCTCTAAACGGGTCTTGAGGGGTTTTTTGAAGCTGC<br>AGGCATGCAAGCTTGGCGTAATCATGGTCATAGCTGTTTCCTGTGT<br>GAAATTGTTATCCGCTCACAATTCCACACAACATACGAGCCGGAAGC<br>ATAAAGTGTAAAGCCTGGGGTGCCTAATGAGTGAGCTAACTCACATT<br>AATTGCGTTGCGCTCACTGCCCGCTTTCCAGTCGGGAAACCTGTCG<br>TGCCAGCTGCATTAATGAATCGGCCAACGCGCGGGGAGAGGCGGT<br>TTGCGTATTGGGCGCTCTTCCGCTTCCTCGCTCACTGACTCGCTGC<br>GCTCGGTCGTTCGGCTGCGGCGAGCGGTATCAGCTCACTCAAAGG<br>CGGTAATACGGTTATCCACAGAATCAGGGGATAACGCAGGAAAGAA<br>CATGTGAGCAAAAGGCCAGCAAAAGGCCAGGAACCGTAAAAAGGC<br>CGCGTTGCTGGCGTTTTTCCATAGGCTCCGCCCCCCTGACGAGCAT<br>CACAAAAATCGACGCTCAAGTCAGAGGTGGCGAAACCCGACAGGAC<br>TATAAAGATACCAGGCGTTTCCCCCTGGAAGCTCCCTCGTGCGCTC<br>TCCTGTTCCGACCCTGCCGCTTACCGGATACCTGTCCGCCTTTCTC<br>CCTTCGGGAAGCGTGGCGCTTTCTCATAGCTCACGCTGTAGGTATC<br>TCAGTTCGGTGTAGGTCGTTCGCTCCAAGCTGGGCTGTGTGCACGA<br>ACCCCCCGTTCAGCCCGACCGCTGCGCCTTATCCGGTAACTATCGT<br>CTTGAGTCCAACCCGGTAAGACACGACTTATCGCCACTGGCAGCAG<br>CCACTGGTAACAGGATTAGCAGAGCGAGGTATGTAGGCGGTGCTAC<br>AGAGTTCTTGAAGTGGTGGCCTAACTACGGCTACACTAGAAGAACA<br>GTATTTGGTATCTGCGCTCTGCTGAAGCCAGTTACCTTCGGAAAAAG<br>AGTTGGTAGCTCTTGATCCGGCAAACAAACCACCGCTGGTAGCGGT<br>GGTTTTTTTGTTTGCAAGCAGCAGATTACGCGCAGAAAAAAAGGATC<br>TCAAGAAGATCCTTTGATCTTTTCTACGGGGTCTGACGCTCAGTGGA<br>ACGAAAACTCACGTTAAGGGATTTTGGTCATGAGATTATCAAAAAGG<br>ATCTTCACCTAGATCCTTTTAAATTAAAAATGAAGTTTTAAATCAATCT<br>AAAGTATATATGAGTAAACTTGGTCTGACAGTTACCAATGCTTAATCA<br>GTGAGGCACCTATCTCAGCGATCTGTCTATTTCGTTCATCCATAGTT<br>GCCTGACTCCCCGTCGTGTAGATAACTACGATACGGGAGGGCTTAC<br>CATCTGGCCCCAGTGCTGCAATGATACCGCGAGACCCACGCTCACC<br>GGCTCCAGATTTATCAGCAATAAACCAGCCAGCCGGAAGGGCCGAG<br>CGCAGAAGTGGTCCTGCAACTTTATCCGCCTCCATCCAGTCTATTAA<br>TTGTTGCCGGGAAGCTAGAGTAAGTAGTTCGCCAGTTAATAGTTTGC<br>GCAACGTTGTTGCCATTGCTACAGGCATCGTGGTGTCACGCTCGTC<br>GTTTGGTATGGCTTCATTCAGCTCCGGTTCCCAACGATCAAGGCGA<br>GTTACATGATCCCCCATGTTGTGCAAAAAAGCGGTTAGCTCCTTCGG<br>TCCTCCGATCGTTGTCAGAAGTAAGTTGGCCGCAGTGTTATCACTCA<br>TGGTTATGGCAGCACTGCATAATTCTCTTACTGTCATGCCATCCGTA<br>AGATGCTTTTCTGTGACTGGTGAGTACTCAACCAAGTCATTCTGAGA<br>ATAGTGTATGCGGCGACCGAGTTGCTCTTGCCCGGCGTCAATACGG<br>GATAATACCGCGCCACATAGCAGAACTTTAAAAGTGCTCATCATTGG<br>AAAACGTTCTTCGGGGCGAAAACTCTCAAGGATCTTACCGCTGTTGA<br>GATCCAGTTCGATGTAACCCACTCGTGCACCCAACTGATCTTCAGCA<br>TCTTTTACTTTCACCAGCGTTTCTGGGTGAGCAAAAACAGGAAGGCA<br>AAATGCCGCAAAAAAGGGAATAAGGGCGACACGGAAATGTTGAATA<br>CTCATACTCTTCCTTTTTCAATATTATTGAAGCATTTATCAGGGTTATT<br>GTCTCATGAGCGGATACATATTTGAATGTATTTAGAAAAATAAACAAA<br>TAGGGGTTCCGCGCACATTTCCCCGAAAAGTGCCACCTGACGTCTA<br>AGAAACCATTATTATCATGACATTAACCTATAAAAATAGGCGTATCAC<br>GAGGCCCTTTCGTCTCGCGCGTTTCGGTGATGACGGTGAAAACCTC<br>TGACACATGCAGCTCCCGGAGACGGTCACAGCTTGTCTGTAAGCGG<br>ATGCCGGGAGCAGACAAGCCCGTCAGGGCGCGTCAGCGGGTGTTG<br>GCGGGTGTCGGGGCTGGCTTAACTATGCGGCATCAGAGCAGATTG |

TABLE 6-continued

Sequences used in this disclosure.

| Sequence Description [SEQ ID NO: __] | Nucleotide or Amino Acid Sequence |
|---|---|
| | TACTGAGAGTGCACCATATGCGGTGTGAAATACCGCACAGATGCGT AAGGAGAAAATACCGCATCAGGCGCCATTCGCCATTCAGGCTGCGC AACTGTTGGGAAGGGCGATCGGTGCGGGCCTCTTCGCTATTACGCC AGCTGGCGAAAGGGGGATGTGCTGCAAGGCGATTAAGTTGGGTAA CGCCAGGGTTTTCCCAGTCACGACGTTGTAAAACGACGGCCAGTGA ATTCGAGCTCGGTACC |
| p23S-HDV 23S RNA [SEQ ID NO: 25] | GGUUAAGCGACUAAGCGUACACGGUGGAUGCCCUGGCAGUCAG AGGCGAUGAAGGACGUGCUAAUCUGCGAUAAGCGUCGGUAAGG UGAUAUGAACCGUUAUAACCGGCGAUUUCCGAAUGGGGAAACCC AGUGUGUUUCGACACACUAUCAUUAACUGAAUCCAUAGGUUAAU GAGGCGAACCGGGGGAACUGAAACAUCUAAGUACCCCGAGGAAA AGAAAUCAACCGAGAUUCCCCCAGUAGCGGCGAGCGAACGGGGA GCAGCCCAGAGCCUGAAUCAGUGUGUGUGUUAGUGGAAGCGUC UGGAAAGGCGCGCGAUACAGGGUGACAGCCCCGUACACAAAAAU GCACAUGCUGUGAGCUCGAUGAGUAGGGCGGGACACGUGGUAU CCUGUCUGAAUAUGGGGGGACCAUCCUCCAAGGCUAAAUACUCC UGACUGACCGAUAGUGAACCAGUACCGUGAGGGAAAGGCGAAAA GAACCCCGGCGAGGGGAGUGAAAAAGAACCUGAAACCGUGUACG UACAAGCAGUGGGAGCACGCUUAGGCGUGUGACUGCGUACCUU UUGUAUAAUGGGUCAGCGACUUAUAUUCUGUAGCAAGGUUAACC GAAUAGGGGAGCCGAAGGGAAACCGAGUCUUAACUGGGCGUUA AGUUGCAGGGUAUAGACCCGAAACCCGGUGAUCUAGCCAUGGG CAGGUUGAAGGUUGGGUAACACUAACUGGAGGACCGAACCGACU AAUGUUGAAAAAUUAGCGGAUGACUUGUGGCUGGGGGUGAAAG GCCAAUCAAACCGGGAGAUAGCUGGUUCUCCCCGAAAGCUAUUU AGGUAGCGCCUCGUGAAUUCAUCUCCGGGGGUAGAGCACUGUU UCGGCAAGGGGGUCAUCCCGACUUACCAACCCGAUGCAAACUGC GAAUACCGGAGAAUGUUAUCACGGGAGACACACGGCGGGUGCU AACGUCCGUCGUGAAGAGGGAAACAACCCAGACCGCCAGCUAAG GUCCCAAAGUCAUGGUUAAGUGGGAAACGAUGUGGGAAGGCCC AGACAGCCAGGAUGUUGGCUUAGAAGCAGCCAUCAUUUAAAGAA AGCGUAAUAGCUCACUGGUCGAGUCGGCCUGCGCGGAAGAUGU AACGGGGCUAAACCAUGCACCGAAGCUGCGGCAGCGACGCUUAU GCGUUGUUGGGUAGGGGAGCGUUCUGUAAGCCUGCGAAGGUGU GCUGUGAGGCAUGCUGGAGGUAUCAGAAGUGCGAAUGCUGACA UAAGUAACGAUAAAGCGGGUGAAAAGCCCGCUCGCCGGAAGACC AAGGGUUCCUGUCCAACGUUAAUCGGGGCAGGGUGAGUCGACC CCUAAGGCGAGGCCGAAAGGCGUAGUCGAUGGGAAACAGGUUA AUAUUCCUGUACUUGGUGUUACUGCGAAGGGGGGACGGAGAG GCUAUGUUGGCCGGGCGACGGUUGUCCCGGUUUAAGCGUGUAG GCUGGUUUUCCAGGCAAAUCCGGAAAAUCAAGGCUGAGGCGUG AUGACGAGGCACUACGGUGCUGAAGCAACAAAUGCCCUGCUUCC AGGAAAAGCCUCUAAGCAUCAGGUAACAUCAAAUCGUACCCCAA CCGACACAGGUGGUCAGGUAGAGAAUACCAAGGCGCUUGAGAGA ACUCGGGUGAAGGAACUAGGCAAAAUGGUGCCGUAACUUCGGG AGAAGGCACGCUGAUAUGUAGGUGAGGUCCCUCGCGGAUGGAG CUGAAAUCAGUCGAAGAUACCAGCUGGCUGCAACUGUUUAUUAA AAACACAGCACUGUGCAAACACGAAAGUGGACGUAUACGGUGUG ACGCCUGCCCGGUGCCGGAAGGUUAAUUGAUGGGGUUAGCGCA AGCGAAGCUCUUGAUCGAAGCCCCGGUAAACGGCGGCCGUAAC UAUAACGGUCCUAAGGUAGCGAAAUUCCUUGUCGGGUAAGUUCC GACCUGCACGAAUGGCGUAAUGAUGGCCAGGCUGUCUCCACCC GAGACUCAGUGAAAUUGAACUCGCUGUGAAGAUGCAGUGUACCC GCGGCAAGACGGAAAGACCCCGUGAACCUUUACUAUAGCUUGAC ACUGAACAUUGAGCCUUGAUGUGUAGGAUAGGUGGGAGGCUUU GAAGUGUGGACGCCAGUCUGCAUGGAGCCGACCUUGAAAUACCA CCCUUUAAUGUUUGAUGUUCUAACGUUGACCCGUAAUCCGGGUU GCGGACAGUGUCUGGUGGGUAGUUUGACUGGGGCGGUCUCCUC CUAAAGAGUAACGGAGGAGCACGAAGGUUGGCUAAUCCUGGUC GGACAUCAGGAGGUUAGUGCAAUGGCAUAAGCCAGCUUGACUG CGAGCGUGACGGCGCGAGCAGGUGCGAAAGCAGGUCAUAGUGA UCCGGUGGUUCUGAAUGGAAGGGCCAUCGCUCAACGGAUAAAA GGUACUCCGGGGAUAACAGGCUGAUACCGCCCAAGAGUUCAUAU CGACGGCGGUGUUUGGCACCUCGAUGUCGGCUCAUCACAUCCU GGGGCUGAAGUAGGUCCCAAGGGUAUGGCUGUUCGCCAUUUAA AGUGGUACGCGAGCUGGGUUUAGAACGUCGUGAGACAGUUCGG UCCCUAUCUGCCGUGGGCGCUGGAGAACUGAGGGGGGCUGCUC CUAGUACGAGAGGACCGGAGUGGACGCAUCACUGGUGUUCGGG UUGUCAUGCCAAUGGCACUGCCCGGUAGCUAAAUGCGGAAGAGA UAAGUGCUGAAAGCAUCUAAGCACGAAACUUGCCCCGAGAUGAG UUCUCCCUGACCCUUUAAGGGUCCUGAAGGAACGUUGAAGACGA CGACGUUGAUAGGCCGGGUGUGUAAGCGCAGCGAUGCGUUGAG CUAACCGGUACUAAUGAACCGUGAGGCUUAACCUUAAGUGGCCG |

TABLE 6-continued

Sequences used in this disclosure.

| Sequence Description [SEQ ID NO: __] | Nucleotide or Amino Acid Sequence |
|---|---|
| | GCAUGGUCCCAGCCUCCUCGCUGGCGCCGGCUGGGCAACAUUC<br>CGAGGGGACCGUCCCCUCGGUAAUGGCGAAUGGGACCCACUAG<br>CAUAACCCCUUGGGGCCUCUAAACGGGUCUUGAGGGGUUUUUU<br>G |
| pT7rrnB DNA [SEQ ID NO: 26] | TTAATACGACTCACTATAGGGGCCGCTGAGAAAAAGCGAAGCGGC<br>ACTGCTCTTTAACAATTTATCAGACAATCTGTGTGGGCACTCGAAG<br>ATACGGATTCTTAACGTCGCAAGACGAAAATGAATACCAAGTCTC<br>AAGAGTGAACACGTAATTCATTACGAAGTTTAATTCTTTGAGCGTCA<br>AACTTTTAAATTGAAGAGTTTGATCATGGCTCAGATTGAACGCTGG<br>CGGCAGGCCTAACACATGCAAGTCGAACGGTAACAGGAAGAAGCT<br>TGCTTCTTTGCTGACGAGTGGCGGACGGGTGAGTAATGTCTGGGA<br>AACTGCCTGATGGAGGGGGATAACTACTGGAAACGGTAGCTAATA<br>CCGCATAACGTCGCAAGACCAAAGAGGGGGACCTTCGGGCCTCTT<br>GCCATCGGATGTGCCCAGATGGGATTAGCTAGTAGGTGGGGTAAC<br>GGCTCACCTAGGCGACGATCCCTAGCTGGTCTGAGAGGATGACCA<br>GCCACACTGGAACTGAGACACGGTCCAGACTCCTACGGGAGGCA<br>GCAGTGGGGAATATTGCACAATGGGCGCAAGCCTGATGCAGCCAT<br>GCCGCGTGTATGAAGAAGGCCTTCGGGTTGTAAAGTACTTTCAGC<br>GGGGAGGAAGGGAGTAAAGTTAATACCTTTGCTCATTGACGTTAC<br>CCGCAGAAGAAGCACCGGCTAACTCCGTGCCAGCAGCCGCGGTA<br>ATACGGAGGGTGCAAGCGTTAATCGGAATTACTGGGCGTAAAGCG<br>CACGCAGGCGGTTTGTTAAGTCAGATGTGAAATCCCCGGGCTCAA<br>CCTGGGAACTGCATCTGATACTGGCAAGCTTGAGTCTCGTAGAGG<br>GGGGTAGAATTCCAGGTGTAGCGGTGAAATGCGTAGAGATCTGGA<br>GGAATACCGGTGGCGAAGGCGGCCCCCTGGACGAAGACTGACGC<br>TCAGGTGCGAAAGCGTGGGGAGCAAACAGGATTAGATACCCTGGT<br>AGTCCACGCCGTAAACGATGTCGACTTGGAGGTTGTGCCCTTGAG<br>GCGTGGCTTCCGGAGCTAACGCGTTAAGTCGACCGCCTGGGGAG<br>TACGGCCGCAAGGTTAAAACTCAAATGAATTGACGGGGGCCCGCA<br>CAAGCGGTGGAGCATGTGGTTTAATTCGATGCAACGCGAAGAACC<br>TTACCTGGTCTTGACATCCACGGAAGTTTTCAGAGATGAGAATGTG<br>CCTTCGGGAACCGTGAGACAGGTGCTGCATGGCTGTCGTCAGCTC<br>GTGTTGTGAAATGTTGGGTTAAGTCCCGCAACGAGCGCAACCCTT<br>ATCCTTTGTTGCCAGCGGTCCGGCCGGGAACTCAAAGGAGACTGC<br>CAGTGATAAACTGGAGGAAGGTGGGGATGACGTCAAGTCATCATG<br>GCCCTTACGACCAGGGCTACACACGTGCTACAATGGCGCATACAA<br>AGAGAAGCGACCTCGCGAGAGCAAGCGGACCTCATAAAGTGCGT<br>CGTAGTCCGGATTGGAGTCTGCAACTCGACTCCATGAAGTCGGAA<br>TCGCTAGTAATCGTGGATCAGAATGCCACGGTGAATACGTTCCCG<br>GGCCTTGTACACACCGCCCGTCACACCATGGGAGTGGGTTGCAAA<br>AGAAGTAGGTAGCTTAACCTTCGGGAGGGCGCTTACCACTTTGTG<br>ATTCATGACTGGGGTGAAGTCGTAACAAGGTAACCGTAGGGGAAC<br>CTGCGGTTGGATCACCTCCTTACCTTAAAGAAGCGTACTTTGTAGT<br>GCTCACACAGATTGTCTGATAGAAAGTGAAAAGCAAGGCGTTTAC<br>GCGTTGGGAGTGAGGCTGAAGAGAATAAGGCCGTTCGCTTTCTAT<br>TAATGAAAGCTCACCCTACACGAAAATATCACGCAACGCGTGATAA<br>GCAATTTTCGTGTCCCCTTCGTCTAGAGGGCCAGGACACCGCCCT<br>TTCACGGCGGTAACAGGGGTTCGAATCCCTAGGGGACGCCACTT<br>GCTGGTTTGTGAGTGAAAGTCGCCGACCTTAATATCTCAAAACTCA<br>TCTTCGGGTGATGTTTGAGATATTTGCTCTTTAAAAATCTGGATCAA<br>GCTGAAAATTGAAACACTGAACAACGAGAGTTGTTCGTGAGTCTCT<br>CAAATTTTCGCAACACGATGATGAATCGAAAGAAACATCTTCGGGT<br>TGTGAGGTTAAGCGACTAAGCGTACACGGTGGATGCCCTGGCAGT<br>CAGAGGCGATGAAGGACGTGCTAATCTGCGATAAGCGTCGGTAAG<br>GTGATATGAACCGTTATAACCGGCGATTTCCGAATGGGAAACCC<br>AGTGTGTTTCGACACACTATCATTAACTGAATCCATAGGTTAATGA<br>GGCGAACCGGGGGAACTGAAACATCTAAGTACCCCGAGGAAAAG<br>AAATCAACCGAGATTCCCCCAGTAGCGGCGAGCGAACGGGGAGC<br>AGCCCAGAGCCTGAATCAGTGTGTGTTAGTGGAAGCGTCTGGA<br>AAGGCGCGCGATACAGGGTGACAGCCCCGTACACAAAAATGCACA<br>TGCTGTGAGCTCGATGAGTAGGGCGGGACACGTGGTATCCTGTCT<br>GAATATGGGGGACCATCCTCCAAGGCTAAATACTCCTGACTGAC<br>CGATAGTGAACCAGTACCGTGAGGGAAAGGCGAAAAGAACCCCG<br>GCGAGGGGAGTGAAAAAGAACCTGAAACCGTGTACGTACAAGCAG<br>TGGGAGCACGCTTAGGCGTGTGACTGCGTACCTTTTGTATAATGG<br>GTCAGCGACTTATATTCGTAGCAAGGTTAACCGAATAGGGGAGC<br>CGAAGGGAAACCGAGTCTTAACTGGGCGTTAAGTTGCAGGGTATA<br>GACCCGAAACCCGGTGATCTAGCCATGGGCAGGTTGAAGGTTGG<br>GTAACACTAACTGGAGGACCGAACCGACTAATGTTGAAAAATTAGC<br>GGATGACTTGTGGCTGGGGGTGAAAGGCCAATCAAACCGGGAGA<br>TAGCTGGTTCTCCCCGAAAGCTATTTAGGTAGCGCCTCGTGAATTC<br>ATCTCCGGGGGTAGAGCACTGTTTCGGCAAGGGGGTCATCCCGA<br>CTTACCAACCCCGATGCAAACTGCGAATACCGGAGAATGTTATCAC |

TABLE 6-continued

Sequences used in this disclosure.

| Sequence Description [SEQ ID NO: __] | Nucleotide or Amino Acid Sequence |
|---|---|
| | GGGAGACACACGGCGGGTGCTAACGTCCGTCGTGAAGAGGGAAA CAACCCAGACCGCCAGCTAAGGTCCCAAAGTCATGGTTAAGTGGG AAACGATGTGGGAAGGCCCAGACAGCCAGGATGTTGGCTTAGAAG CAGCCATCATTTAAAGAAAGCGTAATAGCTCACTGGTCGAGTCGG CCTGCGCGGAAGATGTAACGGGGCTAAACCATGCACCGAAGCTG CGGCAGCGACGCTTATGCGTTGTTGGGTAGGGGAGCGTTCTGTAA GCCTGCGAAGGTGTGCTGTGAGGCATGCTGGAGGTATCAGAAGT GCGAATGCTGACATAAGTAACGATAAAGCGGGTGAAAAGCCCGCT CGCCGGAAGACCAAGGGTTCCTGTCCAACGTTAATCGGGGCAGG GTGAGTCGACCCCTAAGGCGAGGCCGAAAGGCGTAGTCGATGGG AAACAGGTTAATATTCCTGTACTTGGTGTTACTGCGAAGGGGGAC GGGAGAAGGCTATGTTGGCCGGGCGACGGTTGTCCCGGTTTAAGC GTGTAGGCTGGTTTTCCAGGCAAATCCGGAAATCAAGGCTGAGG CGTGATGACGAGGCACTACGGTGCTGAAGCAACAAATGCCCTGCT TCCAGGAAAAGCCTCTAAGCATCAGGTAACATCAAATCGTACCCCA AACCGACACAGGTGGTCAGGTAGAGAATACCAAGGCGCTTGAGAG AACTCGGGTGAAGGAACTAGGCAAAATGGTGCCGTAACTTCGGGA GAAGGCACGCTGATATGTAGGTGAGGTCCCTCGCGGATGGAGCT GAAATCAGTCGAAGATACCAGCTGGCTGCAACTGTTTATTAAAAAC ACAGCACTGTGCAAACACGAAAGTGGACGTATACGGTGTGACGCC TGCCCGGTGCCGGAAGGTTAATTGATGGGGTTAGCGCAAGCGAA GCTCTTGATCGAAGCCCCGGTAAACGGCGGCCGTAACTATAACGG TCCTAAGGTAGCGAAATTCCTTGTCGGGTAAGTTCCGACCTGCAC GAATGGCGTAATGATGGCCAGGCTGTCTCCACCCGAGACTCAGTG AAATTGAACTCGCTGTGAAGATGCAGTGTACCCGCGGCAAGACGG AAAGACCCCGTGAACCTTTACTATAGCTTGACACTGAACATTGAGC CTTGATGTGTAGGATAGGTGGGAGGCTTTGAAGTGTGGACGCCAG TCTGCATGGAGCCGACCTTGAAATACCACCCTTTAATGTTTGATGT TCTAACGTTGACCCGTAATCCGGGTTGCGGACAGTGTCTGGTGGG TAGTTTGACTGGGGCGGTCTCCTCCTAAAGAGTAACGGAGGAGCA CGAAGGTTGGCTAATCCTGGTCGGACATCAGGAGGTTAGTGCAAT GGCATAAGCCAGCTTGACTGCGAGCGTGACGGCGCGAGCAGGTG CGAAAGCAGGTCATAGTGATCCGGTGGTTCTGAATGGAAGGGCCA TCGCTCAACGGATAAAAGGTACTCCGGGGATAACAGGCTGATACC GCCCAAGAGTTCATATCGACGGCGGTGTTTGGCACCTCGATGTCG GCTCATCACATCCTGGGGCTGAAGTAGGTCCCAAGGGTATGGCTG TTCGCCATTTAAAGTGGTACGCGAGCTGGGTTTAGAACGTCGTGA GACAGTTCGGTCCCTATCTGCCGTGGGCGCTGGAGAACTGAGGG GGGCTGCTCCTAGTACGAGAGGACCGGAGTGGACGCATCACTGG TGTTCGGGTTGTCATGCCAATGGCACTGCCCGGTAGCTAAATGCG GAAGAGATAAGTGCTGAAAGCATCTAAGCACGAAACTTGCCCCGA GATGAGTTCTCCCTGACCCTTTAAGGGTCCTGAAGGAACGTTGAA GACGACGACGTTGATAGGCCGGGTGTGTAAGCGCAGCGATGCGT TGAGCTAACCGGTACTAATGAACCGTGAGGCTTAACCTTACAACGC CGAAGCTGTTTTGGCGGATGAGAGAAGATTTTCAGCCTGATACAG ATTAAATCAGAACGCAGAAGCGGTCTGATAAAACAGAATTTGCCTG GCGGCAGTAGCGCGGTGGTCCCACCTGACCCCATGCCGAACTCA GAAGTGAAACGCCGTAGCGCCGATGGTAGTGTGGGGTCTCCCCAT GCGAGAGTAGGGAACTGCCAGGCATCAAATAAAACGAAAGGCTCA GTCGAAAGACTGGGCCTTTCGTTTTATCTGTTGTTTGTCGGTGAAC GCTCTCCTGAGTAGGACAAATCCGCCGGGAGCGGATTTGAACGTT GCGAAGCAACGGCCCGGAGGGTGGCGGGCAGGACGCCCGCCAT AAACTGCCAGGCATCAAATTAAGCAGAAGGCCATCCTGACGGATG GCCTTTTTGCGTTTCTACAAACTCTTCCTGTCGTCATATCTACAAGC CGGCGCGCCAAATTGACAATTACTCATCCGGCTCGAATAATGTGT GGAACTTAAACACACAGGAGGAAAACATATGTCTATCCAGCACT TCCGTGTTGCGCTGATCCCGTTCTTCGCGGCGTTCTGCCTGCCGG TTTTCGCGCACCCGGAAACCCTGGTTAAAGTTAAAGACGCGGAAG ACCAGCTGGGTGCGCGTGTTGGTTACATCGAACTGGACCTGAACT CTGGTAAAATCCTGGAATCTTTCCGTCCGGAAGAACGTTTCCCGAT GATGTCTACCTTCAAAGTTCTGCTGTGCGGTGCGGTTCTGTCTCGT GTTGACGCGGGTCAGGAACAGCTGGGTCGTCGTATCCACTACTCT CAGAACGACCTGGTTGAATACTCTCCCGTTACCGAAAAACACCTGA CCGACGGTATGACCGTTCGTGAACTGTGCTCTGCGGCGATCACCA TGTCTGACAACACCGCAGCGAACCTGCTGCTGACCACCATCGGTG GTCCGAAAGAACTGACCGCGTTCCTGCACAACATGGGCGACCACG TTACCCGTCTGGACCGTTGGGAACCGGAACTGAACGAAGCGATCC CGAACGACGAACGTGACACCACCATGCCTGCGGCGATGGCGACC ACCCTGCGTAAACTGCTGACCGGTGAACTGCTGACCCTGGCATCT CGTCAGCAGCTGATCGACTGGATGGAAGCGGACAAAGTTGCGGG TCCGCTGCTGCGTTCTGCGCTGCCTGCGGGTTGGTTCATCGCGGA CAAATCTGGTGCGGGTGAACGTGGTTCTCGTGGTATCATCGCGGC GCTGGGTCCGGACGGTAAACCGTCTCGTATCGTTGTTATCTACAC CACCGGTTCTCAGGCGACCATGGACGAACGTAACCGTCAGATCGC |

TABLE 6-continued

Sequences used in this disclosure.

| Sequence Description [SEQ ID NO: __] | Nucleotide or Amino Acid Sequence |
|---|---|
| | GGAAATCGGTGCGTCTCTGATTAAACACTGGTAAACTCACTCCTAG<br>CCCGCCTAATAAGCGGGCTTTTTTTCTGCAGACCAAGTTTACTCAT<br>ATATACTTTAGATTGATTTAAAACTTCATTTTTAATTTAAAAGGATCT<br>AGGTGAAGATCCTTTTTGATAATCTCATGACCAAAATCCCTTAACGT<br>GAGTTTTCGTTCCACTGAGCGTCAGACCCCGTAGAAAAGATCAAA<br>GGATCTTCTTGAGATCCTTTTTTTCTGCGCGTAATCTGCTGCTTGC<br>AAACAAAAAAACCACCGCTACCAGCGGTGGTTTGTTTGCCGGATC<br>AAGAGCTACCAACTCTTTTTCCGAAGGTAACTGGCTTCAGCAGAGC<br>GCAGATACCAAATACTGTCCTTCTAGTGTAGCCGTAGTTAGGCCAC<br>CACTTCAAGAACTCTGTAGCACCGCCTACATACCTCGCTCTGCTAA<br>TCCTGTTACCAGTGGCTGCTGCCAGTGGCGATAAGTCGTGTCTTA<br>CCGGGTTGGACTCAAGACGATAGTTACCGGATAAGGCGCAGCGGT<br>CGGGCTGAACGGGGGGTTCGTGCACACAGCCCAGCTTGGAGCGA<br>ACGACCTACACCGAACTGAGATACCTACAGCGTGAGCTATGAGAA<br>AGCGCCACGCTTCCCGAAGGGAGAAAGGCGGACAGGTATCCGGT<br>AAGCGGCAGGGTCGGAACAGGAGAGCGCACGAGGGAGCTTCCAG<br>GGGGAAACGCCTGGTATCTTTATAGTCCTGTCGGGTTTCGCCACC<br>TCTGACTTGAGCGTCGATTTTTGTGATGCTCGTCAGGGGGCGGA<br>GCCTATGGAAAAACGCCAGCAACGCGGCCTTTTTACGGTTCCTGG<br>CCTTTTGCTGG |
| pT7rrnB RNA [SEQ ID NO: 27] | GGGCCGCUGAGAAAAAGCGAAGCGGCACUGCUCUUUAACAAUUU<br>AUCAGACAAUCUGUGUGGGCACUCGAAGAUACGGAUUCUUAACG<br>UCGCAAGACGAAAAAUGAAUACCAAGUCUCAAGAGUGAACACGU<br>AAUUCAUUACGAAGUUUAAUUCUUUGAGCGUCAAACUUUUAAAU<br>UGAAGAGUUUGAUCAUGGCUCAGAUUGAACGCUGGCGGCAGGC<br>CUAACACAUGCAAGUCGAACGGUAACAGGAAGAAGCUUGCUUCU<br>UUGCUGACGAGUGGCGGACGGGUGAGUAAUGUCUGGGAAACUG<br>CCUGAUGGAGGGGGAUAACUACUGGAAACGGUAGCUAAUACCGC<br>AUAACGUCGCAAGACCAAAGAGGGGGACCUUCGGGCCUCUUGC<br>CAUCGGAUGUGCCCAGAUGGGAUUAGCUAGUAGGUGGGGUAAC<br>GGCUCACCUAGGCGACGAUCCCUAGCUGGUCUGAGAGGAUGAC<br>CAGCCACACUGGAACUGAGACACGGUCCAGACUCCUACGGGAGG<br>CAGCAGUGGGGAAUAUUGCACAAUGGGCGCAAGCCUGAUGCAG<br>CCAUGCCGCGUGUAUGAAGAAGGCCUUCGGGUUGUAAAGUACU<br>UUCAGCGGGGAGGAAGGGAGUAAAGUUAAUACCUUUGCUCAUU<br>GACGUUACCCGCAGAAGAAGCACCGGCUAACUCCGUGCCAGCAG<br>CCGCGGUAAUACGGAGGGUGCAAGCGUUAAUCGGAAUUACUGG<br>GCGUAAAGCGCACGCAGGCGGUUUGUUAAGUCAGAUGUGAAAU<br>CCCCGGGCUCAACCUGGGAACUGCAUCUGAUACUGGCAAGCUU<br>GAGUCUCGUAGAGGGGGUAGAAUUCCAGGUGUAGCGGUGAAA<br>UGCGUAGAGAUCUGGAGGAAUACCGGUGGCGAAGGCGGCCCCC<br>UGGACGAAGACUGACGCUCAGGUGCGAAAGCGUGGGGAGCAAA<br>CAGGAUUAGAUACCCUGGUAGUCCACGCCGUAAACGAUGUCGAC<br>UUGGAGGUUGUGCCCUUGAGGCGUGGCUUCCGGAGCUAACGCG<br>UUAAGUCGACCGCCUGGGGAGUACGGCCGCAAGGUUAAAACUCA<br>AAUGAAUUGACGGGGGCCCGCACAAGCGGUGGAGCAUGUGGUU<br>UAAUUCGAUGCAACGCGAAGAACCUUACCUGGUCUUGACAUCCA<br>CGGAAGUUUUCAGAGAUGAGAAUGUGCCUUCGGGAACCGUGAG<br>ACAGGUGCUGCAUGGCUGUCGUCAGCUCGUGUUGUGAAAUGUU<br>GGGUUAAGUCCCGCAACGAGCGCAACCCUUAUCCUUUGUUGCCA<br>GCGGUCCGGCCGGGAACUCAAAGGAGACUGCCAGUGAUAAACU<br>GGAGGAAGGUGGGGAUGACGUCAAGUCAUCAUGGCCCUUACGA<br>CCAGGGCUACACACGUGCUACAAUGGCGCAUACAAAGAGAAGCG<br>ACCUCGCGAGAGCAAGCGGACCUCAUAAAGUGCGUCGUAGUCC<br>GGAUUGGAGUCUGCAACUCGACUCCAUGAAGUCGGAAUCGCUA<br>GUAAUCGUGGAUCAGAAUGCCACGGUGAAUACGUUCCCGGGCC<br>UUGUACACACCGCCCGUCACACCAUGGGAGUGGGUUGCAAAAGA<br>AGUAGGUAGCUUAACCUUCGGGAGGGCGCUUACCACUUUGUGA<br>UUCAUGACUGGGGUGAAGUCGUAACAAGGUAACCGUAGGGGAA<br>CCUGCGGUUGGAUCACCUCCUUACCUUAAAGAAGCGUACUUUGU<br>AGUGCUCACACAGAUUGUCUGAUAGAAAGUGAAAAGCAAGGCGU<br>UUACGCGUUGGGAGUGAGGCUGAAGAGAAUAAGGCCGUUCGCU<br>UUCUAUUAAUGAAAGCUCACCCUACACGAAAAAUAUCACGCAACGC<br>GUGAUAAGCAAUUUUCGUGUCCCCUUCGUCUAGAGGCCCAGGA<br>CACCGCCCUUUCACGGCGGUAACAGGGGUUCGAAUCCCCUAGG<br>GGACGCCACUUGCUGGUUUGUGAGUGAAAGUCGCCGACCUUAA<br>UAUCUCAAAACUCAUCUUCGGGUGAUGUUUGAGAUAUUUGCUCU<br>UUAAAAAUCUGGAUCAAGCUGAAAAUUGAAACACUGACACAGAG<br>AGUUGUUCGUGAGUCUCUCAAAUUUUCGCAACACGAUGAUGAAU<br>CGAAAGAAACAUCUUCGGGUUGUGAGGUUAAGCGACUAAGCGUA<br>CACGGUGGAUGCCCUGGCAGUCAGAGGCGAUGAAGGACGUGCU<br>AAUCUGCGAUAAGCGUCGGUAAGGUGAUAUGAACCGUUAUAACC<br>GGCGAUUUCCGAAUGGGGAAACCCAGUGUGUUUCGACACACUAU |

TABLE 6-continued

Sequences used in this disclosure.

| Sequence Description [SEQ ID NO: __] | Nucleotide or Amino Acid Sequence |
|---|---|
| | CAUUAACUGAAUCCAUAGGUUAAUGAGGCGAACCGGGGGAACUG AAACAUCUAAGUACCCCGAGGAAAAGAAAUCAACCGAGAUUCCCC CAGUAGCGGCGAGCGAACGGGGAGCAGCCCAGAGCCUGAAUCA GUGUGUGUGUUAGUGGAAGCGUCUGGAAAGGCGCGCGAUACAG GGUGACAGCCCCGUACACAAAAAUGCACAUGCUGUGAGCUCGAU GAGUAGGGCGGGACACGUGGUAUCCUGUCUGAAUAUGGGGGA CCAUCCUCCAAGGCUAAAUACUCCUGACUGACCGAUAGUGAACC AGUACCGUGAGGGAAAGGCGAAAAGAACCCCGGCGAGGGGAGU GAAAAAGAACCUGAAACCGUGUACGUACAAGCAGUGGGAGCACG CUUAGGCGUGUGACUGCGUACCUUUUGUAUAAUGGGUCAGCGA CUUAUAUUCUGUAGCAAGGUUAACCGAAUAGGGGAGCCGAAGGG AAACCGAGUCUUAACUGGGCGUUAAGUUGCAGGGUAUAGACCCG AAACCCGGUGAUCUAGCCAUGGGCAGGUUGAAGGUUGGGUAAC ACUAACUGGAGGACCGAACCGACUAAUGUUGAAAAAUUAGCGGA UGACUUGUGGCUGGGGGUGAAAGGCCAAUCAAACCGGGAGAUA GCUGGUUCUCCCCGAAAGCUAUUUAGGUAGCGCCUCGUGAAUU CAUCUCCGGGGUAGAGCACUGUUUCGGCAAGGGGGUCAUCCC GACUUACCAACCCGAUGCAAACUGCGAAUACCGGAGAAUGUUAU CACGGGAGACACACGGCGGGUGCUAACGUCCGUCGUGAAGAGG GAAACAACCCAGACCGCCAGCUAAGGUCCCAAAGUCAUGGUUAA GUGGGAAACGAUGUGGGAAGGCCCAGACAGCCAGGAUGUUGGC UUAGAAGCAGCCAUCAUUUAAAGAAAGCGUAAUAGCUCACUGGU CGAGUCGGCCUGCGCGGAAGAUGUAACGGGGCUAAACCAUGCA CCGAAGCUGCGGCAGCGACGCUUAUGCGUUGUUGGGUAGGGGA GCGUUCUGUAAGCCUGCGAAGGUGUGCUGUGAGGCAUGCUGGA GGUAUCAGAAGUGCGAAUGCUGACAUAAGUAACGAUAAAGCGGG UGAAAAGCCCGCUCGCCGGAAGACCAAGGGUUCCUGUCCAACGU UAAUCGGGGCAGGGUGAGUCGACCCCUAAGGCGAGGCCGAAAG GCGUAGUCGAUGGGAAACAGGUUAAUAUUCCUGUACUUGGUGU UACUGCGAAGGGGGGACGGAGAAGGCUAUGUUGGCCGGGCGAC GGUUGUCCCGGUUUAAGCGUGUAGGCUGGUUUUCCAGGCAAAU CCGGAAAAUCAAGGCUGAGGCGUGAUGACGAGGCACUACGGUG CUGAAGCAACAAAUGCCCUGCUUCCAGGAAAAGCCUCUAAGCAU CAGGUAACAUCAAAUCGUACCCCAAACCGACACAGGUGGUCAGG UAGAGAAUACCAAGGCGCUUGAGAGAACUCGGGUGAAGGAACUA GGCAAAAUGGUGCCGUAACUUCGGGAAAGGCACGCUGAUAUG UAGGUGAGGUCCCUCGCGGAUGGAGCUGAAAUCAGUCGAAGAU ACCAGCUGGCUGCAACUGUUUAUUAAAAACACAGCACUGUGCAA ACACGAAAGUGGACGUAUACGGUGUGACGCCUGCCCGGUGCCG GAAGGUUAAUUGAUGGGGUUAGCGCAAGCGAAGCUCUUGAUCG AAGCCCCGGUAAACGGCGGCCGUAACUAUAACGGUCCUAAGGUA GCGAAAUUCCUUGUCGGGUAAGUUCCGACCUGCACGAAUGGCG UAAUGAUGGCCAGGCUGUCUCCACCCGAGACUCAGUGAAAUUGA ACUCGCUGUGAAGAUGCAGUGUACCCGCGGCAAGACGGAAAGAC CCCGUGAACCUUUACUAUAGCUUGACACUGAACAUUGAGCCUUG AUGUGUAGGAUAGGUGGGAGGCUUUGAAGUGUGGACGCCAGUC UGCAUGGAGCCGACCUUGAAAUACCACCCUUUAAUGUUUGAUGU UCUAACGUUGACCCGUAAUCCGGGUUGCGGACAGUGUCUGGUG GGUAGUUUGACUGGGGCGGUCUCCUCCUAAAGAGUAACGGAGG AGCACGAAGGUUGGCUAAUCCUGGUCGGACAUCAGGAGGUUAG UGCAAUGGCAUAAGCCAGCUUGACUGCGAGCGUGACGGCGCGA GCAGGUGCGAAAGCAGGUCAUAGUGAUCCGGUGGUUCUGAAUG GAAGGGCCAUCGCUCAACGGAUAAAAGGUACUCCGGGGAUAACA GGCUGAUACCGCCCAAGAGUUCAUAUCGACGGCGGUGUUUGGC ACCUCGAUGUCGGCUCAUCACAUCCUGGGGCUGAAGUAGGUCC CAAGGGUAUGGCUGUUCGCCAUUUAAAGUGGUACGCGAGCUGG GUUUAGAACGUCGUGAGACAGUUCGGUCCCUAUCUGCCGUGGG CGCUGGAGAACUGAGGGGGGCUGCUCCUAGUACGAGAGGACCG GAGUGGACGCAUCACUGGUGUUCGGGUUGUCAUGCCAAUGGCA CUGCCCGGUAGCUAAAUGCGGAAGAGAUAAGUGCUGAAAGCAUC UAAGCACGAAACUUGCCCCGAGAUGAGUUCUCCCUGACCCUUUA AGGGUCCUGAAGGAACGUUGAAGACGACGACGUUGAUAGGCCG GGUGUGUAAGCGCAGCGAUGCGUUGAGCUAACCGGUACUAAUG AACCGUGAGGCUUAACCUUACAACGCCGAAGCUGUUUUGGCGGA UGAGAGAAGAUUUUCAGCCUGAUACAGAUUAAAUCAGAACGCAG AAGCGGUCUGAUAAAACAGAAUUUGCCUGGCGGCAGUAGCGCG GUGGUCCCACCUGACCCCAUGCCGAACUCAGAAGUGAAACGCCG UAGCGCCGAUGGUAGUGUGGGGUCUCCCCAUGCGAGAGUAGGG AACUGCCAGGCAUCAAAUAAAACGAAAGGCUCAGUCGAAAGACU GGGCCUUUCGUUUUAUCUGUUGUUUGUCGGUGAACGCUCUCCU GAGUAGGACAAAUCCGCCGGGAGCGGAUUUGAACGUUGCGAAG CAACGGCCCGGAGGGUGGCGGGCAGGACGCCCGCCAUAAACUG CCAGGCAUCAAAUUAAGCAGAAGGCCAUCCUGACGGAUGGCCUU UUUG |

TABLE 6-continued

Sequences used in this disclosure.

| Sequence Description [SEQ ID NO: __] | Nucleotide or Amino Acid Sequence |
|---|---|
| pT7rrnB-CR DNA [SEQ ID NO: 28] | TTAATACGACTCACTATAGGGGCCGCTGAGAAAAAGCGAAGCGGCA CTGCTCTTTAACAATTTATCAGACAATCTGTGTGGGCACTCGAAGAT ACGGATTCTTAACGTCGCAAGACGAAAATGAATACCAAGTCTCAAG AGTGAACACGTAATTCATTACGAAGTTTAATTCTTTGAGCGTCAAACT TTTAAATTGAAGAGTTTGATCATGGCTCAGATTGAACGCTGGCGGCA GGCCTAACACATGCAAGTCGAACGGTAACAGGAAGAAGCTTGCTTC TTTGCTGACGAGTGGCGGACGGGTGAGTAATGTCTGGGAAACTGCC TGATGGAGGGGGATAACTACTGGAAACGGTAGCTAATACCGCATAA CGTCGCAAGACCAAAGAGGGGGACCTTCGGGCCTCTTGCCATCGG ATGTGCCCAGATGGGATTAGCTAGTAGGTGGGGTAACGGCTCACCT AGGCGACGATCCCTAGCTGGTCTGAGAGGATGACCAGCCACACTG GAACTGAGACACGGTCCAGACTCCTACGGGAGGCAGCAGTGGGGA ATATTGCACAATGGGCGCAAGCCTGATGCAGCCATGCCGCGTGTAT GAAGAAGGCCTTCGGGTTGTAAAGTACTTTCAGCGGGGAGGAAGG GAGTAAAGTTAATACCTTTGCTCATTGACGTTACCCGCAGAAGAAGC ACCGGCTAACTCCGTGCCAGCAGCCGCGGTAATACGGAGGGTGCA AGCGTTAATCGGAATTACTGGGCGTAAAGCGCACGCAGGCGGTTTG TTAAGTCAGATGTGAAATCCCCGGGCTCAACCTGGGAACTGCATCT GATACTGGCAAGCTTGAGTCTCGTAGAGGGGGGTAGAATTCCAGGT GTAGCGGTGAAATGCGTAGAGATCTGGAGGAATACCGGTGGCGAA GGCGGCCCCCTGGACGAAGACTGACGCTCAGGTGCGAAAGCGTGG GGAGCAAACAGGATTAGATACCCTGGTAGTCCACGCCGTAAACGAT GTCGACTTGGAGGTTGTGCCCTTGAGGCGTGGCTTCCGGAGCTAAC GCGTTAAGTCGACCGCCTGGGGAGTACGGCCGCAAGGTTAAAACT CAAATGAATTGACGGGGGCCCGCACAAGCGGTGGAGCATGTGGTT TAATTCGATGCAACGCGAAGAACCTTACCTGGTCTTGACATCCACG GAAGTTTTCAGAGATGAGAATGTGCCTTCGGGAACCGTGAGACAGG TGCTGCATGGCTGTCGTCAGCTCGTGTTGTGAAATGTTGGGTTAAG TCCCGCAACGAGCGCAACCCTTATCCTTTGTTGCCAGCGGTCCGGC CGGGAACTCAAAGGAGACTGCCAGTGATAAACTGGAGGAAGGTGG GGATGACGTCAAGTCATCATGGCCCTTACGACCAGGGCTACACACG TGCTACAATGGCGCATACAAAGAGAAGCGACCTCGCGAGAGCAAGC GGACCTCATAAAGTGCGTCGTAGTCCGGATTGGAGTCTGCAACTCG ACTCCATGAAGTCGGAATCGCTAGTAATCGTGGATCAGAATGCCAC GGTGAATACGTTCCCGGGCCTTGTACACACCGCCCGTCACACCATG GGAGTGGGTTGCAAAAGAAGTAGGTAGCTTAACCTTCGGGAGGGC GCTTACCACTTTGTGATTCATGACTGGGGTGAAGTCGTAACAAGGTA ACCGTAGGGGAACCTGCGGTTGGATCACCTCCTTACCTTAAAGAAG CGTACTTTGTAGTGCTCACACAGATTGTCTGATAGAAAGTGAAAAGC AAGGCGTTTACGCGTTGGGAGTGAGGCTGAAGAGAATAAGGCCGTT CGCTTTCTATTAATGAAAGCTCACCCTACACGAAAATATCACGCAAC GCGTGATAAGCAATTTTCGTGTCCCCTTCGTCTAGAGGCCCAGGAC ACCGCCCTTTCACGGCGGTAACAGGGGTTCGAATCCCCTAGGGGA CGCCACTTGCTGGTTTGTGAGTGAAAGTCGCCGACCTTAATATCTCA AAACTCATCTTCGGGTGATGTTTGAGATATTTGCTCTTTAAAAATCTG GATCAAGCTGAAAATTGAAACACTGAACAACGAGAGTTGTTCGTGAG TCTCTCAAATTTTCGCAACACGATGAATCGAAAGAAACATCTTC GGGTTGTGAGGTTAAGCGACTAAGCGTACACGGTGGATGCCCTGG CAGTCAGAGGCGATGAAGGACGTGCTAATCTGCGATAAGCGTCGGT AAGGTGATATGAACCGTTATAACCGGCGATTTCCGAATGGGGAAAC CCAGTGTGTTTCGACACACTATCATTAACTGAATCCATAGGTTAATG AGGCGAACCGGGGGAACTGAAACATCTAAGTACCCCGAGGAAAAG AAATCAACCGAGATTCCCCCAGTAGCGGCGAGCGAACGGGGAGCA GCCCAGAGCCTGAATCAGTGTGTGTGTTAGTGGAAGCGTCTGGAAA GGCGCGCGATACAGGGTGACAGCCCCGTACACAAAAATGCACATG CTGTGAGCTCGATGAGTAGGGCGGGACACGTGGTATCCTGTCTGAA TATGGGGGGACCATCCTCCAAGGCTAAATACTCCTGACTGACCGAT AGTGAACCAGTACCGTGAGGGAAAGGCGAAAAGAACCCCGGCGAG GGGAGTGAAAAAGAACCTGAAACCGTGTACGTACAAGCAGTGGGAG CACGCTTAGGCGTGTGACTGCGTACCTTTTGTATAATGGGTCAGCG ACTTATATTCTGTAGCAAGGTTAACCGAATAGGGGAGCCGAAGGGA AACCGAGTCTTAACTGGGCGTTAAGTTGCAGGGTATAGACCCGAAA CCCGGTGATCTAGCCATGGGCAGGTTGAAGGTTGGGTAACACTAAC TGGAGGACCGAACCGACTAATGTTGAAAAATTAGCGGATGACTTGT GGCTGGGGGTGAAAGGCCAATCAAACCGGGAGATAGCTGGTTCTC CCCGAAAGCTATTTAGGTAGCGCCTCGTGAATTCATCTCCGGGGGT AGAGCACTGTTTCGGCAAGGGGTCATCCCGACTTACCAACCCGAT GCAAACTGCGAATACCGGAGAATGTTATCACGGGAGACACACGCG GGTGCTAACGTCCGTCGTGAAGAGGGAAACAACCCAGACCGCCAG CTAAGGTCCCAAAGTCATGGTTAAGTGGGAAACGATGTGGGAAGGC CCAGACAGCCAGGATGTTGGCTTAGAAGCAGCCATCATTTAAAGAA AGCGTAATAGCTCACTGGTCGAGTCGGCCTGCGCGGAAGATGTAAC GGGGCTAAACCATGCACCGAAGCTGCGGCAGCGACGCTTATGCGT |

TABLE 6-continued

Sequences used in this disclosure.

| Sequence Description [SEQ ID NO: __] | Nucleotide or Amino Acid Sequence |
|---|---|
| | TGTTGGGTAGGGGAGCGTTCTGTAAGCCTGCGAAGGTGTGCTGTGA |
| | GGCATGCTGGAGGTATCAGAAGTGCGAATGCTGACATAAGTAACGA |
| | TAAAGCGGGTGAAAAGCCCGCTCGCCGGAAGACCAAGGGTTCCTG |
| | TCCAACGTTAATCGGGGCAGGGTGAGTCGACCCCTAAGGCGAGGC |
| | CGAAAGGCGTAGTCGATGGGAAACAGGTTAATATTCCTGTACTTGG |
| | TGTTACTGCGAAGGGGGACGGAGAAGGCTATGTTGGCCGGCGA |
| | CGGTTGTCCCGGTTTAAGCGTGTAGGCTGGTTTTCCAGGCAAATCC |
| | GGAAAATCAAGGCTGAGGCGTGATGACGAGGCACTACGGTGCTGA |
| | AGCAACAAATGCCCTGCTTCCAGGAAAAGCCTCTAAGCATCAGGTA |
| | ACATCAAATCGTACCCCAAACCGACACAGGTGGTCAGGTAGAGAAT |
| | ACCAAGGCGCTTGAGAGAACTCGGGTGAAGGAACTAGGCAAAATG |
| | GTGCCGTAACTTCGGGAGAAGGCACGCTGATATGTAGGTGAGGTCC |
| | CTCGCGGATGGAGCTGAAATCAGTCGAAGATACCAGCTGGCTGCAA |
| | CTGTTTATTAAAAACACAGCACTGTGCAAACACGAAAGTGGACGTAT |
| | ACGGTGTGACGCCTGCCCGGTGCCGGAAGGTTAATTGATGGGGTT |
| | AGCGCAAGCGAAGCTCTTGATCGAAGCCCGGTAAACGGCGGCCG |
| | TAACTATAACGGTCCTAAGGTAGCGAAATTCCTTGTCGGGTAAGTTC |
| | CGACCTGCACGAATGGCGTAATGATGGCCAGGCTGTCTCCACCCGA |
| | GACTCAGTGAAATTGAACTCGCTGTGAAGATGCAGTGTACCCGCGG |
| | CAAGACGGTAAGACCCCGTGAACCTTTACTATAGCTTGACACTGAAC |
| | ATTGAGCCTTGATGTGTAGGATAGGTGGGAGGCTTTGAAGTGTGGA |
| | CGCCAGTCTGCATGGAGCCGACCTTGAAATACCACCCTTTAATGTTT |
| | GATGTTCTAACGTTGACCCGTAATCCGGGTTGCGGACAGTGTCTGG |
| | TGGGTAGTTTGACTGGGGCGGTCTCCTCCTAAAGAGTAACGGAGGA |
| | GCACGAAGGTTGGCTAATCCTGGTCGGACATCAGGAGGTTAGTGCA |
| | ATGGCATAAGCCAGCTTGACTGCGAGCGTGACGGCGCGAGCAGGT |
| | GCGAAAGCAGGTCATAGTGATCCGGTGGTTCTGAATGGAAGGGCCA |
| | TCGCTCAACGGATAAAAGGTACTCCGGGGATAACAGGCTGATACCG |
| | CCCAAGAGTTCATATCGACGGCGGTGTTTGGCACCTCGATGTCGGC |
| | TCATCACATCCTGGGGCTGAAGTAGGTCCCAAGGGTATGGCTGTTC |
| | GCCATTTAAAGTGGTACGCGAGCTGGGTTTAGAACGTCGTGAGACA |
| | GTTCGGTCCCTATCTGCCGTGGGCGCTGGAGAACTGAGGGGGGCT |
| | GCTCCTAGTACGAGAGGACCGGAGTGGACGCATCACTGGTGTTCG |
| | GGTTGTCATGCCAATGGCACTGCCCGGTAGCTAAATGCGGAAGAGA |
| | TAAGTGCTGAAAGCATCTAAGCACGAAACTTGCCCCGAGATGAGTT |
| | CTCCCTGACCCTTTAAGGGTCCTGAAGGAACGTTGAAGACGACGAC |
| | GTTGATAGGCCGGGTGTGTAAGCGCAGCGATGCGTTGAGCTAACC |
| | GGTACTAATGAACCGTGAGGCTTAACCTTACAACGCCGAAGCTGTTT |
| | TGGCGGATGAGAGAAGATTTTCAGCCTGATACAGATTAAATCAGAAC |
| | GCAGAAGCGGTCTGATAAAACAGAATTTGCCTGGCGGCAGTAGCGC |
| | GGTGGTCCCACCTGACCCCATGCCGAACTCAGAAGTGAAACGCCGT |
| | AGCGCCGATGGTAGTGTGGGGTCTCCCCATGCGAGAGTAGGGAAC |
| | TGCCAGGCATCAAATAAAACGAAAGGCTCAGTCGAAAGACTGGGCC |
| | TTTCGTTTTATCTGTTGTTTGTCGGTGAACGCTCTCCTGAGTAGGAC |
| | AAATCCGCCGGGAGCGGATTTGAACGTTGCGAAGCAACGGCCCGG |
| | AGGGTGGCGGGCAGGACGCCCGCCATAAACTGCCAGGCATCAAAT |
| | TAAGCAGAAGGCCATCCTGACGGATGGCCTTTTTGCGTTTCTACAAA |
| | CTCTTCCTGTCGTCATATCTACAAGCCGGCGCGCCAAATTGACAATT |
| | ACTCATCCGGCTCGAATAATGTGTGGAACTTAAACACACACAGGAG |
| | GAAAACATATGTCTATCCAGCACTTCCGTGTTGCGCTGATCCCGTTC |
| | TTCGCGGCGTTCTGCCTGCCGGTTTTCGCGCACCCGGAAACCCTG |
| | GTTAAAGTTAAAGACGCGGAAGACCAGCTGGGTGCGCGTGTTGGTT |
| | ACATCGAACTGGACCTGAACTCTGGTAAAATCCTGGAATCTTTCCGT |
| | CCGGAAGAACGTTTCCCGATGATGTCTACCTTCAAAGTTCTGCTGTG |
| | CGGTGCGGTTCTGTCTCGTGTTGACGCGGGTCAGGAACAGCTGGG |
| | TCGTCGTATCCACTACTCTCAGAACGACCTGGTTGAATACTCTCCCG |
| | TTACCGAAAAACACCTGACCGACGGTATGACCGTTCGTGAACTGTG |
| | CTCTGCGGCGATCACCATGTCTGACAACACCGCAGCGAACCTGCTG |
| | CTGACCACCATCGGTGGTCCGAAAGAACTGACCGCGTTCCTGCACA |
| | ACATGGGCGACCACGTTACCCGTCTGGACCGTTGGGAACCGGAAC |
| | TGAACGAAGCGATCCCGAACGACGAACGTGACACCACCATGCCTGC |
| | GGCGATGGCGACCACCCTGCGTAAACTGCTGACCGGTGAACTGCT |
| | GACCCTGGCATCTCGTCAGCAGCTGATCGACTGGATGGAAGCGGA |
| | CAAAGTTGCGGGTCCGCTGCTGCGTTCTGCGCTGCCTGCGGGTTG |
| | GTTCATCGCGGACAAATCTGGTCGGGTGAACGTGGTTCTCGTGGT |
| | ATCATCGCGGCGCTGGGTCCGGACGGTAAACCGTCTCGTATCGTTG |
| | TTATCTACACCACCGGTTCTCAGGCGACCATGGACGAACGTAACCG |
| | TCAGATCGCGGAAATCGGTGCGTCTCTGATTAAACACTGGTAAACTC |
| | ACTCCTAGCCCGCCTAATAAGCGGGCTTTTTTCTGCAGACCAAGTT |
| | TACTCATATATACTTTAGATTGATTTAAAACTTCATTTTTAATTTAAAA |
| | GGATCTAGGTGAAGATCCTTTTTGATAATCTCATGACCAAAATCCCT |
| | TAACGTGAGTTTTCGTTCCACTGAGCGTCAGACCCCGTAGAAAAGAT |
| | CAAAGGATCTTCTTGAGATCCTTTTTTTCTGCGCGTAATCTGCTGCTT |
| | GCAAACAAAAAAACCACCGCTACCAGCGGTGGTTTGTTTGCCGGAT |

TABLE 6-continued

Sequences used in this disclosure.

| Sequence Description [SEQ ID NO: __] | Nucleotide or Amino Acid Sequence |
|---|---|
| | CAAGAGCTACCAACTCTTTTTCCGAAGGTAACTGGCTTCAGCAGAG CGCAGATACCAAATACTGTCCTTCTAGTGTAGCCGTAGTTAGGCCAC CACTTCAAGAACTCTGTAGCACCGCCTACATACCTCGCTCTGCTAAT CCTGTTACCAGTGGCTGCTGCCAGTGGCGATAAGTCGTGTCTTACC GGGTTGGACTCAAGACGATAGTTACCGGATAAGGCGCAGCGGTCG GGCTGAACGGGGGGTTCGTGCACACAGCCCAGCTTGGAGCGAACG ACCTACACCGAACTGAGATACCTACAGCGTGAGCTATGAGAAAGCG CCACGCTTCCCGAAGGGAGAAAGGCGGACAGGTATCCGGTAAGCG GCAGGGTCGGAACAGGAGAGCGCACGAGGGAGCTTCCAGGGGGA AACGCCTGGTATCTTTATAGTCCTGTCGGGTTTCGCCACCTCTGACT TGAGCGTCGATTTTTGTGATGCTCGTCAGGGGGGCGGAGCCTATGG AAAAACGCCAGCAACGCGGCCTTTTTACGGTTCCTGGCCTTTTGCT GG |
| pT7rrnB-CR RNA [SEQ ID NO: 29] | GGGCCGCUGAGAAAAAGCGAAGCGGCACUGCUCUUUAACAAUUU AUCAGACAAUCUGUGUGGGCACUCGAAGAUACGGAUUCUUAACG UCGCAAGACGAAAAAUGAAUACCAAGUCUCAAGAGUGAACACGU AAUUCAUUACGAAGUUUAAUUCUUUGAGCGUCAAACUUUUAAAU UGAAGAGUUUGAUCAUGGCUCAGAUUGAACGCUGGCGGCAGGC CUAACACAUGCAAGUCGAACGGUAACAGGAAGAAGCUUGCUUCU UUGCUGACGAGUGGCGGACGGGUGAGUAAUGUCUGGGAAACUG CCUGAUGGAGGGGGAUAACUACUGGAAACGGUAGCUAAUACCGC AUAACGUCGCAAGACCAAAGAGGGGGACCUUCGGGCCUCUUGC CAUCGGAUGUGCCCAGAUGGGAUUAGCUAGUAGGUGGGGUAAC GGCUCACCUAGGCGACGAUCCCUAGCUGGUCUGAGAGGAUGAC CAGCCACACUGGAACUGAGACACGGUCCAGACUCCUACGGGAGG CAGCAGUGGGGAAUAUUGCACAAUGGGCGCAAGCCUGAUGCAG CCAUGCCGCGUGUAUGAAGAAGGCCUUCGGGUUGUAAAGUACU UUCAGCGGGGAGGAAGGGAGUAAAGUUAAUACCUUUGCUCAUU GACGUUACCCGCAGAAGAAGCACCGGCUAACUCCGUGCCAGCAG CCGCGGUAAUACGGAGGGUGCAAGCGUUAAUCGGAAUUACUGG GCGUAAAGCGCACGCAGGCGGUUUGUUAAGUCAGAUGUGAAAU CCCCGGGCUCAACCUGGGAACUGCAUCUGAUACUGGCAAGCUU GAGUCUCGUAGAGGGGGGUAGAAUUCCAGGUGUAGCGGUGAAA UGCGUAGAGAUCUGGAGGAAUACCGGUGGCGAAGGCGGCCCCC UGGACGAAGACUGACGCUCAGGUGCGAAAGCGUGGGGAGCAAA CAGGAUUAGAUACCCUGGUAGUCCACGCCGUAAACGAUGUCGAC UUGGAGGUUGUGCCCUUGAGGCGUGGCUUCCGGAGCUAACGCG UUAAGUCGACCGCCUGGGGAGUACGGCCGCAAGGUUAAAACUCA AAUGAAUUGACGGGGGCCCGCACAAGCGGUGGAGCAUGUGGUU AAUUCGAUGCAACGCGAAGAACCUUACCUGGUCUUGACAUCCA CGGAAGUUUUCAGAGAUGAGAAUGUGCCUUCGGGAACCGUGAG ACAGGUGCUGCAUGGCUGUCGUCAGCUCGUGUUGUGAAAUGUU GGGUUAAGUCCCGCAACGAGCGCAACCCUUAUCCUUUGUUGCCA GCGGUCCGGCCGGGAACUCAAAGGAGACUGCCAGUGAUAAACU GGAGGAAGGUGGGGAUGACGUCAAGUCAUCAUGGCCCUUACGA CCAGGGCUACACACGUGCUACAAUGGCGCAUACAAAGAGAAGCG ACCUCGCGAGAGCAAGCGGACCUCAUAAAGUGCGUCGUAGUCC GGAUUGGAGUCUGCAACUCGACUCCAUGAAGUCGGAAUCGCUA GUAAUCGUGGAUCAGAAUGCCACGGUGAAUACGUUCCCGGGCC UUGUACACACCGCCCGUCACACCAUGGGAGUGGGUUGCAAAAGA AGUAGGUAGCUUAACCUUCGGGAGGGCGCUUACCACUUUGUGA UUCAUGACUGGGGUGAAGUCGUAACAAGGUAACCGUAGGGGAA CCUGCGGUUGGAUCACCUCCUUACCUUAAAGAAGCGUACUUUGU AGUGCUCACACAGAUUGUCUGAUAGAAAGUGAAAAGCAAGGCGU UUACGCGUUGGGAGUGAGGCUGAAGAGAAUAAGGCCGUUCGCU UUCUAUUAAUGAAAGCUCACCCUACACGAAAAUAUCACGCAACGC GUGAUAAGCAAUUUUCGUGUCCCCUUCGUCUAGAGGCCCAGGA CACCGCCCUUUCACGGCGGUAACAGGGGUUCGAAUCCCCUAGG GGACGCCACUUGCUGGUUUGUGAGUGAAAGUCGCCGACCUUAA UAUCUCAAAACUCAUCUUCGGGUGAUGUUUGAGAUAUUUGCUCU UUAAAAAUCUGGAUCAAGCUGAAAAUUGAAACACUGAACAACGAG AGUUGUUCGUGAGUCUCUCAAAUUUUCGCAACACGAUGAUGAAU CGAAAGAAACAUCUUCGGGUUGUGAGGUUAAGCGACUAAGCGUA CACGGUGGAUGCCCUGGCAGUCAGAGGCGAUGAAGGACGUGCU AAUCUGCGAUAAGCGUCGGUAAGGUGAUAUGAACCGUUAUAACC GGCGAUUUCCGAAUGGGGAAACCCAGUGUGUUUCGACACACUAU CAUUAACUGAAUCCAUAGGUUAAUGAGGCGAACCGGGGGAACUG AAACAUCUAAGUACCCCGAGGAAAAGAAAUCAACCGAGAUUCCC CAGUAGCGGCGAGCGAACGGGGAGCAGCCCAGAGCCUGAAUCA GUGUGUGUGUUAGUGGAAGCGUCUGGAAAGGCGCGCGAUACAG GGUGACAGCCCCGUACACAAAAAUGCACAUGCUGUGAGCUCGAU GAGUAGGGCGGGACACGUGGUAUCCUGUCUGAAUAUGGGGGGA CCAUCCUCCAAGGCUAAAUACUCCUGACUGACCGAUAGUGAACC |

TABLE 6-continued

Sequences used in this disclosure.

| Sequence Description [SEQ ID NO: __] | Nucleotide or Amino Acid Sequence |
|---|---|
| | AGUACCGUGAGGGAAAGGCGAAAAGAACCCCGGCGAGGGGAGU
GAAAAAGAACCUGAAACCGUGUACGUACAAGCAGUGGGAGCACG
CUUAGGCGUGUGACUGCGUACCUUUUGUAUAAUGGGUCAGCGA
CUUAUAUUCUGUAGCAAGGUUAACCGAAUAGGGGAGCCGAAGGG
AAACCGAGUCUUAACUGGGCGUUAAGUUGCAGGGUAUAGACCCG
AAACCCGGUGAUCUAGCCAUGGGCAGGUUGAAGGUUGGGUAAC
ACUAACUGGAGGACCGAACCGACUAAUGUUGAAAAAUUAGCGGA
UGACUUGUGGCUGGGGGUGAAAGGCCAAUCAAACCGGGAGAUA
GCUGGUUCUCCCCGAAAGCUAUUUAGGUAGCGCCUCGUGAAUU
CAUCUCCGGGGUAGAGCACUGUUUCGGCAAGGGGGUCAUCCC
GACUUACCAACCCGAUGCAAACUGCGAAUACCGGAGAAUGUUAU
CACGGGAGACACACGGCGGGUGCUAACGUCCGUCGUGAAGAGG
GAAACAACCCAGACCGCCAGCUAAGGUCCCAAAGUCAUGGUUAA
GUGGGAAACGAUGUGGGAAGGCCCAGACAGCCAGGAUGUUGGC
UUAGAAGCAGCCAUCAUUUAAAGAAAGCGUAAUAGCUCACUGGU
CGAGUCGGCCUGCGCGGAAGAUGUAACGGGGCUAAACCAUGCA
CCGAAGCUGCGGCAGCGACGCUUAUGCGUUGUUGGGUAGGGGA
GCGUUCUGUAAGCCUGCGAAGGUGUGCUGUGAGGCAUGCUGGA
GGUAUCAGAAGUGCGAAUGCUGACAUAAGUAACGAUAAAGCGGG
UGAAAAGCCCGCUCGCCGGAAGACCAAGGGUUCCUGUCCAACGU
UAAUCGGGGCAGGGUGAGUCGACCCCUAAGGCGAGGCCGAAAG
GCGUAGUCGAUGGGAAACAGGUUAAUAUUCCUGUACUUGGUGU
UACUGCGAAGGGGGGACGGAGAAGGCUAUGUUGGCCGGGCGAC
GGUUGUCCCGGUUUAAGCGUGUAGGCUGGUUUUCCAGGCAAAU
CCGGAAAAUCAAGGCUGAGGCGUGAUGACGAGGCACUACGGUG
CUGAAGCAACAAAUGCCCUGCUUCCAGGAAAAGCCUCUAAGCAU
CAGGUAACAUCAAAUCGUACCCCAAACCGACACAGGUGGUCAGG
UAGAGAAUACCAAGGCGCUUGAGAGAACUCGGGUGAAGGAACUA
GGCAAAAUGGUGCCGUAACUUCGGGAGAAGGCACGCUGAUAUG
UAGGUGAGGUCCCUCGCGGAUGGAGCUGAAAUCAGUCGAAGAU
ACCAGCUGGCUGCAACUGUUUAUUAAAAACACAGCACUGUGCAA
ACACGAAAGUGGACGUAUACGUGUGACGCCUGCCCGGUGCCG
GAAGGUUAAUUGAUGGGGUUAGCGCAAGCGAAGCUCUUGAUCG
AAGCCCCGGUAAACGGCGGCCGUAACUAUAACGGUCCUAAGGUA
GCGAAAUUCCUUGUCGGGUAAGUUCCGACCUGCACGAAUGGCG
UAAUGAUGGCCAGGCUGUCUCCACCCGAGACUCAGUGAAAUGA
ACUCGCUGUGAAGAUGCAGUGUACCCGCGGCAAGACGGUAAGA
CCCCGUGAACCUUUACUAUAGCUUGACACUGAACAUUGAGCCUU
GAUGUGUAGGAUAGGUGGGAGGCUUUGAAGUGUGGACGCCAGU
CUGCAUGGAGCCGACCUUGAAAUACCACCCUUUAAUGUUUGAUG
UUCUAACGUUGACCCGUAAUCCGGGUUGCGGACAGUGUCUGGU
GGGUAGUUUGACUGGGGCGGUCUCCUCCUAAAGAGUAACGGAG
GAGCACGAAGGUUGGCUAAUCCUGGUCGGACAUCAGGAGGUUA
GUGCAAUGGCAUAAGCCAGCUUGACUGCGAGCGUGACGGCGCG
AGCAGGUGCGAAAGCAGGUCAUAGUGAUCCGGUGGUUCUGAAU
GGAAGGGCCAUCGCUCAACGGAUAAAAGGUACUCCGGGGAUAAC
AGGCUGAUACCGCCCAAGAGUUCAUAUCGACGGCGGUGUUUGG
CACCUCGAUGUCGGCUCAUCACAUCCUGGGGCUGAAGUAGGUC
CCAAGGGUAUGGCUGUUCGCCAUUUAAAGUGGUACGCGAGCUG
GGUUUAGAACGUCGUGAGACAGUUCGGUCCCUAUCUGCCGUGG
GCGCUGGAGAACUGAGGGGGGCUGCUCCUAGUACGAGAGGACC
GGAGUGGACGCAUCACUGGUGUUCGGGUUGUCAUGCCAAUGGC
ACUGCCCGUAGCUAAAUGCGGAAGAGAUAAGUGCUGAAAGCAU
CUAAGCACGAAACUUGCCCCGAGAUGAGUUCUCCCUGACCCUUU
AAGGGUCCUGAAGGAACGUUGAAGACGACGACGUUGAUAGGCC
GGGUGUGUAAGCGCAGCGAUGCGUUGAGCUAACCGGUACUAAU
GAACCGUGAGGCUUAACCUUACAACGCCGAAGCUGUUUUGGCG
GAUGAGAGAAGAUUUUCAGCCUGAUACAGAUUAAAUCAGAACGC
AGAAGCGGUCUGAUAAAACAGAAUUUGCCUGGCGGCAGUAGCGC
GGUGGUCCCACCUGACCCCAUGCCGAACUCAGAAGUGAAACGCC
GUAGCGCCGAUGGUAGUGUGGGGUCUCCCCAUGCGAGAGUAGG
GAACUGCCAGGCAUCAAAUAAAACGAAAGGCUCAGUCGAAAGAC
UGGGCCUUUCGUUUUAUCUGUUGUUUGUCGGUGAACGCUCUCC
UGAGUAGGACAAAUCCGCCGGGAGCGGAUUUGAACGUUGCGAA
GCAACGCCCGAGGGUGGCGGGCAGGACGCCCGCCAUAAACU
GCCAGGCAUCAAAUUAAGCAGAAGGCCAUCCUGACGGAUGGCCU
UUUUG |
| pT7rrnB-NF DNA [SEQ ID NO: 30] | TTAATACGACTCACTATAGGGGCCGCTGAGAAAAAGCGAAGCGGCA
CTGCTCTTTAACAATTTATCAGACAATCTGTGTGGGCACTCGAAGAT
ACGGATTCTTAACGTCGCAAGACGAAAATGAATACCAAGTCTCAAG
AGTGAACACGTAATTCATTACGAAGTTTAATTCTTTGAGCGTCAAACT
TTTAAATTGAAGAGTTTGATCATGGCTCAGATTGAACGCTGGCGGCA
GGCCTAACACATGCAAGTCGAACGGTAACAGGAAGAAGCTTGCTTC |

TABLE 6-continued

Sequences used in this disclosure.

| Sequence Description [SEQ ID NO: __] | Nucleotide or Amino Acid Sequence |
|---|---|
| | TTTGCTGACGAGTGGCGGACGGGTGAGTAATGTCTGGGAAACTGCC
TGATGGAGGGGGATAACTACTGGAAACGGTAGCTAATACCGCATAA
CGTCGCAAGACCAAAGAGGGGGACCTTCGGGCCTCTTGCCATCGG
ATGTGCCCAGATGGGATTAGCTAGTAGGTGGGGTAACGGCTCACCT
AGGCGACGATCCCTAGCTGGTCTGAGAGGATGACCAGCCACACTG
GAACTGAGACACGGTCCAGACTCCTACGGGAGGCAGCAGTGGGGA
ATATTGCACAATGGGCGCAAGCCTGATGCAGCCATGCCGCGTGTAT
GAAGAAGGCCTTCGGGTTGTAAAGTACTTTCAGCGGGGAGGAAGG
GAGTAAAGTTAATACCTTTGCTCATTGACGTTACCCGCAGAAGAAGC
ACCGGCTAACTCCGTGCCAGCAGCCGCGGTAATACGGAGGGTGCA
AGCGTTAATCGGAATTACTGGGCGTAAAGCGCACGCAGGCGGTTTG
TTAAGTCAGATGTGAAATCCCCGGGCTCAACCTGGGAACTGCATCT
GATACTGGCAAGCTTGAGTCTCGTAGAGGGGGGTAGAATTCCAGGT
GTAGCGGTGAAATGCGTAGAGATCTGGAGGAATACCGGTGGCGAA
GGCGGCCCCCTGGACGAAGACTGACGCTCAGGTGCGAAAGCGTGG
GGAGCAAACAGGATTAGATACCCTGGTAGTCCACGCCGTAAACGAT
GTCGACTTGGAGGTTGTGCCCTTGAGGCGTGGCTTCCGGAGCTAAC
GCGTTAAGTCGACCGCCTGGGGAGTACGGCCGCAAGGTTAAAACT
CAAATGAATTGACGGGGGCCCGCACAAGCGGTGGAGCATGTGGTT
TAATTCGATGCAACGCGAAGAACCTTACCTGGTCTTGACATCCACG
GAAGTTTTCAGAGATGAGAATGTGCCTTCGGGAACCGTGAGACAGG
TGCTGCATGGCTGTCGTCAGCTCGTGTTGTGAAATGTTGGGTTAAG
TCCCGCAACGAGCGCAACCCTTATCCTTTGTTGCCAGCGGTCCGGC
CGGGAACTCAAAGGAGACTGCCAGTGATAAACTGGAGGAAGGTGG
GGATGACGTCAAGTCATCATGGCCCTTACGACCAGGGCTACACACG
TGCTACAATGGCGCATACAAAGAGAAGCGACCTCGCGAGAGCAAGC
GGACCTCATAAAGTGCGTCGTAGTCCGGATTGGAGTCTGCAACTCG
ACTCCATGAAGTCGGAATCGCTAGTAATCGTGGATCAGAATGCCAC
GGTGAATACGTTCCCGGGCCTTGTACACACCGCCCGTCACACCATG
GGAGTGGGTTGCAAAAGAAGTAGGTAGCTTAACCTTCGGGAGGGC
GCTTACCACTTTGTGATTCATGACTGGGGTGAAGTCGTAACAAGGTA
ACCGTAGGGGAACCTGCGGTTGGATCACCTCCTTACCTTAAAGAAG
CGTACTTTGTAGTGCTCACACAGATTGTCTGATAGAAAGTGAAAAGC
AAGGCGTTTACGCGTTGGGAGTGAGGCTGAAGAGAATAAGGCCGTT
CGCTTTCTATTAATGAAAGCTCACCCTACACGAAAATATCACGCAAC
GCGTGATAAGCAATTTTCGTGTCCCCTTCGTCTAGAGGCCCAGGAC
ACCGCCCTTTCACGGCGGTAACAGGGGTTCGAATCCCCTAGGGGA
CGCCACTTGCTGGTTTGTGAGTGAAAGTCGCCGACCTTAATATCTCA
AAACTCATCTTCGGGTGATGTTTGAGATATTTGCTCTTTAAAAATCTG
GATCAAGCTGAAAATTGAAACACTGAACAACGAGAGTTGTTCGTGAG
TCTCTCAAATTTTCGCAACACGATGATGAATCGAAAGAAACATCTTC
GGGTTGTGAGGTTAAGCGACTAAGCGTACACGGTGGATGCCCTGG
CAGTCAGAGGCGATGAAGGACGTGCTAATCTGCGATAAGCGTCGGT
AAGGTGATATGAACCGTTATAACCGGCGATTTCGAATGGGGAAAC
CCAGTGTGTTTCGACACACTATCATTAACTGAATCCATAGGTTAATG
AGGCGAACCGGGGGAACTGAAACATCTAAGTACCCCGAGGAAAAG
AAATCAACCGAGATTCCCCCAGTAGCGGCGAGCGAACGGGGAGCA
GCCCAGAGCCTGAATCAGTGTGTGTGTTAGTGGAAGCGTCTGGAAA
GGCGCGCGATACAGGGTGACAGCCCCGTACACAAAAATGCACATG
CTGTGAGCTCGATGAGTAGGGCGGGACACGTGGTATCCTGTCTGAA
TATGGGGGACCATCCTCCAAGGCTAAATACTCCTGACTGACCGAT
AGTGAACCAGTACCGTGAGGGAAAGGCGAAAAGAACCCCGGCGAG
GGGAGTGAAAAAGAACCTGAAACCGTGTACGTACAAGCAGTGGGAG
CACGCTTAGGCGTGTGACTGCGTACCTTTTGTATAATGGGTCAGCG
ACTTATATTCTGTAGCAAGGTTAACCGAATAGGGGAGCCGAAGGGA
AACCGAGTCTTAACTGGGCGTTAAGTTGCAGGGTATAGACCCGAAA
CCCGGTGATCTAGCCATGGGCAGGTTGAAGGTTGGGTAACACTAAC
TGGAGGACCGAACCGADTAATGTTGAAAAATTAGCGGATGACTTGT
GGCTGGGGTGAAAGGCCAATCAAACCGGGAGATAGCTGGTTCTC
CCCGAAAGCTATTTAGGTAGCGCCTCGTGAATTCATCTCCGGGGGT
AGAGCACTGTTTCGGCAAGGGGGTCATCCCGACTTACCAACCCGAT
GCAAACTGCGAATACCGGAGAATGTTATCACGGGAGACACACGGCG
GGTGCTAACGTCCTCGTGAAGAGGGAAACAACCCAGACCGCCAG
CTAAGGTCCCAAAGTCATGGTTAAGTGGGAAACGATGTGGGAAGGC
CCAGACAGCCAGGATGTTGGCTTAGAAGCAGCCATCATTTAAAGAA
AGCGTAATAGCTCACTGGTCGAGTCGGCCTGCGCGGAAGATGTAAC
GGGGCTAAACCATGCACCGAAGCTGCGGCAGCGACGCTTATGCGT
TGTTGGGTAGGGGAGCGTTCTGTAAGCCTGCGAAGGTGTGCTGTGA
GGCATGCTGGAGGTATCAGAAGTGCGAATGCTGACATAAGTAACGA
TAAAGCGGGTGAAAAGCCCGCTCGCCGGAAGACCAAGGGTTCCTG
TCCAACGTTAATCGGGCAGGGTGAGTCGACCCCTAAGGCGAGGC
CGAAAGGCGTAGTCGATGGGAAACAGGTTAATATTCCTGTACTTGG
TGTTACTGCGAAGGGGGACGGAGAAGGCTATGTTGGCCGGGCGA
CGGTTGTCCCGGTTTAAGCGTGTAGGCTGGTTTTCCAGGCAAATCC |

TABLE 6-continued

Sequences used in this disclosure.

| Sequence Description [SEQ ID NO: __] | Nucleotide or Amino Acid Sequence |
|---|---|
| | GGAAAATCAAGGCTGAGGCGTGATGACGAGGCACTACGGTGCTGA
AGCAACAAATGCCCTGCTTCCAGGAAAAGCCTCTAAGCATCAGGTA
ACATCAAATCGTACCCCAAACCGACACAGGTGGTCAGGTAGAGAAT
ACCAAGGCGCTTGAGAGAACTCGGGTGAAGGAACTAGGCAAAATG
GTGCCGTAACTTCGGGAGAAGGCACGCTGATATGTAGGTGAGGTCC
CTCGCGGATGGAGCTGAAATCAGTCGAAGATACCAGCTGGCTGCAA
CTGTTTATTAAAAACACAGCACTGTGCAAACACGAAAGTGGACGTAT
ACGGTGTGACGCCTGCCCGGTGCCGGAAGGTTAATTGATGGGGTT
AGCGCAAGCGAAGCTCTTGATCGAAGCCCCGGTAAACGGCGGCCG
TAACTATAACGGTCCTAAGGTAGCGAAATTCCTTGTCGGGTAAGTTC
CGACCTGCACGAATGGCGTAATGATGGCCAGGCTGTCTCCACCCGA
GACTCAGTGAAATTGAACTCGCTGTGAAGATGCAGTGTACCCGCGG
CAAGACGGAAAGACCCCGTGAACCTTTACTATAGCTTGACACTGAA
CATTGAGCCTTGATGTGTAGGATAGGTGGGAGGCTTTGAAGTGTGG
ACGCCAGTCTGCATGGAGCCGACCTTGAAATACCACCCTTTAATGTT
TGATGTTCTAACGTTGACCCGTAATCCGGGTTGCGGACAGTGTCTG
GTGGGTAGTTTGACTGGGGCGGTCTCCTCCTAAAGAGTAACGGAGG
AGCACGAAGGTTGGCTAATCCTGGTCGGACATCAGGAGGTTAGTGC
AATGGCATAAGCCAGCTTGACTGCGAGCGTGACGGCGCGAGCAGG
TGCGAAAGCAGGTCATAGTGATCCGGTGGTTCTGAATGGAAGGGCC
ATCGCTCAACGGATAAAAGGTACTCCGGGGATAACAGGCTGATACC
GCCCAAGAGTTCATATCGACGGCGGTGTTTGGCACCTCGATGTCGG
CTCATCACATCCTGGGGCTGAAGTAGGTCCCAAGGGTATGGCTGTT
CGCCATTTAAAGTGGTACGCGAGCTGGGTCTAGAACGTCGTGAGAC
AGTTCGGTCCCTATCTGCCGTGGGCGCTGGAGAACTGAGGGGGGC
TGCTCCTAGTACGAGAGGACCGGAGTGGACGCATCACTGGTGTTCG
GGTTGTCATGCCAATGGCACTGCCCGGTAGCTAAATGCGGAAGAGA
TAAGTGCTGAAAGCATCTAAGCACGAAACTTGCCCCGAGATGAGTT
CTCCCTGACCCTTTAAGGGTCCTGAAGGAACGTTGAAGACGACGAC
GTTGATAGGCCGGGTGTGTAAGCGCAGCGATGCGTTGAGCTAACC
GGTACTAATGAACCGTGAGGCTTAACCTTACAACGCCGAAGCTGTTT
TGGCGGATGAGAGAAGATTTTCAGCCTGATACAGATTAAATCAGAAC
GCAGAAGCGGTCTGATAAAACAGAATTTGCCTGGCGGCAGTAGCGC
GGTGGTCCCACCTGACCCCATGCCGAACTCAGAAGTGAAACGCCGT
AGCGCCGATGGTAGTGTGGGGTCTCCCCATGCGAGAGTAGGGAAC
TGCCAGGCATCAAATAAAACGAAAGGCTCAGTCGAAAGACTGGGCC
TTTCGTTTTATCTGTTGTTTGTCGGTGAACGCTCTCCTGAGTAGGAC
AAATCCGCCGGGAGCGGATTTGAACGTTGCGAAGCAACGGCCCGG
AGGGTGGCGGGCAGGACGCCCGCCATAAACTGCCAGGCATCAAAT
TAAGCAGAAGGCCATCCTGACGGATGGCCTTTTTGCGTTTCTACAAA
CTCTTCCTGTCGTCATATCTACAAGCCGGCGCGCCAAATTGACAATT
ACTCATCCGGCTCGAATAATGTGTGGAACTTAAACACACACAGGAG
GAAAACATATGTCTATCCAGCACTTCCGTGTTGCGCTGATCCCGTTC
TTCGCGGCGTTCTGCCTGCCGGTTTTCGCGCACCCGGAAACCCTG
GTTAAAGTTAAAGACGCGGAAGACCAGCTGGGTGCGCGTGTTGGTT
ACATCGAACTGGACCTGAACTCTGGTAAAATCCTGGAATCTTTCCGT
CCGGAAGAACGTTTCCCGATGATGTCTACCTTCAAAGTTCTGCTGTG
CGGTGCGGTTCTGTCTCGTGTTGACGCGGGTCAGGAACAGCTGGG
TCGTCGTATCCACTACTCTCAGAACGACCTGGTTGAATACTCTCCCG
TTACCGAAAAACACCTGACCGACGGTATGACCGTTCGTGAACTGTG
CTCTGCGGCGATCACCATGTCTGACAACACCGCAGCGAACCTGCTG
CTGACCACCATCGGTGGTCCGAAAGAACTGACCGCGTTCCTGCACA
ACATGGGCGACCACGTTACCCGTCTGGACCGTTGGGAACCGGAAC
TGAACGAAGCGATCCCGAACGACGAACGTGACACCACCATGCCTGC
GGCGATGGCGACCACCCTGCGTAAACTGCTGACCGGTGAACTGCT
GACCCTGGCATCTCGTCAGCAGCTGATCGACTGGATGGAAGCGGA
CAAAGTTGCGGGTCCGCTGCTGCGTTCTGCGCTGCCTGCGGGTTG
GTTCATCGCGGACAAATCTGGTGCGGGTGAACGTGGTTCTCGTGGT
ATCATCGCGGCGCTGGGTCCGGACGGTAAACCGTCTCGTATCGTTG
TTATCTACACCACCGGTTCTCAGGCGACCATGGACGAACGTAACCG
TCAGATCGCGGAAATCGGTGCGTCTCTGATTAAACACTGGTAAACTC
ACTCCTAGCCCGCCTAATAAGCGGGCTTTTTTCTGCAGACCAAGTT
TACTCATATATACTTTAGATTGATTTAAAACTTCATTTTTAATTTAAAA
GGATCTAGGTGAAGATCCTTTTTGATAATCTCATGACCAAAATCCCT
TAACGTGAGTTTTCGTTCCACTGAGCGTCAGACCCCGTAGAAAAGAT
CAAAGGATCTTCTTGAGATCCTTTTTTTCTGCGCGTAATCTGCTGCTT
GCAAACAAAAAAACCACCGCTACCAGCGGTGGTTTGTTTGCCGGAT
CAAGAGCTACCAACTCTTTTTCCGAAGGTAACTGGCTTCAGCAGAG
CGCAGATACCAAATACTGTCCTTCTAGTGTAGCCGTAGTTAGGCCAC
CACTTCAAGAACTCTGTAGCACCGCCTACATACCTCGCTCTGCTAAT
CCTGTTACCAGTGGCTGCTGCCAGTGGCGATAAGTCGTGTCTTACC
GGGTTGGACTCAAGACGATAGTTACCGGATAAGGCGCAGCGGTCG
GGCTGAACGGGGGGTTCGTGCACACAGCCCAGCTTGGAGCGAACG
ACCTACACCGAACTGAGATACCTACAGCGTGAGCTATGAGAAAGCG |

TABLE 6-continued

Sequences used in this disclosure.

| Sequence Description [SEQ ID NO: __] | Nucleotide or Amino Acid Sequence |
|---|---|
| | CCACGCTTCCCGAAGGGAGAAAGGCGGACAGGTATCCGGTAAGCG GCAGGGTCGGAACAGGAGAGCGCACGAGGGAGCTTCCAGGGGGA AACGCCTGGTATCTTTATAGTCCTGTCGGGTTTCGCCACCTCTGACT TGAGCGTCGATTTTTGTGATGCTCGTCAGGGGGGCGGAGCCTATGG AAAAACGCCAGCAACGCGGCCTTTTTACGGTTCCTGGCCTTTTGCT GG |
| pT7rrnB-NF RNA [SEQ ID NO: 31] | GGGGCCGCUGAGAAAAAGCGAAGCGGCACUGCUCUUUAACAAUUU AUCAGACAAUCUGUGUGGGCACUCGAAGAUACGGAUUCUUAACGU CGCAAGACGAAAAAUGAAUACCAAGUCUCAAGAGUGAACACGUAA UUCAUUACGAAGUUUAAUUCUUUGAGCGUCAAACUUUUAAAUUGA AGAGUUUGAUCAUGGCUCAGAUUGAACGCUGGCGGCAGGCCUAA CACAUGCAAGUCGAACGGUAACAGGAAGAAGCUUGCUUCUUUGCU GACGAGUGGCGGACGGGUGAGUAAUGUCUGGGAAACUGCCUGAU GGAGGGGGAUAACUACUGGAAACGGUAGCUAAUACCGCAUAACGU CGCAAGACCAAAGAGGGGGACCUUCGGGCCUCUUGCCAUCGGAU GUGCCCAGAUGGGAUUAGCUAGUAGGUGGGGUAACGGCUCACCU AGGCGACGAUCCCUAGCUGGUCUGAGAGGAUGACCAGCCACACU GGAACUGAGACACGGUCCAGACUCCUACGGGAGGCAGCAGUGGG GAAUAUUGCACAAUGGGCGCAAGCCUGAUGCAGCCAUGCCGCGU GUAUGAAGAAGGCCUUCGGGUUGUAAAGUACUUUCAGCGGGGAG GAAGGGAGUAAAGUUAAUACCUUUGCUCAUUGACGUUACCCGCAG AAGAAGCACCGGCUAACUCCGUGCCAGCAGCCGCGGUAAUACGGA GGGUGCAAGCGUUAAUCGGAAUUACUGGGCGUAAAGCGCACGCA GGCGGUUUGUUAAGUCAGAUGUGAAAUCCCCGGGCUCAACCUGG GAACUGCAUCUGAUACUGGCAAGCUUGAGUCUCGUAGAGGGGGG UAGAAUUCCAGGUGUAGCGGUGAAAUGCGUAGAGAUCUGGAGGA AUACCGGUGGCGAAGGCGGCCCCCUGGACGAAGACUGACGCUCA GGUGCGAAAGCGUGGGGAGCAAACAGGAUUAGAUACCCUGGUAG UCCACGCCGUAAACGAUGUCGACUUGGAGGUUGUGCCCUUGAGG CGUGGCUUCCGGAGCUAACGCGUUAAGUCGACCGCCUGGGGAGU ACGGCCGCAAGGUUAAAACUCAAAUGAAUUGACGGGGCCCGCAC AAGCGGUGGAGCAUGUGGUUUAAUUCGAUGCAACGCGAAGAACC UUACCUGGUCUUGACAUCCACGGAAGUUUUCAGAGAUGAGAAUGU GCCUUCGGGAACCGUGAGACAGGUGCUGCAUGGCUGUCGUCAGC UCGUGUUGUGAAAUGUUGGGUUAAGUCCCGCAACGAGCGCAACC CUUAUCCUUUGUUGCCAGCGGUCCGGCCGGGAACUCAAAGGAGA CUGCCAGUGAUAAACUGGAGGAAGGUGGGGAUGACGUCAAGUCA UCAUGGCCCUUACGACCAGGGCUACACACGUGCUACAAUGGCGCA UACAAAGAGAAGCGACCUCGCGAGAGCAAGCGGACCUCAUAAAGU GCGUCGUAGUCCGGAUUGGAGUCUGCAACUCGACUCCAUGAAGU CGGAAUCGCUAGUAAUCGUGGAUCAGAAUGCCACGGUGAAUACGU UCCCGGGCCUUGUACACACCGCCCGUCACACCAUGGGAGUGGGU UGCAAAAGAAGUAGGUAGCUUAACCUUCGGGAGGGCGCUUACCAC UUUGUGAUUCAUGACUGGGGUGAAGUCGUAACAAGGUAACCGUA GGGGAACCUGCGGUUGGAUCACCUCCUUACCUUAAAGAAGCGUA CUUUGUAGUGCUCACACAGAUUGUCUGAUAGAAAGUGAAAAGCAA GGCGUUUACGCGUUGGGAGUGAGGCUGAAGAGAAUAAGGCCGUU CGCUUUCUAUUAAUGAAAGCUCACCCUACACGAAAAUAUCACGCA ACGCGUGAUAAGCAAUUUUCGUGUCCCCUUCGUCUAGAGGCCCA GGACACCGCCCUUUCACGGCGGUAACAGGGGUUCGAAUCCCCUA GGGGACGCCACUUGCUGGUUUGUGAGUGAAAGUCGCCGACCUUA AUAUCUCAAAACUCAUCUUCGGGUGAUGUUUGAGAUAUUUGCUCU UUAAAAAUCUGGAUCAGCUGAAAAUUGAAACACUGAACAACGAGA GUUGUUCGUGAGUCUCUCAAAUUUUCGCAACACGAUGAUGAAUCG AAAGAAACAUCUUCGGUUGUGAGGUUAAGCGACUAAGCGUACAC GGUGGAUGCCCUGGCAGUCAGAGGCGAUGAAGGACGUGCUAAUC UGCGAUAAGCGUCGGUAAGGUGAUAUGAACCGUUAUAACCGGCG AUUUCCGAAUGGGGAAACCCAGUGUGUUUCGACACACUAUCAUUA ACUGAAUCCAUAGGUUAAUGAGGCGAACCGGGGAACUGAAACAU CUAAGUACCCCGAGGAAAAGAAAUCAACCGAGAUUCCCCCAGUAG CGGCGAGCGAACGGGGAGCAGCCCAGAGCCUGAAUCAGUGUGUG UGUUAGUGGAAGCGUCUGGAAAGGCGCGCGAUACAGGGUGACAG CCCCGUACACAAAAAUGCACAUGCUGUGAGCUCGAUGAGUAGGGC GGGACACGUGGUAUCCUGUCUGAAUAUGGGGGGACCAUCCUCCA AGGCUAAAUACUCCUGACUGACCGAUAGUGAACCAGUACCGUGAG GGAAAGGCGAAAAGAACCCCGGCGAGGGGAGUGAAAAAGAACCUG AAACCGUGUACGUACAAGCAGUGGGAGCACGCUUAGGCGUGUGA CUGCGUACCUUUUGUAUAAUGGGUCAGCGACUUAUAUUCUGUAG CAAGGUUAACCGAAUAGGGGAGCCGAAGGGAAACCGAGUCUUAAC UGGGCGUUAAGUUGCAGGGUAUAGACCCGAAACCCGGUGAUCUA GCCAUGGGCAGGUUGAAGGUUGGGUAACACUAACUGGAGGACCG AACCGACUAAUGUUGAAAAAUUAGCGGAUGACUUGUGGCUGGGG GUGAAAGGCCAAUCAAACCGGGAGAUAGCUGGUUCUCCCCGAAAG |

TABLE 6-continued

Sequences used in this disclosure.

| Sequence Description [SEQ ID NO: __] | Nucleotide or Amino Acid Sequence |
|---|---|
| | CUAUUUAGGUAGCGCCUCGUGAAUUCAUCUCCGGGGGUAGAGCA |
| | CUGUUUCGGCAAGGGGGUCAUCCCGACUUACCAACCCGAUGCAAA |
| | CUGCGAAUACCGGAGAAUGUUAUCACGGGAGACACACGGCGGGU |
| | GCUAACGUCCGUCGUGAAGAGGGAAACAACCCAGACCGCCAGCUA |
| | AGGUCCCAAAGUCAUGGUUAAGUGGGAAACGAUGUGGGAAGGCC |
| | CAGACAGCCAGGAUGUUGGCUUAGAAGCAGCCAUCAUUUAAAGAA |
| | AGCGUAAUAGCUCACUGGUCGAGUCGGCCUGCGCGGAAGAUGUA |
| | ACGGGGCUAAACCAUGCACCGAAGCUGCGGCAGCGACGCUUAUG |
| | CGUUGUUGGGUAGGGGAGCGUUCUGUAAGCCUGCGAAGGUGUG |
| | CUGUGAGGCAUGCUGGAGGUAUCAGAAGUGCGAAUGCUGACAUA |
| | AGUAACGAUAAAGCGGGUGAAAAGCCCGCUCGCCGGAAGACCAAG |
| | GGUUCCUGUCCAACGUUAAUCGGGGCAGGGUGAGUCGACCCCUA |
| | AGGCGAGGCCGAAAGGCGUAGUCGAUGGGAAACAGGUUAAUAUU |
| | CCUGUACUUGGUGUUACUGCGAAGGGGGGACGGAGAAGGCUAUG |
| | UUGGCCGGGCGACGGUUGUCCCGGUUUAAGCGUGUAGGCUGGU |
| | UUUCCAGGCAAAUCCGGAAAAUCAAGGCUGAGGCGUGAUGACGA |
| | GGCACUACGGUGCUGAAGCAACAAAUGCCCUGCUUCCAGGAAAAG |
| | CCUCUAAGCAUCAGGUAACAUCAAAUCGUACCCCAAACCGACACA |
| | GGUGGUCAGGUAGAGAAUACCAAGGCGCUUGAGAGAACUCGGGU |
| | GAAGGAACUAGGCAAAAUGGUGCCGUAACUUCGGGAGAAGGCAC |
| | GCUGAUAUGUAGGUGAGGUCCCUCGCGGAUGGAGCUGAAAUCAG |
| | UCGAAGAUACCAGCUGGCUGCAACUGUUUAUUAAAAACACAGCAC |
| | UGUGCAAACACGAAAGUGGACGUAUACGGUGUGACGCCUGCCCG |
| | GUGCCGGAAGGUUAAUUGAUGGGGUUAGCGCAAGCGAAGCUCUU |
| | GAUCGAAGCCCCGGUAAACGGCGGCCGUAACUAUAACGGUCCUAA |
| | GGUAGCGAAAUUCCUUGUCGGGUAAGUUCCGACCUGCACGAAUG |
| | GCGUAAUGAUGGCCAGGCUGUCUCCACCCGAGACUCAGUGAAAU |
| | UGAACUCGCUGUGAAGAUGCAGUGUACCCGCGGCAAGACGGAAA |
| | GACCCCGUGAACCUUUACUAUAGCUUGACACUGAACAUUGAGCCU |
| | UGAUGUGUAGGAUAGGUGGGAGGCUUUGAAGUGUGGACGCCAGU |
| | CUGCAUGGAGCCGACCUUGAAAUACCACCCUUUAAUGUUUGAUGU |
| | UCUAACGUUGACCCGUAAUCCGGGUUGCGGACAGUGUCUGGUGG |
| | GUAGUUUGACUGGGGCGGUCUCCUCCUAAAGAGUAACGGAGGAG |
| | CACGAAGGUUGGCUAAUCCUGGUCGGACAUCAGGAGGUUAGUGC |
| | AAUGGCAUAAGCCAGCUUGACUGCGAGCGUGACGGCGCGAGCAG |
| | GUGCGAAAGCAGGUCAUAGUGAUCCGUGGUUCUGAAUGGAAGG |
| | GCCAUCGCUCAACGGAUAAAAGGUACUCCGGGGAUAACAGGCUGA |
| | UACCGCCCAAGAGUUCAUAUCGACGGCGGUGUUUGGCACCUCGA |
| | UGUCGGCUCAUCACAUCCUGGGGCUGAAGUAGGUCCCAAGGGUA |
| | UGGCUGUUCGCCAUUUAAAGUGGUACGCGAGCUGGGUCUAGAAC |
| | GUCGUGAGACAGUUCGGUCCCUAUCUGCCGUGGGCGCUGGAGAA |
| | CUGAGGGGGCUGCUCCUAGUACGAGAGGACCGGAGUGGACGCA |
| | UCACUGGUGUUCGGGUUGUCAUGCCAAUGGCACUGCCCGGUAGC |
| | UAAAUGCGGAAGAGAUAAGUGCUGAAAGCAUCUAAGCACGAAACU |
| | UGCCCCGAGAUGAGUUCUCCCUGACCCUUUAAGGGUCCUGAAGG |
| | AACGUUGAAGACGACGUUGAUAGGCCGGGUGUGUAAGCGCA |
| | GCGAUGCGUUGAGCUAACCGGUACUAAUGAACCGUGAGGCUUAA |
| | CCUUACAACGCCGAAGCUGUUUUGGCGGAUGAGAGAAGAUUUUCA |
| | GCCUGAUACAGAUUAAAUCAGAACGCAGAAGCGGUCUGAUAAAAC |
| | AGAAUUUGCCUGGCGGCAGUAGCGCGGUGGUCCCACCUGACCCC |
| | AUGCCGAACUCAGAAGUGAAACGCCGUAGCGCCGAUGGUAGUGU |
| | GGGGUCUCCCCAUGCGAGAGUAGGGAACUGCCAGGCAUCAAAUA |
| | AAACGAAAGGCUCAGUCGAAAGACUGGGCCUUUCGUUUUAUCUGU |
| | UGUUUGUCGGUGAACGCUCUCCUGAGUAGGACAAAUCCGCCGGG |
| | AGCGGAUUUGAACGUUGCGAAGCAACGGCCCGGAGGGUGGCGGG |
| | CAGGACGCCCGCCAUAAACUGCCAGGCAUCAAAUUAAGCAGAAGG |
| | CCAUCCUGACGGAUGGCCUUUUUG |

All references, including publications, patent applications, and patents, cited herein are hereby incorporated by reference to the same extent as if each reference were individually and specifically indicated to be incorporated by reference and were set forth in its entirety herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in

What is claimed is:

1. A platform for preparing a sequence defined biopolymer in vitro, the platform comprising:
    (a) a ribosome-depleted cellular extract comprising an S150 bacterial extract harvested from mid-exponential growth phase to late-exponential growth phase at an $OD_{600}$ greater than 3 and up to 5, the ribosome-depleted cellular extract having a protein concentration of greater than about 5 mg/ml, the ribosome-depleted cellular extract having a polyamine at a concentration of 1.0-5.0 mM, and the ribosome-depleted cellular extract having a concentration of salts from about 50 mM to about 300 mM;
    (b) ribosomal RNAs prepared by in vitro transcription; and
    (c) purified ribosomal proteins depleted of ribosomal RNAs.

2. The platform according to claim 1, wherein the polyamine is selected from the group consisting of spermine, spermidine and putrescine.

3. The platform according to claim 1, further comprising at least one exogenous DNA template encoding ribosomal RNAs and at least one exogenous DNA template encoding a mRNA for the sequence defined biopolymer.

4. The platform according to claim 1, wherein the ribosomal RNAs are prepared from an isolated nucleic acid comprising SEQ ID NO: 26, or variants thereof.

5. The platform according to claim 1, wherein the ribosomal RNAs comprise transcripts produced from one or more isolated nucleic acids.

6. The platform according to claim 1, wherein ribosomes assemble from the ribosomal RNA and the ribosomal proteins to produce biopolymers.

7. The platform according to claim 1, wherein the platform is configured for fed-batch operation or continuous operation.

8. The platform according to claim 1, wherein at least one substrate is replenished.

9. The platform according to claim 1, further comprising a DNA-dependent RNA polymerase.

10. The platform according to claim 1, further comprising at least one macromolecular crowding or volume-excluding agent.

11. The platform according to claim 1, further comprising at least one reducing agent.

12. A method for preparing a sequence defined biopolymer in vitro, the method comprising:
    (a) providing the platform according to claim 1;
    (b) adding the purified ribosomal proteins depleted of ribosomal RNA to the ribosomal RNAs prepared by in vitro transcription in the presence of the ribosome-depleted extract to provide a translation platform mixture; and
    (c) providing an RNA transcription template encoding the sequence defined biopolymer to the translational platform mixture to prepare the sequence defined biopolymer in vitro.

13. A method for preparing a sequence defined biopolymer in vitro, the method comprising:
    (a) providing a translation platform mixture, wherein the translation platform mixture is prepared from a platform of claim 1 by adding the purified ribosomal proteins depleted of ribosomal RNA of part (c) to the ribosomal RNAs prepared by in vitro transcription of part (b) in the presence of the ribosome-depleted extract of part (a); and
    (b) providing an RNA transcription template encoding the sequence defined biopolymer to the translation platform mixture to prepare the sequence defined biopolymer in vitro.

14. A platform for preparing a sequence defined biopolymer in vitro, the platform comprising:
    (a) a ribosome-depleted cellular extract prepared from an S150 bacterial extract harvested at about 3 $OD_{600}$, the ribosome-depleted cellular extract having a protein concentration of greater than about 5 mg/ml, the ribosome-depleted cellular extract having a polyamine at a concentration of 1.0-5.0 mM, and the ribosome-depleted cellular extract having a concentration of salts from about 50 mM to about 300 mM;
    (b) ribosomal RNAs prepared by in vitro transcription; and
    purified ribosomal proteins depleted of ribosomal RNAs.

15. A platform for preparing a sequence defined biopolymer in vitro, the platform comprising:
    (a) a ribosome-depleted cellular extract comprising an S150 bacterial extract harvested from mid-exponential growth phase to late-exponential growth phase at an $OD_{600}$ greater than 3 and up to 5, the ribosome-depleted cellular extract having a protein concentration of greater than about 5 mg/ml, the ribosome-depleted cellular extract having a polyamine at a concentration of 1.0-5.0 mM, and the ribosome-depleted cellular extract having a concentration of salts from about 50 mM to about 300 mM;
    (b) ribosomal RNAs prepared by in vitro transcription, wherein the ribosomal RNAs are transcribed from an rRNA-encoding template comprising a synthetic 3' gene modification that enables highly efficient termination of the transcribed ribosomal RNAs; and
    (c) purified ribosomal proteins depleted of ribosomal RNAs.

16. The platform of claim 15, wherein the synthetic 3' gene modification is a hammerhead ribozyme.

17. The platform of claim 15, wherein the synthetic 3' gene modification is a transcription terminator.

18. A platform for preparing a sequence defined biopolymer in vitro, the platform comprising:
    (a) a ribosome-depleted cellular extract comprising an S150 bacterial extract harvested from mid-exponential growth phase to late-exponential growth phase at an $OD_{600}$ greater than 3 and up to 5, the ribosome-depleted cellular extract having a protein concentration of greater than about 5 mg/ml, the ribosome-depleted cellular extract having a polyamine at a concentration of 1.0-5.0 mM, and the ribosome-depleted cellular extract having a concentration of salts from about 50 mM to about 300 mM;
    (b) ribosomal RNAs prepared by in vitro transcription, wherein the ribosomal RNAs are transcribed from an rRNA-encoding template comprising native operon structure and RNA processing sites that enhance synthesis and stoichiometric balancing of the rRNA; and
    (c) purified ribosomal proteins depleted of ribosomal RNAs.

19. A method for preparing a sequence defined biopolymer in vitro, the method comprising:
    (a) providing the platform according to claim 15;
    (b) adding the purified ribosomal proteins depleted of ribosomal RNA to the ribosomal RNAs prepared by in vitro transcription in the presence of the ribosome-depleted extract to provide a translation platform mixture; and (c) providing an RNA transcription template encoding the sequence defined biopolymer to the translational platform mixture to prepare the sequence defined biopolymer in vitro.

20. A method for preparing a sequence defined biopolymer in vitro, the method comprising:
 (a) providing the platform according to claim 18;
 (b) adding the purified ribosomal proteins depleted of ribosomal RNA to the ribosomal RNAs prepared by in vitro transcription in the presence of the ribosome-depleted extract to provide a translation platform mixture; and
 (c) providing an RNA transcription template encoding the sequence defined biopolymer to the translational platform mixture to prepare the sequence defined biopolymer in vitro.

\* \* \* \* \*